US010801027B2

(12) United States Patent
Hautbergue et al.

(10) Patent No.: US 10,801,027 B2
(45) Date of Patent: Oct. 13, 2020

(54) INHIBITORS OF SRSF1 TO TREAT NEURODEGENERATIVE DISORDERS

(71) Applicant: University of Sheffield, Sheffield (GB)

(72) Inventors: Guillaume Hautbergue, Sheffield (GB); Mimoun Azzouz, Sheffield (GB); Alexander Whitworth, Cambridge (GB); Pamela Shaw, Sheffield (GB)

(73) Assignee: University of Sheffield, Sheffield (GB)

( * ) Notice: Subject to any disclaimer, the term of this patent is extended or adjusted under 35 U.S.C. 154(b) by 0 days.

(21) Appl. No.: 16/304,487

(22) PCT Filed: May 30, 2017

(86) PCT No.: PCT/GB2017/051539
§ 371 (c)(1),
(2) Date: Nov. 26, 2018

(87) PCT Pub. No.: WO2017/207979
PCT Pub. Date: Dec. 7, 2017

(65) Prior Publication Data
US 2019/0194660 A1    Jun. 27, 2019

(30) Foreign Application Priority Data
Jun. 1, 2016   (GB) .................................. 1609597.8

(51) Int. Cl.
| | |
|---|---|
| A61K 48/00 | (2006.01) |
| C07H 21/04 | (2006.01) |
| C12N 15/113 | (2010.01) |
| C12N 9/12 | (2006.01) |
| A61P 35/00 | (2006.01) |
| A61K 38/00 | (2006.01) |

(52) U.S. Cl.
CPC ............ *C12N 15/113* (2013.01); *A61P 35/00* (2018.01); *C12N 9/1205* (2013.01); *C12Y 207/11001* (2013.01); *A61K 38/00* (2013.01); *C12N 2310/11* (2013.01); *C12N 2310/14* (2013.01); *C12N 2310/531* (2013.01); *C12N 2740/16043* (2013.01)

(58) Field of Classification Search
CPC ..................... A61K 31/713; C12N 15/115
See application file for complete search history.

(56) References Cited

U.S. PATENT DOCUMENTS

2015/0376622 A1* 12/2015 Bradburne ......... C12N 15/1131
                                                    514/44 A

FOREIGN PATENT DOCUMENTS

| CN | 102747083 B | 4/2014 |
|---|---|---|
| WO | WO 2004/048511 A2 | 6/2004 |
| WO | WO 2013/106934 A1 | 7/2013 |
| WO | WO 2016/040167 A1 | 3/2016 |
| WO | WO 2016/077687 A1 | 5/2016 |

OTHER PUBLICATIONS

Wee et al. (PLoS One, Dec. 15, 2014;9(12):e115205).*
Crunkhorn (Nature Reviews, Drug Discovery, vol. 14, No. 6, p. 386, 2015).*
Orafidiya et al. (Future Sci. OA, 2015, 1(2), FSO47, pp. 1-10).*
Shi et al. (Journal of Biological Chemistry, vol. 286, No. 16, 2011, pp. 14639-14648).*
Anczuków et al., "The splicing factor SRSF1 regulates apoptosis and proliferation to promote mammary epithelial cell transformation," *Nat Struct Mol Biol.* 19:220-228, 2012.
Crunkhorn et al., "Neurodegenerative disease: Phosphatase inhibitor prevents protein-misfolding diseases," *Nat Rev Drug Discov.* 14:386, 2015.
Daniilidou et al., "Detection of elevated antibodies against SR protein kinase 1 in the serum of Alzheimer's disease patients," *J Neuroimmunol.* 238:67-72, 2011.
Das and Krainer, "Emerging functions of SRSF1, splicing factor and oncoprotein, in RNA metabolism and cancer," *Mol Cancer Res.* 12:1195-1204, 2014.
Guo et al., "HnRNP A1/A2 and SF2/ASF Regulate Alternative Splicing of Interferon Regulatory Factor-3 and Affect Immunomodulatory Functions in Human Non-Small Cell Lung Cancer Cells," *PLoS One* 8:e62729, 2013.
Hautbergue et al., "SRSF1-dependent nuclear export inhibition of C9ORF72 repeat transcripts prevents neurodegeneration and associated motor deficits," *Nat Commun.* 8:16063, 2017.
Khan et al., "RNA-dependent dynamic histone acetylation regulates MCL1 alternative splicing," *Nucleic Acids Res.*42:1656-1670, 2014.
Marcel et al., "Modulation of p53β and p53γ expression by regulating the alternative splicing of TP53 gene modifies cellular response," *Cell Death Differ.*21:1377-1387, 2014.
Mavrou et al., "Serine-arginine protein kinase 1 (SRPK1) inhibition as a potential novel targeted therapeutic strategy in prostate cancer," *Oncogene* 34:4311-4319, 2015.
Oltean et al., "SRPK1 inhibition in vivo: modulation of VEGF splicing and potential treatment for multiple diseases," *Biochem Soc Trans.* 40: 831-835, 2012.
Wee et al., "Targeting SR proteins improves SMN expression in spinal muscular atrophy cells," *PLoS One* 9:e115205, 2014 (with Supplementary Table and References).
Zamiri et al., "TMPyP4 Porphyrin Distorts RNA G-quadruplex Structures of the Disease-associated r(GGGGCC)n Repeat of the C9orf72 Gene and Blocks Interaction of RNA-binding Proteins," *J Biol Chem.* 289:4653-4659, 2014.
Zhao et al., "Splicing factor 2/alternative splicing factor contributes to extracellular signal-regulated kinase activation in hepatocellular carcinoma cells," *Mol Med Rep.* 12:3890-3894, 2015.
GB 1609597.8 Search Report dated Mar. 2, 2017 (9 pages).
PCT/GB2017/051539 International Search Report & Written Opinion dated Aug. 24, 2017 (18 pages).

* cited by examiner

*Primary Examiner* — Amy H Bowman
(74) *Attorney, Agent, or Firm* — Klarquist Sparkman, LLP

(57) ABSTRACT

The present disclosure relates to antagonists that target Serine/Arginine-Rich Splicing Factor 1 (SRSF1); expression vectors comprising SRSF1 antagonists; and the use of such antagonists in therapy for the treatment of neurodegenerative disorders and cancer and screening methods that identify agents that inhibit the expression or activity of SRSF1.

24 Claims, 57 Drawing Sheets

Specification includes a Sequence Listing.

Figure 4A 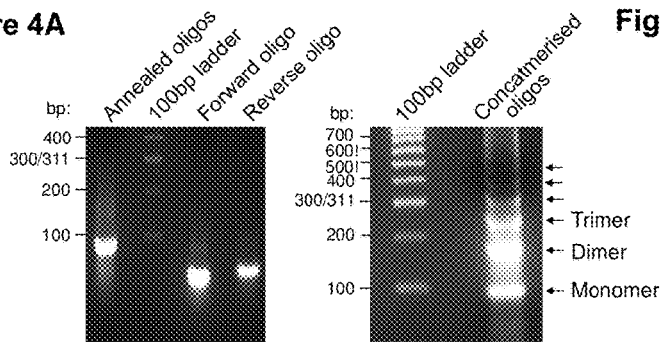 Figure 4B 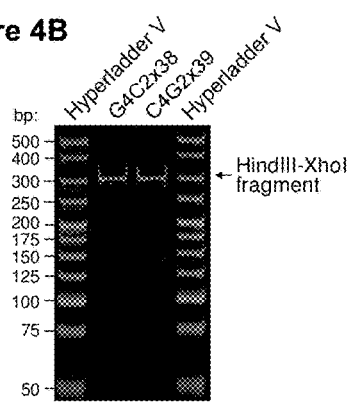

Figure 4C 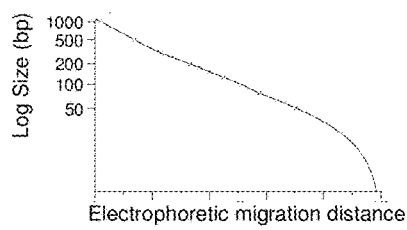

Figure 4D

| Construct | Theoretical Size | Calculated Size |
|---|---|---|
| G4C2x38 | 317 bp | 315 bp |
| C4G2x39 | 316 bp | 316 bp |

Figure 4E RAN-G4C2x38 sense-repeats (SEQ ID NO: 40)

...TGGCTT ATGAAATTAATACGACTCACTATAGGGAGACCCAAGCTGGCTAGTTAAGCTTGGTACCGAGCTCGGATCCACTA
GTCCAGTGTGGTGGAATTGGGCCCGGCCGCCGGCCGGCCGGCCGGCCGGCCGGCCGGCCGGCCGGCCGGCCGGCCGGCC
GGCCGGCCGGCCGGCCGGCCGGCCGGCCGGCCGGCCGGCCGGCCGGCCGGCCGGCCGGCCGGCCGGCCGGCCGGCCGGCC
GGAATTCTGCAGATATCCAGCACAGTGGCGGCCGCTCGAGTCTAGAGGGCCCTTCGAACAAAAACTCATCTCAGAAGAGGATCTG
AATATGCATACCGGTCATCATCACCATCACCATTGAGTTTAAACCCGCTGATCAGCCT CGACTG...

RAN-C4G2x39 antisense-repeats: (SEQ ID NO: 41)

...TGGCTT ATGAAATTAATACGACTCACTATAGGGAGACCCAAGCTGGCTAGTTAAGCTTGGTACCGAGCTCGGATCCACTA
GTCCAGTGTGGTGGAATTGGGCCCGGCCGCCGGCCGGCCGGCCGGCCGGCCGGCCGGCCGGCCGGCCGGCCGGCCGGCC
GGCCGGCCGGCCGGCCGGCCGGCCGGCCGGCCGGCCGGCCGGCCGGCCGGCCGGCCGGCCGGCCGGCCGGCCGGCCGGCC
CAATTCTGCAGATATCCAGCACAGTGGCGGCCGCTCGAGTCTAGAGGGCCCTTCGAACAAAAACTCATCTCAGAAGAGGATCTG
ATATGCATACCGGTCATCATCACCATCACCATTGAGTTTAAACCCGCTGATCAGCCT CGACTG...

Figure 6A
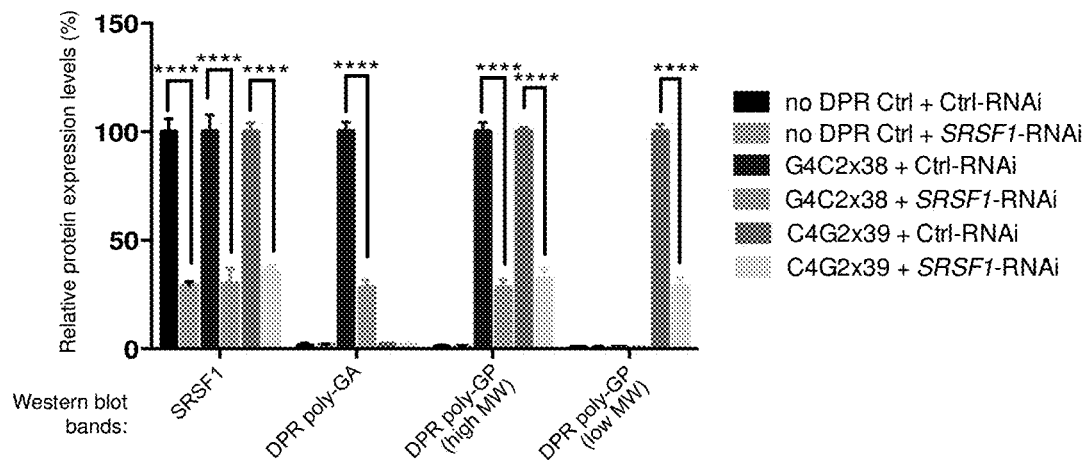

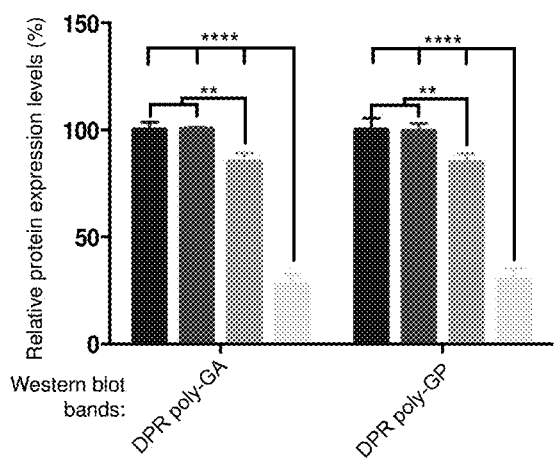
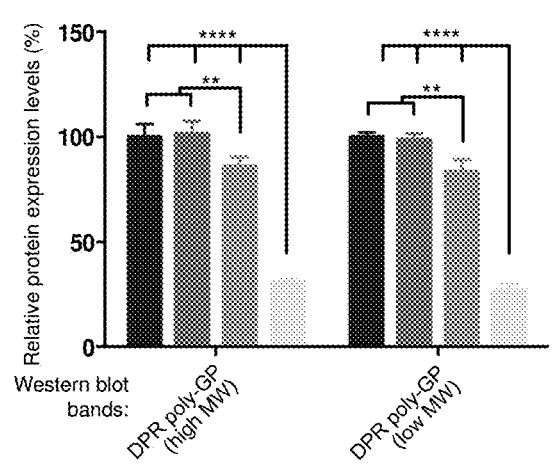

Figure 12A

(SEQ ID NO 1)

```
1     atgtcggagg tggtgtgatt cgtggccccg
241   cagggaacaa cgattgccgc atctacgtgg gtaacttacc tccagacatc cgaaccaagg
301   acattgagga cgtgttctac aaatacggcg ctatccgcga catcgacctc aagaatcgcc
361   gcggggacc gcccttcgcc ttcgttgagt tcgaggaccc gcgagacgcg gaagacgcgg
421   tgtatggtcg cgacggctat gattacgatg gtaccgtct gcggtggag tttcctcgaa
481   gcggccgtgg aacaggccga ggcggcggcg ggggtggagg tggcggagct ccccgaggtc
541   gctatggccc cccatccagg cggtctgaaa acagagtggt tgtctctgga ctgcctccaa
601   gtggaagttg gcaggattta aaggatcaca tgcgtgaagc aggtgatgta tgttatgctg
661   atgtttaccg agatggcact ggtgtcgtgg agtttgtacg gaaagaagat atgacctatg
721   cagttcgaaa actggataac actaagttta gatctcatga gggagaaact gcctacatcc
781   gggttaaagt tgatgggccc agaagtccaa gttatggaag atctcgatct cgaagccgta
841   gtcgtagcag aagccgtagc agaagcaaca gcaggagtcg cagttactcc ccaaggagaa
901   gcagaggatc accacgctat tctccccgtc atagcagatc tcgctctcgt acataa
```

Figure 12B

(SEQ ID NO 2):
MSGGGVIRGPAGNNDCRIYVGNLPPDIRTKDIEDVFYKYGAIRDIDLKNRRGGPPFAFV
EFEDPRDAEDAVYGRDGYDYDGYRLRVEFPRSGRGTGRGGGGGGGGAPRGRYGP
PSRRSENRVVVSGLPPSGSWQDLKDHMREAGDVCYADVYRDGTGVVEFVRKEDMTY
AVRKLDNTKFRSHEGETAYIRVKVDGPRSPSYGRSRSRSRSRSRSRSNSRSRSYS
PRRSRGSPRYSPRHSRSRSRT

Figure 12C
(SEQ ID NO: 3)

```
      atgtcggagg tggtgtgatt cgtggccccg
241   cagggaacaa cgattgccgc atctacgtgg gtaacttacc tccagacatc cgaaccaagg
301   acattgagga cgtgttctac aaatacggcg ctatccgcga catcgacctc aagaatcgcc
361   gcggggacc gcccttcgcc ttcgttgagt tcgaggaccc gcgagacgcg gaagacgcgg
421   tgtatggtcg cgacggctat gattacgatg gtaccgtct gcggtggag tttcctcgaa
481   gcggccgtgg aacaggccga ggcggcggcg ggggtggagg tggcggagct ccccgaggtc
541   gctatggccc cccatccagg cggtctgaaa acagagtggt tgtctctgga ctgcctccaa
601   gtggaagttg gcaggattta aaggatcaca tgcgtgaagc aggtgatgta tgttatgctg
661   atgtttaccg agatggcact ggtgtcgtgg agtttgtacg gaaagaagat atgacctatg
721   cagttcgaaa actggataac actaagttta gatctcatga ggtaggttat acacgtattc
781   ttttctttga ccagaattgg atacagtggt cttaa
```

Figure 12D
(SEQ ID NO: 4)
MSGGGVIRGPAGNNDCRIYVGNLPPDIRTKDIEDVFYKYGAIRDIDLKNRRGGPPFAFV
EFEDPRDAEDAVYGRDGYDYDGYRLRVEFPRSGRGTGRGGGGGGGGAPRGRYGP
PSRRSENRVVVSGLPPSGSWQDLKDHMREAGDVCYADVYRDGTGVVEFVRKEDMTY
AVRKLDNTKFRSHEVGYTRILFFDQNWIQWS

Figure 12E
(SEQ ID NO 23)

```
1     gttgcgctcc cgcgcgtgcg tgttgggatc gaatcgctgt ttccttccgc ttctcttcct
61    ctgtctcccc cccatatccg tgcgccgagc tgataaaggc gccattttgg aggggccgcg
121   ggagacgtgg tgccgctgcg ggctcgctct gccgtgcgct aggcttggtg ggaaggcctg
181   ttctcgagtc cgcgcttttc gtcaccgcca tgtcggagg tggtgtgatt cgtggcccg
241   cagggaacaa cgattgccgc atctacgtgg gtaacttacc tccagacatc cgaaccaagg
301   acattgagga cgtgttctac aaatacggcg ctatccgcga catcgacctc aagaatcgcc
361   gcggggacc gcccttcgcc ttcgttgagt tcgaggaccc gcgagacgcg gaagacgcgg
421   tgtatggtcg cgacggctat gattacgatg ggtaccgtct gcgggtggag tttcctcgaa
481   gcggccgtgg aacaggccga ggcggcggcg ggggtggagg tggcggagct ccccgaggtc
541   gctatggccc cccatccagg cggtctgaaa acagagtggt tgtctctgga ctgcctccaa
601   gtggaagttg gcaggattta aaggatcaca tgcgtgaagc aggtgatgta tgttatgctg
661   atgtttaccg agatggcact ggtgtcgtgg agtttgtacg gaaagaagat atgacctatg
721   cagttcgaaa actggataac actaagttta gatctcatga ggtaggttat acacgtattc
781   ttttctttga ccagaattgg atacagtggt cttaacagtg gaatttcaag gtaaggattc
841   aggcaaggtt gtccaagtaa attgccagat ttctggtttt agttacattg tattcattca
901   gcatgtctga agatagatga aagcttagat ctttcaatgg aaagttctgt ctatccaata
961   gggagaaact gcctacatcc gggttaaagt tgatgggccc agaagtccaa gttatggaag
1021  atctcgatct cgaagccgta gtcgtagcag aagccgtagc agaagcaaca gcaggagtcg
1081  cagttactcc ccaaggagaa gcagaggatc accacgctat tctccccgtc atagcagatc
1141  tcgctctcgt acataagatg attggtgaca cttttgtag aacccatgtt gtatacagtt
1201  ttcctttatt cagtacaatc ttttcatttt ttaattcaaa ctgttttgtt cagaatgggc
1261  taaagtgttg aattgcattc ttgtaatatc cccttgctcc taacatctac attcccttcg
1321  tgtctttgat aaattgtatt ttaagtgatg tcatagacag gattgtttaa atttagttaa
1381  ctccatactc ttcagactgt gatattgtgt aaatgtctat ctgccctggt tgtgtgaac
1441  tgggatgttg ggggtgtttg tggttatctt acctggggaa gttcttatgt ttatcttgct
1501  tttcatgtgt ctttctgtag acatatctga agagatggat taagaatgct ttggattaag
1561  gattgtggag cacatttcaa tcatttagg attgtcaaaa ggaggattga ggaggatcag
1621  atcaataatg gaggcaatgg tttggattgg agagggctca ctggatccca atccttggag
1681  ctggatcatt ggattcaaat cataatgtgg atagatagg gaggatgaat taccaggatt
1741  catggagcgg gatcagatta ccaggaacat aggagtggat tcctgcccca accaaaccgc
1801  attcgtgtgg atttttttat tcaacttaat tggctattcc aaagattttt ttttcctat
1861  ttttgacgat tggagcccct aagatgcacg atggaattgt gttttgcgtt ttttggtaaa
1921  aggagcaaag cgaggacctg gagataaacg ctggagcaat ctccttggaa ggattcagca
1981  cgagtagatg gtaaacattt aaaggggaaa gggggggttt gtttaaaata gtaaatcagt
2041  aagtcacttc taaatttaaa gaaaacaaaa ttggagttga agaataagta ggtttccaat
2101  tggctattgc cgttttcttt gaaaaaataa acatttttta aaaaactatg catggttgtc
2161  ctttttcctc ttcatgtaag attctaactg ggtctatcag ttaatcttta aattgttaag
2221  taagataaga ttttgactct tgtgttaatg tgttagcaaa ttaaaagttc ttaaaaggca
2281  atctaatggt attagccatc ttttattgtt aattgtaaaa gtcttcaggg gaaagcaaaa
2341  ggggagaata aggcatttgt gtatgtaact tggtaaatga cggtggggga tggatctagc
2401  atctgaaaga taagcttctc tactttgtta taaagtggtt aaaaaactat agatgctgct
2461  tattttctgg tggtcataga caacataggc ttttgtgcaa aattggttga tggctactaa
2521  tgttcacttg gagatagctt ttgatattct caatgaaact catctcaaaa aaaggtaagt
2581  attaaatgtt aacatcagca cagatgtatt agaactgttt tttgttttg agacagagtc
2641  tcgctctgtt ctccagactg gagggcagtg tgtgatcta ggctcactgc aacctccacc
2701  cctggatttg agtgattctc gtgcctcagt ctcccaagta gctgagacta caagtgtgtg
2761  ccacccttgc ccggctaatt ttgtattttt agtagagatg tggtttctct gttacccca
2821  ggctggtccc aaaactcctg gcctcaagtg atctgcctgc cttggcctcc caaagtgtta
2881  ggattacagg tgtgagccac catgctcagc ctgtagaact tttaacccaa gtctcatttc
2941  tttttttgaaa gggaagagtg cacaagatta actgcttctt tggatgaatc attgttaata
```

Figure 12F

```
3001 aaaagctggg catttagaat tttgccttat aagcccttct ccaaccataa gattattttg
3061 taccaaaaac tttggtgttc tctaccaaag cagttaaaaa cttttagcct gctacttctt
3121 gtatttgtct actgacagcc ccttggtact atttaggttg ggggagggga cctaaaataa
3181 atagacttta acatttccct tgggtgctaa tcatagttgg aagttgaatt taaggtgatt
3241 atttgggtga caattaaaaa cctaaggaaa accagaaatc ttggtagtgg aagaaatgtg
3301 taaggtcacc ccaatcggta gattttaatg aacgttgtgg aatgttggga agaggggatg
3361 ttaagttgaa tgcagaattt cactaagtac ttagtgtaag tttaaggatg tagctctttt
3421 tatctaagaa ttcaatgtaa tggccaaaag gcagatttac tgtttaaaaa tttgaataat
3481 tttacatgac attcttgaaa ttctaagaag ttttatgtgt agaacatttt aaaaattcat
3541 cagattatta aagggaaaat aaatgattaa tgataatttt ggaaggttaa tgtgagctag
3601 acttaagtaa actttggttc atttgtgttc attgaatgtt ttggaaatga ccaaaaaatg
3661 taaatggcct tcactcaagt ttgagtgttt aaagttgaaa gatgtgctct actaaaagtt
3721 atagtaattc taacctcaca ttgaaatgag acagtattcc ttgttataca ggctgaattt
3781 gaagattaga gaggatctaa tgtttactta ggtaaagggg cataggtttt gtagttaaga
3841 tgaccagaca gctaaaagct gtgatggaa gtatggactg ctcctattta tagtctcaga
3901 aaatggacct ttaggtctct atccgtattg gcaattatta gaagaaagtt acacccttt
3961 gaaactacaa aagctgtctt ggaatttccc cctcttctcc ctatttatgt cccccttagaa
4021 tattttaggg agcctataat tatttcctaa ccaaggaaaa acttaagtct ctttaagaag
4081 caattacttt tcataacatc agattgaata acccaccttg ctgttcagcc cacatcctac
4141 tggaaacaaa aggtaagaaa cccatttttct ggttcttgat tgtttgggtc tgaattttgt
4201 ttttaaaact aagctaagtt taatgttttt taaaatgctg tttggaatat gaatagattc
4261 cccgtaaaat gattttcct aagttttatg ctttagtaaa tattcagtgc tcacgtctgt
4321 gcatcatagt gcttgcgttt aatatgattt attgtagaat ctcaacttttt cttggtgttt
4381 gttgtctttg aaacattgtc ttggtcatta gggctggtgt tttcacattt ctgtggtcaa
4441 ggtggatttc ttatgtgtgc ctttttgctt actttgtata tgaattttgt aatttaaatt
4501 gcaagtaagt tatatatatg tatttaccat aaatagtatt aaaagatgag aaactgttag
4561 actgaagttc tgttgtaaca taaccattat ttccatcaca gtatgaagac tgcaaacgca
4621 gaaaacagat tacagtctct tatccatttt ttgaaatcca aaaactacga aaacaaaga
4681 ttttctgttg ttgagctaat taaatgtgaa ccctgaccag aaaaaaaaaa aaaaaaaaaa
4741 aaaaaaa
```

Figure 12G

(SEQ ID NO 24)
```
1   atgtcgggaggt ggtgtgatcc
121 gtggcccggc ggggaacaac gactgccgca tctacgtggg taacctacct ccggatatcc
181 gaaccaagga catcgaggac gtgttttaca aatacggcgc catccgcgac atcgacctga
241 agaaccgccg cggggaccg cccttcgcct tcgttgagtt cgaggacccg cgagacgcgg
301 aagatgcggt gtacggtcgc gacggctacg actacgacgg ctaccggctg cgggtagagt
361 ttccccgaag cggccgcggg accggccgag gcggcggcgg gggtggaggc ggcggcgccc
421 cgagaggccg ctatggcccg ccgtccaggc ggtccgagaa cagagtggtt gtctctggac
481 tgcctccgag tggaagctgg caggacttaa aggatcacat gcgtgaggca ggtgatgtat
541 gttacgctga tgtttaccga gatggcactg gtgtcgtgga gtttgtacgg aaagaagata
601 tgacgtatgc agttcgaaaa ctggataaca ctaagtttag atctcacgag ggagaaactg
661 cctacatccg ggttaaagtt gatgggccca gaagtccaag ttatggaaga tctcgatctc
721 gaagccgtag tcgtagcaga agccgtagca gaagcaacag caggagtcgc agttactccc
781 caaggagaag cagaggatca ccacgctatt ctccccgtca tagcagatct cgctctcgta
841 cataa
```

Figure 12H

(SEQ ID NO 25)
MSGGGVIRGPAGNNDCRIYVGNLPPDIRTKDIEDVFYKYGAIRDIDLKNRRGGPPFAFV
EFEDPRDAEDAVYGRDGYDYDGYRLRVEFPRSGRGTGRGGGGGGGGAPRGRYGP
PSRRSENRVVVSGLPPSGSWQDLKDHMREAGDVCYADVYRDGTGVVEFVRKEDMTY
AVRKLDNTKFRSHEGETAYIRVKVDGPRSPSYGRSRSRSRSRSRSRSRSNSRSRSYS
PRRSRGSPRYSPRHSRSRSRT

Figure 12I

(SEQ ID NO 26)
```
   1    atgt cgggaggtgg
 481    tgtgatccgt ggcccggcgg ggaacaacga ctgccgcatc tacgtgggta acctacctcc
 541    ggatatccga accaaggaca tcgaggacgt gttttacaaa tacggcgcca tccgcgacat
 601    cgacctgaag aaccgccgcg ggggaccgcc cttcgccttc gttgagttcg aggacccgcg
 661    agacgcggaa gatgcggtgt acgtcgcga cggctacgac tacgacggct accggctgcg
 721    ggtagagttt ccccgaagcg gccgcgggac cggccgaggc ggcggcgggg gtggaggcgg
 781    cggcgccccg agaggccgct atggcccgcc gtccaggcgg tccgagaaca gagtggttgt
 841    ctctggactg cctccgagtg gaagctggca ggacttaaag gatcacatgc gtgaggcagg
 901    tgatgtatgt tacgctgatg tttaccgaga tggcactggt gtcgtggagt ttgtacggaa
 961    agaagatatg acgtatgcag ttcgaaaact ggataacact aagtttagat ctcacgaggg
1021    agaaactgcc tacatccggg ttaaagttga tgggcccaga agtccaagtt atggaagatc
1081    tcgatctcga agccgtagtc gtagcagaag ccgtagcaga agcaacagca ggagtcgcag
1141    ttactcccca aggagaagca gaggatcacc acgctattct ccccgtcata gcagatctcg
1201    ctctcgtaca taa
```

Figure 12J

(SEQ ID NO 27)
MSGGGVIRGPAGNNDCRIYVGNLPPDIRTKDIEDVFYKYGAIRDIDLKNRRGGPPFAFV
EFEDPRDAEDAVYGRDGYDYDGYRLRVEFPRSGRGTGRGGGGGGGGAPRGRYGP
PSRRSENRVVVSGLPPSGSWQDLKDHMREAGDVCYADVYRDGTGVVEFVRKEDMTY
AVRKLDNTKFRSHEGETAYIRVKVDGPRSPSYGRSRSRSRSRSRSRSRSNSRSRSYS
PRRSRGSPRYSPRHSRSRSRT

Figure 12K
(SEQ ID NO 28)
```
   1    atgt cgggaggtgg
 481    tgtgatccgt ggcccggcgg ggaacaacga ctgccgcatc tacgtgggta acctacctcc
 541    ggatatccga accaaggaca tcgaggacgt gttttacaaa tacggcgcca tccgcgacat
 601    cgacctgaag aaccgccgcg ggggaccgcc cttcgccttc gttgagttcg aggacccgcg
 661    agacgcggaa gatgcggtgt acgtcgcga cggctacgac tacgacggct accggctgcg
 721    ggtagagttt ccccgaagcg gccgcgggac cggccgaggc ggcggcgggg gtggaggcgg
 781    cggcgccccg agaggccgct atggcccgcc gtccaggcgg tccgagaaca gagtggttgt
 841    ctctggactg cctccgagtg gaagctggca ggacttaaag gatcacatgc gtgaggcagg
 901    tgatgtatgt tacgctgatg tttaccgaga tggcactggt gtcgtggagt ttgtacggaa
 961    agaagatatg acgtatgcag ttcgaaaact ggataacact aagtttagat ctcacgaggt
1021    aggttataca cttattcttt ttttggcca gaattggata cagttttctt aa
```

Figure 12L
(SEQ ID NO 29)
MSGGGVIRGPAGNNDCRIYVGNLPPDIRTKDIEDVFYKYGAIRDIDLKNRRGGPPFAFV
EFEDPRDAEDAVYGRDGYDYDGYRLRVEFPRSGRTGRGGGGGGGGAPRGRYGP
PSRRSENRVVVSGLPPSGSWQDLKDHMREAGDVCYADVYRDGTGVVEFVRKEDMTY
AVRKLDNTKFRSHEVGYTLILFFGQNWIQFS

Figure 13A
(SEQ ID NO 16)

MSGGGVIRGPAGNNDCRIYVGNLPPDIRTKDIEDVFYKYGAIRDIDLKNRRGGPPFAFV
EFEDPRDAEDAVYGRDGYDYDGYRLRVEFPASGAGTGRGGGGGGGGAPRGRYGP
PSAASENRVVVSGLPPSGSWQDLKDHMREAGDVCYADVYRDGTGVVEFVRKEDMTY
AVRKLDNTKFRSHEGETAYIRVKVDG

Figure 13B
(SEQ ID NO 17):
MAGNNDCRIYVGNLPPDIRTKDIEDVFYKYGAIRDIDLKNRRGGPPFAFVEFEDPRDAE
DAVYGRDGYDYDGYRLRVEFPASGAGTGRGGGGGGGGAPRGRYGPPSAASENRV
VVSGLPPSGSWQDLKDHMREAGDVCYADVYRDGTGVVEFVRKEDMTYAVRKLDNTK
FRSHEGETAYIRVKVDG

Figure 13C
(SEQ ID NO 152):
MSGGGVIRGPAGNNDCRIYVGNLPPDIRTKDIEDVFYKYGAIRDIDLKNRRGGPP
FAFVEFEDPRDAEDAVYGRDGYDYDGYRLRVEFPASGAGTGRGGGGGGGGA
PRGRYGPPSAASENRVVVSGLPPSGSWQDLKDHMREAGDVCYADVYRDGTGV
VEFVRKEDMTYAVRKLDNTKFRSHEGETAYIRVKVDGPRSPSYGRSRSRSRSRS
RSRSRSNSRSRSYSPRRSRGSPRYSPRHSRSRSRT

Figure 14
(SEQ ID NO 15):
PRSGRGTGRGGGGGGGGGAPRGRYGPPSRRSE

Figure 15A
(SEQ ID NO: 18)

```
1     atggag cggaaagtgc ttgcgctcca ggcccgaaag aaaaggacca aggccaagaa
181   ggacaaagcc caaaggaaat ctgaaactca gcaccgaggc tctgctcccc actctgagag
241   tgatctacca gagcaggaag aggagattct gggatctgat gatgatgagc aagaagatcc
301   taatgattat tgtaaggag gttatcatct tgtgaaaatt ggagatctat tcaatgggag
361   ataccatgtg atccgaaagt taggctgggg acactttca acagtatggt tatcatggga
421   tattcagggg aagaaatttg tggcaatgaa agtagttaaa agtgctgaac attacactga
481   aacagcacta gatgaaatcc ggttgctgaa gtcagttcgc aattcagacc ctaatgatcc
541   aaatagagaa atggttgttc aactactaga tgactttaaa atatcaggag ttaatggaac
601   acatatctgc atggtatttg aagttttggg gcatcatctg ctcaagtgga tcatcaaatc
661   caattatcag gggcttccac tgccttgtgt caaaaaaatt attcagcaag tgttacaggg
721   tcttgattat ttacatacca agtgccgtat catccacact gacattaaac cagagaacat
781   cttattgtca gtgaatgagc agtacattcg gaggctggct gcagaagcaa cagaatggca
841   gcgatctgga gctcctccgc cttccggatc tgcagtcagt actgctcccc agcctaaacc
901   agctgacaaa atgtcaaaga ataagaagaa gaaattgaag aagaagcaga agcgccaggc
961   agaattacta gagaagcgaa tgcaggaaat tgaggaaatg gagaaagagt cgggccctgg
1021  gcaaaaaaga ccaaacaagc aagaagaatc agagagtcct gttgaaagac ccttgaaaga
1081  gaacccacct aataaaatga cccaagaaaa acttgaagag tcaagtacca ttggccagga
1141  tcaaacgctt atggaacgtg atacagaggg tggtgcagca gaaattaatt gcaatggagt
1201  gattgaagtc attaattata ctcagaacag taataatgaa acattgagac ataaagagga
1261  tctacataat gctaatgact gtgatgtcca aaatttgaat caggaatcta gtttcctaag
1321  ctcccaaaat ggagacagca gcacatctca agaaacagac tcttgtacac ctataacatc
1381  tgaggtgtca gacaccatgg tgtgccagtc ttcctcaact gtaggtcagt cattcagtga
1441  acaacacatt agccaacttc aagaaagcat tcgggcagag ataccctgtg aagatgaaca
1501  agagcaagaa cataacggac cactggacaa caaaggaaaa tccacggctg gaaattttct
1561  tgttaatccc cttgagccaa aaaatgcaga aaagctcaag gtgaagattg ctgaccttgg
1621  aaatgcttgt tgggtgcaca acatttcac tgaagatatt caaacaaggc aatatcgttc
1681  cttggaagtt ctaatcggat ctggctataa taccctgct gacatttgga gcacggcatg
1741  catggccttt gaactggcca caggtgacta tttgttgaa cctcattcag gggaagagta
1801  cactcgagat gaagatcaca ttgcattgat catagaactt ctggggaagg tgcctcgcaa
1861  gctcattgtg gcaggaaaat attccaagga atttttcacc aaaaaaggtg acctgaaaca
1921  tatcacgaag ctgaaacctt ggggccttt tgaggttcta gtggagaagt atgagtggtc
1981  gcaggaagag gcagctggct tcacagattt cttactgccc atgttggagc tgatccctga
2041  gaagagcc actgccgccg agtgtctccg gcaccttgg cttaactcct aa
```

Figure 15B

SEQ ID NO: 19

MERKVLALQARKKRTKAKKDKAQRKSETQHRGSAPHSESDLPEQEEEILGSDDDEQE
DPNDYCKGGYHLVKIGDLFNGRYHVIRKLGWGHFSTVWLSWDIQGKKFVAMKVVKSA
EHYTETALDEIRLLKSVRNSDPNDPNREMVVQLLDDFKISGVNGTHICMVFEVLGHHLL
KWIIKSNYQGLPLPCVKKIIQQVLQGLDYLHTKCRIIHTDIKPENILLSVNEQYIRRLAAEAT
EWQRSGAPPPSGSAVSTAPQPKPADKMSKNKKKKLKKKQKRQAELLEKRMQEIEEME
KESGPGQKRPNKQEESESPVERPLKENPPNKMTQEKLEESSTIGQDQTLMERDTEGG
AAEINCNGVIEVINYTQNSNNETLRHKEDLHNANDCDVQNLNQESSFLSSQNGDSSTS
QETDSCTPITSEVSDTMVCQSSSTVGQSFSEQHISQLQESIRAEIPCEDEQEQEHNGPL
DNKGKSTAGNFLVNPLEPKNAEKLKVKIADLGNACWVHKHFTEDIQTRQYRSLEVLIGS
GYNTPADIWSTACMAFELATGDYLFEPHSGEEYTRDEDHIALIIELLGKVPRKLIVAGKY
SKEFFTKKGDLKHITKLKPWGLFEVLVEKYEWSQEEAAGFTDFLLPMLELIPEKRATAAE
CLRHPWLNS

Figure 16A
(SEQ ID NO: 20)
mRNA sequence:

```
   1  gtgcatgacc cgccccgcgg cggagacgcg ctcgctgcgt catcagtgtt ttcgagacga
  61  gtctcgacgc agcagctgtc agctccattt tgttgttggt gcgcgacgca gtcagctgcg
 121  tgattcccgt gattgcgtta caagctttgt ctccttcgac ttggagtctt tgtccaggac
 181  g▓▓agacac tcaaagagaa cttactgtcc tgattgggat gacaaggatt gggattatgg
 241  aaaatggagg agcagcagca gtcataaaag aaggaagaga tcacatagca gtgcccagga
 301  gaacaagcgc tgcaaataca atcactctaa aatgtgtgat agccattatt ggaaagcag
 361  gtctataaat gagaaagatt atcatagtcg acgctacatt gatgagtaca gaaatgacta
 421  cactcaagga tgtgaacctg gacatcgcca agagaccat gaaagccggt atcagaacca
 481  tagtagcaag tcttctggta gaagtggaag aagtagttat aaaagcaaac acaggattca
 541  ccacagtact tcacatcgtc gttcacatgg gaagagtcac cgaaggaaaa gaaccaggag
 601  tgtagaggat gatgaggagg gtcacctgat ctgtcagagt ggagacgtac taagtgcaag
 661  atatgaaatt gttgatactt taggtgaagg agcttttgga aaagttgtgg agtgcatcga
 721  tcataaagcg ggaggtagac atgtagcagt aaaaatagtt aaaaatgtgg atagatactg
 781  tgaagctgct cgctcagaaa tacaagttct ggaacatctg aatacaacag accccaacag
 841  tactttccgc tgtgtccaga tgttggaatg gtttgagcat catggtcaca tttgcattgt
 901  ttttgaacta tgggactta gtacttacga cttcattaaa gaaaatggtt ttctaccatt
 961  tcgactggat catatcagaa agatggcata tcagatatgc aagtctgtga attttttgca
1021  cagtaataag ttgactcaca cagacttaaa gcctgaaaac atcttatttg tgcagtctga
1081  ctacacagag gcgtataatc ccaaaataaa acgtgatgaa cgcaccttaa taaatccaga
1141  tattaaagtt gtagactttg gtagtgcaac atatgatgac gaacatcaca gtacattggt
1201  atctacaaga cattatagag cacctgaagt tattttagcc ctagggtggt cccaaccatg
1261  tgatgtctgg agcatagat gcattcttat tgaatactat cttggtttta ccgtatttcc
1321  aacacacgat agtaaggagc atttagcaat gatggaaagg attcttggac ctctaccaaa
1381  acatatgata cagaaaacca ggaaacgtaa atattttcac cacgatcgat tagactggga
1441  tgaacacagt tctgccggca gatatgtttc aagacgctgt aaacctctga aggaatttat
1501  gctttctcaa gatgttgaac atgagcgtct ctttgacctc attcagaaaa tgttggagta
1561  tgatccagcc aaaagaatta ctctcagaga agcttaaag catcctttct ttgaccttct
1621  gaagaaaagt ata▓▓atct gtaattggac agctctctcg aagagatctt acagactgta
1681  tcagtctaat ttttaaattt taagttattt tgtacagctt tgtaaattct taacattttt
1741  atattgccat gtttattttg tttgggtaat ttggttcatt aagtacatag ctaaggtaat
1801  gaacatcttt ttcagtaatt gtaaagtgat ttattcagaa taaattttt gtgcttatga
1861  agttgatatg tatctgaaca gtttgttcta agtaccattt ttcttcctac ttctattaaa
1921  gaatggacat aga
```

Figure 16B
[SEQ ID NO: 21]

MRHSKRTYCPDWDDKDWDYGKWRSSSSHKRRKRSHSSAQENKRCKYNHSKMCDS
HYLESRSINEKDYHSRRYIDEYRNDYTQGCEPGHRQRDHESRYQNHSSKSSGRSGRS
SYKSKHRIHHSTSHRRSHGKSHRRKRTRSVEDDEEGHLICQSGDVLSARYEIVDTLGE
GAFGKVVECIDHKAGGRHVAVKIVKNVDRYCEAARSEIQVLEHLNTTDPNSTFRCVQM
LEWFEHHGHICIVFELLGLSTYDFIKENGFLPFRLDHIRKMAYQICKSVNFLHSNKLTHTD
LKPENILFVQSDYTEAYNPKIKRDERTLINPDIKVVDFGSATYDDEHHSTLVSTRHYRAP
EVILALGWSQPCDVWSIGCILIEYYLGFTVFPTHDSKEHLAMMERILGPLPKHMIQKTRK
RKYFHHDRLDWDEHSSAGRYVSRRCKPLKEFMLSQDVEHERLFDLIQKMLEYDPAKRI
TLREALKHPFFDLLKKSI

Figure 17A
[SEQ ID NO: 22]
mRNA sequence (coding sequence 30-1022nt)

```
   1  gggcaaggag ctgctggctg gacggcggc  gtccgacag cgagaagctc aacctggact
  61  cgatcatcgg gcgcctgctg gaagtgcagg gctcgcggcc tggcaagaat gtacagctga
 121  cagagaacga gatccgcggt ctgtgcctga atcccggga gattttctg agccagccca
 181  ttcttctgga gctggaggca cccctcaaga tctgcggtga catacacggc cagtactacg
 241  accttctgcg actatttgag tatggcggtt tccctcccga gcaactac ctctttctgg
 301  gggactatgt ggacaggggc aagcagtcct tggagaccat ctgcctgctg ctggcctata
 361  agatcaagta ccccgagaac ttcttcctgc tccgtgggaa ccacgagtgt gccagcatca
 421  accgcatcta tggtttctac gatgagtgca agagacgcta caacatcaaa ctgtggaaaa
 481  ccttcactga ctgcttcaac tgcctgccca tcgcggccat agtggacgaa aagatcttct
 541  gctgccacgg aggcctgtcc ccggacctgc agtctatgga gcagattcgg cggatcatgc
 601  ggcccacaga tgtgcctgac cagggcctgc tgtgtgacct gctgtggtct gaccctgaca
 661  aggacgtgca gggctggggc gagaacgacc gtggcgtctc ttttaccttt ggagccgagg
 721  tggtggccaa gttcctccac aagcacgact tggacctcat ctgccgagca caccaggtgg
 781  tagaagacgg ctatgagttc tttgccaagc ggcagctggt gacacttttc tcagctccca
 841  actactgtgg cgagtttgac aatgctggcg ccatgatgag tgtggacgag accctcatgt
 901  gctctttcca gatcctcaag cccgccgaca gaacaaggg gaagtacggg cagttcagtg
 961  gcctgaaccc tggaggccga cccatcaccc caccccgcaa ttccgccaaa gccaagaaa
1021  ccccccgca caccaccctg tgcccagat gatggattga ttgtacagaa atcatgctgc
1081  catgctgggg gggggtcacc ccgaccccta aggcccacct gtcacgggga acatggagcc
1141  ttggtgtatt tttctttct tttttaatg aatcaatagc agcgtccagt cccccagggc
1201  tgcttcctgc ctgcacctgc ggtactgtga gcaggatcct ggggccgagg ctgcagctca
1261  gggcaacggc aggccaggtc gtgggtctcc agccgtgctt ggcctcaggc tggcagcccg
1321  gatcctgggg caacccatct ggtctcttga ataaaggtca aagctgg
```

Figure 17B
(SEQ ID NO 30)

MSDSEKLNLDSIIGRLLEVQGSRPGKNVQLTENEIRGLCLKSREIFLSQPILLELEAPLKIC
GDIHGQYYDLLRLFEYGGFPPESNYLFLGDYVDRGKQSLETICLLLAYKIKYPENFFLLR
GNHECASINRIYGFYDECKRRYNIKLWKTFTDCFNCLPIAAIVDEKIFCCHGGLSPDLQS
MEQIRRIMRPTDVPDQGLLCDLLWSDPDKDVQGWGENDRGVSFTFGAEVVAKFLHKH
DLDLICRAHQVVEDGYEFFAKRQLVTLFSAPNYCGEFDNAGAMMSVDETLMCSFQILK
PADKNKGKYGQFSGLNPGGRPITPPRNSAKAKK

Figure 18A
(SEQ ID NO 31)
GACATTGATTATTGACTAGTTATTAATAGTAATCAATTACGGGGTCATTAGTTCATAG
CCCATATATGGAGTTCCGCGTTACATAACTTACGGTAAATGGCCCGCCTGGCTGAC
CGCCCAACGACCCCGCCCATTGACGTCAATAATGACGTATGTTCCCATAGTAACG
CCAATAGGGACTTTCCATTGACGTCAATGGGTGGAGTATTTACGGTAAACTGCCCA
CTTGGCAGTACATCAAGTGTATCATATGCCAAGTACGCCCCTATTGACGTCAATGA
CGGTAAATGGCCCGCCTGGCATTATGCCCAGTACATGACCTTATGGGACTTTCCTA
CTTGGCAGTACATCTACGTATTAGTCATCGCTATTACCATGGTCGAGGTGAGCCCC
ACGTTCTGCTTCACTCTCCCCATCTCCCCCCCTCCCCACCCCAATTTTGTATTTA
TTTATTTTTTAATTATTTTGTGCAGCGATGGGGCGGGGGGGGGGGGGGGCCCC
CCCCAGGCGGGGCGGGGCGGGGCGAGGGGCGGGGCGGGGCGAGGCGGAAAGG
TGCGGCGGCAGCCAATCAGAGCGGCGCGCTCCGAAAGTTTCCTTTTATGGCGAGG
CGGCGGCGGCGGCCCTATAAAAGCGAAGCGCGCGGCGGGCG

Figure 18B
(SEQ ID NO 32)
ACGCGTTGACATTGATTATTGACTAGTTATTAATAGTAATCAATTACGGGGTCATTAG
TTCATAGCCCATATATGGAGTTCCGCGTTACATAACTTACGGTAAATGGCCCGCCT
GGCTGACCGCCCAACGACCCCGCCCATTGACGTCAATAATGACGTATGTTCCCAT
AGTAACGCCAATAGGGACTTTCCATTGACGTCAATGGGTGGACTATTTACGGTAAA
CTGCCCACTTGGCAGTACATCAAGTGTATCATATGCCAAGTACGCCCCTATTGAC
GTCAATGACGGTAAATGGCCCGCCTGGCATTATGCCCAGTACATGACCTTATGGGA
CTTTCCTACTTGGCAGTACATCTACGTATTAGTCATCGCTATTACCATGGTGATGCG
GTTTTGGCAGTACATCAATGGGCGTGGATAGCGGTTTGACTCACGGGGATTTCCAA
GTCTCCACCCCATTGACGTCAATGGGAGTTTGTTTTGGCACCAAAATCAACGGGAC
TTTCCAAAATGTCGTAACAACTCCGCCCCATTGACGCAAATGGGCGGTAGGCGTGT
ACGGTGGGAGGTCTATATAAGCAGAGCTCTCTGGCTAACTAGAGAACCCACTGCTT
ACTGGCTTATCGAAATTAATACGACTCACTATAGGGAGACCCAAGCTGGCTAGCGT
TTAAACTTAAGCTTGGTACCGAGCTCGGATCCACTAGTCCAGTGTGGTG

Figure 18C
(SEQ ID NO 33)
TCGAGGTGAGCCCCACGTTCTGCTTCACTCTCCCCATCTCCCCCCCTCCCCACCC
CAATTTTGTATTTATTTATTTTTAATTATTTTGTGCAGCGATGGGGCGGGGGGG
GGGGGGGGCCCCCCCAGGCGGGGCGGGGCGGGGCGAGGGGCGGGGCGGG
GCGAGGCGGAAAGGTGCGGCGGCAGCCAATCAGAGCGGCGCGCTCCGAAAGTTT
CCTTTTATGGCGAGGCGGCGGCGGCGGCGGCCCTATAAAAGCGAAGCGCGCGG
CGGGCG

Figure 18D
(SEQ ID NO 34)
CTGCAGAGGGCCCTGCGTATGAGTGCAAGTGGGTTTTAGGACCAGGATGAGGCGG
GGTGGGGGTGCCTACCTGACGACCGACCCCGACCCACTGGACAAGCACCCAACC
CCCATTCCCCAAATTGCGCATCCCCTATCAGAGAGGGGGAGGGGAAACAGGATGC
GGCGAGGCGCGTGCGCACTGCCAGCTTCAGCACCGCGGACAGTGCCTTCGCCCC
CGCCTGGCGGCGCGCCACCGCCGCCTCAGCACTGAAGGCGCGCTGACGTCAC
TCGCCGGTCCCCGCAAACTCCCCTTCCCGGCCACCTTGGTCGCGTCCGCGCCGC
CGCCGGCCCAGCCGGACCGCACCACGCGAGGCGCGAGATAGGGGGGCACGGGC
GCGACCATCTGCGCTGCGGCG

Figure 18E
(SEQ ID NO 35)
GTCTGCAAGCAGACCTGGCAGCATTGGGCTGGCCGCCCCCAGGGCCTCCTCTTC
ATGCCCAGTGAATGACTCACCTTGGCACAGACACAATGTTCGGGGTGGGCACAGT
GCCTGCTTCCCGCCGCACCCCAGCCCCCTCAAATGCCTTCCGAGAAGCCCATTG
AGTAGGGGGCTTGCATTGCACCCCAGCCTGACAGCCTGGCATCTTGGGATAAAAG
CAGCACAGCCCCTAGGGGCTGCCCTTGCTGTGTGGCGCCACCGGCGGTGGAGA
ACAAGGCTCTATTCAGCCTGTGCCCAGGAAAGGGGATCAGGGGATGCCCAGGCAT
GGACAGTGGGTGGCAGGGGGGAGAGGAGGGCTGTCTGCTTCCCAGAAGTCCAA
GGACACAAATGGGTGAGGGGACTGGGCAGGGTTCTGACCCTGTGGGACCAGAGT
GGAGGGCGTAGATGGACCTGAAGTCTCCAGGGACAACAGGGCCCAGGTCTCAGG
CTCCTAGTTGGGCCCAGTGGCTCCAGCGTTTCCAAACCCATCCATCCCCAGAGGTT
CTTCCCATCTCTCCAGGCTGATGTGTGGGAACTCGAGGAAATAAATCTCCAGTGGG
AGACGGAGGGGTGGCCAGGGAAACGGGGCGCTGCAGGAATAAAGACGAGCCAGC
ACAGCCAGCTCATGCGTAACGGCTTTGTGGAGCTGTCAAGGCCTGGTCTCTGGGA
GAGAGGCACAGGGAGGCCAGACAAGGAAGGGGTGACCTGGAGGGACAGATCCAG
GGGCTAAAGTCCTGATAAGGCAAGAGAGTGCCGGCCCCTCTTGCCCTATCAGGA
CCTCCACTGCCACATAGAGGCCATGATTGACCCTTAGACAAAGGGCTGGTGTCCAA
TCCCAGCCCCAGCCCCAGAACTCCAGGGAATGAATGGGCAGAGAGCAGGAATGT
GGGACATCTGTGTTCAAGGGAAGGACTCCAGGAGTCTGCTGGGAATGAGGCCTAG
TAGGAAATGAGGTGGCCCTTGAGGGTACAGAACAGGTTCATTCTTCGCCAAATTCC
CAGCACCTTGCAGGCACTTACAGCTGAGTGAGATAATGCCTGGGTTATGAAATCAA
AAAGTTGGAAAGCAGGTCAGAGGTCATCTGGTACAGCCCTTCCTTCCCTTTTTTTTT
TTTTTTTTTTTTGTGAGACAAGGTCTCTCTGTTGCCCAGGCTGGAGTGGCGCAA
ACACAGCTCACTGCAGCCTCAACCTACTGGGCTCAAGCAATCCTCCAGCCTCAGCC
TCCCAAAGTGCTGGGATTACAAGCATGAGCCACCCCACTCAGCCCTTTCCTTCCTT
TTTAATTGATGCATAATAATTGTAAGTATTCATCATGGTCCAACCAACCCTTTCTTGA
CCCACCTTCCTAGAGAGGGTCCTCTTGATTCAGCGGTCAGGGCCCCAGACCCA
TGGTCTGGCTCCAGGTACCACCTGCCTCATGCAGGAGTTGGCGTGCCCAGGAAGC
TCTGCCTCTGGGCACAGTGACCTCAGTGGGGTGAGGGGAGCTCTCCCCATAGCTG
GGCTGCGGCCCAACCCCACCCCCTCAGGCTATGCCAGGGGGTGTTGCCAGGGGC
ACCCGGGCATCGCCAGTCTAGCCCACTCCTTCATAAAGCCCTCGCATCCCAGGAG
CGAGCAGAGCCAGAGCAT

Figure 18F
(SEQ ID NO 36)
GAATCCTATGCTTCGAACGCTGACGTCATCAACCCGCTCCAAGGAATCGCGGGCC
CAGTGTCACTAGGCGGGAACACCCAGCGCGCGTGCGCCCTGGCAGGAAGATGGC
TGTGAGGGACAGGGGAGTGGCGCCCTGCAATATTTGCATGTCGCTATGTGTTCTG
GGAAATCACCATAAACGTGAAATGTCTTTGGATTTGGGAGTCTTATAAGTTCTGTAT
GAGACCACTCTTTCCCATGGTCTTCATCCTATCTAGACA

Figure 18G (SEQ ID NO 37)
GCCGCCCCTTCACCGAGGGCCTATTTCCCATGATTCCTTCATATTTGCATATACGA
TACAAGGCTGTTAGAGAGATAATTGGAATTAATTTGACTGTAAACACAAAGATATTA
GTACAAAATACGTGACGTAGAAAGTAATAATTTCTTGGGTAGTTTGCAGTTTTAAAAT
TATGTTTTAAAATGGACTATCATATGCTTACCGTAACTTGAAAGTATTTCGATTTCTT
GGCTTTATATATCTTGTGGAAAGGACGAAAC

Figure 18H
H1_pLVTHM promoter (SEQ ID NO 143)
GAACGCTGACGTCATCAACCCGCTCCAAGGAATCGCGGGCCCAGTGTCACTA
GGCGGGAACACCCAGCGCGGTGCGCCCTGGCAGGAAGATGGCTGTGAGGGA
CAGGGGAGTGGCGCCCTGCAATATTTGCATGTCGCTATGTGTTCTGGGAAATC
ACCATAAACGTGAAATGTCTTTGGATTTGGGAATCTTATAAGTTCTGTATGAG
ACCAC

Figure 18I
H1 promoter in scAAV backbone (SEQ ID NO 144)
ATATTTGCATGTCGCTATGTGTTCTGGGAAATCACCATAAACGTGAAATGTCT
TTGGATTTGGGAATCTTATAAGTTCTGTATGAGACCAC

Figure 18J
U6 promoter(SEQ ID NO 145)
GAGGGCCTATTTCCCATGATTCCTTCATATTTGCATATACGATACAAGGCTGT
TAGAGAGATAATTGGAATTAATTTGACTGTAAACACAAAGATATTAGTACAA
AATACGTGACGTAGAAAGTAATAATTTCTTGGGTAGTTTGCAGTTTTAAAATT
ATGTTTTAAAATGGACTATCATATGCTTACCGTAACTTGAAAGTATTTCGATT
TCTTGGCTTTATATATCTTGTGGAAGGAC

Figure 18K
Chicken-β-actin promoter (CBA)(SEQ ID NO 146)
TCGAGGTGAGCCCCACGTTCTGCTTCACTCTCCCCATCTCCCCCCCCTCCCCA
CCCCCAATTTTGTATTTATTTATTTTTAATTATTTTGTGCAGCGATGGGGGCG
GGGGGGGGGGGGGGCGCGCGCCAGGCGGGGCGGGGCGGGGCGAGGGGCG
GGGCGGGGCGAGGCGGAGAGGTGCGGCGGCAGCCAATCAGAGCGGCGCGCT
CCGAAAGTTTCCTTTTATGGCGAGGCGGCGGCGGCGGCGGCCCTATAAAAAG
CGAAGCGCGCGGCGGGCG

Figure 18L
CAG promoter (hybrid chicken b-actin promoter)(SEQ ID NO 147)
GACATTGATTATTGACTAGTTATTAATAGTAATCAATTACGGGGTCATTAGTT
CATAGCCCATATATGGAGTTCCGCGTTACATAACTTACGGTAAATGGCCCGCC
TGGCTGACCGCCCAACGACCCCCGCCCATTGACGTCAATAATGACGTATGTT
CCCATAGTAACGCCAATAGGGACTTTCCATTGACGTCAATGGGTGGAGTATTT
ACGGTAAACTGCCCACTTGGCAGTACATCAAGTGTATCATATGCCAAGTACG
CCCCCTATTGACGTCAATGACGGTAAATGGCCCGCCTGGCATTATGCCCAGT
ACATGACCTTATGGGACTTTCCTACTTGGCAGTACATCTACGTATTAGTCATC
GCTATTACCATGGTCGAGGTGAGCCCCACGTTCTGCTTCACTCTCCCCATCTC
CCCCCCCTCCCCACCCCCAATTTTGTATTTATTTATTTTTAATTATTTTGTGCA
GCGATGGGGGCGGGGGGGGGGGGGGGGCCCCCCCCAGGCGGGGCGGGGCG
GGGCGAGGGGCGGGGCGGGGCGAGGCGGAAAGGTGCGGCGGCAGCCAATC
AGAGCGGCGCGCTCCGAAAGTTTCCTTTTATGGCGAGGCGGCGGCGGCGGCG
GCCCTATAAAAAGCGAAGCGCGCGGCGGGCG

Figure 18M
Mouse PGK_promoter from LV-LacZ (SEQ ID NO 148)
GGGTAGGGGAGGCGCTTTTCCCAAGGCAGTCTGGAGCATGCGCTTTAGCAGC
CCCGCTGGGCACTTGGCGCTACACAAGTGGCCTCTGGCCTCGCACACATTCC
ACATCCACCGGTAGGCGCCAACCGGCTCCGTTCTTTGGTGGCCCCTTCGCGCC
ACCTTCTACTCCTCCCTAGTCAGGAAGTTCCCCCCCGCCCCGCAGCTCGCGT
CGTGCAGGACGTGACAAATGGAAGTAGCACGTCTCACTAGTCTCGTGCAGAT
GGACAGCACCGCTGAGCAATGGAAGCGGGTAGGCCTTTGGGGCAGCGGCCA
ATAGCAGCTTTGCTCCTTCGCTTTCTGGGCTCAGAGGCTGGGAAGGGGTGGGT
CCGGGGGCGGGCTCAGGGGCGGGCTCAGGGGCGGGGCGGGCGCCCGAAGGT
CCTCCGGAGGCCCGGCATTCTGCACGCTTCAAAAGCGCACGTCTGCCGCGCT
GTTCTCCTCTTCCTCATCTCCGGGCCTTTCG

Figure 18N
Elongation factor short 1α (EFS1α)(SEQ ID NO 149)
GGGCAGAGCGCACATCGCCCACAGTCCCCGAGAAGTTGGGGGGAGGGGTCG
GCAATTGATCCGGTGCCTAGAGAAGGTGGCGCGGGGTAAACTGGGAAAGTG
ATGTCGTGTACTGGCTCCGCCTTTTCCCGAGGGTGGGGAGAACCGTATATA
AGTGCAGTAGTCGCCGTGAACGTTCTTTTCGCAACGGGTTTGCCGCCAGAAC
ACAG

Figure 18O
CMV enhancer:(SEQ ID NO 150)
GACATTGATTATTGACTAGTTATTAATAGTAATCAATTACGGGGTCATTAGTT
CATAGCCCATATATGGAGTTCCGCGTTACATAACTTACGGTAAATGGCCCGCC
TGGCTGACCGCCCAACGACCCCCGCCCATTGACGTCAATAATGACGTATGTT
CCCATAGTAACGCCAATAGGGACTTTCCATTGACGTCAATGGGTGGAGTATTT
ACGGTAAACTGCCCACTTGGCAGTACATCAAGTGTATCATATGCCAAGTACG
CCCCCTATTGACGTCAATGACGGTAAATGGCCCGCCTGGCATTATGCCCAGT
ACATGACCTTATGGGACTTTCCTACTTGGCAGTACATCTACGTATTAGTCATC
GCTATTACCATG

Figure 18P
CMV promoter:(SEQ ID NO 151)
GTGATGCGGTTTTGGCAGTACATCAATGGGCGTGGATAGCGGTTTGACTCAC
GGGGATTTCCAAGTCTCCACCCCATTGACGTCAATGGGAGTTTGTTTTGGCAC
CAAAATCAACGGGACTTTCCAAAATGTCGTAACAACTCCGCCCCATTGACGC
AAATGGGCGGTAGGCGTGTACGGTGGGAGGTCTATATAAGCAGAGCT

Figure 19A

(SEQ ID NO 38)
AAAGCTTCCCGGGGGGATCTGGGCCACTCCCTCTCTGCGCGCTCGCTCGCTCACT
GAGGCCGGGCGACCAAAGGTCGCCCGACGCCCGGGCTTTGCCCGGGCGGCCTCA
GTGAGCGAGCGAGCGCGCAGAGAGGGAGTGGCCAACTCCATCACTAGGGGTTCC
TGGAGGGGTGGAGTCGTGACCCCTAAAATGGGCAAACATTGCGCTAGCGCGGCCG
CGGTACCTACCGATGTACGGGCCAGATATACGCGTGGAGCTAGTTATTAATAGTAA
TCAATTACGGGGTCATTAGTTCATAGCCCATATATGGAGTTCCGCGTTACATAACTT
ACGGTAAATGGCCCGCCTGGCTGACCGCCCAACGACCCCGCCCATTGACGTCAA
TAATGACGTATGTTCCCATAGTAACGCCAATAGGGACTTTCCATTGACGTCAATGGG
TGGAGTATTTACGGTAAACTGCCCACTTGGCAGTACATCAAGTGTATCATATGCCAA
GTACGCCCCTATTGACGTCAATGACGGTAAATGGCCCGCCTGGCATTATGCCCAG
TACATGACCTTATGGGACTTTCCTACTTGGCAGTACATCTACGTATTAGTCATCGCT
ATTACCATGGTGATGCGGTTTTGGCAGTACATCAATGGGCGTGGATAGCGGTTTGA
CTCACGGGGATTTCCAAGTCTCCACCCCATTGACGTCAATGGGAGTTTGTTTTGGC
ACCAAAATCAACGGGACTTTCCAAAATGTCGTAACAACTCCGCCCCATTGACGCAA
ATGGGCGGTAGGCGTGTACGGTGGGAGGTCTATATAAGCAGAGCTCGTTTAGTGA
ACCGTCAGATCGCCTGGAGACGCCATCCACGCTGTTTTGACCTCCATAGAAGACAC
CGGGACCGATCCAGCCTGAATTCTGCAGTCGACGGTACCGCGGGCCCGGGATCC
ACCGGTCGCCACCATGGTGAGCAAGGGCGAGGAGCTGTTCACCGGGGTGGTGCC
CATCCTGGTCGAGCTGGACGGCGACGTAAACGGCCACAAGTTCAGCGTGTCCGGC
GAGGGCGAGGGCGATGCCACCTACGGCAAGCTGACCCTGAAGTTCATCTGCACCA
CCGGCAAGCTGCCCGTGCCCTGGCCCACCCTCGTGACCACCCTGACCTACGGCGT
GCAGTGCTTCAGCCGCTACCCCGACCACATGAAGCAGCACGACTTCTTCAAGTCC
GCCATGCCCGAAGGCTACGTCCAGGAGCGCACCATCTTCTTCAAGGACGACGGCA
ACTACAAGACCCGCGCCGAGGTGAAGTTCGAGGGCGACACCCTGGTGAACCGCAT
CGAGCTGAAGGGCATCGACTTCAAGGAGGACGGCAACATCCTGGGGCACAAGCTG
GAGTACAACTACAACAGCCACAACGTCTATATCATGGCCGACAAGCAGAAGAACGG
CATCAAGGTGAACTTCAAGATCCGCCACAACATCGAGGACGGCAGCGTGCAGCTC
GCCGACCACTACCAGCAGAACACCCCCATCGGCGACGGCCCCGTGCTGCTGCCC
GACAACCACTACCTGAGCACCCAGTCCGCCCTGAGCAAAGACCCCAACGAGAAGC
GCGATCACATGGTCCTGCTGGAGTTCGTGACCGCCGCGGGATCACTCTCGGCAT
GGACGAGCTGTACAAGTAAAGCGGCCGCGACTCTAGAGTCGACCTGCAGGGAAGA
CCAAGCTGACCTGACTCGATGCTTTATTTGTGAAATTTGTGATGCTATTGCTTTATTT
GTAACCATTATAAGCTGCAATAAACAAGTTAACAACAACAATTGCATTCATTTTATGT
TTCAGGTTCAGGGGGAGGTGTGGGAGGTTTTTTAAACTAGTCCACTCCCTCTCTGC
GCGCTCGCTCGCTCACTGAGGCCGGGCGACCAAAGGTCGCCCGACGCCCGGGCT
TTGCCCGGGCGGCCTCAGTGAGCGAGCGAGCGCGCAGAGAGGGACAGATCCGGG
CCCGCATGCGTCGACAATTCACTGGCCGTCGTTTTACAACGTCGTGACTGGGAAAA
CCCTGGCGTTACCCAACTTAATCGCCTTGCAGCACATCCCCCTTTCGCCAGCTGGC
GTAATAGCGAAGAGGCCCGCACCGATCGCCCTTCCCAACAGTTGCGCAGCCTGAA
TGGCGAATGGCGCCTGATGCGGTATTTTCTCCTTACGCATCTGTGCGGTATTTCAC
ACCGCATATGGTGCACTCTCAGTACAATCTGCTCTGATGCCGCATAGTTAAGCCAG

Figure 19B

```
CCCCGACACCCGCCAACACCCGCTGACGCGCCCTGACGGGCTTGTCTGCTCCCG
GCATCCGCTTACAGACAAGCTGTGACCGTCTCCGGGAGCTGCATGTGTCAGAGGT
TTTCACCGTCATCACCGAAACGCGCGAGACGAAAGGGCCTCGTGATACGCCTATTT
TTATAGGTTAATGTCATGATAATAATGGTTTCTTAGACGTCAGGTGGCACTTTTCGG
GGAAATGTGCGCGGAACCCCTATTTGTTTATTTTTCTAAATACATTCAAATATGTATC
CGCTCATGAGACAATAACCCTGATAAATGCTTCAATAATATTGAAAAAGGAAGAGTA
TGAGTATTCAACATTTCCGTGTCGCCCTTATTCCCTTTTTTGCGGCATTTTGCCTTCC
TGTTTTTGCTCACCCAGAAACGCTGGTGAAAGTAAAAGATGCTGAAGATCAGTTGG
GTGCACGAGTGGGTTACATCGAACTGGATCTCAACAGCGGTAAGATCCTTGAGAGT
TTTCGCCCCGAAGAACGTTTTCCAATGATGAGCACTTTTAAAGTTCTGCTATGTGGC
GCGGTATTATCCCGTATTGACGCCGGGCAAGAGCAACTCGGTCGCCGCATACACT
ATTCTCAGAATGACTTGGTTGAGTACTCACCAGTCACAGAAAAGCATCTTACGGATG
GCATGACAGTAAGAGAATTATGCAGTGCTGCCATAACCATGAGTGATAACACTGCG
GCCAACTTACTTCTGACAACGATCGGAGGACCGAAGGAGCTAACCGCTTTTTGCA
CAACATGGGGGATCATGTAACTCGCCTTGATCGTTGGGAACCGGAGCTGAATGAA
GCCATACCAAACGACGAGCGTGACACCACGATGCCTGTAGCAATGGCAACAACGT
TGCGCAAACTATTAACTGGCGAACTACTTACTCTAGCTTCCCGGCAACAATTAATAG
ACTGGATGGAGGCGGATAAAGTTGCAGGACCACTTCTGCGCTCGGCCCTTCCGGC
TGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACG
GGGAGTCAGGCAACTATGGATGAACGAAATAGACAGATCGCTGAGATAGGTGCCT
CACTGATTAAGCATTGGTAACTGTCAGACCAAGTTTACTCATATATACTTTAGATTGA
TTTAAAACTTCATTTTTAATTTAAAAGGATCTAGGTGAAGATCCTTTTTGATAATCTCA
TGACCAAAATCCCTTAACGTGAGTTTTCGTTCCACTGAGCGTCAGACCCCGTAGAA
AAGATCAAAGGATCTTCTTGAGATCCTTTTTTTCTGCGCGTAATCTGCTGCTTGCAA
ACAAAAAAACCACCGCTACCAGCGGTGGTTTGTTTGCCGGATCAAGAGCTACCAAC
TCTTTTTCCGAAGGTAACTGGCTTCAGCAGAGCGCAGATACCAAATACTGTTCTTCT
AGTGTAGCCGTAGTTAGGCCACCACTTCAAGAACTCTGTAGCACCGCCTACATACC
TCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAA
CGGGGGGTTCGTGCACACAGCCCAGCTTGGAGCGAACGACCTACACCGAACTGAG
ATACCTACAGCGTGAGCTATGAGAAAGCGCCACGCTTCCCGAAGGGAGAAAGGCG
GACAGGTATCCGGTAAGCGGCAGGGTCGGAACAGGAGAGCGCACGAGGGAGCTT
CCAGGGGGAAACGCCTGGTATCTTTATAGTCCTGTCGGGTTTCGCCACCTCTGACT
TGAGCGTCGATTTTGTGATGCTCGTCAGGGGGCGGAGCCTATGGAAAAACGCC
AGCAACGCGGCCTTTTTACGGTTCCTGGCCTTTTGCTGGCCTTTTGCTCACATGTTC
TTTCCTGCGTTATCCCCTGATTCTGTGGATAACCGTATTACCGCCTTTGAGTGAGCT
GATACCGCTCGCCGCAGCCGAACGACCGAGCGCAGCGAGTCAGTGAGCGAGGAA
GCGGAAGAGCGCCCAATACGCAAACCGCCTCTCCCCGCGCGTTGGCCGATTCATT
AATGCAGCTGGCACGACAGGTTTCCCGACTGGAAAGCGGGCAGTGAGCGCAACGC
```

Figure 19C

AATTAATGTGAGTTAGCTCACTCATTAGGCACCCCAGGCTTTACACTTTATGCTTCC
GGCTCGTATGTTGTGTGGAATTGTGAGCGGATAACAATTTCACACAGGAAACAGCT
ATGACCATGATTACGCCAAGCTCTCGAGATCTAG

Figure 19D

(SEQ ID NO 39)
ATGCCGGGGTTTTACGAGATTGTGATTAAGGTCCCCAGCGACCTTGACGGGCATCT
GCCCGGCATTTCTGACAGCTTTGTGAACTGGGTGGCCGAGAAGGAATGGGAGTTG
CCGCCAGATTCTGACATGGATCTGAATCTGATTGAGCAGGCACCCCTGACCGTGG
CCGAGAAGCTGCAGCGCGACTTTCTGACGGAATGGCGCCGTGTGAGTAAGGCCCC
GGAGGCCCTTTTCTTTGTGCAATTTGAGAAGGGAGAGAGCTACTTCCACATGCACG
TGCTCGTGGAAACCACCGGGGTGAAATCCATGGTTTTGGGACGTTTCCTGAGTCAG
ATTCGCGAAAAACTGATTCAGAGAATTTACCGCGGGATCGAGCCGACTTTGCCAAA
CTGGTTCGCGGTCACAAAGACCAGAAATGGCGCCGGAGGCGGGAACAAGGTGGT
GGATGAGTGCTACATCCCCAATTACTTGCTCCCCAAAACCCAGCCTGAGCTCCAGT
GGGCGTGGACTAATATGGAACAGTATTTAAGCGCCTGTTTGAATCTCACGGAGCGT
AAACGGTTGGTGGCGCAGCATCTGACGCACGTGTCGCAGACGCAGGAGCAGAACA
AAGAGAATCAGAATCCCAATTCTGATGCGCCGGTGATCAGATCAAAAACTTCAGCC
AGGTACATGGAGCTGGTCGGGTGGCTCGTGGACAAGGGGATTACCTCGGAGAAGC
AGTGGATCCAGGAGGACCAGGCCTCATACATCTCCTTCAATGCGGCCTCCAACTCG
CGGTCCCAAATCAAGGTGCCTTGGACAATGCGGGAAAGATTATGAGCCTGACTAAA
ACCGCCCCCGACTACCTGGTGGGCCAGCAGCCCGTGGAGGACATTTCCAGCAATC
GGATTTATAAAATTTTGGAACTAAACGGGTACGATCCCCAATATGCGGCTTCCGTCT
TTCTGGGATGGGCCACGAAAAAGTTCGGCAAGAGGAACACCATCTGGCTGTTTGG
GCCTGCAACTACCGGGAAGACCAACATCGCGGAGGCCATAGCCCACACTGTGCCC
TTCTACGGGTGCGTAAACTGGACCAATGAGAACTTTCCCTTCAACGACTGTGTCGA
CAAGATGGTGATCTGGTGGGAGGAGGGGAAGATGACCGCCAAGGTCGTGGAGTC
GGCCAAAGCCATTCTCGGAGGAAGCAAGGTGCGCGTGGACCAGAAATGCAAGTCC
TCGGCCCAGATAGACCCGACTCCCGTGATCGTCACCTCCAACACCAACATGTGCG
CCGTGATTGACGGGAACTCAACGACCTTCGAACACCAGCAGCCGTTGCAAGACCG
GATGTTCAAATTTGAACTCACCCGCCGTCTGGATCATGACTTTGGGAAGGTCACCA
AGCAGGAAGTCAAAGACTTTTTCCGGTGGGCAAAGGATCACGTGGTTGAGGTGGA
GCATGAATTCTACGTCAAAAAGGGTGGAGCCAAGAAAAGACCCGCCCCAGTGAC
GCAGATATAAGTGAGCCCAAACGGGTGCGCGAGTCAGTTGCGCAGCCATCGACGT
CAGACGCGGAAGCTTCGATCAACTACGCGGACAGGTACCAAAACAAATGTTCTCGT
CACGTGGGCATGAATCTGATGCTGTTTCCCTGCAGACAATGCGAGAGACTGAATCA
GAATTCAAATATCTGCTTCACTCACGGTGTCAAAGACTGTTTAGAGTGCTTTCCCGT
GTCAGAATCTCAACCCGTTTCTGTCGTCAAAAAGGCGTATCAGAAACTGTGCTACAT
TCATCACATCATGGGAAAGGTGCCAGACGCTTGCACTGCTTGCGACCTGGTCAATG
TGGACTTGGATGACTGTGTTTCTGAACAATAAATGACTTAAACCAGGTATGGCTGCC
GATGGTTATCTTCCAGATTGGCTCGAGGACAACCTTAGTGAAGGAATTCGCGAGTG
GTGGGCTTTGAAACCTGGAGCCCCTCAACCCAAGGCAAATCAACAACATCAAGACA

Figure 19E

ACGCTCGAGGTCTTGTGCTTCCGGGTTACAAATACCTTGGACCCGGCAACGGACTC
GACAAGGGGGAGCCGGTCAACGCAGCAGACGCGGCGGCCCTCGAGCACGACAAG
GCCTACGACCAGCAGCTCAAGGCCGGAGACAACCCGTACCTCAAGTACAACCACG
CCGACGCCGAGTTCCAGGAGCGGCTCAAAGAAGATACGTCTTTTGGGGGCAACCT
CGGGCGAGCAGTCTTCCAGGCCAAAAAGAGGCTTCTTGAACCTCTTGGTCTGGTTG
AGGAAGCGGCTAAGACGGCTCCTGGAAAGAAGAGGCCTGTAGAGCAGTCTCCTCA
GGAACCGGACTCCTCCGCGGGTATTGGCAAATCGGGTGCACAGCCCGCTAAAAAG
AGACTCAATTTCGGTCAGACTGGCGACACAGAGTCAGTCCCAGACCCTCAACCAAT
CGGAGAACCTCCCGCAGCCCCCTCAGGTGTGGGATCTCTTACAATGGCTTCAGGT
GGTGGCGCACCAGTGGCAGACAATAACGAAGGTGCCGATGGAGTGGGTAGTTCCT
CGGGAAATTGGCATTGCGATTCCCAATGGCTGGGGACAGAGTCATCACCACCAG
CACCCGAACCTGGGCCCTGCCCACCTACAACAATCACCTCTACAAGCAAATCTCCA
ACAGCACATCTGGAGGATCTTCAAATGACAACGCCTACTTCGGCTACAGCACCCCC
TGGGGGTATTTTGACTTCAACAGATTCCACTGCCACTTCTCACCACGTGACTGGCA
GCGACTCATCAACAACAACTGGGGATTCCGGCCTAAGCGACTCAACTTCAAGCTCT
TCAACATTCAGGTCAAAGAGGTTACGGACAACAATGGAGTCAAGACCATCGCCAAT
AACCTTACCAGCACGGTCCAGGTCTTCACGGACTCAGACTATCAGCTCCCGTACGT
GCTCGGGTCGGCTCACGAGGGCTGCCTCCCGCCGTTCCCAGCGGACGTTTTCATG
ATTCCTCAGTACGGGTATCTGACGCTTAATGATGGAAGCCAGGCCGTGGGTCGTTC
GTCCTTTTACTGCCTGGAATATTTCCCGTCGCAAATGCTAAGAACGGGTAACAACTT
CCAGTTCAGCTACGAGTTTGAGAACGTACCTTTCCATAGCAGCTACGCTCACAGCC
AAAGCCTGGACCGACTAATGAATCCACTCATCGACCAATACTTGTACTATCTCTCAA
AGACTATTAACGGTTCTGGACAGAATCAACAAACGCTAAAATTCAGTGTGGCCGGA
CCCAGCAACATGGCTGTCCAGGGAAGAAACTACATACCTGGACCCAGCTACCGAC
AACAACGTGTCTCAACCACTGTGACTCAAAACAACAACAGCGAATTTGCTTGGCCT
GGAGCTTCTTCTTGGGCTCTCAATGGACGTAATAGCTTGATGAATCCTGGACCTGC
TATGGCCAGCCACAAAGAAGGAGAGGACCGTTTCTTTCCTTTGTCTGGATCTTTAAT
TTTTGGCAAACAAGGAACTGGAAGAGACAACGTGGATGCGGACAAAGTCATGATAA
CCAACGAAGAAGAAATTAAAACTACTAACCCGGTAGCAACGGAGTCCTATGGACAA
GTGGCCACAAACCACCAGAGTGCCCAAGCACAGGCGCAGACCGGCTGGGTTCAAA
ACCAAGGAATACTTCCGGGTATGGTTTGGCAGGACAGAGATGTGTACCTGCAAGGA
CCCATTTGGGCCAAAATTCCTCACACGGACGGCAACTTTCACCCTTCTCCGCTGAT
GGGAGGGTTTGGAATGAAGCACCCGCCTCCTCAGATCCTCATCAAAAACACACCTG
TACCTGCGGATCCTCCAACGGCCTTCAACAAGGACAAGCTGAACTCTTTCATCACC
CAGTATTCTACTGGCCAAGTCAGCGTGGAGATCGAGTGGGAGCTGCAGAAGGAAA
ACAGCAAGCGCTGGAACCCGGAGATCCAGTACACTTCCAACTATTACAAGTCTAAT
AATGTTGAATTTGCTGTTAATACTGAAGGTGTATATAGTGAACCCGCCCCATTGGC
ACCAGATACCTGACTCGTAATCTGTAATTGCTTGTTAATCAATAAACCGTTTAATTCG
TTTCAGTTGAACTTTGGTCTCTGCGAAGGGCGAATTCGTTTAAACCTGCAGGACTA
GAGGTCCTGTATTAGAGGTCACGTGAGTGTTTTGCGACATTTTGCGACACCATGTG
GTCACGCTGGGTATTTAAGCCCGAGTGAGCACGCAGGGTCTCCATTTTGAAGCGG
GAGGTTTGAACGCGCAGCCGCCAAGCCGAATTCTGCAGATATCCATCACACTGGC

Figure 19F

GGCCGCTCGACTAGAGCGGCCGCCACCGCGGTGGAGCTCCAGCTTTTGTTCCCTT
TAGTGAGGGTTAATTGCGCGCTTGGCGTAATCATGGTCATAGCTGTTTCCTGTGTG
AAATTGTTATCCGCTCACAATTCCACACAACATACGAGCCGGAAGCATAAAGTGTAA
AGCCTGGGGTGCCTAATGAGTGAGCTAACTCACATTAATTGCGTTGCGCTCACTGC
CCGCTTTCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCACTGACT
CGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAG
GCCAGCAAAAGGCCAGGAACCGTAAAAAGGCCGCGTTGCTGGCGTTTTTCCATAG
GCTCCGCCCCCCTGACGAGCATCACAAAAATCGACGCTCAAGTCAGAGGTGGCGA
AACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACCGCTGC
GCCTTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGTGCT
ACAGAGTTCTTGAAGTGGTGGCCTAACTACGGCTACACTAGAAGGACAGTATTTGG
TATCTGCGCTCTGCTGAAGCCAGTTACCTTCGGAAAAAGAGTTGGTAGCTCTTGAT
CCGGCAAACAAACCACCGCTGGTAGCGGTGGTTTTTTGTTTGCAAGCAGCAGATT
ACGCGCAGAAAAAAGGATCTCAAGAAGATCCTTTGATCTTTTCTACGGGGTCTGA
CGCTCAGTGGAACGAAAACTCACGTTAAGGGATTTTGGTCATGAGATTATCAAAAA
GGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTC
AGCGATCTGTCTATTTCGTTCATCCATAGTTGCCTGACTCCCCGTCGTGTAGATAAC
TACGATACGGGAGGGCTTACCATCTGGCCCCAGTGCTGCAATGATACCGCGAGAC
CCACGCTCACCGGCTCCAGATTTATCAGCAATAAACCAGCCAGCCGGAAGGGCCG
AGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATT
GCTACAGGCATCGTGGTGTCACGCTCGTCGTTTGGTATGGCTTCATTCAGCTCCGG
TTCCCAACGATCAAGGCGAGTTACATGATCCCCCATGTTGTGCAAAAAAGCGGTTA
GCTCCTTCGGTCCTCCGATCGTTGTCAGAAGTAAGTTGGCCGCAGTGTTATCACTC
ATGGTTATGGCAGCACTGCATAATTCTCTTACTGTCATGCCATCCGTAAGATGCTTT
CTGTGACTGGTGAGTACTCAACCAAGTCATTCTGAGAATAGTGTATGCGGCGACCG
AGTTGCTCTTGCCCGGCGTCAATACGGGATAATACCGCGCCACATAGCAGAACTTT
AAAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGCA
TCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCA
ATATTATTGAAGCATTTATCAGGGTTATTGTCTCATGAGCGGATACATATTTGAATGT
ATTTAGAAAAATAAACAAATAGGGGTTCCGCGCACATTTCCCCGAAAAGTGCCACCT
AAATTGTAAGCGTTAATATTTTGTTAAAATTCGCGTTAAATTTTTGTTAAATCAGCTCA
TTTTTTAACCAATAGGCCGAAATCGGCAAAATCCCTTATAAATCAAAAGAATAGACC

Figure 19G

```
GAGATAGGGTTGAGTGTTGTTCCAGTTTGGAACAAGAGTCCACTATTAAAGAACGT
GGACTCCAACGTCAAAGGGCGAAAAACCGTCTATCAGGGCGATGGCCCACTACGT
GAACCATCACCCTAATCAAGTTTTTTGGGGTCGAGGTGCCGTAAAGCACTAAATCG
GAACCCTAAAGGGAGCCCCCGATTTAGAGCTTGACGGGGAAAGCCGGCGAACGTG
GCGAGAAAGGAAGGGAAGAAAGCGAAAGGAGCGGGCGCTAGGGCGCTGGCAAGT
GTAGCGGTCACGCTGCGCGTAACCACCACACCCGCCGCGCTTAATGCGCCGCTAC
AGGGCGCGTCCCATTCGCCATTCAGGCTGCGCAACTGTTGGGAAGGGCGATCGGT
GCGGGCCTCTTCGCTATTACGCCAGCTGGCGAAAGGGGGATGTGCTGCAAGGCGA
TTAAGTTGGGTAACGCCAGGGTTTTCCCAGTCACGACGTTGTAAAACGACGGCCAG
TGAGCGCGCGTAATACGACTCACTATAGGGCGAATTGGGTACCGGGCCCCCCTC
GATCGAGGTCGACGGTATCGGGGGAGCTCGGATCCACTAGTAACGGCCGCCAGT
GTGCTGGATTCGGCTTTATTTAAGCCCGAGTGAGCACGCAGGGTCTCCATTTTGAA
GCGGGAGGTTTGAACGCGCAGCCGCC
```

Figure 20A

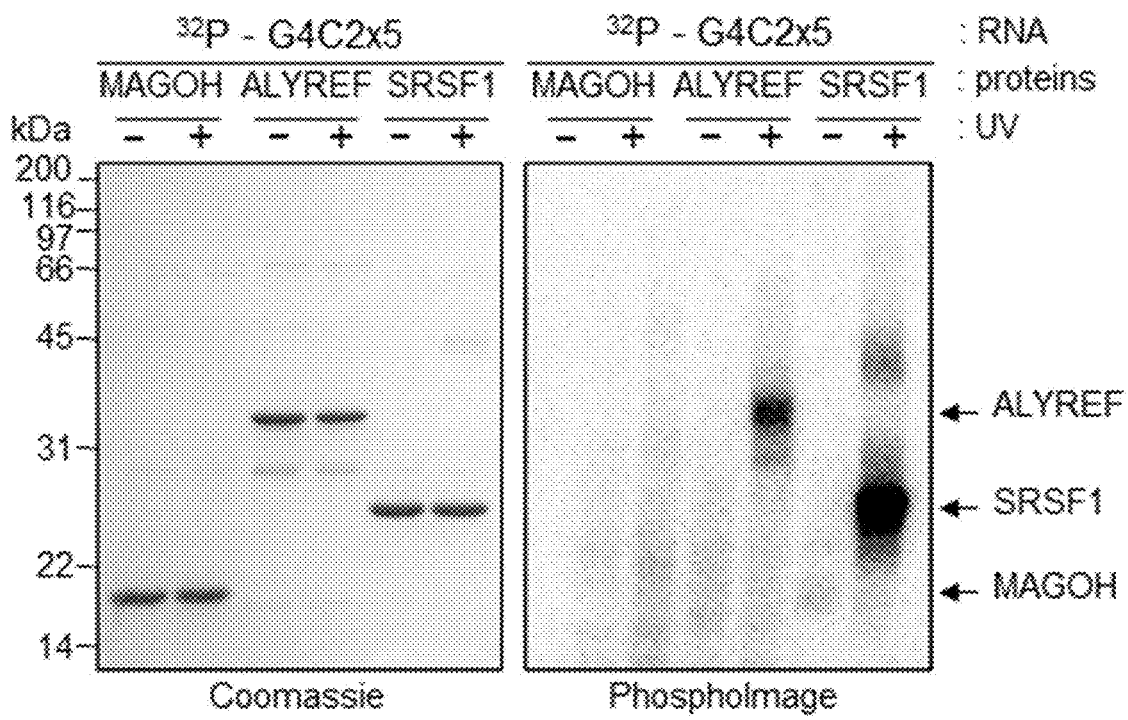

Figure 20C
Case 1
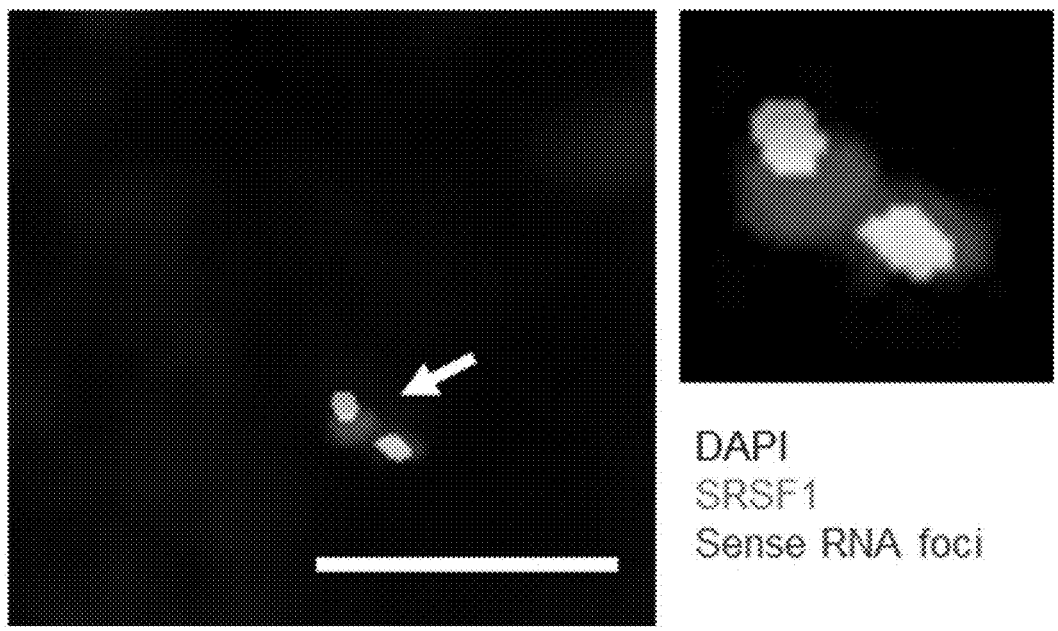
Case 2
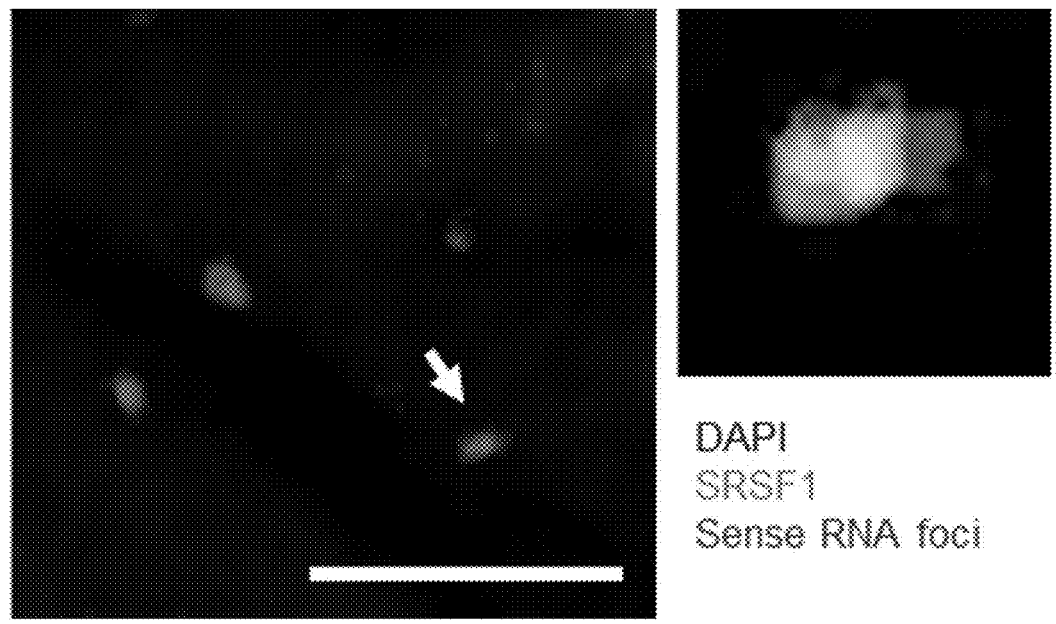

Figure 26A

Expression of synthetic poly-Gly-Pro x36 DPRs independent of G4C2 repeats. (SEQ ID NO: 42)

```
ATG GGC AAA CTG ATT CCG AAC CCG CTG CTG GGC CTG GAT AGC ACC CTC GAG AAT GAT CCC ACC ATG
GGC CCT GGC CCT GGA CCA GGA CCT GGC CCC GGA CCC GGT CCA GGT CCC GGC CCA GGC CCC GGT CCC
GGC CCT GGA CCA GGA CCA GGA CCA GGC CCA GGT CCC GGA CCA GGA CCC GGA CCT GGC CCA
GGC CCT GGC CCT GGC CCT GGC CCC GGA CCA GGT CCT GGA CCC GGC CCT GGT CCC GGC CCA GGA CCC
GGA CCA GGA CCT GGC CCT TAA
```

Figure 26B

Expression of synthetic poly-Gly-Ala x36 DPRs independent of G4C2 repeats. (SEQ ID NO: 43)

```
ATG GGC AAA CTG ATT CCG AAC CCG CTG CTG GGC CTG GAT AGC ACC CTC GAG AAT GAT CCC ACC ATG
GGA GCT GGT GCT GGT GCA GGC GCT GGC GCA GGG GCA GGC GCT GGT GCT GGG GCT GGT GCC GGG GCT
GGG GCA GGC GCA GGG GCT GGT GCC GGT GCA GGC GCA GGG GCT GGG GCT GGC GCT GGT GCC GGC GCA
GGC GCG GGT GCC GGC GCA GGG GCT GGT GCA GGG GCC GGT GCT GGC GCG GGT GCA GGG GCC GGT GCA
GGG GCA GGC GCA GGC GCT TAA
```

Figure 27A

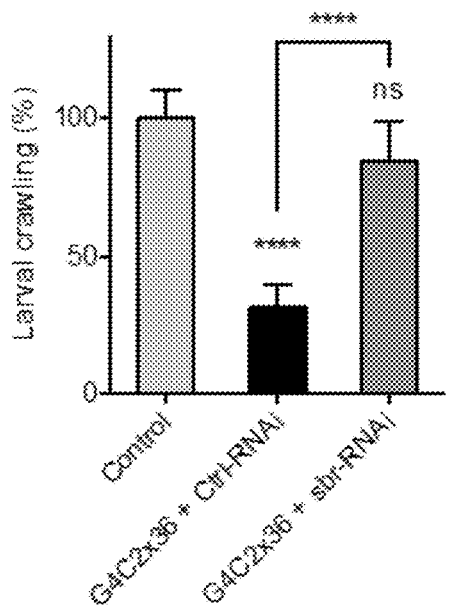

Figure 27B

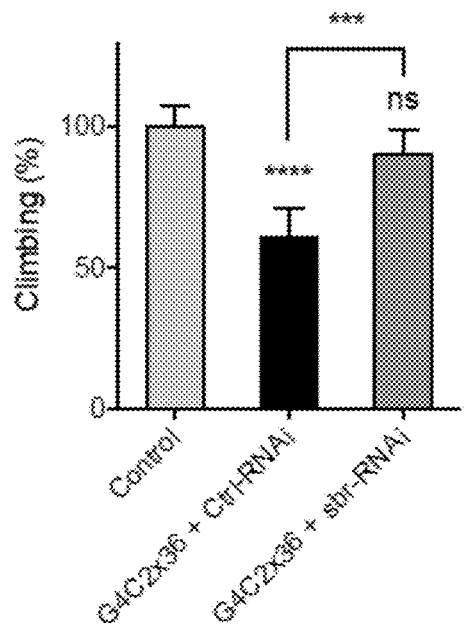

Figure 29

RAN-G4C2x38 sense-repeats with 3x V5 tags
```
...CTTATCGAAATTAATACGACTCACTATAGGGAGACCCAAGCTGGCTAGTTAAGCTTGGTACCGAGCTCGGATCCACTAGTCCAGTGTGGTGGAA
TTGGGGCCCGGGGCCGGGGCCGGGGCCGGGGCCGGGGCCGGGGCCGGGGCCGGGGCCGGGGCCGGGGCCGGGGCCGGGGCCGGGGCCGGGGCCGGGGC
CGGGGCCGGGGCCGGGGCCGGGGCCGGGGCCGGGGCCGGGGCCGGGGCCGGGGCCGGGGCCGGGGCCGGGGCCGGGGCCGGGGCCGGGGCCGGGGCCG
GGGCCGGGGCCGGGGCCGGGGCCGGGGCCGGGGCCGGGGCCGGGGAATTCTGCAGATATCCAGCACAGTG GCGGCCGC TG GGCAAGCCCATC
CCCAACCCCCTGCTCGGTCTGGACAGCACCGGCTAA C GGCAAGCCCATCCCCAACCCCCTGCTCGGTCTGGACAGCACCGGCTAA C GGCAAGC
CCATCCCCAACCCCCTGCTCGGTCTGGACAGCACCGGCTAA CTCGAGTCTAGATCTAGAGGGCCCTTCGAACAAAAACTCATCTCAGAAGAGGATC
TGAATATGCATACCGGTCATCATCACCATCACCATTGAGTTTAAACCCGCTGATCAGCCT CGA...
```

Figure 30

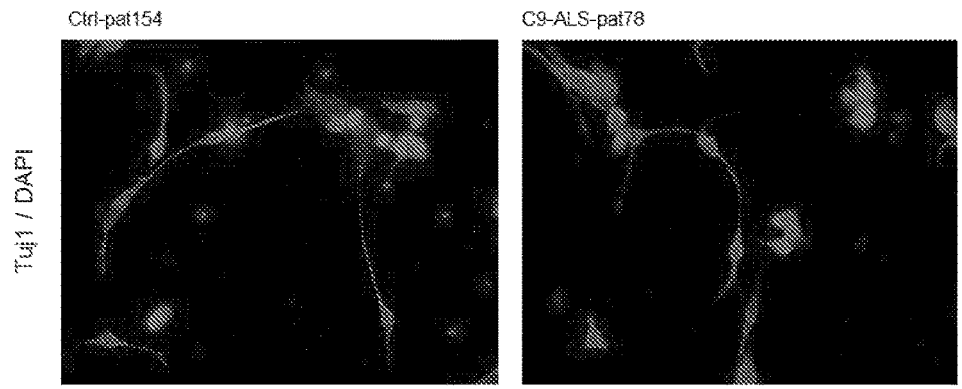

Figure 31

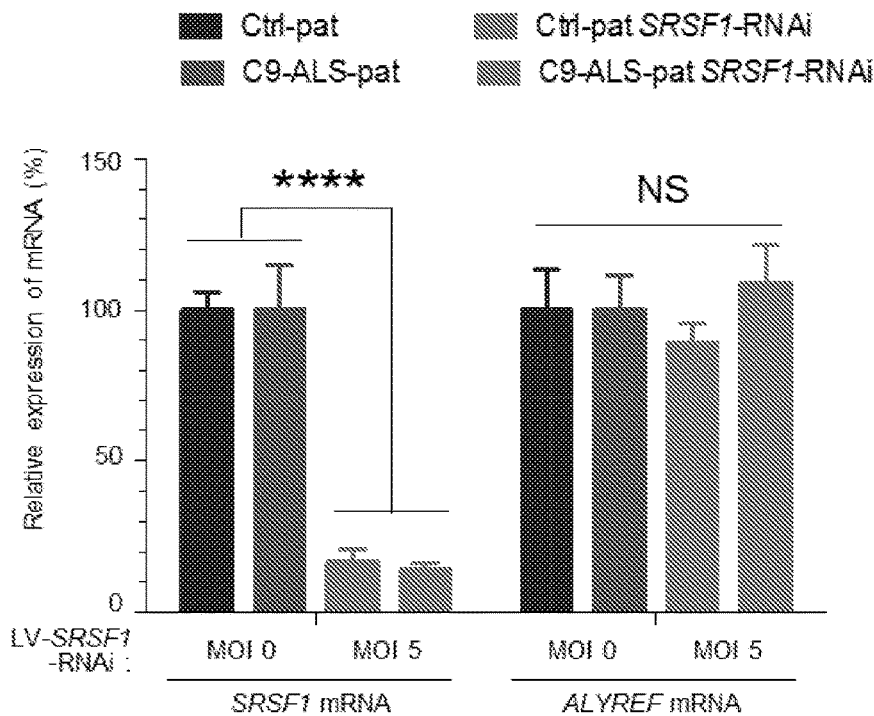

```
                      SEQUENCE LISTING

<160> NUMBER OF SEQ ID NOS: 158

<210> SEQ ID NO 1
<211> LENGTH: 747
<212> TYPE: DNA
<213> ORGANISM: homo sapiens

<400> SEQUENCE: 1
atgtcgggag gtggtgtgat tcgtggcccc gcagggaaca acgattgccg catctacgtg      60
ggtaacttac ctccagacat ccgaaccaag gacattgagg acgtgttcta caaatacggc     120
gctatccgcg acatcgacct caagaatcgc cgcggggac cgcccttcgc cttcgttgag      180
ttcgaggacc cgcgagacgc ggaagacgcg gtgtatggtc gcgacggcta tgattacgat     240
gggtaccgtc tgcgggtgga gtttcctcga agcggccgtg gaacaggccg aggcggcggc     300 ggggtggag gtggcggagc tccccgaggt cgctatggcc ccccatccag gcggtctgaa      360
aacagagtgg ttgtctctgg actgcctcca agtggaagtt ggcaggattt aaaggatcac     420
atgcgtgaag caggtgatgt atgttatgct gatgtttacc gagatggcac tggtgtcgtg     480
gagtttgtac ggaaagaaga tatgacctat gcagttcgaa aactggataa cactaagttt     540
agatctcatg agggagaaac tgcctacatc cgggttaaag ttgatgggcc cagaagtcca     600
```

-continued

```
agttatggaa gatctcgatc tcgaagccgt agtcgtagca gaagccgtag cagaagcaac    660
agcaggagtc gcagttactc cccaaggaga agcagaggat caccacgcta ttctcccgt     720 catagcagat ctcgctctcg tacataa                                        747
```

<210> SEQ ID NO 2
<211> LENGTH: 248
<212> TYPE: PRT
<213> ORGANISM: Homo sapiens

<400> SEQUENCE: 2

```
Met Ser Gly Gly Gly Val Ile Arg Gly Pro Ala Gly Asn Asn Asp Cys
1               5                   10                  15

Arg Ile Tyr Val Gly Asn Leu Pro Pro Asp Ile Arg Thr Lys Asp Ile
            20                  25                  30

Glu Asp Val Phe Tyr Lys Tyr Gly Ala Ile Arg Asp Ile Asp Leu Lys
        35                  40                  45

Asn Arg Arg Gly Gly Pro Pro Phe Ala Phe Val Glu Phe Glu Asp Pro
    50                  55                  60

Arg Asp Ala Glu Asp Ala Val Tyr Gly Arg Asp Gly Tyr Asp Tyr Asp
65                  70                  75                  80

Gly Tyr Arg Leu Arg Val Glu Phe Pro Arg Ser Gly Arg Gly Thr Gly
                85                  90                  95

Arg Gly Gly Gly Gly Gly Gly Gly Gly Ala Pro Arg Gly Arg Tyr
            100                 105                 110

Gly Pro Pro Ser Arg Arg Ser Glu Asn Arg Val Val Val Ser Gly Leu
        115                 120                 125

Pro Pro Ser Gly Ser Trp Gln Asp Leu Lys Asp His Met Arg Glu Ala
    130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175

Asn Thr Lys Phe Arg Ser His Glu Gly Glu Thr Ala Tyr Ile Arg Val
            180                 185                 190

Lys Val Asp Gly Pro Arg Ser Pro Ser Tyr Gly Arg Ser Arg Ser Arg
        195                 200                 205

Ser Arg Ser Arg Ser Arg Ser Arg Ser Asn Ser Arg Ser Arg
    210                 215                 220

Ser Tyr Ser Pro Arg Arg Ser Arg Gly Ser Pro Arg Tyr Ser Pro Arg
225                 230                 235                 240

His Ser Arg Ser Arg Ser Arg Thr
                245
```

<210> SEQ ID NO 3
<211> LENGTH: 606
<212> TYPE: DNA
<213> ORGANISM: Homo sapiens

<400> SEQUENCE: 3

```
atgtcgggag gtggtgtgat tcgtggcccc gcagggaaca acgattgccg catctacgtg    60
ggtaacttac ctccagacat ccgaaccaag acattgagg acgtgttcta caaatacggc    120
gctatccgcg acatcgacct caagaatcgc gcgggggac cgcccttcgc cttcgttgag    180
ttcgaggacc cgcgagacgc ggaagacgcg gtgtatggtc gcgacggcta tgattacgat    240
```

-continued

```
gggtaccgtc tgcgggtgga gtttcctcga agcggccgtg aacaggccg aggcggcggc    300 gggggtggag gtggcggagc tccccgaggt cgctatggcc cccatccag gcggtctgaa    360 aacagagtgg ttgtctctgg actgcctcca agtggaagtt ggcaggattt aaaggatcac   420
atgcgtgaag caggtgatgt atgttatgct gatgtttacc gagatggcac tggtgtcgtg   480
gagtttgtac ggaaagaaga tatgacctat gcagttcgaa aactggataa cactaagttt   540
agatctcatg aggtaggtta tacacgtatt cttttctttg accagaattg gatacagtgg   600
tcttaa                                                               606
```

<210> SEQ ID NO 4
<211> LENGTH: 201
<212> TYPE: PRT
<213> ORGANISM: Homo sapiens

<400> SEQUENCE: 4

```
Met Ser Gly Gly Gly Val Ile Arg Gly Pro Ala Gly Asn Asn Asp Cys
 1               5                  10                  15

Arg Ile Tyr Val Gly Asn Leu Pro Pro Asp Ile Arg Thr Lys Asp Ile
            20                  25                  30

Glu Asp Val Phe Tyr Lys Tyr Gly Ala Ile Arg Asp Ile Asp Leu Lys
        35                  40                  45

Asn Arg Arg Gly Gly Pro Pro Phe Ala Phe Val Glu Phe Glu Asp Pro
    50                  55                  60

Arg Asp Ala Glu Asp Ala Val Tyr Gly Arg Asp Gly Tyr Asp Tyr Asp
65                  70                  75                  80

Gly Tyr Arg Leu Arg Val Glu Phe Pro Arg Ser Gly Arg Gly Thr Gly
                85                  90                  95

Arg Gly Gly Gly Gly Gly Gly Gly Ala Pro Arg Gly Arg Tyr
            100                 105                 110

Gly Pro Pro Ser Arg Arg Ser Glu Asn Arg Val Val Val Ser Gly Leu
        115                 120                 125

Pro Pro Ser Gly Ser Trp Gln Asp Leu Lys Asp His Met Arg Glu Ala
    130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175

Asn Thr Lys Phe Arg Ser His Glu Val Gly Tyr Thr Arg Ile Leu Phe
            180                 185                 190

Phe Asp Gln Asn Trp Ile Gln Trp Ser
        195                 200
```

<210> SEQ ID NO 5
<211> LENGTH: 21
<212> TYPE: DNA
<213> ORGANISM: artificial sequence
<220> FEATURE:
<223> OTHER INFORMATION: inhibitory RNA

<400> SEQUENCE: 5

```
aactgcctac atccgggtta a                                              21
```

<210> SEQ ID NO 6
<211> LENGTH: 21
<212> TYPE: DNA
<213> ORGANISM: artificial sequence
<220> FEATURE:

```
<223> OTHER INFORMATION: inhibitory RNA

<400> SEQUENCE: 6
ttaaagttga tgggcccaga a                                              21

<210> SEQ ID NO 7
<211> LENGTH: 21
<212> TYPE: DNA
<213> ORGANISM: artificial sequence
<220> FEATURE:
<223> OTHER INFORMATION: inhibitory RNA

<400> SEQUENCE: 7
gggcccagaa gtccaagtta t                                              21

<210> SEQ ID NO 8
<211> LENGTH: 21
<212> TYPE: DNA
<213> ORGANISM: artificial sequence
<220> FEATURE:
<223> OTHER INFORMATION: inhibitory RNA

<400> SEQUENCE: 8
agcagaggat caccacgcta t                                              21

<210> SEQ ID NO 9
<211> LENGTH: 21
<212> TYPE: DNA
<213> ORGANISM: artificial sequence
<220> FEATURE:
<223> OTHER INFORMATION: inhibitory RNA

<400> SEQUENCE: 9
tcaataatgg aggcaatggt a                                              21

<210> SEQ ID NO 10
<211> LENGTH: 21
<212> TYPE: DNA
<213> ORGANISM: artificial sequence
<220> FEATURE:
<223> OTHER INFORMATION: inhibitory RNA

<400> SEQUENCE: 10
aatggtatga ctccaagtgc t                                              21

<210> SEQ ID NO 11
<211> LENGTH: 21
<212> TYPE: DNA
<213> ORGANISM: artificial sequence
<220> FEATURE:
<223> OTHER INFORMATION: inhibitory RNA

<400> SEQUENCE: 11
gctaatttgt cacagtgctt a                                              21

<210> SEQ ID NO 12
<211> LENGTH: 21
<212> TYPE: DNA
<213> ORGANISM: artificial sequence
<220> FEATURE:
<223> OTHER INFORMATION: inhibitory RNA

<400> SEQUENCE: 12
gttaatgtgt gacctgctgt t                                              21
```

-continued

<210> SEQ ID NO 13
<211> LENGTH: 21
<212> TYPE: DNA
<213> ORGANISM: artificial sequence
<220> FEATURE:
<223> OTHER INFORMATION: inhibitory RNA

<400> SEQUENCE: 13
actgctaaat ctgcatgtcc t                                              21

<210> SEQ ID NO 14
<211> LENGTH: 21
<212> TYPE: DNA
<213> ORGANISM: artificial sequence
<220> FEATURE:
<223> OTHER INFORMATION: inhibitory RNA

<400> SEQUENCE: 14
tgatagagcg ttgctatttc a                                              21

<210> SEQ ID NO 15
<211> LENGTH: 32
<212> TYPE: PRT
<213> ORGANISM: artificial sequence
<220> FEATURE:
<223> OTHER INFORMATION: antagonistic agent

<400> SEQUENCE: 15

Pro Arg Ser Gly Arg Gly Thr Gly Arg Gly Gly Gly Gly Gly
1               5                   10                  15

Gly Gly Ala Pro Arg Gly Arg Tyr Gly Pro Pro Ser Arg Ser Glu
            20                  25                  30

<210> SEQ ID NO 16
<211> LENGTH: 196
<212> TYPE: PRT
<213> ORGANISM: artificial sequence
<220> FEATURE:
<223> OTHER INFORMATION: modified protein

<400> SEQUENCE: 16

Met Ser Gly Gly Gly Val Ile Arg Gly Pro Ala Gly Asn Asn Asp Cys
1               5                   10                  15

Arg Ile Tyr Val Gly Asn Leu Pro Pro Asp Ile Arg Thr Lys Asp Ile
            20                  25                  30

Glu Asp Val Phe Tyr Lys Tyr Gly Ala Ile Arg Asp Ile Asp Leu Lys
        35                  40                  45

Asn Arg Arg Gly Gly Pro Pro Phe Ala Phe Val Glu Phe Glu Asp Pro
    50                  55                  60

Arg Asp Ala Glu Asp Ala Val Tyr Gly Arg Asp Gly Tyr Asp Tyr Asp
65                  70                  75                  80

Gly Tyr Arg Leu Arg Val Glu Phe Pro Ala Ser Gly Ala Gly Thr Gly
                85                  90                  95

Arg Gly Gly Gly Gly Gly Gly Gly Gly Ala Pro Arg Gly Arg Tyr
            100                 105                 110

Gly Pro Pro Ser Ala Ala Ser Glu Asn Arg Val Val Ser Gly Leu
        115                 120                 125

Pro Pro Ser Gly Ser Trp Gln Asp Leu Lys Asp His Met Arg Glu Ala
    130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175

Asn Thr Lys Phe Arg Ser His Glu Gly Glu Thr Ala Tyr Ile Arg Val
            180                 185                 190

Lys Val Asp Gly
        195

<210> SEQ ID NO 17
<211> LENGTH: 187
<212> TYPE: PRT
<213> ORGANISM: artificial sequence
<220> FEATURE:
<223> OTHER INFORMATION: modified protein

<400> SEQUENCE: 17

Met Ala Gly Asn Asn Asp Cys Arg Ile Tyr Val Gly Asn Leu Pro Pro
1               5                   10                  15

Asp Ile Arg Thr Lys Asp Ile Glu Asp Val Phe Tyr Lys Tyr Gly Ala
            20                  25                  30

Ile Arg Asp Ile Asp Leu Lys Asn Arg Arg Gly Gly Pro Pro Phe Ala
        35                  40                  45

Phe Val Glu Phe Glu Asp Pro Arg Asp Ala Glu Asp Ala Val Tyr Gly
    50                  55                  60

Arg Asp Gly Tyr Asp Tyr Asp Gly Tyr Arg Leu Arg Val Glu Phe Pro
65                  70                  75                  80

Ala Ser Gly Ala Gly Thr Gly Arg Gly Gly Gly Gly Gly Gly Gly Gly
                85                  90                  95

Gly Ala Pro Arg Gly Arg Tyr Gly Pro Pro Ser Ala Ala Ser Glu Asn
            100                 105                 110

Arg Val Val Val Ser Gly Leu Pro Pro Ser Gly Ser Trp Gln Asp Leu
        115                 120                 125

Lys Asp His Met Arg Glu Ala Gly Asp Val Cys Tyr Ala Asp Val Tyr
    130                 135                 140

Arg Asp Gly Thr Gly Val Val Glu Phe Val Arg Lys Glu Asp Met Thr
145                 150                 155                 160

Tyr Ala Val Arg Lys Leu Asp Asn Thr Lys Phe Arg Ser His Glu Gly
                165                 170                 175

Glu Thr Ala Tyr Ile Arg Val Lys Val Asp Gly
            180                 185

<210> SEQ ID NO 18
<211> LENGTH: 1968
<212> TYPE: DNA
<213> ORGANISM: homo sapiens

<400> SEQUENCE: 18
atggagcgga aagtgcttgc gctccaggcc cgaaagaaaa ggaccaaggc caagaaggac      60
aaagcccaaa ggaaatctga aactcagcac cgaggctctg ctccccactc tgagagtgat     120
ctaccagagc aggaagagga gattctggga tctgatgatg atgagcaaga agatcctaat     180
gattattgta aggaggttta tcatcttgtg aaaattggag atctattcaa tgggagatac     240
catgtgatcc gaagttaggg ctggggcacac ttttcaacag tatggttatc atgggatatt     300
caggggaaga aatttgtggc aatgaaagta gttaaaagtg ctgaacatta cactgaaaca     360
gcactagatg aaatccggtt gctgaagtca gttcgcaatt cagacccwaa tgatccaaat     420
agagaaatgg ttgttcaact actagatgac tttaaaatat caggagttaa tggaacacat     480

-continued

```
atctgcatgg tatttgaagt tttggggcat catctgctca agtggatcat caaatccaat    540
tatcaggggc ttccactgcc ttgtgtcaaa aaaattattc agcaagtgtt acagggtctt    600
gattatttac ataccaagtg ccgtatcatc cacactgaca ttaaaccaga gaacatctta    660
ttgtcagtga atgagcagta cattcggagg ctggctgcag aagcaacaga atggcagcga    720
tctggagctc ctccgccttc cggatctgca gtcagtactg ctccccagcc taaaccagct    780
gacaaaatgt caagaataaa gaagaagaaa ttgaagaaga agcagaagcg ccaggcagaa    840
ttactagaga agcgaatgca ggaaattgag gaaatggaga aagagtcggg ccctgggcaa    900
aaaagaccaa acaagcaaga agaatcgagag agtcctgttg aaagacccct tgaaagagaac    960 ccacctaata aaatgaccca agaaaaactt gaagagtcaa gtaccattgg ccaggatcaa   1020
acgcttatgg aacgtgatac agagggtggt gcagcagaaa ttaattgcaa tggagtgatt   1080
gaagtcatta attatactca gaacagtaat aatgaaacat gagacataa agaggatcta   1140 cataatgcta atgactgtga tgtccaaaat ttgaatcagg aatctagttt cctaagctcc   1200
caaaatggag acagcagcac atctcaagaa acagactctt gtacacctat aacatctgag   1260
gtgtcagaca ccatggtgtg ccagtcttcc tcaactgtag gtcagtcatt cagtgaacaa   1320
cacattagcc aacttcaaga aagcattcgg gcagagatac cctgtgaaga tgaacaagag   1380
caagaacata acggaccact ggacaacaaa ggaaaatcca cggctggaaa ttttcttgtt   1440
aatccccttg agccaaaaaa tgcagaaaag ctcaaggtga agattgctga ccttggaaat   1500
gcttgttggg tgcacaaaca tttcactgaa gatattcaaa caaggcaata tcgttccttg   1560
gaagttctaa tcggatctgg ctataatacc cctgctgaca tttggagcac ggcatgcatg   1620
gcctttgaac tggccacagg tgactatttg tttgaacctc attcagggga agagtacact   1680
cgagatgaag atcacattgc attgatcata gaacttctgg ggaaggtgcc tcgcaagctc   1740
attgtggcag gaaaatattc caaggaattt ttcaccaaaa aaggtgacct gaaacatatc   1800
acgaagctga aaccttgggg cctttttgag gttctagtgg agaagtatga gtggtcgcag   1860
gaagaggcag ctggcttcac agatttctta ctgcccatgt tggagctgat ccctgagaag   1920
agagccactg ccgccgagtg tctccggcac ccttggctta actcctaa               1968
```

<210> SEQ ID NO 19
<211> LENGTH: 655
<212> TYPE: PRT
<213> ORGANISM: homo sapiens

<400> SEQUENCE: 19

```
Met Glu Arg Lys Val Leu Ala Leu Gln Ala Arg Lys Lys Arg Thr Lys
1               5                   10                  15

Ala Lys Lys Asp Lys Ala Gln Arg Lys Ser Glu Thr Gln His Arg Gly
            20                  25                  30

Ser Ala Pro His Ser Glu Ser Asp Leu Pro Glu Gln Glu Glu Glu Ile
        35                  40                  45

Leu Gly Ser Asp Asp Asp Glu Gln Glu Asp Pro Asn Asp Tyr Cys Lys
    50                  55                  60

Gly Gly Tyr His Leu Val Lys Ile Gly Asp Leu Phe Asn Gly Arg Tyr
65                  70                  75                  80

His Val Ile Arg Lys Leu Gly Trp Gly His Phe Ser Thr Val Trp Leu
                85                  90                  95

Ser Trp Asp Ile Gln Gly Lys Lys Phe Val Ala Met Lys Val Val Lys
            100                 105                 110
```

```
Ser Ala Glu His Tyr Thr Glu Thr Ala Leu Asp Glu Ile Arg Leu Leu
            115                 120                 125
Lys Ser Val Arg Asn Ser Asp Pro Asn Asp Pro Asn Arg Glu Met Val
        130                 135                 140
Val Gln Leu Leu Asp Asp Phe Lys Ile Ser Gly Val Asn Gly Thr His
145                 150                 155                 160
Ile Cys Met Val Phe Glu Val Leu Gly His His Leu Leu Lys Trp Ile
                165                 170                 175
Ile Lys Ser Asn Tyr Gln Gly Leu Pro Leu Pro Cys Val Lys Lys Ile
            180                 185                 190
Ile Gln Gln Val Leu Gln Gly Leu Asp Tyr Leu His Thr Lys Cys Arg
        195                 200                 205
Ile Ile His Thr Asp Ile Lys Pro Glu Asn Ile Leu Leu Ser Val Asn
        210                 215                 220
Glu Gln Tyr Ile Arg Arg Leu Ala Ala Glu Ala Thr Glu Trp Gln Arg
225                 230                 235                 240
Ser Gly Ala Pro Pro Ser Gly Ser Ala Val Ser Thr Ala Pro Gln
                245                 250                 255
Pro Lys Pro Ala Asp Lys Met Ser Lys Asn Lys Lys Lys Leu Lys
            260                 265                 270
Lys Lys Gln Lys Arg Gln Ala Glu Leu Leu Glu Lys Arg Met Gln Glu
        275                 280                 285
Ile Glu Glu Met Glu Lys Glu Ser Gly Pro Gly Gln Lys Arg Pro Asn
        290                 295                 300
Lys Gln Glu Glu Ser Glu Ser Pro Val Glu Arg Pro Leu Lys Glu Asn
305                 310                 315                 320
Pro Pro Asn Lys Met Thr Gln Glu Lys Leu Glu Glu Ser Ser Thr Ile
                325                 330                 335
Gly Gln Asp Gln Thr Leu Met Glu Arg Asp Thr Glu Gly Gly Ala Ala
            340                 345                 350
Glu Ile Asn Cys Asn Gly Val Ile Glu Val Ile Asn Tyr Thr Gln Asn
        355                 360                 365
Ser Asn Asn Glu Thr Leu Arg His Lys Glu Asp Leu His Asn Ala Asn
        370                 375                 380
Asp Cys Asp Val Gln Asn Leu Asn Gln Glu Ser Ser Phe Leu Ser Ser
385                 390                 395                 400
Gln Asn Gly Asp Ser Ser Thr Ser Gln Glu Thr Asp Ser Cys Thr Pro
                405                 410                 415
Ile Thr Ser Glu Val Ser Asp Thr Met Val Cys Gln Ser Ser Ser Thr
            420                 425                 430
Val Gly Gln Ser Phe Ser Glu Gln His Ile Ser Gln Leu Gln Glu Ser
        435                 440                 445
Ile Arg Ala Glu Ile Pro Cys Glu Asp Glu Gln Glu Gln Glu His Asn
        450                 455                 460
Gly Pro Leu Asp Asn Lys Gly Lys Ser Thr Ala Gly Asn Phe Leu Val
465                 470                 475                 480
Asn Pro Leu Glu Pro Lys Asn Ala Glu Lys Leu Lys Val Lys Ile Ala
                485                 490                 495
Asp Leu Gly Asn Ala Cys Trp Val His Lys His Phe Thr Glu Asp Ile
            500                 505                 510
Gln Thr Arg Gln Tyr Arg Ser Leu Glu Val Leu Ile Gly Ser Gly Tyr
        515                 520                 525
Asn Thr Pro Ala Asp Ile Trp Ser Thr Ala Cys Met Ala Phe Glu Leu
```

```
                530             535             540
Ala Thr Gly Asp Tyr Leu Phe Glu Pro His Ser Gly Glu Glu Tyr Thr
545                 550                 555                 560

Arg Asp Glu Asp His Ile Ala Leu Ile Ile Glu Leu Leu Gly Lys Val
                565                 570                 575

Pro Arg Lys Leu Ile Val Ala Gly Lys Tyr Ser Lys Glu Phe Phe Thr
                580                 585                 590

Lys Lys Gly Asp Leu Lys His Ile Thr Lys Leu Lys Pro Trp Gly Leu
            595                 600                 605

Phe Glu Val Leu Val Glu Lys Tyr Glu Trp Ser Gln Glu Glu Ala Ala
            610                 615                 620

Gly Phe Thr Asp Phe Leu Leu Pro Met Leu Glu Leu Ile Pro Glu Lys
625                 630                 635                 640

Arg Ala Thr Ala Ala Glu Cys Leu Arg His Pro Trp Leu Asn Ser
                645                 650                 655

<210> SEQ ID NO 20
<211> LENGTH: 1933
<212> TYPE: DNA
<213> ORGANISM: Homo sapiens

<400> SEQUENCE: 20
gtgcatgacc cgccccgcgg cggagacgcg ctcgctgcgt catcagtgtt ttcgagacga    60
gtctcgacgc agcagctgtc agctccattt tgttgttggt gcgcgacgca gtcagctgcg   120
tgattcccgt gattgcgtta caagctttgt ctccttcgac ttggagtctt tgtccaggac   180
gatgagacac tcaaagagaa cttactgtcc tgattgggat gacaaggatt gggattatgg   240
aaaatggagg agcagcagca gtcataaaag aaggaagaga tcacatagca gtgcccagga   300
gaacaagcgc tgcaaataca atcactctaa aatgtgtgat agccattatt ggaaagcag    360 gtctataaat gagaaagatt atcatagtcg acgctacatt gatgagtaca gaatgactac   420
cactcaagga tgtgaacctg acatcgccaa agagaccat gaaagccggt atcagaacca    480
tagtagcaag tcttctggta gaagtggaag aagtagttat aaaagcaaac acaggattca   540
ccacagtact tcacatcgtc gttcacatgg gaagagtcac cgaaggaaaa gaaccaggag   600
tgtagaggat gatgaggagg tcacctgat ctgtcagagt ggagacgtac taagtgcaag    660
atatgaaatt gttgatactt taggtgaagg agcttttgga aaagttgtgg agtgcatcga   720
tcataaagcg ggaggtagac atgtagcagt aaaaatagtt aaaaatgtgg atagatactg   780
tgaagctgct cgctcagaaa tacaagttct ggaacatctg aatacaacag accccaacag   840
tactttccgc tgtgtccaga tgttggaatg gtttgagcat catggtcaca tttgcattgt   900
ttttgaacta ttgggactta gtacttacga cttcattaaa gaaaatggtt ttctaccatt   960
tcgactggat catatcagaa agatggcata tcagatatgc aagtctgtga atttttgca   1020 cagtaataag ttgactcaca cagacttaaa gcctgaaaac atcttatttg tgcagtctga   1080
ctacacagag gcgtataatc ccaaaataaa acgtgatgaa cgcaccttaa taaatccaga   1140
tattaaagtt gtagactttg gtagtgcaac atatgatgac gaacatcaca gtacattggt   1200
atctacaaga cattatagag cacctgaagt tattttagcc ctagggtggt cccaaccatg   1260
tgatgtctgg agcataggat gcattcttat tgaatactat cttgggttta ccgtatttcc   1320
aacacacgat agtaaggagc atttagcaat gatggaaagg attcttggac ctctaccaaa   1380
acatatgata cagaaaacca ggaaacgtaa atattttcac cacgatcgat tagactggga   1440
```

-continued

```
tgaacacagt tctgccggca gatatgtttc aagacgctgt aaacctctga aggaatttat      1500
gctttctcaa gatgttgaac atgagcgtct ctttgacctc attcagaaaa tgttggagta      1560
tgatccagcc aaaagaatta ctctcagaga agccttaaag catcctttct ttgaccttct      1620
gaagaaaagt atatagatct gtaattggac agctctctcg aagagatctt acagactgta      1680
tcagtctaat ttttaaattt taagttattt tgtacagctt tgtaaattct taacattttt      1740
atattgccat gtttattttg tttgggtaat ttggttcatt aagtacatag ctaaggtaat      1800
gaacatcttt ttcagtaatt gtaaagtgat ttattcagaa taaattttt gtgcttatga       1860 agttgatatg tatctgaaca gtttgttcta agtaccattt tcttcctac ttctattaaa       1920 gaatggacat aga                                                         1933
```

<210> SEQ ID NO 21
<211> LENGTH: 484
<212> TYPE: PRT
<213> ORGANISM: homo sapiens

<400> SEQUENCE: 21

```
Met Arg His Ser Lys Arg Thr Tyr Cys Pro Asp Trp Asp Asp Lys Asp
1               5                   10                  15

Trp Asp Tyr Gly Lys Trp Arg Ser Ser Ser His Lys Arg Arg Lys
                20                  25                  30

Arg Ser His Ser Ala Gln Glu Asn Lys Arg Cys Lys Tyr Asn His
            35                  40                  45

Ser Lys Met Cys Asp Ser His Tyr Leu Glu Ser Arg Ser Ile Asn Glu
50                  55                  60

Lys Asp Tyr His Ser Arg Arg Tyr Ile Asp Glu Tyr Arg Asn Asp Tyr
65                  70                  75                  80

Thr Gln Gly Cys Glu Pro Gly His Arg Gln Arg Asp His Glu Ser Arg
                85                  90                  95

Tyr Gln Asn His Ser Ser Lys Ser Ser Gly Arg Ser Gly Arg Ser Ser
            100                 105                 110

Tyr Lys Ser Lys His Arg Ile His His Ser Thr Ser His Arg Arg Ser
        115                 120                 125

His Gly Lys Ser His Arg Arg Lys Arg Thr Arg Ser Val Glu Asp Asp
130                 135                 140

Glu Glu Gly His Leu Ile Cys Gln Ser Gly Asp Val Leu Ser Ala Arg
145                 150                 155                 160

Tyr Glu Ile Val Asp Thr Leu Gly Glu Gly Ala Phe Gly Lys Val Val
                165                 170                 175

Glu Cys Ile Asp His Lys Ala Gly Gly Arg His Val Ala Val Lys Ile
            180                 185                 190

Val Lys Asn Val Asp Arg Tyr Cys Glu Ala Ala Arg Ser Glu Ile Gln
        195                 200                 205

Val Leu Glu His Leu Asn Thr Thr Asp Pro Asn Ser Thr Phe Arg Cys
210                 215                 220

Val Gln Met Leu Glu Trp Phe Glu His His Gly His Ile Cys Ile Val
225                 230                 235                 240

Phe Glu Leu Leu Gly Leu Ser Tyr Asp Phe Ile Lys Glu Asn Gly
                245                 250                 255

Phe Leu Pro Phe Arg Leu Asp His Ile Arg Lys Met Ala Tyr Gln Ile
            260                 265                 270

Cys Lys Ser Val Asn Phe Leu His Ser Asn Lys Leu Thr His Thr Asp
        275                 280                 285
```

```
Leu Lys Pro Glu Asn Ile Leu Phe Val Gln Ser Asp Tyr Thr Glu Ala
    290                 295                 300

Tyr Asn Pro Lys Ile Lys Arg Asp Glu Arg Thr Leu Ile Asn Pro Asp
305                 310                 315                 320

Ile Lys Val Val Asp Phe Gly Ser Ala Thr Tyr Asp Asp Glu His His
                325                 330                 335

Ser Thr Leu Val Ser Thr Arg His Tyr Arg Ala Pro Glu Val Ile Leu
                340                 345                 350

Ala Leu Gly Trp Ser Gln Pro Cys Asp Val Trp Ser Ile Gly Cys Ile
            355                 360                 365

Leu Ile Glu Tyr Tyr Leu Gly Phe Thr Val Phe Pro Thr His Asp Ser
    370                 375                 380

Lys Glu His Leu Ala Met Met Glu Arg Ile Leu Gly Pro Leu Pro Lys
385                 390                 395                 400

His Met Ile Gln Lys Thr Arg Lys Arg Lys Tyr Phe His His Asp Arg
                405                 410                 415

Leu Asp Trp Asp Glu His Ser Ser Ala Gly Arg Tyr Val Ser Arg Arg
            420                 425                 430

Cys Lys Pro Leu Lys Glu Phe Met Leu Ser Gln Asp Val Glu His Glu
    435                 440                 445

Arg Leu Phe Asp Leu Ile Gln Lys Met Leu Glu Tyr Asp Pro Ala Lys
450                 455                 460

Arg Ile Thr Leu Arg Glu Ala Leu Lys His Pro Phe Phe Asp Leu Leu
465                 470                 475                 480

Lys Lys Ser Ile

<210> SEQ ID NO 22
<211> LENGTH: 1367
<212> TYPE: DNA
<213> ORGANISM: Homo sapiens

<400> SEQUENCE: 22
gggcaaggag ctgctggctg acggcggca tgtccgacag cgagaagctc aacctggact      60
cgatcatcgg gcgcctgctg aagtgcagg gctcgcggcc tggcaagaat gtacagctga     120
cagagaacga gatccgcggt ctgtgcctga atcccgggaa gattttctg agccagccca     180
ttcttctgga gctggaggca ccctcaaga tctgcggtga catacaccgg cagtactacg     240
accttctgcg actatttgag tatggcggtt ccctcccga gagcaactac ctctttctgg     300
gggactatgt ggacaggggc aagcagtcct tggagaccat ctgcctgctg ctggcctata     360
agatcaagta ccccgagaac ttcttcctgc tccgtgggaa ccacgagtgt gccagcatca     420
accgcatcta tggtttctac gatgagtgca agagacgcta caacatcaaa ctgtggaaaa     480
ccttcactga ctgcttcaac tgcctgccca tcgcggccat agtggacgaa aagatcttct     540
gctgccacgg aggcctgtcc ccggacctgc agtctatgga gcagattcgg cggatcatgc     600
ggcccacaga tgtgcctgac cagggcctgc tgtgtgacct gctgtggtct gaccctgaca     660
aggacgtgca gggctgggc gagaacgacc gtggcgtctc tttttacctttt ggagccgagg     720
tggtggccaa gttcctccac aagcacgact ggacctcat ctgccgagca caccaggtgg     780
tagaagacgg ctatgagttc tttgccaagc ggcagctggt gacacttttc tcagctccca     840
actactgtgg cgagtttgac aatgctggcg ccatgatgag tgtggacgag accctcatgt     900
gctcttttcca gatcctcaag cccgccgaca agaacaaggg gaagtacggg cagttcagtg     960
```

|  |  |
|---|---|
| gcctgaaccc tggaggccga cccatcaccc caccccgcaa ttccgccaaa gccaagaaat | 1020 |
| agccccccgca caccaccctg tgccccagat gatggattga ttgtacagaa atcatgctgc | 1080 |
| catgctgggg gggggtcacc ccgaccccta aggcccacct gtcacgggga acatggagcc | 1140 |
| ttggtgtatt tttcttttct ttttttaatg aatcaatagc agcgtccagt cccccagggc | 1200 |
| tgcttcctgc ctgcacctgc ggtactgtga gcaggatcct ggggccgagg ctgcagctca | 1260 |
| ggcaacggc aggccaggtc gtgggtctcc agccgtgctt ggcctcaggc tggcagcccg | 1320 |
| gatcctgggg caacccatct ggtctcttga ataaaggtca aagctgg | 1367 |

<210> SEQ ID NO 23
<211> LENGTH: 4747
<212> TYPE: DNA
<213> ORGANISM: Homo sapiens

<400> SEQUENCE: 23

|  |  |
|---|---|
| gttgcgctcc cgcgcgtgcg tgttgggatc gaatcgctgt ttccttccgc ttctcttcct | 60 |
| ctgtctcccc cccatatccg tgcgccgagc tgataaaggc gccattttgg aggggccgcg | 120 |
| ggagacgtgg tgccgctgcg ggctcgctct gccgtgcgct aggcttggtg gaaggcctg | 180 |
| ttctcgagtc cgcgcttttc gtcaccgcca tgtcggagg tggtgtgatt cgtggccccg | 240 |
| cagggaacaa cgattgccgc atctacgtgg gtaacttacc tccagacatc cgaaccaagg | 300 |
| acattgagga cgtgttctac aaatacggcg ctatccgcga catcgacctc aagaatcgcc | 360 |
| gcggggacc gcccttcgcc ttcgttgagt tcgaggaccc gcgagacgcg gaagacgcgg | 420 |
| tgtatggtcg cgacggctat gattacgatg ggtaccgtct gcgggtggag tttcctcgaa | 480 |
| gcggccgtgg aacaggccga ggcggcggcg ggggtggagg tggcggagct ccccgaggtc | 540 |
| gctatggccc cccatccagg cggtctgaaa acagagtggt tgtctctgga ctgcctccaa | 600 |
| gtggaagttg gcaggattta aaggatcaca tgcgtgaagc aggtgatgta tgttatgctg | 660 |
| atgtttaccg agatggcact ggtgtcgtgg agtttgtacg gaagaagat atgacctatg | 720 |
| cagttcgaaa actggataac actaagttta gatctcatga ggtaggttat acacgtattc | 780 |
| ttttctttga ccagaattgg atacagtggt cttaacagtg gaatttcaag gtaaggattc | 840 |
| aggcaaggtt gtccaagtaa attgccagat ttctggtttt agttacattg tattcattca | 900 |
| gcatgtctga agatagatga aagcttagat cttttcaatgg aaagttctgt ctatccaata | 960 |
| gggagaaaact gcctacatcc gggttaaagt tgatgggccc agaagtccaa gttatggaag | 1020 |
| atctcgatct cgaagccgta gtcgtagcag aagccgtagc agaagcaaca gcaggagtcg | 1080 |
| cagttactcc ccaaggagaa gcagaggatc accacgctat tctccccgtc atagcagatc | 1140 |
| tcgctctcgt acataagatg attggtgaca ctttttgtag aacccatgtt gtatacagtt | 1200 |
| ttcctttatt cagtacaatc ttttcatttt ttaattcaaa ctgttttgtt cagaatgggc | 1260 |
| taaagtgttg aattgcattc ttgtaatatc cccttgctcc taacatctac attcccttcg | 1320 |
| tgtctttgat aaattgtatt ttaagtgatg tcatagacag gattgtttaa atttagttaa | 1380 |
| ctccatactc ttcagactgt gatattgtgt aaatgtctat ctgccctggt ttgtgtgaac | 1440 |
| tgggatgttg ggggtgtttg tggttatctt acctggggaa gttcttatgt ttatcttgct | 1500 |
| tttcatgtgt ctttctgtag acatatctga agagatggat taagaatgct ttggattaag | 1560 |
| gattgtggag cacatttcaa tcattttagg attgtcaaaa ggaggattga ggaggatcag | 1620 |
| atcaataatg gaggcaatgg tttggattgg agagggctca ctggatccca atccttggag | 1680 |
| ctggatcatt ggattcaaat cataatgtgg ataggatagg gaggatgaat taccaggatt | 1740 |

```
catggagcgg gatcagatta ccaggaacat aggagtggat tcctgcccca accaaaccgc    1800
attcgtgtgg atttttttat tcaacttaat tggctattcc aaagattttt tttttcctat    1860
ttttgacgat tggagccctt aagatgcacg atggaattgt gttttgcgtt ttttggtaaa    1920
aggagcaaag cgaggacctg agataaacg ctggagcaat ctccttggaa ggattcagca    1980
cgagtagatg gtaaacattt aagggggaaa ggggggtttt gtttaaaata gtaaatcagt    2040
aagtcacttc taaatttaaa gaaacaaaa ttggagttga agaataagta ggtttccaat    2100
tggctattgc cgttttcttt gaaaaaataa acatttttta aaaactatg catggttgtc     2160 cttttttcctc ttcatgtaag attctaactg ggtctatcag ttaatcttta aattgttaag    2220
taagataaga ttttgactct tgtgttaatg tgttagcaaa ttaaaagttc ttaaaaggca    2280
atctaatggt attagccatc ttttattgtt aattgtaaaa gtcttcaggg gaaagcaaaa    2340
ggggagaata aggcatttgt gtatgtaact tggtaaatga cggtggggga tggatctagc    2400
atctgaaaga taagcttctc tactttgtta taaagtggtt aaaaaactat agatgctgct    2460
tattttctgg tggtcataga caacataggc ttttgtgcaa aattggttga tggctactaa    2520
tgttcacttg gagatagctt ttgatattct caatgaaact catctcaaaa aaaggtaagt    2580
attaaatgtt aacatcagca cagatgtatt agaactgttt tttgtttttg agacagagtc    2640
tcgctctgtt ctccagactg gagggcagtg gtgtgatcta ggctcactgc aacctccacc    2700
cctggatttg agtgattctc gtgcctcagt ctcccaagta gctgagacta caagtgtgtg    2760
ccacccttgc ccggctaatt ttgtattttt agtagagatg tggtttctct gtgttaccca    2820
ggctggtccc aaaactcctg gcctcaagtg atctgcctgc cttggcctcc caagtgtta     2880 ggattacagg tgtgagccac catgctcagc ctgtagaact tttaacccaa gtctcatttc    2940 tttttttgaaa gggaagagtg cacaagatta actgcttctt tggatgaatc attgttaata    3000
aaaagctggg catttagaat tttgccttat aagcccttct ccaaccataa gattattttg    3060
taccaaaaac tttggtgttc tctaccaaag cagttaaaaa cttttagcct gctacttctt    3120
gtatttgtct actgacagcc ccttggtact atttaggttg ggggagggga cctaaaataa    3180 atagactta acatttccct tgggtgctaa tcatagttgg aagttgaatt taaggtgatt    3240
atttgggtga caattaaaaa cctaaggaaa accagaaatc ttggtagtgg aagaaatgtg    3300
taaggtcacc ccaatcggta gattttaatg aacgttgtgg aatgttggga agaggggatg    3360
ttaagttgaa tgcagaattt cactaagtac ttagtgtaag tttaaggatg tagctctttt    3420
tatctaagaa ttcaatgtaa tggccaaaag gcagatttac tgtttaaaaa tttgaataat    3480
tttacatgac attcttgaaa ttctaagaag ttttatgtgt agaacatttt aaaaattcat    3540
cagattatta aagggaaaat aaatgattaa tgataatttt ggaaggttaa tgtgagctag    3600
acttaagtaa actttggttc atttgtgttc attgaatgtt ttggaaatga ccaaaaaatg    3660
taaatggcct tcactcaagt ttgagtgttt aagttgaaa gatgtgctct actaaaagtt     3720
atagtaattc taacctcaca ttgaaatgag acagtattcc ttgttataca ggctgaattt    3780
gaagattaga gaggatctaa tgtttactta ggtaaagggg cataggtttt gtagttaaga    3840
tgaccagaca gctaaaagct gtgatgggaa gtatggactg ctcctatta tagtctcaga     3900 aaatggacct ttaggtctct atccgtattg gcaattatta aagaaagtt accccttttt     3960 gaaactacaa aagctgtctt ggaatttccc cctcttctcc ctatttatgt ccccttagaa    4020
tattttaggg agcctataat tatttttctaa ccaaggaaaa acttaagtct ctttaagaag    4080
```

```
caattactttt tcataacatc agattgaata acccaccttg ctgttcagcc cacatcctac    4140
tggaaacaaa aggtaagaaa cccatttcct ggttcttgat tgtttgggtc tgaatttgt     4200 ttttaaaact aagctaagtt taatgttttt taaaatgctg tttggaatat gaatagattc    4260
cccgtaaaat gattttcct aagttttatg ctttagtaaa tattcagtgc tcacgtctgt    4320
gcatcatagt gcttgcgttt aatatgattt attgtagaat ctcaactttt cttggtgttt    4380
gttgtctttg aaacattgtc ttggtcatta gggctggtgt tttcacattt ctgtggtcaa    4440
ggtggatttc ttatgtgtgc cttttgctt actttgtata tgaattttgt aatttaaatt    4500
gcaagtaagt tatatatatg tatttaccat aaatagtatt aaaagatgag aaactgttag    4560
actgaagttc tgttgtaaca taaccattat ttccatcaca gtatgaagac tgcaaacgca    4620
gaaaacagat tacagtctct tatccatttt ttgaaatcca aaaactacga aaacaaaga    4680 ttttctgttg ttgagctaat taaatgtgaa ccctgaccag aaaaaaaaaa aaaaaaaaa    4740 aaaaaaa                                                                  4747
```

<210> SEQ ID NO 24
<211> LENGTH: 747
<212> TYPE: DNA
<213> ORGANISM: Mus musulus

<400> SEQUENCE: 24

```
atgtcgggag gtggtgtgat ccgtggcccg gcggggaaca acgactgccg catctacgtg     60
ggtaacctac ctccggatat ccgaaccaag gacatcgagg acgtgtttta caaatacggc    120
gccatccgcg acatcgacct gaagaaccgc cgcgggggac cgccctttcgc cttcgttgag    180 ttcgaggacc cgcgagacgc ggaagatgcg gtgtacggtc gcgacggcta cgactacgac    240
ggctaccggc tgcgggtaga gttccccga agcggccgcg ggaccggccg aggcggcggc    300 ggggtggag cggcggcgc cccgagaggc cgctatggcc cgccgtccag gcggtccgag    360
aacagagtgg ttgtctctgg actgcctccg agtggaagct ggcaggactt aaaggatcac    420
atgcgtgagg caggtgatgt atgttacgct gatgtttacc gagatggcac tggtgtcgtg    480
gagtttgtac ggaaagaaga tatgacgtat gcagttcgaa aactggataa cactaagttt    540
agatctcacg agggagaaac tgcctacatc cgggttaaag ttgatgggcc cagaagtcca    600
agttatggaa gatctcgatc tcgaagccgt agtcgtagca gaagccgtag cagaagcaac    660
agcaggagtc gcagttactc cccaaggaga agcagaggat caccacgcta ttctccccgt    720
catagcagat ctcgctctcg tacataa                                            747
```

<210> SEQ ID NO 25
<211> LENGTH: 248
<212> TYPE: PRT
<213> ORGANISM: Mus musulus

<400> SEQUENCE: 25

```
Met Ser Gly Gly Val Ile Arg Gly Pro Ala Gly Asn Asn Asp Cys
1               5                   10                  15

Arg Ile Tyr Val Gly Asn Leu Pro Pro Asp Ile Arg Thr Lys Asp Ile
                20                  25                  30

Glu Asp Val Phe Tyr Lys Tyr Gly Ala Ile Arg Asp Ile Asp Leu Lys
            35                  40                  45

Asn Arg Arg Gly Gly Pro Pro Phe Ala Phe Val Glu Phe Glu Asp Pro
        50                  55                  60

Arg Asp Ala Glu Asp Ala Val Tyr Gly Arg Asp Gly Tyr Asp Tyr Asp
```

```
                65                  70                  75                  80
Gly Tyr Arg Leu Arg Val Glu Phe Pro Arg Ser Gly Arg Gly Thr Gly
                85                  90                  95

Arg Gly Gly Gly Gly Gly Gly Gly Ala Pro Arg Gly Arg Tyr
                100                 105                 110

Gly Pro Pro Ser Arg Arg Ser Glu Asn Arg Val Val Ser Gly Leu
                115                 120                 125

Pro Pro Ser Gly Ser Trp Gln Asp Leu Lys Asp His Met Arg Glu Ala
    130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175

Asn Thr Lys Phe Arg Ser His Glu Gly Glu Thr Ala Tyr Ile Arg Val
                180                 185                 190

Lys Val Asp Gly Pro Arg Ser Pro Ser Tyr Gly Arg Ser Arg Ser Arg
                195                 200                 205

Ser Arg Ser Arg Ser Arg Ser Arg Ser Asn Ser Arg Ser Arg
        210                 215                 220

Ser Tyr Ser Pro Arg Arg Ser Arg Gly Ser Pro Arg Tyr Ser Pro Arg
225                 230                 235                 240

His Ser Arg Ser Arg Ser Arg Thr
                245
```

<210> SEQ ID NO 26
<211> LENGTH: 747
<212> TYPE: DNA
<213> ORGANISM: Mus musculus

<400> SEQUENCE: 26

```
atgtcgggag gtggtgtgat ccgtggcccg gcggggaaca acgactgccg catctacgtg      60
ggtaacctac ctccggatat ccgaaccaag gacatcgagg acgtgtttta caaatacggc    120
gccatccgcg acatcgacct gaagaaccgc cgcggggggac cgcccttcgc cttcgttgag    180
ttcgaggacc cgcgagacgc ggaagatgcg gtgtacggtc gcgacggcta cgactacgac    240
ggctaccggc tgcgggtaga gtttccccga agcggccgcg ggaccggccg aggcggcggc    300
gggggtggag gcggcggcgc cccgagaggc cgctatggcc cgccgtccag gcggtccgag    360
aacagagtgg ttgtctctgg actgcctccg agtggaagct ggcaggactt aaaggatcac    420
atgcgtgagg caggtgatgt atgttacgct gatgtttacc gagatggcac tggtgtcgtg    480
gagtttgtac ggaaagaaga tatgacgtat gcagttcgaa aactggataa cactaagttt    540
agatctcacg agggagaaac tgcctacatc cgggttaaag ttgatgggcc agaagtccca    600
agttatggaa gatctcgatc tcgaagccgt agtcgtagca gaagccgtag cagaagcaac    660
agcaggagtc gcagttactc cccaaggaga agcagaggat caccacgcta ttctccccgt    720
catagcagat ctcgctctcg tacataa                                        747
```

<210> SEQ ID NO 27
<211> LENGTH: 248
<212> TYPE: PRT
<213> ORGANISM: Mus musulus

<400> SEQUENCE: 27

```
Met Ser Gly Gly Gly Val Ile Arg Gly Pro Ala Gly Asn Asn Asp Cys
1               5                   10                  15
```

Arg Ile Tyr Val Gly Asn Leu Pro Pro Asp Ile Arg Thr Lys Asp Ile
            20                  25                  30

Glu Asp Val Phe Tyr Lys Tyr Gly Ala Ile Arg Asp Ile Asp Leu Lys
        35                  40                  45

Asn Arg Arg Gly Gly Pro Pro Phe Ala Phe Val Glu Phe Glu Asp Pro
 50                  55                  60

Arg Asp Ala Glu Asp Ala Val Tyr Gly Arg Asp Gly Tyr Asp Tyr Asp
 65                  70                  75                  80

Gly Tyr Arg Leu Arg Val Glu Phe Pro Arg Ser Gly Arg Gly Thr Gly
                85                  90                  95

Arg Gly Gly Gly Gly Gly Gly Gly Ala Pro Arg Gly Arg Tyr
            100                 105                 110

Gly Pro Pro Ser Arg Arg Ser Glu Asn Arg Val Val Ser Gly Leu
            115                 120                 125

Pro Pro Ser Gly Ser Trp Gln Asp Leu Lys Asp His Met Arg Glu Ala
            130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175

Asn Thr Lys Phe Arg Ser His Glu Gly Glu Thr Ala Tyr Ile Arg Val
            180                 185                 190

Lys Val Asp Gly Pro Arg Ser Pro Ser Tyr Gly Arg Ser Arg Ser Arg
            195                 200                 205

Ser Arg Ser Arg Ser Arg Ser Arg Ser Arg Asn Ser Arg Ser Arg
            210                 215                 220

Ser Tyr Ser Pro Arg Arg Ser Arg Gly Ser Pro Arg Tyr Ser Pro Arg
225                 230                 235                 240

His Ser Arg Ser Arg Ser Arg Thr
            245

<210> SEQ ID NO 28
<211> LENGTH: 606
<212> TYPE: DNA
<213> ORGANISM: Mus musulus

<400> SEQUENCE: 28
atgtcgggag gtggtgtgat ccgtggcccg gcggggaaca acgactgccg catctacgtg      60
ggtaacctac ctccggatat ccgaaccaag gacatcgagg acgtgtttta caaatacggc     120
gccatccgcg acatcgacct gaagaaccgc cgcgggggac cgcccttcgc cttcgttgag     180
ttcgaggacc cgcgagacgc ggaagatgcg gtgtacggtc gcgacggcta cgactacgac     240
ggctaccggc tgcgggtaga gtttccccga agcggccgcg gaccggccg aggcggcggc     300 gggggtggag gcggcggcgc cccgagaggc cgctatggcc cgccgtccag gcggtccgag     360
aacagagtgg ttgtctctgg actgcctccg agtggaagct ggcaggactt aaaggatcac     420
atgcgtgagg caggtgatgt atgttacgct gatgtttacc gagatggcac tggtgtcgtg     480
gagtttgtac ggaaagaaga tatgacgtat gcagttcgaa aactggataa cactaagttt     540
agatctcacg aggtaggtta tacacttatt ctttttttg gccagaattg gatacagttt     600
tcttaa                                                                606

<210> SEQ ID NO 29
<211> LENGTH: 201

<212> TYPE: PRT
<213> ORGANISM: Mus musulus

<400> SEQUENCE: 29

Met Ser Gly Gly Gly Val Ile Arg Gly Pro Ala Gly Asn Asn Asp Cys
1               5                   10                  15

Arg Ile Tyr Val Gly Asn Leu Pro Pro Asp Ile Arg Thr Lys Asp Ile
            20                  25                  30

Glu Asp Val Phe Tyr Lys Tyr Gly Ala Ile Arg Asp Ile Asp Leu Lys
        35                  40                  45

Asn Arg Arg Gly Gly Pro Pro Phe Ala Phe Val Glu Phe Glu Asp Pro
    50                  55                  60

Arg Asp Ala Glu Asp Ala Val Tyr Gly Arg Asp Gly Tyr Asp Tyr Asp
65                  70                  75                  80

Gly Tyr Arg Leu Arg Val Glu Phe Pro Arg Ser Gly Arg Gly Thr Gly
                85                  90                  95

Arg Gly Gly Gly Gly Gly Gly Gly Ala Pro Arg Gly Arg Tyr
            100                 105                 110

Gly Pro Pro Ser Arg Arg Ser Glu Asn Arg Val Val Val Ser Gly Leu
        115                 120                 125

Pro Pro Ser Gly Ser Trp Gln Asp Leu Lys Asp His Met Arg Glu Ala
    130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175

Asn Thr Lys Phe Arg Ser His Glu Val Gly Tyr Thr Leu Ile Leu Phe
            180                 185                 190

Phe Gly Gln Asn Trp Ile Gln Phe Ser
        195                 200

<210> SEQ ID NO 30
<211> LENGTH: 330
<212> TYPE: PRT
<213> ORGANISM: Homo sapiens

<400> SEQUENCE: 30

Met Ser Asp Ser Glu Lys Leu Asn Leu Asp Ser Ile Ile Gly Arg Leu
1               5                   10                  15

Leu Glu Val Gln Gly Ser Arg Pro Gly Lys Asn Val Gln Leu Thr Glu
            20                  25                  30

Asn Glu Ile Arg Gly Leu Cys Leu Lys Ser Arg Glu Ile Phe Leu Ser
        35                  40                  45

Gln Pro Ile Leu Leu Glu Leu Glu Ala Pro Leu Lys Ile Cys Gly Asp
    50                  55                  60

Ile His Gly Gln Tyr Tyr Asp Leu Leu Arg Leu Phe Glu Tyr Gly Gly
65                  70                  75                  80

Phe Pro Pro Glu Ser Asn Tyr Leu Phe Leu Gly Asp Tyr Val Asp Arg
                85                  90                  95

Gly Lys Gln Ser Leu Glu Thr Ile Cys Leu Leu Leu Ala Tyr Lys Ile
            100                 105                 110

Lys Tyr Pro Glu Asn Phe Phe Leu Leu Arg Gly Asn His Glu Cys Ala
        115                 120                 125

Ser Ile Asn Arg Ile Tyr Gly Phe Tyr Asp Glu Cys Lys Arg Arg Tyr
    130                 135                 140

```
Asn Ile Lys Leu Trp Lys Thr Phe Thr Asp Cys Phe Asn Cys Leu Pro
145                 150                 155                 160

Ile Ala Ala Ile Val Asp Glu Lys Ile Phe Cys Cys His Gly Gly Leu
            165                 170                 175

Ser Pro Asp Leu Gln Ser Met Glu Gln Ile Arg Arg Ile Met Arg Pro
        180                 185                 190

Thr Asp Val Pro Asp Gln Gly Leu Leu Cys Asp Leu Leu Trp Ser Asp
    195                 200                 205

Pro Asp Lys Asp Val Gln Gly Trp Gly Glu Asn Asp Arg Gly Val Ser
210                 215                 220

Phe Thr Phe Gly Ala Glu Val Val Ala Lys Phe Leu His Lys His Asp
225                 230                 235                 240

Leu Asp Leu Ile Cys Arg Ala His Gln Val Val Glu Asp Gly Tyr Glu
            245                 250                 255

Phe Phe Ala Lys Arg Gln Leu Val Thr Leu Phe Ser Ala Pro Asn Tyr
        260                 265                 270

Cys Gly Glu Phe Asp Asn Ala Gly Ala Met Met Ser Val Asp Glu Thr
    275                 280                 285

Leu Met Cys Ser Phe Gln Ile Leu Lys Pro Ala Asp Lys Asn Lys Gly
290                 295                 300

Lys Tyr Gly Gln Phe Ser Gly Leu Asn Pro Gly Gly Arg Pro Ile Thr
305                 310                 315                 320

Pro Pro Arg Asn Ser Ala Lys Ala Lys Lys
            325                 330

<210> SEQ ID NO 31
<211> LENGTH: 659
<212> TYPE: DNA
<213> ORGANISM: Homo sapiens

<400> SEQUENCE: 31
gacattgatt attgactagt tattaatagt aatcaattac ggggtcatta gttcatagcc      60
catatatgga gttccgcgtt acataactta cggtaaatgg cccgcctggc tgaccgccca     120 acgaccccg cccattgacg tcaataatga cgtatgttcc catagtaacg ccaataggga     180
ctttccattg acgtcaatgg gtggagtatt tacggtaaac tgcccacttg cagtacatc     240 aagtgtatca tatgccaagt acgccccta ttgacgtcaa tgacggtaaa tggcccgcct     300
ggcattatgc ccagtacatg accttatggg actttcctac ttggcagtac atctacgtat     360
tagtcatcgc tattaccatg gtcgaggtga gccccacgtt ctgcttcact ctccccatct     420 ccccccctc ccaccccca attttgtatt tatttatttt ttaattattt tgtgcagcga     480
tgggggcggg gggggggggg gggcccccc caggcgggc ggggcgggc gaggggcggg     540 gcgggcgag gcggaaaggt gcggcggcag ccaatcagag cggcgcgctc cgaaagtttc     600
cttttatggc gaggcggcgg cggcggcggc cctataaaaa gcgaagcgcg cggcgggcg     659

<210> SEQ ID NO 32
<211> LENGTH: 724
<212> TYPE: DNA
<213> ORGANISM: Homo sapiens

<400> SEQUENCE: 32
acgcgttgac attgattatt gactagttat taatagtaat caattacggg gtcattagtt      60
catagcccat atatggagtt ccgcgttaca taacttacgg taaatggccc gcctggctga     120
ccgcccaacg accccgccc attgacgtca ataatgacgt atgttccat agtaacgcca     180
```

```
ataggggactt tccattgacg tcaatgggtg gactatttac ggtaaactgc ccacttggca    240
gtacatcaag tgtatcatat gccaagtacg ccccctattg acgtcaatga cggtaaatgg    300
cccgcctggc attatgccca gtacatgacc ttatgggact ttcctacttg gcagtacatc    360
tacgtattag tcatcgctat taccatggtg atgcggtttt ggcagtacat caatgggcgt    420
ggatagcggt ttgactcacg gggatttcca agtctccacc ccattgacgt caatgggagt    480
ttgttttggc accaaaatca acgggacttt ccaaaatgtc gtaacaactc cgccccattg    540
acgcaaatgg gcggtaggcg tgtacggtgg gaggtctata taagcagagc tctctggcta    600
actagagaac ccactgctta ctggcttatc gaaattaata cgactcacta tagggagacc    660
caagctggct agcgtttaaa cttaagcttg gtaccgagct cggatccact agtccagtgt    720
ggtg                                                                724

<210> SEQ ID NO 33
<211> LENGTH: 278
<212> TYPE: DNA
<213> ORGANISM: Homo sapiens

<400> SEQUENCE: 33
tcgaggtgag ccccacgttc tgcttcactc tccccatctc ccccccctcc caccccccaa     60
ttttgtattt atttattttt taattatttt gtgcagcgat ggggggcgggg gggggggggg    120 ggcccccccc aggcggggcg gggcggggcg aggggcgggg cggggcgagg cggaaaggtg    180
cggcggcagc caatcagagc ggcgcgctcc gaaagtttcc ttttatggcg aggcggcggc    240
ggcggcggcc ctataaaaag cgaagcgcgc ggcgggcg                            278

<210> SEQ ID NO 34
<211> LENGTH: 401
<212> TYPE: DNA
<213> ORGANISM: Homo sapiens

<400> SEQUENCE: 34
ctgcagaggg ccctgcgtat gagtgcaagt gggttttagg accaggatga ggcggggtgg     60
gggtgcctac ctgacgaccg accccgaccc actggacaag cacccaaccc ccattcccca    120
aattgcgcat cccctatcag agaggggag ggggaaacagg atgcggcgag gcgcgtgcgc    180
actgccagct tcagcaccgc ggacagtgcc ttcgcccccg cctggcggcg cgcgccaccg    240
ccgcctcagc actgaaggcg cgctgacgtc actcgccggt ccccccgcaaa ctcccccttcc    300 cggccacctt ggtcgcgtcc gcgccgccgc cggcccagcc ggaccgcacc acgcgaggcg    360
cgagataggg gggcacgggc gcgaccatct gcgctgcggc g                       401

<210> SEQ ID NO 35
<211> LENGTH: 1675
<212> TYPE: DNA
<213> ORGANISM: Homo sapiens

<400> SEQUENCE: 35
gtctgcaagc agacctggca gcattgggct ggccgccccc cagggcctcc tcttcatgcc     60
cagtgaatga ctcaccttgg cacagacaca atgttcgggg tggcacagt gcctgcttcc    120 cgccgcaccc cagcccccct caaatgcctt ccgagaagcc cattgagtag ggggcttgca    180
ttgcacccca gcctgacagc ctggcatctt gggataaaag cagcacagcc cctaggggc    240 tgcccttgct gtgtggcgcc accggcggtg gagaacaagg ctctattcag cctgtgccca    300
```

```
ggaaagggga tcaggggatg cccaggcatg acagtgggt ggcagggggg gagaggaggg      360
ctgtctgctt cccagaagtc caaggacaca aatgggtgag gggactgggc agggttctga      420
ccctgtggga ccagagtgga gggcgtagat ggacctgaag tctccaggga caacagggcc      480
caggtctcag gctcctagtt gggcccagtg gctccagcgt ttccaaaccc atccatcccc      540
agaggttctt cccatctctc caggctgatg tgtgggaact cgaggaaata aatctccagt      600
gggagacgga ggggtggcca gggaaacggg gcgctgcagg aataaagacg agccagcaca      660
gccagctcat gcgtaacggc tttgtggagc tgtcaaggcc tggtctctgg gagagaggca      720
cagggaggcc agacaaggaa ggggtgacct ggagggacag atccagggc taaagtcctg       780 ataaggcaag agagtgccgg cccccctcttg ccctatcagg acctccactg ccacatagag     840
gccatgattg accttagac aaagggctgg tgtccaatcc cagccccag ccccagaact       900 ccagggaatg aatgggcaga gagcaggaat gtgggacatc tgtgttcaag ggaaggactc      960
caggagtctg ctgggaatga ggcctagtag gaaatgaggt ggcccttgag ggtacagaac      1020
aggttcattc ttcgccaaat tcccagcacc ttgcaggcac ttacagctga gtgagataat      1080
gcctgggtta tgaaatcaaa aagttggaaa gcaggtcaga ggtcatctgg tacagccctt      1140
ccttcccttt tttttttttt tttttttttg tgagacaagg tctctctctg ttgcccaggc      1200
tggagtggcg caaacacagc tcactgcagc ctcaacctac tgggctcaag caatcctcca      1260
gcctcagcct cccaaagtgc tgggattaca agcatgagcc accccactca gcccttcct       1320 tcctttttaa ttgatgcata ataattgtaa gtattcatca tggtccaacc aacccttctct    1380 tgacccacct tcctagagag agggtcctct tgattcagcg gtcagggccc cagacccatg     1440
gtctggctcc aggtaccacc tgcctcatgc aggagttggc gtgcccagga agctctgcct     1500
ctgggcacag tgacctcagt ggggtgaggg gagctctccc catagctggg ctgcggccca     1560
accccacccc ctcaggctat gccaggggt gttgccaggg gcacccgggc atcgccagtc     1620
tagcccactc cttcataaag ccctcgcatc ccaggagcga gcagagccag agcat          1675
```

<210> SEQ ID NO 36
<211> LENGTH: 260
<212> TYPE: DNA
<213> ORGANISM: Homo sapiens

<400> SEQUENCE: 36

```
gaatcctatg cttcgaacgc tgacgtcatc aacccgctcc aaggaatcgc gggcccagtg      60
tcactaggcg ggaacaccca gcgcgcgtgc gccctggcag gaagatggct gtgagggaca      120
ggggagtggc gccctgcaat atttgcatgt cgctatgtgt tctgggaaat caccataaac      180
gtgaaatgtc tttggatttg ggagtcttat aagttctgta tgagaccact ctttcccatg      240
gtcttcatcc tatctagaca                                                  260
```

<210> SEQ ID NO 37
<211> LENGTH: 261
<212> TYPE: DNA
<213> ORGANISM: Homo sapiens

<400> SEQUENCE: 37

```
gccgcccct tcaccgaggg cctatttccc atgattcctt catatttgca tatacgatac       60
aaggctgtta gagagataat tggaattaat ttgactgtaa acacaaagat attagtacaa      120 atacgtgac gtagaaagta ataatttctt gggtagtttg cagttttaaa attatgtttt       180
aaaatggact atcatatgct taccgtaact tgaaagtatt tcgatttctt ggctttatat     240
```
atcttgtgga aaggacgaaa c                                          261

<210> SEQ ID NO 38
<211> LENGTH: 4661
<212> TYPE: DNA
<213> ORGANISM: Adenovirus

<400> SEQUENCE: 38

```
aaagcttccc ggggggatct gggccactcc ctctctgcgc gctcgctcgc tcactgaggc    60
cgggcgacca aggtcgcccg acgcccggg ctttgcccgg gcggcctcag tgagcgagcg   120
agcgcgcaga gagggagtgg ccaactccat cactaggggt tcctggaggg gtggagtcgt   180
gacccctaaa atgggcaaac attgcgctag cgcggccgcg gtacctaccg atgtacgggc   240
cagatatacg cgtggagcta gttattaata gtaatcaatt acgggtcat  tagttcatag   300
cccatatatg gagttccgcg ttacataact tacggtaaat ggcccgcctg gctgaccgcc   360
caacgacccc cgcccattga cgtcaataat gacgtatgtt cccatagtaa cgccaatagg   420
gactttccat tgacgtcaat gggtggagta tttacggtaa actgcccact tggcagtaca   480
tcaagtgtat catatgccaa gtacgccccc tattgacgtc aatgacggta atggcccgc    540
ctggcattat gcccagtaca tgaccttatg ggactttcct acttggcagt acatctacgt   600
attagtcatc gctattacca tggtgatgcg gttttggcag tacatcaatg ggcgtggata   660
gcggtttgac tcacggggat ttccaagtct ccaccccatt gacgtcaatg ggagtttgtt   720
ttggcaccaa aatcaacggg actttccaaa atgtcgtaac aactccgccc cattgacgca   780
aatgggcggt aggcgtgtac ggtgggaggt ctatataagc agagctcgtt tagtgaaccg   840
tcagatcgcc tggagacgcc atccacgctg ttttgacctc catagaagac accgggaccg   900
atccagcctg aattctgcag tcgacggtac cgcgggcccg ggatccaccg gtcgccacca   960
tggtgagcaa gggcgaggag ctgttcaccg gggtggtgcc catcctggtc gagctggacg  1020
gcgacgtaaa cggccacaag ttcagcgtgt ccggcgaggg cgagggcgat gccacctacg  1080
gcaagctgac cctgaagttc atctgcacca ccggcaagct gcccgtgccc tggcccaccc  1140
tcgtgaccac cctgacctac ggcgtgcagt gcttcagccg ctaccccgac cacatgaagc  1200
agcacgactt cttcaagtcc gccatgcccg aaggctacgt ccaggagcgc accatcttct  1260
tcaaggacga cggcaactac aagacccgcg ccgaggtgaa gttcgagggc gacaccctgg  1320
tgaaccgcat cgagctgaag ggcatcgact tcaaggagga cggcaacatc ctggggcaca  1380
agctggagta caactacaac agccacaacg tctatatcat ggccgacaag cagaagaacg  1440
gcatcaaggt gaacttcaag atccgccaca acatcgagga cggcagcgtg cagctcgccg  1500
accactacca gcagaacacc cccatcggcg acggccccgt gctgctgccc gacaaccact  1560
acctgagcac ccagtccgcc ctgagcaaag accccaacga aagcgcgat cacatggtcc  1620
tgctggagtt cgtgaccgcc gccgggatca ctctcggcat ggacgagctg tacaagtaaa  1680
gcggccgcga ctctagagtc gacctgcagg gaagaccaag ctgacctgac tcgatgcttt  1740
atttgtgaaa tttgtgatgc tattgcttta tttgtaacca ttataagctg caataaacaa  1800
gttaacaaca acaattgcat tcattttatg tttcaggttc agggggaggt gtgggaggtt  1860
ttttaaacta gtccactccc tctctgcgcg ctcgctcgct cactgaggcc gggcgaccaa  1920
aggtcgcccg acgcccgggc tttgcccggg cggcctcagt gagcgagcga gcgcgcagag  1980
agggacagat ccgggcccgc atgcgtcgac aattcactgg ccgtcgtttt acaacgtcgt  2040
```

```
gactgggaaa accctggcgt tacccaactt aatcgccttg cagcacatcc ccctttcgcc    2100
agctggcgta atagcgaaga gcccgcacc gatcgccctt cccaacagtt gcgcagcctg     2160
aatggcgaat ggcgcctgat gcggtatttt ctccttacgc atctgtgcgg tatttcacac    2220
cgcatatggt gcactctcag tacaatctgc tctgatgccg catagttaag ccagccccga    2280
cacccgccaa cacccgctga cgcgccctga cgggcttgtc tgctcccggc atccgcttac    2340
agacaagctg tgaccgtctc cgggagctgc atgtgtcaga ggttttcacc gtcatcaccg    2400
aaacgcgcga gacgaaaggg cctcgtgata cgcctatttt tataggttaa tgtcatgata    2460
ataatggttt cttagacgtc aggtggcact tttcggggaa atgtgcgcgg aaccctatt     2520
tgtttatttt tctaaataca ttcaaatatg tatccgctca tgagacaata accctgataa    2580
atgcttcaat aatattgaaa aaggaagagt atgagtattc aacatttccg tgtcgccctt    2640
attcccttt ttgcggcatt ttgccttcct gttttgctc acccagaaac gctggtgaaa      2700
gtaaaagatg ctgaagatca gttgggtgca cgagtgggtt acatcgaact ggatctcaac    2760
agcggtaaga tccttgagag ttttcgcccc gaagaacgtt ttccaatgat gagcactttt    2820
aaagttctgc tatgtggcgc ggtattatcc cgtattgacg ccgggcaaga gcaactcggt    2880
cgccgcatac actattctca gaatgacttg gttgagtact caccagtcac agaaaagcat    2940
cttacggatg gcatgacagt aagagaatta tgcagtgctg ccataaccat gagtgataac    3000
actgcggcca acttacttct gacaacgatc ggaggaccga aggagctaac cgcttttttg    3060
cacaacatgg gggatcatgt aactcgcctt gatcgttggg aaccggagct gaatgaagcc    3120
ataccaaacg acgagcgtga caccacgatg cctgtagcaa tggcaacaac gttgcgcaaa    3180
ctattaactg gcgaactact tactctagct tcccggcaac aattaataga ctggatggag    3240
gcggataaag ttgcaggacc acttctgcgc tcggcccttc cggctggctg gtttattgct    3300
gataaatctg gagccggtga gcgtgggtct cgcggtatca ttgcagcact ggggccagat    3360
ggtaagccct cccgtatcgt agttatctac acgacgggga gtcaggcaac tatggatgaa    3420
cgaaatagac agatcgctga gataggtgcc tcactgatta agcattggta actgtcagac    3480
caagtttact catatatact ttagattgat ttaaaacttc atttttaatt taaaaggatc    3540
taggtgaaga tcctttttga atctcatg accaaaatcc cttaacgtga gttttcgttc      3600
cactgagcgt cagaccccgt agaaaagatc aaaggatctt cttgagatcc ttttttctg     3660
cgcgtaatct gctgcttgca acaaaaaaa ccaccgctac cagcggtggt ttgtttgccg     3720
gatcaagagc taccaactct ttttccgaag gtaactggct tcagcagagc gcagatacca    3780
aatactgttc ttctagtgta gccgtagtta ggccaccact tcaagaactc tgtagcaccg    3840
cctacatacc tcgctctgct aatcctgtta ccagtggctg ctgccagtgg cgataagtcg    3900
tgtcttaccg ggttggactc aagacgatag ttaccggata aggcgcagcg gtcgggctga    3960
acggggggtt cgtgcacaca gcccagcttg gagcgaacga cctacaccga actgagatac    4020
ctacagcgtg agctatgaga aagcgccacg cttcccgaag ggagaaaggc ggacaggtat    4080
ccggtaagcg gcagggtcgg aacaggagag cgcacgaggg agcttccagg gggaaacgcc    4140
tggtatcttt atagtcctgt cgggtttcgc cacctctgac ttgagcgtcg atttttgtga    4200
tgctcgtcag ggggggcggag cctatggaaa aacgccagca acgcggcctt tttacggttc    4260
ctggcctttt gctggccttt tgctcacatg ttctttcctg cgttatcccc tgattctgtg    4320
gataaccgta ttaccgcctt tgagtgagct gataccgctc gccgcagccg aacgaccgag    4380
cgcagcgagt cagtgagcga ggaagcggaa gagcgcccaa tacgcaaacc gcctctcccc    4440
```

```
gcgcgttggc cgattcatta atgcagctgg cacgacaggt ttcccgactg gaaagcgggc    4500
agtgagcgca acgcaattaa tgtgagttag ctcactcatt aggcacccca ggctttacac    4560
tttatgcttc cggctcgtat gttgtgtgga attgtgagcg gataacaatt tcacacagga    4620
aacagctatg accatgatta cgccaagctc tcgagatcta g                       4661

<210> SEQ ID NO 39
<211> LENGTH: 7390
<212> TYPE: DNA
<213> ORGANISM: Adenovirus

<400> SEQUENCE: 39
atgccggggt tttacgagat tgtgattaag gtccccagcg accttgacgg gcatctgccc      60
ggcatttctg acagctttgt gaactgggtg gccgagaagg aatgggagtt gccgccagat     120
tctgacatgg atctgaatct gattgagcag gcaccctga ccgtggccga aagctgcag      180 cgcgactttc tgacggaatg gcgccgtgtg agtaaggccc cggaggccct tttctttgtg     240
caatttgaga agggagagag ctacttccac atgcacgtgc tcgtggaaac caccggggtg     300
aaatccatgt ttttgggacg tttcctgagt cagattcgcg aaaaactgat tcagagaatt     360
taccgcggga tcgagccgac tttgccaaac tggttcgcgg tcacaaagac cagaaatggc     420 gccgaggcg ggaacaaggt ggtggatgag tgctacatcc ccaattactt gctccccaaa     480
acccagcctg agctccagtg ggcgtggact aatatggaac agtatttaag cgcctgtttg     540
aatctcacgg agcgtaaacg gttggtggcg cagcatctga cgcacgtgtc gcagacgcag     600
gagcagaaca aagagaatca gaatcccaat tctgatgcgc cggtgatcag atcaaaaact     660
tcagccaggt acatggagct ggtcgggtgg ctcgtggaca agggattac ctcggagaag      720 cagtggatcc aggaggacca ggcctcatac atctccttca tgcggcctc caactcgcgg     780 tcccaaatca aggtgccttg gacaatgcgg gaaagattat gagcctgact aaaaccgccc     840
ccgactacct ggtgggccag cagcccgtgg aggacatttc cagcaatcgg atttataaaa     900
ttttggaact aaacgggtac gatccccaat atgcggcttc cgtctttctg ggatgggcca     960
cgaaaaagtt cggcaagagg aacaccatct ggctgtttgg gcctgcaact accgggaaga    1020
ccaacatcgc ggaggccata gcccacactg tgcccttcta cgggtgcgta aactggacca    1080
atgagaactt tccttcaac gactgtgtcg acaagatggt gatctggtgg gaggagggga     1140
agatgaccgc caaggtcgtg gagtcggcca agccattct cggaggaagc aaggtgcgcg    1200
tggaccagaa atgcaagtcc tcggcccaga tagacccgac tcccgtgatc gtcacctcca    1260
acaccaacat gtgcgccgtg attgacggga actcaacgac cttcgaacac cagcagccgt    1320
tgcaagaccg gatgttcaaa tttgaactca cccgccgtct ggatcatgac tttgggaagg    1380
tcaccaagca ggaagtcaaa gactttttcc ggtgggcaaa ggatcacgtg ttgaggtgg     1440 agcatgaatt ctacgtcaaa aagggtggag ccaagaaaag acccgccccc agtgacgcag    1500
atataagtga gcccaaacgg gtgcgcgagt cagttgcgca gccatcgacg tcagacgcgg    1560
aagcttcgat caactacgcg gacaggtacc aaaacaaatg ttctcgtcac gtgggcatga    1620
atctgatgct gtttccctgc agacaatgcg agagactgaa tcagaattca aatatctgct    1680
tcactcacgg tgtcaaagac tgtttagagt gctttcccgt gtcagaatct caacccgttt    1740
ctgtcgtcaa aaaggcgtat cagaaactgt gctacattca tcacatcatg gaaaggtgc    1800 cagacgcttg cactgcttgc gacctggtca atgtggactt ggatgactgt gtttctgaac    1860
```

-continued

```
aataaatgac ttaaaccagg tatggctgcc gatggttatc ttccagattg gctcgaggac    1920
aaccttagtg aaggaattcg cgagtggtgg gctttgaaac ctggagcccc tcaacccaag    1980
gcaaatcaac aacatcaaga caacgctcga ggtcttgtgc ttccgggtta caaataccct    2040
ggacccggca acggactcga caaggggag ccggtcaacg cagcagacgc ggcggccctc     2100
gagcacgaca aggcctacga ccagcagctc aaggcggag acaacccgta cctcaagtac     2160
aaccacgccg acgccgagtt ccaggagcgg ctcaaagaag atacgtcttt tgggggcaac    2220
ctcgggcgag cagtcttcca ggccaaaaag aggcttcttg aacctcttgg tctggttgag    2280
gaagcggcta agacggctcc tggaaagaag aggcctgtag agcagtctcc tcaggaaccg    2340
gactcctccg cgggtattgg caaatcgggt gcacagcccg ctaaaaagag actcaatttc    2400
ggtcagactg cgacacagag gtcagtccca gaccctcaac caatcggaga acctcccgca    2460 gcccctcag gtgtgggatc tcttacaatg gcttcaggtg gtggcgcacc agtggcagac     2520
aataacgaag gtgccgatgg agtgggtagt tcctcgggaa attggcattg cgattcccaa    2580
tggctggggg acagagtcat caccaccagc acccgaacct gggccctgcc cacctacaac    2640
aatcacctct acaagcaaat ctccaacagc acatctggag gatcttcaaa tgacaacgcc    2700
tacttcggct acagcacccc ctgggggtat tttgacttca acagattcca ctgccacttc    2760
tcaccacgtg actggcagcg actcatcaac aacaactggg gattccggcc taagcgactc    2820
aacttcaagc tcttcaacat tcaggtcaaa gaggttacgg acaacaatgg agtcaagacc    2880
atcgccaata accttaccag cacggtccag gtcttcacgg actcagacta tcagctcccg    2940
tacgtgctcg gtcggctca cgagggctgc ctcccgccgt tcccagcgga cgttttcatg     3000
attcctcagt acgggtatct gacgcttaat gatggaagcc aggccgtggg tcgttcgtcc    3060
ttttactgcc tggaatattt cccgtcgcaa atgctaagaa cgggtaacaa cttccagttc    3120
agctacgagt ttgagaacgt acctttccat agcagctacg ctcacagcca aagcctggac    3180
cgactaatga atccactcat cgaccaatac ttgtactatc tctcaaagac tattaacggt    3240
tctggacaga atcaacaaac gctaaaattc agtgtggccg gacccagcaa catggctgtc    3300
cagggaagaa actacatacc tggacccagc taccgacaac aacgtgtctc aaccactgtg    3360
actcaaaaca caacagcga atttgcttgg cctggagctt cttcttgggc tctcaatgga    3420
cgtaatagct tgatgaatcc tggacctgct atggccagcc acaaagaagg agaggaccgt    3480
ttctttcctt tgtctggatc tttaattttt ggcaaacaag gaactggaag agacaacgtg    3540
gatgcggaca aagtcatgat aaccaacgaa gaagaaatta aaactactaa cccggtagca    3600
acggagtcct atggacaagt ggccacaaac caccagagtg cccaagcaca ggcgcagacc    3660
ggctgggttc aaaaccaagg aatacttccg ggtatggttt ggcaggacag agatgtgtac    3720
ctgcaaggac ccatttgggc caaaattcct cacacggacg gcaactttca cccttctccg    3780
ctgatgggag ggtttggaat gaagcaccg cctcctcaga tcctcatcaa aaacacacct    3840
gtacctgcgg atcctccaac ggccttcaac aaggacaagc tgaactcttt catcacccag    3900
tattctactg gccaagtcag cgtggagatc gagtgggagc tgcagaagga aaacagcaag    3960
cgctggaacc cggagatcca gtacacttcc aactattaca agtctaataa tgttgaattt    4020
gctgttaata ctgaaggtgt atatagtgaa ccccgcccca ttggcaccag atacctgact    4080
cgtaatctgt aattgcttgt taatcaataa accgttaat tcgtttcagt tgaactttgg    4140
tctctgcgaa gggcgaattc gtttaaacct gcaggactag aggtcctgta ttagaggtca    4200
cgtgagtgtt ttgcgacatt ttgcgacacc atgtggtcac gctgggtatt taagcccgag    4260
```

```
tgagcacgca gggtctccat tttgaagcgg gaggtttgaa cgcgcagccg ccaagccgaa    4320
ttctgcagat atccatcaca ctggcggccg ctcgactaga gcggccgcca ccgcggtgga    4380
gctccagctt ttgttccctt tagtgagggt taattgcgcg cttggcgtaa tcatggtcat    4440
agctgtttcc tgtgtgaaat tgttatccgc tcacaattcc acacaacata cgagccggaa    4500
gcataaagtg taaagcctgg ggtgcctaat gagtgagcta actcacatta attgcgttgc    4560
gctcactgcc cgctttccag tcgggaaacc tgtcgtgcca gctgcattaa tgaatcggcc    4620
aacgcgcggg gagaggcggt ttgcgtattg ggcgctcttc cgcttcctcg ctcactgact    4680
cgctgcgctc ggtcgttcgg ctgcggcgag cggtatcagc tcactcaaag gcggtaatac    4740
ggttatccac agaatcaggg gataacgcag gaaagaacat gtgagcaaaa ggccagcaaa    4800
aggccaggaa ccgtaaaaag gccgcgttgc tggcgttttt ccataggctc cgcccccctg    4860
acgagcatca caaaaatcga cgctcaagtc agaggtggcg aaacccgaca ggactataaa    4920
gataccaggc gtttccccct ggaagctccc tcgtgcgctc tcctgttccg accctgccgc    4980
ttaccggata cctgtccgcc tttctccctt cgggaagcgt ggcgctttct catagctcac    5040
gctgtaggta tctcagttcg gtgtaggtcg ttcgctccaa gctgggctgt gtgcacgaac    5100
cccccgttca gcccgaccgc tgcgccttat ccggtaacta tcgtcttgag tccaacccgg    5160
taagacacga cttatcgcca ctggcagcag ccactggtaa caggattagc agagcgaggt    5220
atgtaggcgg tgctacagag ttcttgaagt ggtggcctaa ctacggctac actagaagga    5280
cagtatttgg tatctgcgct ctgctgaagc cagttacctt cggaaaaaga gttggtagct    5340
cttgatccgg caaacaaacc accgctggta gcggtggttt ttttgtttgc aagcagcaga    5400
ttacgcgcag aaaaaaagga tctcaagaag atcctttgat cttttctacg ggtctgacg    5460 ctcagtggaa cgaaaactca cgttaaggga ttttggtcat gagattatca aaaaggatct    5520
tcacctagat ccttttaaat taaaaatgaa gttttaaatc aatctaaagt atatatgagt    5580
aaacttggtc tgacagttac caatgcttaa tcagtgaggc acctatctca gcgatctgtc    5640
tatttcgttc atccatagtt gcctgactcc ccgtcgtgta gataactacg atacgggagg    5700
gcttaccatc tggccccagt gctgcaatga taccgcgaga cccacgctca ccggctccag    5760
atttatcagc aataaaccag ccagccggaa gggccgagcg cagaagtggt cctgcaactt    5820
tatccgcctc catccagtct attaattgtt gccgggaagc tagagtaagt agttcgccag    5880
ttaatagttt gcgcaacgtt gttgccattg ctacaggcat cgtggtgtca cgctcgtcgt    5940
ttggtatggc ttcattcagc tccggttccc aacgatcaag gcgagttaca tgatccccca    6000
tgttgtgcaa aaaagcggtt agctccttcg gtcctccgat cgttgtcaga agtaagttgg    6060
ccgcagtgtt atcactcatg gttatggcag cactgcataa ttctcttact gtcatgccat    6120
ccgtaagatg cttttctgtga ctggtgagta ctcaaccaag tcattctgag aatagtgtat    6180
gcggcgaccg agttgctctt gcccggcgtc aatacgggat aataccgcgc cacatagcag    6240
aactttaaaa gtgctcatca ttggaaaacg ttcttcgggg cgaaaactct caaggatctt    6300
accgctgttg agatccagtt cgatgtaacc cactcgtgca cccaactgat cttcagcatc    6360
ttttactttc accagcgttt ctgggtgagc aaaaacagga aggcaaaatg ccgcaaaaaa    6420
gggaataagg gcgacacgga aatgttgaat actcatactc ttcctttttc aatattattg    6480
aagcatttat cagggttatt gtctcatgag cggatacata tttgaatgta tttagaaaaa    6540
taaacaaata ggggttccgc gcacatttcc ccgaaaagtg ccacctaaat tgtaagcgtt    6600
```

```
aatattttgt taaaattcgc gttaaatttt tgttaaatca gctcattttt taaccaatag    6660
gccgaaatcg gcaaaatccc ttataaatca aaagaataga ccgagatagg gttgagtgtt    6720
gttccagttt ggaacaagag tccactatta agaacgtgg  actccaacgt caaagggcga    6780
aaaaccgtct atcagggcga tggcccacta cgtgaaccat caccctaatc aagttttttg    6840
gggtcgaggt gccgtaaagc actaaatcgg aaccctaaag ggagccccg  atttagagct    6900 tgacggggaa agccggcgaa cgtggcgaga aggaaggga  agaaagcgaa aggagcgggc    6960
gctagggcgc tggcaagtgt agcggtcacg ctgcgcgtaa ccaccacacc cgccgcgctt    7020
aatgcgccgc tacagggcgc gtcccattcg ccattcaggc tgcgcaactg ttgggaaggg    7080
cgatcggtgc gggcctcttc gctattacgc cagctggcga aggggggatg tgctgcaagg    7140
cgattaagtt gggtaacgcc agggttttcc cagtcacgac gttgtaaaac gacgccagt     7200 gagcgcgcgt aatacgactc actatagggc gaattgggta ccgggccccc cctcgatcga    7260
ggtcgacggt atcggggag  ctcggatcca ctagtaacgg ccgccagtgt gctggattcg    7320
gctttattta agcccgagtg agcacgcagg gtctccattt tgaagcggga ggtttgaacg    7380
cgcagccgcc                                                           7390

<210> SEQ ID NO 40
<211> LENGTH: 479
<212> TYPE: DNA
<213> ORGANISM: artificial sequence
<220> FEATURE:
<223> OTHER INFORMATION: RAN-G4C2x38 sense-repeats

<400> SEQUENCE: 40
cttatcgaaa ttaatacgac tcactatagg gagacccaag ctggctagtt aagcttggta      60
ccgagctcgg atccactagt ccagtgtggt ggaattgggg cccggggccg gggccggggc     120
cggggccggg gccggggccg gggccgggc  cggggccggg gccggggccg gggccggggc     180
cggggccggg gccggggccg gggccgggc  cggggccggg gccggggccg gggccggggc     240
cggggccggg gccggggccg gggccgggc  cggggccggg gccggggccg gggccggggc     300
cggggccggg gccggggccg gggccgggc  cgggaattc  tgcagatatc cagcacagtg     360
gcggccgctc gagtctagag ggcccttcga acaaaaactc atctcagaag aggatctgaa     420
tatgcatacc ggtcatcatc accatcacca ttgagtttaa acccgctgat cagcctcga     479

<210> SEQ ID NO 41
<211> LENGTH: 478
<212> TYPE: DNA
<213> ORGANISM: artificial sequence
<220> FEATURE:
<223> OTHER INFORMATION: RAN-C4G2x39 antisense-repeats:

<400> SEQUENCE: 41
cttatcgaaa ttaatacgac tcactatagg gagacccaag ctggctagtt aagcttggta      60
ccgagctcgg atccactagt ccagtgtggt ggaattcccc ggccccggcc ccggccccgg     120
ccccggcccc ggccccggcc ccggccccgg ccccggcccc ggccccggcc ccggccccgg     180
ccccggcccc ggccccggcc ccggccccgg ccccggcccc ggccccggcc ccggccccgg     240
ccccggcccc ggccccggcc ccggccccgg ccccggcccc ggccccggcc ccggccccgg     300
ccccggcccc ggccccggcc ccggccccgg ccccaattct gcagatatcc agcacagtgg     360
cggccgctcg agtctagagg gcccttcgaa caaaaactca tctcagaaga ggatctgaat     420
atgcataccg gtcatcatca ccatcaccat tgagtttaaa cccgctgatc agcctcga      478
```

-continued

<210> SEQ ID NO 42
<211> LENGTH: 285
<212> TYPE: DNA
<213> ORGANISM: artificial sequence
<220> FEATURE:
<223> OTHER INFORMATION: poly-Gly-Pro x36 DPRs independent of G4C2
      repeats

<400> SEQUENCE: 42

```
atgggcaaac cgattccgaa cccgctgctg ggcctggata gcaccctcga gaatgatccc      60
accatgggcc ctggccctgg accaggacct ggccccggac ccgtccagg  tcccggccca    120
ggccccggtc ccggccctgg accaggccca ggaccaggac caggcccagg tcccggacca    180
ggacccggac ctggcccagg ccctggcccc ggccctggcc ccggaccagg ccctggaccc    240
ggccctggtc ccggcccagg acccggacca ggacctggcc cttaa                    285
```

<210> SEQ ID NO 43
<211> LENGTH: 285
<212> TYPE: DNA
<213> ORGANISM: artificial sequence
<220> FEATURE:
<223> OTHER INFORMATION: poly-Gly-Ala x36 DPRs independent of G4C2
      repeats

<400> SEQUENCE: 43

```
atgggcaaac cgattccgaa cccgctgctg ggcctggata gcaccctcga gaatgatccc      60
accatgggag ctggtgctgg tgcaggcgct ggcgcagggg caggcgctgg tgctgggggct   120
ggtgccgggg ctggggcagg cgcaggggct ggtgccggtg caggcgcagg ggctggggct   180
ggcgctggtg ccggcgcagg cgcgggtgcc ggcgcagggg ctggtgcagg gccggtgct    240
ggcgcgggtg caggggccgg tgcaggggca ggcgcaggcg cttaa                    285
```

<210> SEQ ID NO 44
<211> LENGTH: 634
<212> TYPE: DNA
<213> ORGANISM: artificial sequence
<220> FEATURE:
<223> OTHER INFORMATION: RAN-G4C2x38 sense-repeats with 3x V5 tags

<400> SEQUENCE: 44

```
cttatcgaaa ttaatacgac tcactatagg gagacccaag ctggctagtt aagcttggta      60
ccgagctcgg atccactagt ccagtgtggt ggaattgggg ccggggccg  gggccggggc    120
cggggccggg gccggggccg gggccggggc cggggccggg gccggggccg gggccggggc    180
cggggccggg gccggggccg gggccggggc cggggccggg gccggggccg gggccggggc    240
cggggccggg gccggggccg gggccggggc cggggccggg gccggggccg gggccggggc    300
cggggccggg gccggggccg gggccggggc cgggaattc tgcagatatc cagcacagtg    360
gcggccgctg gcaagcccca tccccaaccc cctgctcggt ctggacagca ccggctaacg    420
gcaagcccat ccccaacccc ctgctcggtc tggacagcac cggctaacgg caagcccatc    480
cccaaccccc tgctcggtct ggacagcacc ggctaactcg agtctagatc tagagggccc    540
ttcgaacaaa aactcatctc agaagaggat ctgaatatgc ataccggtca tcatcaccat    600
caccattgag tttaaacccg ctgatcagcc tcga                                634
```

<210> SEQ ID NO 45
<211> LENGTH: 21
<212> TYPE: DNA

```
<213> ORGANISM: artificial sequence
<220> FEATURE:
<223> OTHER INFORMATION: inhibitory RNA

<400> SEQUENCE: 45
ttctgggccc atcaacttta a                                              21

<210> SEQ ID NO 46
<211> LENGTH: 21
<212> TYPE: DNA
<213> ORGANISM: artificial sequence
<220> FEATURE:
<223> OTHER INFORMATION: inhibitory RNA

<400> SEQUENCE: 46
agcacttgga gtcataccat t                                              21

<210> SEQ ID NO 47
<211> LENGTH: 21
<212> TYPE: DNA
<213> ORGANISM: artificial sequence
<220> FEATURE:
<223> OTHER INFORMATION: inhibitory RNA

<400> SEQUENCE: 47
gggatcgaat cgctgtttcc t                                              21

<210> SEQ ID NO 48
<211> LENGTH: 21
<212> TYPE: DNA
<213> ORGANISM: artificial sequence
<220> FEATURE:
<223> OTHER INFORMATION: inhibitory RNA

<400> SEQUENCE: 48
gctgtttcct tccgcttctc t                                              21

<210> SEQ ID NO 49
<211> LENGTH: 21
<212> TYPE: DNA
<213> ORGANISM: artificial sequence
<220> FEATURE:
<223> OTHER INFORMATION: inhibitory RNA

<400> SEQUENCE: 49
gggcccagaa gtccaagtta t                                              21

<210> SEQ ID NO 50
<211> LENGTH: 21
<212> TYPE: DNA
<213> ORGANISM: artificial sequence
<220> FEATURE:
<223> OTHER INFORMATION: inhibitory RNA

<400> SEQUENCE: 50
gctgatgttt accgagatgg c                                              21

<210> SEQ ID NO 51
<211> LENGTH: 21
<212> TYPE: DNA
<213> ORGANISM: artificial sequence
<220> FEATURE:
<223> OTHER INFORMATION: inhibitory RNA

<400> SEQUENCE: 51
aatgtctatt ctgctctggt t                                              21
```

<210> SEQ ID NO 52
<211> LENGTH: 21
<212> TYPE: DNA
<213> ORGANISM: artificial sequence
<220> FEATURE:
<223> OTHER INFORMATION: inhibitory RNA

<400> SEQUENCE: 52
aaattgcaga tgggagcaat a                                            21

<210> SEQ ID NO 53
<211> LENGTH: 21
<212> TYPE: DNA
<213> ORGANISM: artificial sequence
<220> FEATURE:
<223> OTHER INFORMATION: inhibitory RNA

<400> SEQUENCE: 53
ttgcagatgg gagcaatagt t                                            21

<210> SEQ ID NO 54
<211> LENGTH: 21
<212> TYPE: DNA
<213> ORGANISM: artificial sequence
<220> FEATURE:
<223> OTHER INFORMATION: inhibitory RNA

<400> SEQUENCE: 54
tgggagcaat agtttaggtt t                                            21

<210> SEQ ID NO 55
<211> LENGTH: 21
<212> TYPE: DNA
<213> ORGANISM: artificial sequence
<220> FEATURE:
<223> OTHER INFORMATION: inhibitory RNA

<400> SEQUENCE: 55
ttaggtttag gtgggtagta a                                            21

<210> SEQ ID NO 56
<211> LENGTH: 21
<212> TYPE: DNA
<213> ORGANISM: artificial sequence
<220> FEATURE:
<223> OTHER INFORMATION: inhibitory RNA

<400> SEQUENCE: 56
taggtttagg tgggtagtaa t                                            21

<210> SEQ ID NO 57
<211> LENGTH: 359
<212> TYPE: DNA
<213> ORGANISM: artificial sequence
<220> FEATURE:
<223> OTHER INFORMATION: inverted repeat sequence

<400> SEQUENCE: 57
atgccgacga tgcggtgaag gcgcgcgacg gctacgacta cgatgggtat cgtctgcgcg    60
tggagttccc gcggggcggt ggtcctggaa gctaccgcgg cggcaaccgc aatgaccgaa   120
gccgcgacgg tggggacgg atgggcggac gcggaccgcc agccaagcgc tcgcagtacc   180
gcgtcatggt tactggactg cccgcctccg gatcgtggca agatctcaag gatcacatgc   240

```
gcgaggccgg cgacgtctgc ttcgcggaca cttacaagga tggttccggc gtcgttgagt    300
tcctgcgcca cgaggacatg aagtacgcaa tcaaaaaatt ggacgactct cgcttccga     359
```

<210> SEQ ID NO 58
<211> LENGTH: 381
<212> TYPE: DNA
<213> ORGANISM: artificial sequence
<220> FEATURE:
<223> OTHER INFORMATION: FlyBase ID = FBst0450381

<400> SEQUENCE: 58

```
ggtccgataa agaaggcggc agtgcactac gatcgctccg gtcgctcgtt gggcaccgct    60
gacgtgattt tcgaacgtcg cgccgacgcc ttgaaggcca ttaaacagta ccatggcgta    120
cctttggacg gacgccctat gaccattcag ctggccgtct cagacgtggc cgtgttgacc    180
cgtcccgtag ccgccaccga tgtcaagcgt cgcgtgggtg gtactgcacc aacttcattc    240
aagcgtggtg gtggccaagc tggtggcacg gcgcgtcgcg gcttcaaacg tccggtcggt    300
ggcaagccgg cggcaggcgg ccagcgacgg gagcgcaagg ccccgcccac tgctgaggag    360
ctggacgccg aactggactc a                                             381
```

<210> SEQ ID NO 59
<211> LENGTH: 324
<212> TYPE: DNA
<213> ORGANISM: artificial sequence
<220> FEATURE:
<223> OTHER INFORMATION: FlyBase ID = FBst0476329

<400> SEQUENCE: 59

```
gtcgaacttg ataaagcgca tttctaaata caataaatac agcatcaaat gtatttcagt    60
tatcttaaca tccgccgcat tggcaaaact aacaattaat ggataaatgc gcaagtggtt    120
gattgatttg atgtccgatg ctttcaaaga tctgctcctg ggcgcggcgt tgtcgatgcg    180
tttgcattta tgtaccatgc ggggggtgtc catatggtag gcttaaaact atagattggg    240
ctgctcttct attcttgtta gactaattca gactattcac tatttagatc ttcatgtcgt    300
tgatgtatga gtccagttcg gcgt                                          324
```

<210> SEQ ID NO 60
<211> LENGTH: 21
<212> TYPE: DNA
<213> ORGANISM: artificial sequence
<220> FEATURE:
<223> OTHER INFORMATION: inhibitory RNA

<400> SEQUENCE: 60

```
gcatctgaaa gataagcttc t                                             21
```

<210> SEQ ID NO 61
<211> LENGTH: 64
<212> TYPE: DNA
<213> ORGANISM: artificial sequence
<220> FEATURE:
<223> OTHER INFORMATION: human/mouse SRSF1 - miR1 -Top strand

<400> SEQUENCE: 61

```
tgctgttctg ggcccatcaa ctttaagttt tggccactga ctgacttaaa gtttgggccc    60
agaa                                                                64
```

<210> SEQ ID NO 62
<211> LENGTH: 64

```
<212> TYPE: DNA
<213> ORGANISM: artificial sequence
<220> FEATURE:
<223> OTHER INFORMATION: human/mouse/rat SRSF1 - miR1 - Bottom strand:

<400> SEQUENCE: 62
cctgttctgg gcccaaactt taagtcagtc agtggccaaa acttaaagtt gatgggccca    60
gaac                                                                 64

<210> SEQ ID NO 63
<211> LENGTH: 64
<212> TYPE: DNA
<213> ORGANISM: artificial sequence
<220> FEATURE:
<223> OTHER INFORMATION: human SRSF1 - miR2 - Top strand

<400> SEQUENCE: 63
tgctgagcac ttggagtcat accattgttt tggccactga ctgacaatgg tatctccaag    60
tgct                                                                 64

<210> SEQ ID NO 64
<211> LENGTH: 64
<212> TYPE: DNA
<213> ORGANISM: artificial sequence
<220> FEATURE:
<223> OTHER INFORMATION: human SRSF1 - miR2 - Bottom strand

<400> SEQUENCE: 64
cctgagcact tggagatacc attgtcagtc agtggccaaa acaatggtat gactccaagt    60
gctc                                                                 64

<210> SEQ ID NO 65
<211> LENGTH: 21
<212> TYPE: DNA
<213> ORGANISM: artificial sequence
<220> FEATURE:
<223> OTHER INFORMATION: Targeted mouse SRSF1 miR2 sequence

<400> SEQUENCE: 65
aatgtctatt ctgctctggt t                                              21

<210> SEQ ID NO 66
<211> LENGTH: 21
<212> TYPE: DNA
<213> ORGANISM: artificial sequence
<220> FEATURE:
<223> OTHER INFORMATION: Targeted mouse SRSF1 miR2 sequence

<400> SEQUENCE: 66
aatgtctatt ctgctctggt t                                              21

<210> SEQ ID NO 67
<211> LENGTH: 64
<212> TYPE: DNA
<213> ORGANISM: artificial sequence
<220> FEATURE:
<223> OTHER INFORMATION: mouse SRSF1 - miR2 - Top strand

<400> SEQUENCE: 67
tgctgaacca gagcagaata gacattgttt tggccactga ctgacaatgt ctactgctct    60
ggtt                                                                 64

<210> SEQ ID NO 68
```

<211> LENGTH: 64
<212> TYPE: DNA
<213> ORGANISM: artificial sequence
<220> FEATURE:
<223> OTHER INFORMATION: mouse SRSF1 - miR2 - Bottom strand

<400> SEQUENCE: 68
cctgaaccag agcagtagac attgtcagtc agtggccaaa acaatgtcta ttctgctctg    60
gttc    64

<210> SEQ ID NO 69
<211> LENGTH: 6
<212> TYPE: DNA
<213> ORGANISM: artificial sequence
<220> FEATURE:
<223> OTHER INFORMATION: hexanucleotide sense GGGGCCx38

<400> SEQUENCE: 69 ggggcc    6

<210> SEQ ID NO 70
<211> LENGTH: 6
<212> TYPE: DNA
<213> ORGANISM: artificial sequence
<220> FEATURE:
<223> OTHER INFORMATION: hexanucleotide antisense CCCCGGx39

<400> SEQUENCE: 70 ccccgg    6

<210> SEQ ID NO 71
<211> LENGTH: 12
<212> TYPE: DNA
<213> ORGANISM: artificial sequence
<220> FEATURE:
<223> OTHER INFORMATION: synthetic oligonucleotides

<400> SEQUENCE: 71
ccccggcccc gg    12

<210> SEQ ID NO 72
<211> LENGTH: 45
<212> TYPE: DNA
<213> ORGANISM: artificial sequence
<220> FEATURE:
<223> OTHER INFORMATION: primer

<400> SEQUENCE: 72
actctagagg taccacgtga tcattctcga gggtgctatc caggc    45

<210> SEQ ID NO 73
<211> LENGTH: 45
<212> TYPE: DNA
<213> ORGANISM: artificial sequence
<220> FEATURE:
<223> OTHER INFORMATION: primer

<400> SEQUENCE: 73
gcctggatag caccctcgag aatgatcacg tggtacctct agagt    45

<210> SEQ ID NO 74
<211> LENGTH: 20
<212> TYPE: DNA
<213> ORGANISM: artificial sequence
<220> FEATURE:
<223> OTHER INFORMATION: primer

```
<400> SEQUENCE: 74
taccgcgtca tggttactgg                                          20

<210> SEQ ID NO 75
<211> LENGTH: 20
<212> TYPE: DNA
<213> ORGANISM: artificial sequence
<220> FEATURE:
<223> OTHER INFORMATION: primer

<400> SEQUENCE: 75
gtacgcgaat gtaggcaacc                                          20

<210> SEQ ID NO 76
<211> LENGTH: 21
<212> TYPE: DNA
<213> ORGANISM: artificial sequence
<220> FEATURE:
<223> OTHER INFORMATION: primer

<400> SEQUENCE: 76
cgatatgtac gacggaccga a                                        21

<210> SEQ ID NO 77
<211> LENGTH: 21
<212> TYPE: DNA
<213> ORGANISM: artificial sequence
<220> FEATURE:
<223> OTHER INFORMATION: primer

<400> SEQUENCE: 77
cggaccaaag tcgttgaaga g                                        21

<210> SEQ ID NO 78
<211> LENGTH: 20
<212> TYPE: DNA
<213> ORGANISM: artificial sequence
<220> FEATURE:
<223> OTHER INFORMATION: inhibitory RNA

<400> SEQUENCE: 78
tgggcccgtc tggaccacaa                                          20

<210> SEQ ID NO 79
<211> LENGTH: 20
<212> TYPE: DNA
<213> ORGANISM: artificial sequence
<220> FEATURE:
<223> OTHER INFORMATION: primer

<400> SEQUENCE: 79
tcgccgtcac cggagtccat                                          20

<210> SEQ ID NO 80
<211> LENGTH: 22
<212> TYPE: DNA
<213> ORGANISM: artificial sequence
<220> FEATURE:
<223> OTHER INFORMATION: primer

<400> SEQUENCE: 80
ttccaaccta tggaactgat ga                                       22

<210> SEQ ID NO 81
```

<211> LENGTH: 23
<212> TYPE: DNA
<213> ORGANISM: artificial sequence
<220> FEATURE:
<223> OTHER INFORMATION: primer

<400> SEQUENCE: 81
ggttttcctc attaaaggca ttc                                    23

<210> SEQ ID NO 82
<211> LENGTH: 20
<212> TYPE: DNA
<213> ORGANISM: artificial sequence
<220> FEATURE:
<223> OTHER INFORMATION: primer

<400> SEQUENCE: 82
ccgcatctac gtgggtaact                                        20

<210> SEQ ID NO 83
<211> LENGTH: 20
<212> TYPE: DNA
<213> ORGANISM: artificial sequence
<220> FEATURE:
<223> OTHER INFORMATION: primer

<400> SEQUENCE: 83
tcgaactcaa cgaaggcgaa                                        20

<210> SEQ ID NO 84
<211> LENGTH: 20
<212> TYPE: DNA
<213> ORGANISM: artificial sequence
<220> FEATURE:
<223> OTHER INFORMATION: primer

<400> SEQUENCE: 84
tctggtcgca gcttaggaac                                        20

<210> SEQ ID NO 85
<211> LENGTH: 21
<212> TYPE: DNA
<213> ORGANISM: artificial sequence
<220> FEATURE:
<223> OTHER INFORMATION: primer

<400> SEQUENCE: 85
ccacctctgt ttacgctctg t                                      21

<210> SEQ ID NO 86
<211> LENGTH: 20
<212> TYPE: DNA
<213> ORGANISM: artificial sequence
<220> FEATURE:
<223> OTHER INFORMATION: primer

<400> SEQUENCE: 86
ccatgatcac gaaggtggtt                                        20

<210> SEQ ID NO 87
<211> LENGTH: 20
<212> TYPE: DNA
<213> ORGANISM: artificial sequence
<220> FEATURE:
<223> OTHER INFORMATION: primer

<400> SEQUENCE: 87

-continued

```
atgcagtcga gtttcccaca                                               20

<210> SEQ ID NO 88
<211> LENGTH: 31
<212> TYPE: DNA
<213> ORGANISM: artificial sequence
<220> FEATURE:
<223> OTHER INFORMATION: primer

<400> SEQUENCE: 88
cttgtgaaac aaaatgcttt ttaacatcca t                                  31

<210> SEQ ID NO 89
<211> LENGTH: 25
<212> TYPE: DNA
<213> ORGANISM: artificial sequence
<220> FEATURE:
<223> OTHER INFORMATION: primer

<400> SEQUENCE: 89
gaatgtgagc accttccttc ttttt                                         25

<210> SEQ ID NO 90
<211> LENGTH: 20
<212> TYPE: DNA
<213> ORGANISM: artificial sequence
<220> FEATURE:
<223> OTHER INFORMATION: primer

<400> SEQUENCE: 90
gaactgcaca bccagaacac                                               20

<210> SEQ ID NO 91
<211> LENGTH: 19
<212> TYPE: DNA
<213> ORGANISM: artificial sequence
<220> FEATURE:
<223> OTHER INFORMATION: primer

<400> SEQUENCE: 91
tgggttgaag ttgctgagg                                                19

<210> SEQ ID NO 92
<211> LENGTH: 20
<212> TYPE: DNA
<213> ORGANISM: artificial sequence
<220> FEATURE:
<223> OTHER INFORMATION: primer

<400> SEQUENCE: 92
gggcccttcg aaccccgtc                                                20

<210> SEQ ID NO 93
<211> LENGTH: 20
<212> TYPE: DNA
<213> ORGANISM: artificial sequence
<220> FEATURE:
<223> OTHER INFORMATION: primer

<400> SEQUENCE: 93
gggaggggca aacaacagat                                               20

<210> SEQ ID NO 94
<211> LENGTH: 20
<212> TYPE: DNA
```

```
<213> ORGANISM: artificial sequence
<220> FEATURE:
<223> OTHER INFORMATION: primer

<400> SEQUENCE: 94
tcaaacagcg acaagttccg                                               20

<210> SEQ ID NO 95
<211> LENGTH: 20
<212> TYPE: DNA
<213> ORGANISM: artificial sequence
<220> FEATURE:
<223> OTHER INFORMATION: primer

<400> SEQUENCE: 95
gtcgacatga ctgcattcca                                               20

<210> SEQ ID NO 96
<211> LENGTH: 20
<212> TYPE: DNA
<213> ORGANISM: artificial sequence
<220> FEATURE:
<223> OTHER INFORMATION: primer

<400> SEQUENCE: 96
ggagagaggg tgggaaaaac                                               20

<210> SEQ ID NO 97
<211> LENGTH: 21
<212> TYPE: DNA
<213> ORGANISM: artificial sequence
<220> FEATURE:
<223> OTHER INFORMATION: inhibitory RNA

<400> SEQUENCE: 97
gcatctacgt gggtaactta c                                             21

<210> SEQ ID NO 98
<211> LENGTH: 21
<212> TYPE: DNA
<213> ORGANISM: artificial sequence
<220> FEATURE:
<223> OTHER INFORMATION: inhibitory RNA

<400> SEQUENCE: 98
ggaacaacga ttgccgcatc t                                             21

<210> SEQ ID NO 99
<211> LENGTH: 21
<212> TYPE: DNA
<213> ORGANISM: artificial sequence
<220> FEATURE:
<223> OTHER INFORMATION: inhibitory RNA

<400> SEQUENCE: 99
ggagtttgta cggaaagaag a                                             21

<210> SEQ ID NO 100
<211> LENGTH: 21
<212> TYPE: DNA
<213> ORGANISM: artificial sequence
<220> FEATURE:
<223> OTHER INFORMATION: inhibitory RNA

<400> SEQUENCE: 100
ggaagttggc aggatttaaa g                                             21
```

```
<210> SEQ ID NO 101
<211> LENGTH: 21
<212> TYPE: DNA
<213> ORGANISM: artificial sequence
<220> FEATURE:
<223> OTHER INFORMATION: inhibitory RNA

<400> SEQUENCE: 101
ggtaggttat acacgtattc t                                              21

<210> SEQ ID NO 102
<211> LENGTH: 21
<212> TYPE: DNA
<213> ORGANISM: artificial sequence
<220> FEATURE:
<223> OTHER INFORMATION: inhibitory RNA

<400> SEQUENCE: 102
gcaggtgatg tatgttatgc t                                              21

<210> SEQ ID NO 103
<211> LENGTH: 21
<212> TYPE: DNA
<213> ORGANISM: artificial sequence
<220> FEATURE:
<223> OTHER INFORMATION: inhibitory RNA

<400> SEQUENCE: 103
gctgatgttt accgagatgg c                                              21

<210> SEQ ID NO 104
<211> LENGTH: 21
<212> TYPE: DNA
<213> ORGANISM: artificial sequence
<220> FEATURE:
<223> OTHER INFORMATION: inhibitory RNA

<400> SEQUENCE: 104
gaagttggca ggatttaaag g                                              21

<210> SEQ ID NO 105
<211> LENGTH: 21
<212> TYPE: DNA
<213> ORGANISM: artificial sequence
<220> FEATURE:
<223> OTHER INFORMATION: inhibitory RNA

<400> SEQUENCE: 105
gaaagaagat atgacctatg c                                              21

<210> SEQ ID NO 106
<211> LENGTH: 21
<212> TYPE: DNA
<213> ORGANISM: artificial sequence
<220> FEATURE:
<223> OTHER INFORMATION: inhibitory RNA

<400> SEQUENCE: 106
gcgtgaagca ggtgatgtat g                                              21

<210> SEQ ID NO 107
<211> LENGTH: 21
<212> TYPE: DNA
<213> ORGANISM: artificial sequence
<220> FEATURE:
```

<223> OTHER INFORMATION: inhibitory RNA

<400> SEQUENCE: 107
gtaagttacc cacgtagatg c                                           21

<210> SEQ ID NO 108
<211> LENGTH: 7
<212> TYPE: DNA
<213> ORGANISM: artificial sequence
<220> FEATURE:
<223> OTHER INFORMATION: inhibitory RNA

<400> SEQUENCE: 108 taagtta                                                            7

<210> SEQ ID NO 109
<211> LENGTH: 21
<212> TYPE: DNA
<213> ORGANISM: artificial sequence
<220> FEATURE:
<223> OTHER INFORMATION: inhibitory RNA

<400> SEQUENCE: 109
agatgcggca atcgttgttc c                                           21

<210> SEQ ID NO 110
<211> LENGTH: 7
<212> TYPE: DNA
<213> ORGANISM: artificial sequence
<220> FEATURE:
<223> OTHER INFORMATION: inhibitory RNA

<400> SEQUENCE: 110 gatgcgg                                                            7

<210> SEQ ID NO 111
<211> LENGTH: 21
<212> TYPE: DNA
<213> ORGANISM: artificial sequence
<220> FEATURE:
<223> OTHER INFORMATION: inhibitory RNA

<400> SEQUENCE: 111
tcttctttcc gtacaaactc c                                           21

<210> SEQ ID NO 112
<211> LENGTH: 7
<212> TYPE: DNA
<213> ORGANISM: artificial sequence
<220> FEATURE:
<223> OTHER INFORMATION: inhibitory RNA

<400> SEQUENCE: 112 cttcttt                                                            7

<210> SEQ ID NO 113
<211> LENGTH: 21
<212> TYPE: DNA
<213> ORGANISM: artificial sequence
<220> FEATURE:
<223> OTHER INFORMATION: inhibitory RNA

<400> SEQUENCE: 113
ctttaaatcc tgccaacttc c                                           21

```
<210> SEQ ID NO 114
<211> LENGTH: 7
<212> TYPE: DNA
<213> ORGANISM: artificial sequence
<220> FEATURE:
<223> OTHER INFORMATION: inhibitory RNA

<400> SEQUENCE: 114 tttaaat                                                                  7

<210> SEQ ID NO 115
<211> LENGTH: 21
<212> TYPE: DNA
<213> ORGANISM: artificial sequence
<220> FEATURE:
<223> OTHER INFORMATION: inhibitory RNA

<400> SEQUENCE: 115
agaatacgtg tataacctac c                                                 21

<210> SEQ ID NO 116
<211> LENGTH: 7
<212> TYPE: DNA
<213> ORGANISM: artificial sequence
<220> FEATURE:
<223> OTHER INFORMATION: inhibitory RNA

<400> SEQUENCE: 116 gaatacg                                                                  7

<210> SEQ ID NO 117
<211> LENGTH: 21
<212> TYPE: DNA
<213> ORGANISM: artificial sequence
<220> FEATURE:
<223> OTHER INFORMATION: inhibitory RNA

<400> SEQUENCE: 117
agcataacat acatcacctg c                                                 21

<210> SEQ ID NO 118
<211> LENGTH: 7
<212> TYPE: DNA
<213> ORGANISM: artificial sequence
<220> FEATURE:
<223> OTHER INFORMATION: inhibitory RNA

<400> SEQUENCE: 118 gcataac                                                                  7

<210> SEQ ID NO 119
<211> LENGTH: 21
<212> TYPE: DNA
<213> ORGANISM: artificial sequence
<220> FEATURE:
<223> OTHER INFORMATION: inhibitory RNA

<400> SEQUENCE: 119
gccatctcgg taaacatcag c                                                 21

<210> SEQ ID NO 120
<211> LENGTH: 7
<212> TYPE: DNA
<213> ORGANISM: artificial sequence
<220> FEATURE:
<223> OTHER INFORMATION: inhibitory RNA
```

<400> SEQUENCE: 120 ccatctc                                                                7

<210> SEQ ID NO 121
<211> LENGTH: 21
<212> TYPE: DNA
<213> ORGANISM: artificial sequence
<220> FEATURE:
<223> OTHER INFORMATION: inhibitory RNA

<400> SEQUENCE: 121
cctttaaatc ctgccaactt c                                                21

<210> SEQ ID NO 122
<211> LENGTH: 7
<212> TYPE: DNA
<213> ORGANISM: artificial sequence
<220> FEATURE:
<223> OTHER INFORMATION: inhibitory RNA

<400> SEQUENCE: 122 ctttaaa                                                                7

<210> SEQ ID NO 123
<211> LENGTH: 21
<212> TYPE: DNA
<213> ORGANISM: artificial sequence
<220> FEATURE:
<223> OTHER INFORMATION: inhibitory RNA

<400> SEQUENCE: 123
gcataggtca tatcttcttt c                                                21

<210> SEQ ID NO 124
<211> LENGTH: 7
<212> TYPE: DNA
<213> ORGANISM: artificial sequence
<220> FEATURE:
<223> OTHER INFORMATION: inhibitory RNA

<400> SEQUENCE: 124 cataggt                                                                7

<210> SEQ ID NO 125
<211> LENGTH: 21
<212> TYPE: DNA
<213> ORGANISM: artificial sequence
<220> FEATURE:
<223> OTHER INFORMATION: inhibitory RNA

<400> SEQUENCE: 125
catacatcac ctgcttcacg c                                                21

<210> SEQ ID NO 126
<211> LENGTH: 7
<212> TYPE: DNA
<213> ORGANISM: artificial sequence
<220> FEATURE:
<223> OTHER INFORMATION: inhibitory RNA

<400> SEQUENCE: 126 atacatc                                                                7

<210> SEQ ID NO 127
<211> LENGTH: 22

```
<212> TYPE: DNA
<213> ORGANISM: artificial sequence
<220> FEATURE:
<223> OTHER INFORMATION: inhibitory RNA

<400> SEQUENCE: 127
gcgctatccg cgacatcgac ct                                              22

<210> SEQ ID NO 128
<211> LENGTH: 7
<212> TYPE: RNA
<213> ORGANISM: artificial sequence
<220> FEATURE:
<223> OTHER INFORMATION: inhibitory RNA

<400> SEQUENCE: 128 ggucgau                                                                7

<210> SEQ ID NO 129
<211> LENGTH: 22
<212> TYPE: DNA
<213> ORGANISM: artificial sequence
<220> FEATURE:
<223> OTHER INFORMATION: inhibitory RNA

<400> SEQUENCE: 129
tggccccgca gggaacaacg at                                              22

<210> SEQ ID NO 130
<211> LENGTH: 7
<212> TYPE: RNA
<213> ORGANISM: artificial sequence
<220> FEATURE:
<223> OTHER INFORMATION: inhibitory RNA

<400> SEQUENCE: 130 ucguugu                                                                7

<210> SEQ ID NO 131
<211> LENGTH: 22
<212> TYPE: DNA
<213> ORGANISM: artificial sequence
<220> FEATURE:
<223> OTHER INFORMATION: inhibitory RNA

<400> SEQUENCE: 131
tcgcgacggc tatgattacg at                                              22

<210> SEQ ID NO 132
<211> LENGTH: 7
<212> TYPE: RNA
<213> ORGANISM: artificial sequence
<220> FEATURE:
<223> OTHER INFORMATION: inhibitory RNA

<400> SEQUENCE: 132 ucguaau                                                                7

<210> SEQ ID NO 133
<211> LENGTH: 22
<212> TYPE: DNA
<213> ORGANISM: artificial sequence
<220> FEATURE:
<223> OTHER INFORMATION: inhibitory RNA

<400> SEQUENCE: 133
```
cggcgctatc cgcgacatcg ac                                    22

<210> SEQ ID NO 134
<211> LENGTH: 7
<212> TYPE: RNA
<213> ORGANISM: artificial sequence
<220> FEATURE:
<223> OTHER INFORMATION: inhibitory RNA

<400> SEQUENCE: 134 ucgaugu                                                      7

<210> SEQ ID NO 135
<211> LENGTH: 22
<212> TYPE: DNA
<213> ORGANISM: artificial sequence
<220> FEATURE:
<223> OTHER INFORMATION: inhibitory RNA

<400> SEQUENCE: 135
agggaacaac gattgccgca tc                                    22

<210> SEQ ID NO 136
<211> LENGTH: 7
<212> TYPE: RNA
<213> ORGANISM: artificial sequence
<220> FEATURE:
<223> OTHER INFORMATION: inhibitory RNA

<400> SEQUENCE: 136 augcggc                                                      7

<210> SEQ ID NO 137
<211> LENGTH: 22
<212> TYPE: DNA
<213> ORGANISM: artificial sequence
<220> FEATURE:
<223> OTHER INFORMATION: inhibitory RNA

<400> SEQUENCE: 137
gcggtgtatg gtcgcgacgg ct                                    22

<210> SEQ ID NO 138
<211> LENGTH: 7
<212> TYPE: RNA
<213> ORGANISM: artificial sequence
<220> FEATURE:
<223> OTHER INFORMATION: inhibitory RNA

<400> SEQUENCE: 138 gccgucg                                                      7

<210> SEQ ID NO 139
<211> LENGTH: 22
<212> TYPE: DNA
<213> ORGANISM: artificial sequence
<220> FEATURE:
<223> OTHER INFORMATION: inhibitory RNA

<400> SEQUENCE: 139
ctgcgggtgg agtttcctcg aa                                    22

<210> SEQ ID NO 140
<211> LENGTH: 7
<212> TYPE: RNA
<213> ORGANISM: artificial sequence
<220> FEATURE:
<223> OTHER INFORMATION: inhibitory RNA

<400> SEQUENCE: 140 ucgagga                                                                     7

<210> SEQ ID NO 141
<211> LENGTH: 22
<212> TYPE: DNA
<213> ORGANISM: artificial sequence
<220> FEATURE:
<223> OTHER INFORMATION: inhibitory RNA

<400> SEQUENCE: 141
gtggagtttc ctcgaagcgg cc                                                   22

<210> SEQ ID NO 142
<211> LENGTH: 7
<212> TYPE: RNA
<213> ORGANISM: artificial sequence
<220> FEATURE:
<223> OTHER INFORMATION: inhibitory RNA

<400> SEQUENCE: 142 gccgcuu                                                                     7

<210> SEQ ID NO 143
<211> LENGTH: 214
<212> TYPE: DNA
<213> ORGANISM: artificial sequence
<220> FEATURE:
<223> OTHER INFORMATION: promoter

<400> SEQUENCE: 143
gaacgctgac gtcatcaacc cgctccaagg aatcgcgggc ccagtgtcac taggcgggaa           60
cacccagcgc ggtgcgccct ggcaggaaga tggctgtgag ggacagggga gtggcgccct          120
gcaatatttg catgtcgcta tgtgttctgg gaaatcacca taaacgtgaa atgtctttgg          180
atttgggaat cttataagtt ctgtatgaga ccac                                     214

<210> SEQ ID NO 144
<211> LENGTH: 91
<212> TYPE: DNA
<213> ORGANISM: artificial sequence
<220> FEATURE:
<223> OTHER INFORMATION: promoter

<400> SEQUENCE: 144
atatttgcat gtcgctatgt gttctgggaa atcaccataa acgtgaaatg tctttggatt           60
tgggaatctt ataagttctg tatgagacca c                                         91

<210> SEQ ID NO 145
<211> LENGTH: 241
<212> TYPE: DNA
<213> ORGANISM: artificial sequence
<220> FEATURE:
<223> OTHER INFORMATION: promoter

<400> SEQUENCE: 145
gagggcctat ttcccatgat tccttcatat ttgcatatac gatacaaggc tgttagagag           60
ataattggaa ttaatttgac tgtaaacaca agatattag tacaaaatac gtgacgtaga          120
aagtaataat ttcttgggta gtttgcagtt ttaaaattat gttttaaaat ggactatcat         180

```
atgcttaccg taacttgaaa gtatttcgat ttcttggctt tatatatctt gtggaaagga    240
c                                                                    241
```

```
<210> SEQ ID NO 146
<211> LENGTH: 278
<212> TYPE: DNA
<213> ORGANISM: artificial sequence
<220> FEATURE:
<223> OTHER INFORMATION: promoter

<400> SEQUENCE: 146
tcgaggtgag ccccacgttc tgcttcactc tccccatctc cccccctcc ccaccccaa      60
ttttgtattt atttatttt taattatttt gtgcagcgat ggggcgggg ggggggggg      120
ggcgcgcgcc aggcggggcg gggcggggcg aggggcgggg cggggcgagg cggagaggtg   180
cggcggcagc caatcagagc ggcgcgctcc gaaagtttcc ttttatggcg aggcggcggc   240
ggcggcggcc ctataaaaag cgaagcgcgc ggcgggcg                           278
```

```
<210> SEQ ID NO 147
<211> LENGTH: 659
<212> TYPE: DNA
<213> ORGANISM: artificial sequence
<220> FEATURE:
<223> OTHER INFORMATION: promoter

<400> SEQUENCE: 147
gacattgatt attgactagt tattaatagt aatcaattac ggggtcatta gttcatagcc    60
catatatgga gttccgcgtt acataactta cggtaaatgg cccgcctggc tgaccgccca   120
acgacccccg cccattgacg tcaataatga cgtatgttcc catagtaacg ccaataggga   180
ctttccattg acgtcaatgg gtggagtatt tacggtaaac tgcccacttg gcagtacatc   240
aagtgtatca tatgccaagt acgccccta ttgacgtcaa tgacggtaaa tggcccgcct   300
ggcattatgc ccagtacatg acctatggg actttcctac ttggcagtac atctacgtat   360
tagtcatcgc tattaccatg gtcgaggtga gccccacgtt ctgcttcact ctccccatct   420
ccccccctc ccacccca attttgtatt tattatttt ttaattattt tgtgcagcga   480
tggggggcgg ggggggggg gggccccccc caggcggggc gggcggggc gaggggcggg   540
gcggggcgag gcgaaaggt gcggcggcag ccaatcagag cggcgcgctc cgaaagtttc   600
cttttatggc gaggcggcgg cggcggcggc cctataaaaa gcgaagcgcg cggcgggcg   659
```

```
<210> SEQ ID NO 148
<211> LENGTH: 500
<212> TYPE: DNA
<213> ORGANISM: artificial sequence
<220> FEATURE:
<223> OTHER INFORMATION: promoter

<400> SEQUENCE: 148
gggtagggga ggcgcttttc ccaaggcagt ctggagcatg cgctttagca gccccgctgg    60
gcacttggcg ctacacaagt ggcctctggc ctcgcacaca ttccacatcc accggtaggc   120
gccaaccggc tccgttcttt ggtggcccct tcgcgccacc ttctactcct ccctagtca    180
ggaagttccc ccccgccccg cagctcgcgt cgtgcaggac gtgacaaatg gaagtagcac   240
gtctcactag tctcgtgcag atggacagca ccgctgagca atggaagcgg gtaggccttt   300
ggggcagcgg ccaatagcag ctttgctcct tcgctttctg ggctcagagg ctgggaaggg   360
gtgggtccgg gggcgggctc agggggcggc tcaggggcgg ggcggcgcc cgaaggtcct   420
```

```
ccggaggccc ggcattctgc acgcttcaaa agcgcacgtc tgccgcgctg ttctcctctt      480
cctcatctcc gggcctttcg                                                  500

<210> SEQ ID NO 149
<211> LENGTH: 212
<212> TYPE: DNA
<213> ORGANISM: artificial sequence
<220> FEATURE:
<223> OTHER INFORMATION: promoter

<400> SEQUENCE: 149
gggcagagcg cacatcgccc acagtccccg agaagttggg gggagggtc ggcaattgat       60 ccggtgccta gagaaggtgg cgcggggtaa actgggaaag tgatgtcgtg tactggctcc     120 gccttttttcc cgagggtggg ggagaaccgt atataagtgc agtagtcgcc gtgaacgttc    180
tttttcgcaa cgggtttgcc gccagaacac ag                                   212

<210> SEQ ID NO 150
<211> LENGTH: 380
<212> TYPE: DNA
<213> ORGANISM: artificial sequence
<220> FEATURE:
<223> OTHER INFORMATION: promoter

<400> SEQUENCE: 150
gacattgatt attgactagt tattaatagt aatcaattac ggggtcatta gttcatagcc      60
catatatgga gttccgcgtt acataactta cggtaaatgg cccgcctggc tgaccgccca    120 acgaccccg cccattgacg tcaataatga cgtatgttcc catagtaacg ccaataggga     180
ctttccattg acgtcaatgg gtggagtatt tacggtaaac tgcccacttg gcagtacatc    240
aagtgtatca tatgccaagt acgccccta ttgacgtcaa tgacggtaaa tggcccgcct    300
ggcattatgc ccagtacatg acctatggg actttcctac ttggcagtac atctacgtat    360
tagtcatcgc tattaccatg                                                 380

<210> SEQ ID NO 151
<211> LENGTH: 204
<212> TYPE: DNA
<213> ORGANISM: artificial sequence
<220> FEATURE:
<223> OTHER INFORMATION: promoter

<400> SEQUENCE: 151
gtgatgcggt tttggcagta catcaatggg cgtggatagc ggtttgactc acggggattt      60
ccaagtctcc accccattga cgtcaatggg agtttgtttt ggcaccaaaa tcaacgggac    120
tttccaaaat gtcgtaacaa ctccgcccca ttgacgcaaa tgggcggtag cgtgtacgg    180 tgggaggtct atataagcag agct                                            204

<210> SEQ ID NO 152
<211> LENGTH: 248
<212> TYPE: PRT
<213> ORGANISM: artificial sequence
<220> FEATURE:
<223> OTHER INFORMATION: inhibitory RNA

<400> SEQUENCE: 152

Met Ser Gly Gly Gly Val Ile Arg Gly Pro Ala Gly Asn Asn Asp Cys
1               5                   10                  15

Arg Ile Tyr Val Gly Asn Leu Pro Pro Asp Ile Arg Thr Lys Asp Ile
```

```
                 20                  25                  30
Glu Asp Val Phe Tyr Lys Tyr Gly Ala Ile Arg Asp Ile Asp Leu Lys
             35                  40                  45

Asn Arg Arg Gly Gly Pro Pro Phe Ala Phe Val Glu Phe Glu Asp Pro
         50                  55                  60

Arg Asp Ala Glu Asp Ala Val Tyr Gly Arg Asp Gly Tyr Asp Tyr Asp
 65                  70                  75                  80

Gly Tyr Arg Leu Arg Val Glu Phe Pro Ala Ser Gly Ala Gly Thr Gly
                 85                  90                  95

Arg Gly Gly Gly Gly Gly Gly Gly Ala Pro Arg Gly Arg Tyr
             100                 105                 110

Gly Pro Pro Ser Ala Ala Ser Glu Asn Arg Val Val Ser Gly Leu
         115                 120                 125

Pro Pro Ser Gly Ser Trp Gln Asp Leu Lys Asp His Met Arg Glu Ala
         130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                 165                 170                 175

Asn Thr Lys Phe Arg Ser His Glu Gly Glu Thr Ala Tyr Ile Arg Val
             180                 185                 190

Lys Val Asp Gly Pro Arg Ser Pro Ser Tyr Gly Arg Ser Arg Ser Arg
                 195                 200                 205

Ser Arg Ser Arg Ser Arg Ser Arg Ser Asn Ser Arg Ser Arg
         210                 215                 220

Ser Tyr Ser Pro Arg Arg Ser Arg Gly Ser Pro Arg Tyr Ser Pro Arg
225                 230                 235                 240

His Ser Arg Ser Arg Ser Arg Thr
                 245

<210> SEQ ID NO 153
<211> LENGTH: 61
<212> TYPE: PRT
<213> ORGANISM: artificial sequence
<220> FEATURE:
<223> OTHER INFORMATION: antagonistic peptide

<400> SEQUENCE: 153

Pro Arg Ser Gly Arg Gly Thr Gly Arg Gly Gly Gly Gly Gly Gly Gly
  1               5                  10                  15

Gly Gly Ala Pro Arg Gly Arg Tyr Gly Pro Pro Ser Arg Ser Glu
             20                  25                  30

Gly Gly Gly Lys Pro Ile Pro Asn Pro Leu Leu Gly Leu Asp Ser Thr
         35                  40                  45

Gly Gly Tyr Gly Arg Lys Lys Arg Gln Arg Arg
         50                  55                  60

<210> SEQ ID NO 154
<211> LENGTH: 21
<212> TYPE: DNA
<213> ORGANISM: artificial sequence
<220> FEATURE:
<223> OTHER INFORMATION: inhibitory RNA

<400> SEQUENCE: 154
ggaaagaaga tatgacctat g                                           21
```

```
<210> SEQ ID NO 155
<211> LENGTH: 21
<212> TYPE: DNA
<213> ORGANISM: artificial sequence
<220> FEATURE:
<223> OTHER INFORMATION: inhibitory RNA

<400> SEQUENCE: 155
agggagaaac tgcctacatc c                                          21

<210> SEQ ID NO 156
<211> LENGTH: 21
<212> TYPE: DNA
<213> ORGANISM: artificial sequence
<220> FEATURE:
<223> OTHER INFORMATION: inhibitory RNA

<400> SEQUENCE: 156
gggactaatg tgggaagaac t                                          21

<210> SEQ ID NO 157
<211> LENGTH: 21
<212> TYPE: DNA
<213> ORGANISM: artificial sequence
<220> FEATURE:
<223> OTHER INFORMATION: inhibitory RNA

<400> SEQUENCE: 157
gcaaccacga aacctgtaat a                                          21

<210> SEQ ID NO 158
<211> LENGTH: 21
<212> TYPE: DNA
<213> ORGANISM: artificial sequence
<220> FEATURE:
<223> OTHER INFORMATION: inhibitory RNA

<400> SEQUENCE: 158
gggatcagat taccaggaac a                                          21
```

INHIBITORS OF SRSF1 TO TREAT NEURODEGENERATIVE DISORDERS

CROSS REFERENCE TO RELATED APPLICATIONS

This is the U.S. National Stage of International Application No. PCT/GB2017/051539, filed May 30, 2017, which was published in English under PCT Article 21(2), which in turn claims the benefit of GB Application No. 1609597.8 filed Jun. 1, 2016.

FIELD OF THE DISCLOSURE

The present disclosure relates to antagonists that target Serine/Arginine-Rich Splicing Factor 1 (SRSF1); expression vectors comprising SRSF1 antagonists; and the use of such antagonists in therapy for the treatment of neurodegenerative disorders and cancer.

BACKGROUND THE DISCLOSURE

Amyotrophic lateral sclerosis (ALS) and frontotemporal dementia (FTD) are adult-onset neurodegenerative diseases with no effective treatment. FTD is a common cause of early onset dementia characterised by a progressive loss of neuronal cells in frontal and temporal lobe leading to alterations of cognitive function and personality features, leaving patients unable to care for themselves and resulting in death from between 2-15 years from disease onset. ALS is the premature degeneration of motor neurons leading to muscle atrophy and paralysis leading to death from respiratory failure within 2 to 3 years from symptom onset. MND is a degenerative disease of motor neurons of the nerve cells which control muscles. MND leads to progressive paralysis and death within 2-5 years from when symptoms appear. The disease prevalence is around 6-8/100,000 people.

Neuroprotective treatment options are currently extremely limited and the anti-glutamatergic agent riluzole prolongs survival in ALS patients by only approximately 3 months or around 6 months of life extension in MND patients. ALS and FTD show a substantial clinical and pathological overlap, 40-50% of ALS patients present FTD dysfunctions, whereas in about 5-10% FTD cases patients develop ALS and are therefore proposed to constitute one disease spectrum.

A number of genes have been discovered and are thought to be responsible for ALS such as SOD1, TARDBP, FUS, OPTN and VCP. Moreover, both diseases are characterised by the presence of protein transactivation response DNA-binding protein (TDP-43) inclusions throughout the central nervous system. However the most commonly identified genetic cause of ALS and FTD involves polymorphic repeat expansions composed of hundreds to thousands of the GGGGCC hexanucleotide-repeat sequence (hereafter abbreviated G4C2) in the first intron of the C9ORF72 gene, with autosomal dominant inheritance and incomplete penetrance (1, 2). The C9ORF72 gene is located on the short arm of chromosome 9 open reading frame 72 and occurs in two isoforms. This protein is found in many regions of the brain in the cytoplasm of neurons as well as in presynaptic terminals, and is also found mutated in diseases such as frontotemporal lobar dementia (FTLD), Huntington's like disorder, primary lateral sclerosis, progressive muscular atrophy, corticobasal syndrome, Alzheimer's disease and Dementia with Lewy Bodies. The pathophysiology potentially involves three extensively-studied mechanisms which may co-exist: (i) RNA toxic gain-of-function by sequestration of RNA-binding factors (5-9), (ii) protein toxic gain-of-function due to repeat associated non-ATG (RAN) translation that occurs in all sense and antisense reading frames to produce five dipeptide-repeat proteins (DPRs (10-14) and (iii) haplo-insufficiency due to decreased expression of the C9ORF72 protein (1, 15, 16).

Typically, therapeutic approaches have targeted C9ORF72. WO2016/024205 discloses oligomers complimentary to the C9ORF72 gene and in particular compositions for targeting RNA containing a pathological number of hexanucleotide repeats for use in the treatment of a neurological disorder selected from the group of ALS and FTD. WO2014/062691 discloses compositions and methods for reducing the expression of C9ORF72 mRNA and protein in an animal for the treatment of ALS, FTD, corticalbasal degeneration syndrome, atypical Parkinson syndrome and olivopontocerebellar degeneration by the delivery of antisense RNA directed against C9ORF27 nucleic acids. The nucleic acids are administered into the central nervous system intrathecally or intraventriculary. Only two antisense drugs have been approved; fomivirsen for the treatment of cytomegalovirus retinitis and mipomersen for the treatment of homozygous familial hypercholesterolemia. Viral vectors present an alternative form of delivery vehicle for genetic material. Viral vector systems, based on adeno-associated viruses and lentiviruses, are ideally suited to mediate RNAi because they can safely transduce a wide range of tissues and provide sustained levels of gene expression.

Nuclear export of mRNA is mediated by NXF1 (nuclear export factor 1) protein and export adaptors such as SRSF1 (serine/arginine-rich splicing factor 1) and ALYREF (Aly/REF export factor) are thought to increase the affinity for mature mRNAs, preventing the export of unprocessed transcripts. Immunohistochemistry in central nervous system tissue from C9orf72+ patients with ALS demonstrated co-localization of GGGGCC repeat RNA with SRSF2, hnRNP H1/F, ALYREF and hnRNP A1 in cerebellar granule cells and with SRSF2, hnRNP H1/F and ALYREF in motor neurons, the primary target of pathology in ALS. Direct binding of proteins to GGGGCC repeat RNA was also confirmed.

The present disclosure has identified that excessive binding of nuclear export adaptor(s) onto G4C2-repeat transcripts forces interactions with NXF1, overriding the normal nuclear retention mechanisms and teaches that depletion of factors such as SRSF (also known as SF2 or ASF) 1 confers neuroprotection.

STATEMENTS OF INVENTION

According to an aspect of the invention there is provided an antagonistic agent that inhibits the expression of a nucleic acid molecule encoding Serine/Arginine-Rich Splice Factor 1 [SRSF1] or inhibits the activity of a SRSF1 protein.

Inhibition of expression defines the reduction of expression ranging from 1-100% when compared to expression of the nucleic acid/protein found in the wild type.

According to a further aspect of the invention there is provided a transcription cassette comprising: a nucleic acid molecule encoding an antagonistic agent wherein said agent inhibits the expression of a nucleic acid encoding a Serine/Arginine-Rich Splice Factor [SRSF1] or inhibits the activity of a SRSF1 protein wherein said nucleic acid molecule is operably linked to a promoter adapted to express said agent.

In a preferred embodiment of the invention SRSF1 is encoded by a nucleic acid molecule comprising a nucleotide sequence as set forth in SEQ ID NO: 1, or polymorphic sequence variant that has 90%-99% sequence identity over the full length nucleotide sequence as set forth in SEQ ID NO:1.

In a preferred embodiment of the invention SRSF1 is encoded by a nucleic acid molecule comprising a nucleotide sequence as set forth in SEQ ID NO: 3 or polymorphic sequence variant that has 90%-99% sequence identity over the full length nucleotide sequence as set forth in SEQ ID NO: 3.

In a preferred embodiment of the invention SRSF1 is represented by the amino acid sequence as set forth in SEQ ID NO:2, or a polymorphic sequence variant that has 90-99% sequence identity over the full length amino acid sequence as set forth in SEQ ID NO: 2.

In an preferred embodiment of the invention SRSF1 is represented by the amino acid sequence as set forth in SEQ ID NO: 4, or a polymorphic sequence variant that has 90-99% sequence identity over the full length amino acid sequence as set forth in SEQ ID NO: 4.

In a preferred embodiment of the invention said nucleic acid molecule encodes nucleic acid based agent.

In a preferred embodiment of the invention said nucleic acid molecule encodes an antisense nucleic acid.

In a preferred embodiment of the invention said nucleic acid based molecule is an inhibitory RNA.

In a preferred embodiment of the invention said inhibitory RNA is a siRNA or shRNA or miRNA molecule.

A technique to specifically ablate gene function is through the introduction of double stranded RNA, also referred to as small inhibitory or interfering RNA (siRNA), into a cell which results in the destruction of mRNA complementary to the sequence included in the siRNA molecule. The siRNA molecule comprises two complementary strands of RNA (a sense strand and an antisense strand) annealed to each other to form a double stranded RNA molecule. The siRNA molecule is typically derived from exons of the gene which is to be ablated. The mechanism of RNA interference is being elucidated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

In a preferred embodiment of the invention said inhibitory RNA molecule is between 19 nucleotides [nt] and 29 nt in length. More preferably still said inhibitory RNA molecule is between 21 nt and 27 nt in length. Preferably said inhibitory RNA molecule is about 21 nt in length.

In a preferred embodiment of the invention said inhibitory RNA comprises or consists of a nucleotide sequences set forth in SEQ ID NO: 5, 6, 7, 8, 9, 10, 11, 12, 13 or 14.

In a preferred embodiment of the invention said inhibitory RNA comprises or consists of a nucleotide sequences set forth in SEQ ID NO: 97, 98, 99, 100, 101, 102, 103, 104, 105 or 106.

In a preferred embodiment of the invention said inhibitory RNA comprises or consists of a nucleotide sequences set forth in SEQ ID NO: 107, 109, 111, 113, 115, 117, 119, 121, 123 or 125.

In a preferred embodiment of the invention said inhibitory RNA comprises or consists of a nucleotide sequences set forth in SEQ ID NO: 127, 129, 131, 133, 135, 137, 139 or 141.

In a preferred embodiment of the invention said inhibitory RNA comprises or consists of a nucleotide sequences set forth in SEQ ID NO: 47, 48, 50, 99, 154, 155, 156, 157, 158 or 60.

In a preferred embodiment of the invention said nucleic acid based agent comprises modified nucleotides.

In an alternative embodiment of the invention said agent is a peptide.

In a preferred embodiment of the invention said peptide comprises an amino acid sequence that is at least 32 amino acids in length and comprises the amino acid sequence set forth in SEQ ID NO: 15.

In a preferred embodiment of the invention said peptide is at least 35, 40, 45, 50, 55, 60, 65, 70, 75, 80, 85, 90, 95 or at least 100 amino acids in length but less than the full length amino acid sequence set forth in SEQ ID NO: 2 or 4.

In a preferred embodiment of the invention said peptide consists of an amino sequence as set forth in SEQ ID NO: 15.

In a preferred embodiment of the invention said peptide is modified, for example said peptide is cyclised.

In an alternative embodiment of the invention said protein is a dominant negative protein comprising a modification of the amino acid sequence set forth in SEQ ID NO: 2 or 4.

In a preferred embodiment of the invention said dominant negative protein comprises or consists of an amino acid sequence as set forth in SEQ ID NO: 2 or 4 wherein said amino acid sequence is modified by addition, deletion or substitution of one or more amino acid residues.

In a preferred embodiment of the invention said modified protein comprises or consists of the amino acid sequence as set forth in SEQ ID NO: 16 or 17.

In a preferred embodiment of the invention said antagonist agent is a protein kinase specific for SRSF1 to maintain the phosphorylation state of SRSF1.

In a preferred embodiment of the invention said protein kinase is SRPK1.

In a preferred embodiment of the invention SRPK1 is encoded by a nucleic acid molecule comprising a nucleotide sequence as set forth in SEQ ID NO: 18.

In an alternative embodiment of the invention SRPK1 comprises an amino acid sequence as set forth in SEQ ID NO: 19.

In an alternative embodiment of the invention said protein kinase is CDC like kinase 1.

In a preferred embodiment of the invention CDC like kinase 1 is encoded by a nucleic acid molecule comprising a nucleotide sequence as set forth in SEQ ID NO: 20.

In an alternative embodiment of the invention CDC like kinase 1 comprises an amino acid sequence as set forth in SEQ ID NO: 21.

In an alternative embodiment of the invention said antagonist agent is a phosphatase inhibitor specific for human protein phosphatase-1.

In a preferred embodiment of the invention said antagonist inhibits expression or activity of human protein phosphatase-1.

In a preferred embodiment of the invention human protein phosphatase-1 is encoded by a nucleotide sequence as set forth in SEQ ID NO: 22.

In a preferred embodiment of the invention said antagonist is an inhibitory RNA.

In a preferred embodiment of the invention said promoter is a constitutive promoter.

In an alternative embodiment of the invention said promoter is a regulated promoter, for example an inducible or cell specific promoter.

According to a further aspect of the invention there is provided an expression vector comprising a transcription cassette according to the invention.

A number of viruses are commonly used as vectors for the delivery of exogenous genes. Commonly employed vectors include recombinantly modified enveloped or non-enveloped DNA and RNA viruses, for example baculoviridiae, parvoviridiae, picornoviridiae, herpesveridiae, poxviridae, adenoviridiae, picornnaviridiae or retroviridae. Chimeric vectors may also be employed which exploit advantageous elements of each of the parent vector properties (See e.g., Feng, et al (1997) Nature Biotechnology 15:866-870). Such viral vectors may be wild-type or may be modified by recombinant DNA techniques to be replication deficient, conditionally replicating or replication competent. Conditionally replicating viral vectors are used to achieve selective expression in particular cell types while avoiding untoward broad spectrum infection. Examples of conditionally replicating vectors are described in Pennisi, E. (1996) Science 274:342-343; Russell, and S. J. (1994) Eur. J. of Cancer 30A(8):1165-1171.

Preferred vectors are derived from the adenoviral, adeno-associated viral and retroviral genomes.

In a preferred embodiment of the invention said expression vector is a viral based expression vector.

In a preferred embodiment of the invention said viral based vector is an adeno-associated virus [AAV].

In a preferred embodiment of the invention said viral based vector is AAV9.

In an alternative preferred embodiment of the invention said viral based vector is a lentiviral vector.

According to a further aspect of the invention there is provided a pharmaceutical composition comprising an expression vector according to the invention and an excipient or carrier.

The agent or expression vector compositions of the present invention are administered in pharmaceutically acceptable preparations. Such preparations may routinely contain pharmaceutically acceptable concentrations of salt, buffering agents, preservatives, compatible carriers and supplementary therapeutic agents'. The agent or expression vector compositions of the invention can be administered by any conventional route, including injection or by gradual infusion over time.

The agent or expression vector compositions of the invention are administered in effective amounts. An "effective amount" is that amount of the agent or expression vector that alone, or together with further doses, produces the desired response. In the case of treating a disease, the desired response is inhibiting the progression of the disease. This may involve only slowing the progression of the disease temporarily, although more preferably, it involves halting the progression of the disease permanently. This can be monitored by routine methods. Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The agent or expression vector compositions used in the foregoing methods preferably are sterile and contain an effective amount of agent or expression vector according to the invention for producing the desired response in a unit of weight or volume suitable for administration to a patient. The doses of agent or vector administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. Other protocols for the administration of agent or vector compositions will be known to one of ordinary skill in the art, in which the dose amount, schedule of injections, sites of injections, mode of administration and the like vary from the foregoing. The administration of compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the agent or expression vector compositions of the invention are applied in pharmaceutically-acceptable amounts and in pharmaceutically-acceptable compositions. The term "pharmaceutically acceptable" means a non-toxic material that does not interfere with the effectiveness of the biological activity of the active agent. Such preparations may routinely contain salts, buffering agents, preservatives, compatible carriers, and optionally other therapeutic agents' (e.g. those typically used in the treatment of the specific disease indication). When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The pharmaceutical compositions containing the agents or expression vectors according to the invention may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

The agent or expression vector compositions may conveniently be presented in unit dosage form and may be prepared by any of the methods well-known in the art of pharmacy. All methods include the step of bringing the active agent into association with an agent or vector which constitutes one or more accessory ingredients. The preparation may be formulated according to known methods using suitable dispersing or wetting agents and suspending agents.

The sterile injectable preparation also may be a sterile injectable solution or suspension in a non-toxic parenterally-acceptable diluent or solvent, for example, as a solution in 1, 3-butanediol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

According to a further aspect of the invention there is provided an antagonistic agent according to the invention for use as a medicament.

According to a further aspect of the invention there is provided an expression vector according to the invention for use as a medicament.

According to an aspect of the invention there is provided an antagonistic agent according to the invention for use in the treatment of a neurodegenerative disease.

According to a further aspect of the invention there is provided an expression vector according to the invention for use in the treatment of a neurodegenerative disease.

In a preferred embodiment of the invention said neurodegenerative disease is selected from the group consisting of: motor neurone disease, frontotemporal lobar dementia (FTLD), Huntington's like disorder, primary lateral sclerosis, progressive muscular atrophy, corticobasal syndrome, Alzheimer's disease and Dementia with Lewy Bodies.

In a preferred embodiment of the invention said neurodegenerative disease is motor neurone disease.

According to a further aspect of the invention there is provided a method for the treatment of a neurodegenerative disease comprising administering a therapeutically effective amount of an antagonistic agent according to the invention to prevent and/or treat said neurodegenerative disease.

According to a further aspect of the invention there is provided a method for the treatment of a neurodegenerative disease comprising administering a therapeutically effective amount of an expression vector according to the invention to prevent and/or treat said neurodegenerative disease.

According to an aspect of the invention there is provided an antagonistic agent according to the invention for use in the treatment of cancer, in particular metastatic cancer.

According to a further aspect of the invention there is provided an expression vector according to the invention for use in the treatment of cancer, in particular metastatic cancer.

Cancer includes reference to tumours. For example adenocarcinomas include malignancies such as most colon cancers, renal-cell carcinoma, prostate cancer, testicular tumours, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumours composed of carcinomatous and sarcomatous tissues. An "adenocarcinoma" refers to a carcinoma derived from glandular tissue or in which the tumor cells form recognizable glandular structures.

In general, doses of antagonistic agents, for example, antisense oligonucleotide, siRNA or shRNA will be between 1 nM-1 µM generally will be formulated and administered according to standard procedures. Preferably doses can range from 1 nM-500 nM, 5 nM-200 nM, and 10 nM-100 nM. In addition dosages of peptides and/or protein antagonist are formulated and administered in doses between 1 ng and 1 mg, and preferably between 10 ng and 100 µg.

According to a further aspect of the invention there is provided the use of a nucleic acid molecule encoding SRSF1, or a protein with the activity associated with SRSF1 in the identification of an agent that inhibits the expression or activity of SRSF1.

According to a further aspect of the invention there is provided a screening method for the identification of an agent that inhibits the expression of SRSF1 or the activity of a protein with activity associated with SRSF1 comprising the steps:
  i) providing a cell that expresses SRSF1;
  ii) contacting the cell with one or more agents to be tested for inhibitory activity with respect to a nucleic acid encoding SRSF1 or a SRSF1 protein;
  iii) monitoring the effect of said agent[s] on the expression or activity of SRSF1 compared to a cell that has not been contacted with said agent[s].

In a preferred method of the invention said cell is a nerve cell, for example an astrocyte.

In a preferred method of the invention said cell is modified to recombinantly express SRSF1.

In a preferred method of the invention said agent is a nucleic acid based agent.

In a preferred method of the invention said nucleic acid based agent comprises modified nucleotides.

The term "modified" as used herein describes a nucleic acid molecule in which:
i) at least two of its nucleotides are covalently linked via a synthetic internucleotide linkage (i.e., a linkage other than a phosphodiester linkage between the 5' end of one nucleotide and the 3' end of another nucleotide). Alternatively or preferably said linkage may be the 5' end of one nucleotide linked to the 5' end of another nucleotide or the 3' end of one nucleotide with the 3' end of another nucleotide; and/or
ii) a chemical group, such as cholesterol, not normally associated with nucleic acids has been covalently attached to the single-stranded nucleic acid.

Preferred synthetic internucleotide linkages are phosphorothioates, alkylphosphonates, phosphorodithioates, phosphate esters, alkylphosphonothioates, phosphoramidates, carbamates, phosphate triesters, acetamidates, peptides, and carboxymethyl esters.

The term "modified" also encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine; 5-(carboxyhydroxylmethyl) uracil; 5-fluorouracil; 5-bromouracil; 5-carboxymethylaminomethyl-2-thiouracil; 5 carboxymethylaminomethyl uracil; dihydrouracil; inosine; N6-isopentyl-adenine; I-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; beta-D-mannosylqueosine; 5-methoxycarbonylmethyluracil; 5-methoxyuracil; 2 methylthio-N6-isopentenyladenine; uracil-5-oxyacetic acid methyl ester; pseudouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine. Modified double stranded nucleic acids also can include base analogs such as C-5 propyne modified bases (see Wagner et al., Nature Biotechnology 14:840-844, 1996). The use of modified nucleotides confers, amongst other properties, resistance to nuclease digestion and improved stability.

In an alternative method of the invention said agent is a peptide or protein agent.

In a preferred method of the invention said peptide agent comprises one or more modified amino acids or are cyclised.

Cyclisation is known in the art, (see Scott et al Chem Biol (2001), 8:801-815; Gellerman et al J. Peptide Res (2001), 57: 277-291; Dutta et al J. Peptide Res (2000), 8: 398-412; Ngoka and Gross J Amer Soc Mass Spec (1999), 10:360-363.

In a further method of the invention said agent is a small organic agent.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

An embodiment of the invention will now be described by example only and with reference to the following figures:

FIGS. 4A-4E: Generation of RAN-dependent uninterrupted G4C2-sense and C4G2-antisense repeat constructs. (A) Agarose gels confirming both the annealing and concatemerisation of the G4C2×15 oligonucleotides. Arrows point to monomeric and multimeric forms of annealed oligonucleotides. (B) Trimeric oligonucleotides were treated with Mung Bean nuclease for blunt cloning. 8% acrylamide gel of HindIII/XhoI digests of pcDNA3.1/RAN constructs containing uninterrupted G4C2-sense and C4G2-antisense repeats with 5' and 3' flanking regions. (C) Standard curve generated from the acrylamide gel analysis using the Gene Tools Image software. (D) Table showing theroretical and experimental base pair size information for HindIII/XhoI inserts. The RAN constructs contain at least 38 G4C2-sense or 39 C4G2-antisense uninterrupted repeats based on the experimental size of the inserts (see sequences in E). (E) Sanger sequencing using betaine was also performed in the 5' and 3' directions using the T7 and T3 promoter sequencing primers respectively. Each sequence read covered the 5' or 3' flanking region and 9-16 G4C2 or C4G2 repeats prior to interruption. Sequencing traces are available on request. The RNA transcripts generated from these constructs are highlighted in blue (flanking regions) and red (sense or antisense repeats). Sequences highlighted in black/underlined correspond to the 3'end of the promoter sequence and in black/italics to the start of the terminator sequence. Note the absence of initiating codons (ATG) in both sense and antisense transcripts generated from the RAN-dependent DPR-expression constructs. Stop codons are shown in all frames in bold (SEQ ID NO 40 and 41). The constructs expressing 15 repeats in sense or antisense orientation are identical except that they only contain 15 repeats. Sequencing and size analysis further showed that the number of repeats remained stable over multiple rounds of transformation and replication in *E. coli*;

FIGS. 6A-6F: SRSF1 depletion and inhibition of the SRSF1:NXF1 interaction inhibit the nuclear export of hexanucleotide-repeat RAN-translated transcripts and the production of DPRs. Western blot quantification of DPRs. (A) Western blots from N2A cells co-transfected with either a Ctrl or SRSF1-RNAi vector and control backbone plasmid (no DPR Ctrl) or the same plasmid expressing 38 uninterrupted G4C2-sense-repeats (G4C2×38) or 39 uninterrupted C4G2-antisense-repeats (C4G2×39) were quantified in triplicate experiments (Mean±SEM; two-way ANOVA, **: $p<0.001$; N=3). One replicate of western blots is presented in FIG. 11A. (B and C) Western blots from N2A cells co-transfected with either G4C2×38 (B) or C4G2×39 (C) plasmids and control (FLAG Ctrl) or FLAG-tagged SRSF1 aa11-196 wild type (SRSF1), SRSF1-m2 or SRSF1-m4 were quantified in triplicate experiments (Mean±SEM; two-way ANOVA, : $p<0.01$, **: $p<0.001$; N=3). One replicate of each western blots is presented in FIG. 11C; (d, e,) Western blots shown in FIG. 11A** for the GP36 (d) and GA36 (e) panels were quantified in triplicate experiments (mean±SEM; two-way ANOVA; N=3). (f) Total extracts from N2A cells transfected with either FLAG control (FLAG ctrl) and either FLAG-tagged SRSF1 aa11-196 wild type (SRSF1), SRSF1-m2 or SRSF1-m4 are subjected to anti-FLAG immunoprecipitation. Co-immunoprecipitation of endogenous NXF1 is assessed using anti-NXF1 antibodies;

FIGS. 12A-12L: DNA sequences used to generate recombinant gene therapy vectors; (A) Human sequences of SRSF1; (A) NCBI accession number NM_006924.4 (mRNA sequence, transcript variant 1)—Coding sequence CDS: 210-956; (B) Amino acid sequence encoded by NM_006924.4; (C) NCBI accession number NM_001078166.1 (mRNA sequence, transcript variant 2)—Coding sequence CDS: 210-815; (D) Amino acid sequence encoded by NM_001078166.1; (E-F) NCBI accession number NR_034041.1 (mRNA sequence, transcript variant 3)—Considered non-coding as potential substrate for non-sense mediated decay; (G) Mouse sequences of SRSF1; B1)_NCBI accession number BC046773.1 (mRNA sequence)—Coding sequence CDS: 99-845; (H) Amino acid sequence encoded by BC046773.1; (I) NCBI accession number NM_173374.4 (mRNA sequence, transcript variant 1)—Coding sequence CDS: 467-1213. Encodes the same sequence of amino acids as BC046773.1; (J) Amino acid sequence encoded by NM_173374.4; (K) NCBI accession number NM_001078167.2 (mRNA sequence, transcript variant 2)—Coding sequence CDS: 467-1072; (L) Amino acid sequence encoded by NM_001078167.2;

FIGS. 13A-13C Expression or cell-permeable fusion of SRSF1 sequences encoding a dominant negative mutant which does not interact with NXF1. Use of any sequences encompassing the expression of human SRSF1 or orthologous sequences encoding the two RNA Recognition Motifs (amino acid 11-196) and mutations of arginines 90, 93, 117, 118 in the linker region between the two 2 RNA Recognition Motifs. These correspond to the following amino acids for human SRSF1 including mutations of arginines 90, 93, 117, 118 into alanine (labelled in bold): Other amino acids can be used for substitution e.g., glycine, valine, etc. (A) SRSF1 amino acids 1-196 R90, 93, 117, 11, (B) SRSF1 amino acids 11-196 R90,93,117,118A; (C); SRSF1 amino acids 1-248 R90,93,117,118A;

FIG. 14 Expression or cell-permeable fusion of SRSF1 sequences encoding antagonistic peptides which interact with NXF1. Use of any orthologous SRSF1 sequences encoding peptides which bind to NXF1. These encompass amino acids 89-120 of human SRSF1;

FIGS. 15A-15B Expression of SRPK1 amino-acids 1-655 to maintain phosphorylation state of SRSF1 for inhibiting interaction of SRSF1 with NXF1 (A) NCBI accession number NM_003137.4 (mRNA sequence, transcript variant 1)—Coding sequence CDS: 125-2092; (B) Amino acids sequence encoded by NM_003137.4;

FIG. 16A nucleotide sequence of CLK1 or Clk/Sty (*Homo sapiens* CDC like kinase 1 (CLK1), transcript variant 1, mRNA)—NCBI Reference Sequence: NM_004071.3;

FIG. 16B amino acid sequence of CLK1;

FIG. 17A nucleotide sequence of PP1 (Human protein phosphatase-1 catalytic subunit mRNA, complete cds)—GenBank: M63960.1; amino acid sequence of human PP1;

FIG. 17B is the amino acid sequence of PP1;

FIGS. 18A-18P Promoters sequences used to generate recombinant gene therapy vectors; (A) 6.1/CMV early enhancer/hybrid Chicken b-actin promoter (CAG); (B) CMV promoter; (C) CBA promoter (Chicken b-actin) (D) Neuronal specific promoter (Synapsin 1); (E) Glial specific promoter (GFAP); (F) H1 promoter; (G) U6 promoter; and (H) H1_pLVTHM promoter, I) H1 promoter in scAAV backbone, J) U6 promoter, (K) Chicken-β-actin promoter (CBA), L) CAG promoter (hybrid chicken b-actin promoter), M) Mouse PGK_promoter from LV-LacZ, N) Elongation factor short 1α (EFS1α), O) CMV enhancer or P) CMV promoter;

FIGS. 19A-19G Adeno-associated virus serotype 1, 2, 5, 6, 8, 9, 10 (A-C; SEQ ID NO: 38) Self-complementary AAV-CMV-GFP; (D-G; SEQ ID NO: 39) pAAV2/9—For construction of scAAV9;

FIGS. 20A-20C: Purified ALYREF and SRSF1 proteins directly interact with hexanucleotide repeat sense and antisense RNA. (A,B) Protein:RNA UV crosslinking assays using purified recombinant proteins and 32P-end-radiolabeled G4C2×5 (A) and C4G2×5 (B) repeat RNA probes. Proteins are visualised on SDS-PAGE stained with Coomassie blue (left panels) and covalently linked RNA:protein complexes by autoradiography on PhosphoImages (Right panels). UV exposure is indicated by +. (C) Fluorescence confocal microscopy images show co-localization of SRSF1 (labeled in green by immunofluorescence) and sense RNA foci (labeled in red using Fluorescence In Situ Hybridization) in motor neurons from post-mortem spinal cord tissues of two human C9ORF72-ALS cases. Nuclei are stained in blue by DAPI. Scale bar: 3 µm;

FIGS. 26A-26B: Generation of synthetic constructs expressing DPRs independently of RAN-translation and G4C2 repeat hexanucleotides. (A) Nucleotide sequence encoding poly-Gly-Pro ×36 DPRs; SEQ ID NO: 42. (B) Nucleotide sequence encoding poly-Gly-Ala ×36 DPRs; SEQ ID NO: 43. The DPR sequence is highlighted in blue. The ATG start codon is highlighted in red while the TAA stop codon is highlighted in bold. A V5-tag is also present and highlighted in green.

FIGS. 27A-27B: Partial loss of sbr/NXF1 restore locomotor deficits in G4C2×36 expressing flies. Neuronal expression of G4C2×36 causes larval crawling (A) and adult climbing (B) deficits that are both restored by sbr depletion (mean±95% Cl normalized to Control; N (larvae)=10; N (adults)=Control (GAL4/luciferase-RNAi): 105, G4C2×36+ Ctrl-RNAi: 70, G4C2×36+sbr-RNAi: 72);

Figure 3:
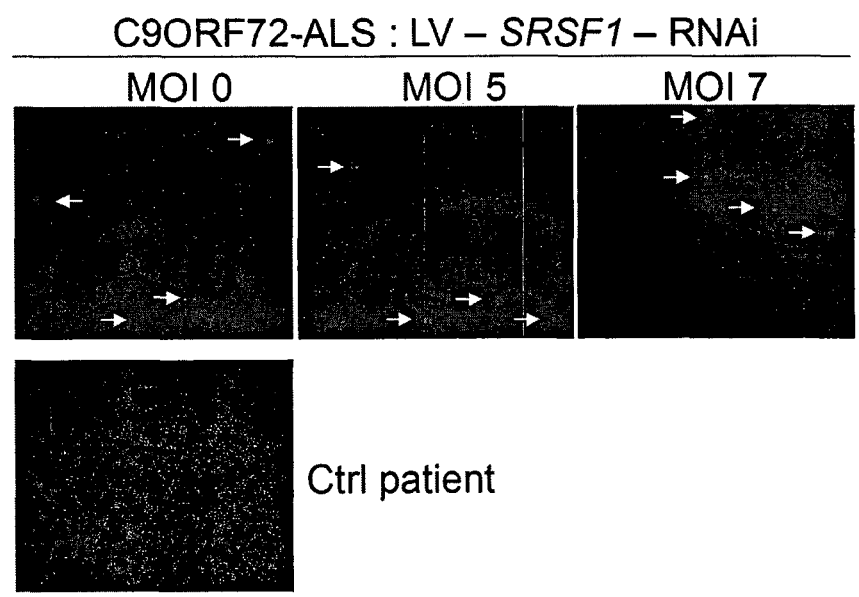
FIG. 3: Depletion of SRSF1 leads to cytoplasmic reduction and nuclear accumulation of sense RNA foci. Representative images of sense RNA foci visualized using Cy3-CCCCGG Fluorescence In Situ Hybridization (red) by confocal microscopy in untransduced/transduced i-Astrocytes. The nuclei were stained in blue using DAPI. Arrows point to RNA foci. Cells with detectable RNA foci represent approximately 15-40% of the cell population depending on the individual patient-derived iAstrocyte line. Quantification was performed on 20-25 cells containing RNA foci (see Additional Data table 1 and table 4 for individual counts and FIG. 10E for bar chart)
Figure 6B:
Figure 6C:
Figure 6D:
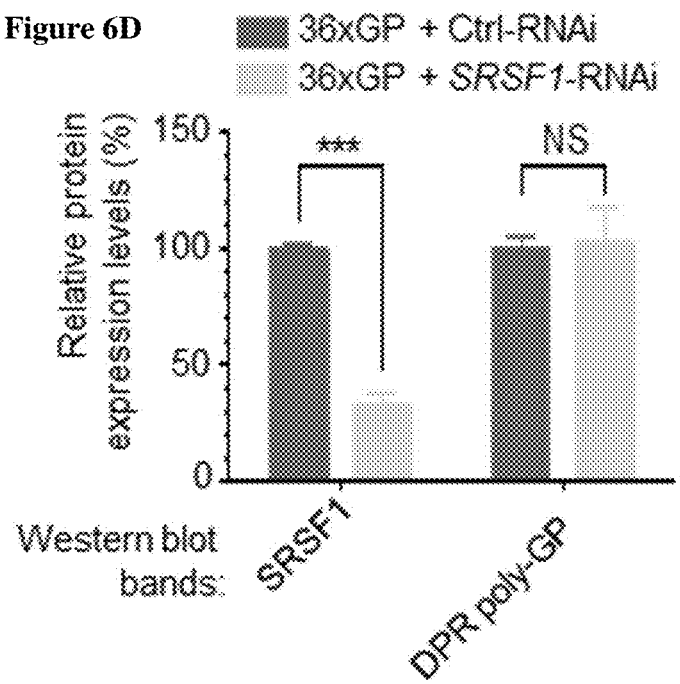
Figure 6E:
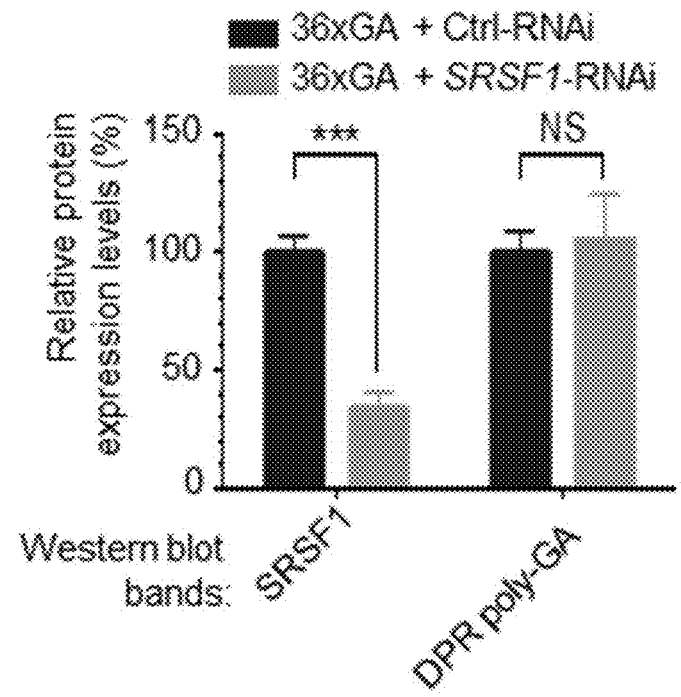
Figure 6F:
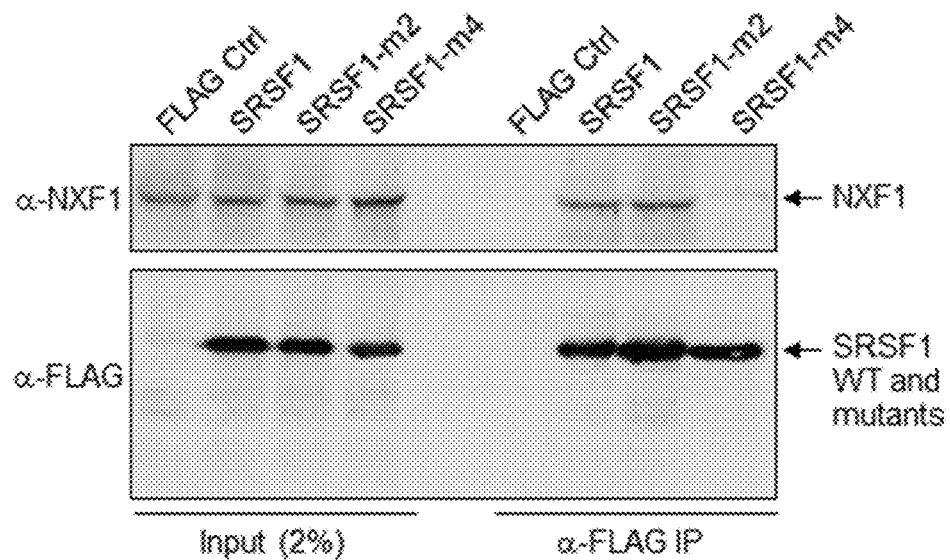
Figure 32:
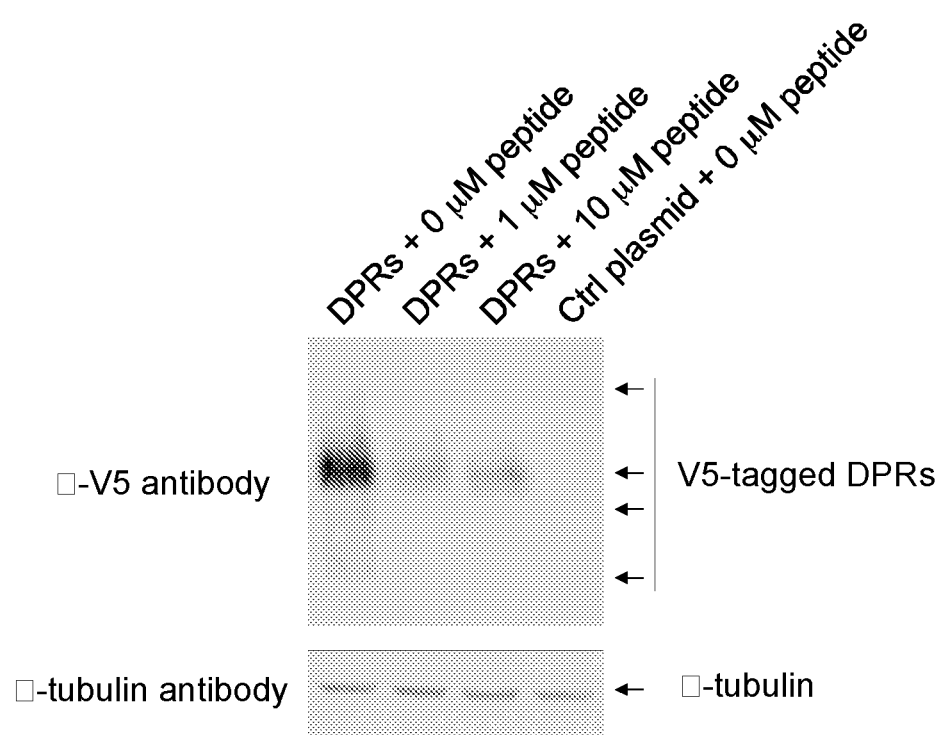

(A) N2A cells co-transfected with G4C2×38 and either Ctrl or SRSF1-RNAi plasmids (left part) and either FLAG-tagged SRSF1 aa11-196 wild type (SRSF1) or SRSF1-m4 (right part) were subjected to cellular fractionation using hypotonic lysis to yield cytoplasmic fractions (FIG. 6e). Total and cytoplasmic G4C2-repeat sense transcript levels were normalized to U1 snRNA levels in triplicate experiments (mean±SEM; one-way ANOVA; N (qRT-PCR reactions)=6). (B) Drosophila expressing G4C2×36 and either control (Ctrl)-RNAi or SRSF1-RNAi. Whole flies were subjected to cellular fractionation using hypotonic lysis to yield cytoplasmic fractions (FIG. 6g). Total cytoplasmic G4C2-repeat sense transcript levels were normalized to Tub84b levels in triplicate experiments (mean±SEM; paired t-test; N (qRT-PCR reactions)=3);

FIG. 29 Transcript sequence. Boxes represent the HindIII (AAGCTT) and XhoI (CTCGAG) cloning sites used to clone the G4C2×38 annealed oligonucleotides (FIG. 3). A synthetic construct encoding for the 3×V5 tags (sequences highlighted in orange, green and violet) with 3 stop codons (TAA, underlined/bold) were cloned in a second step using the NotI (GCGGCCGC) and XbaI (TCTAGA) sites. The RNA transcript generated from this construct is highlighted in blue (flanking regions) and red (38 G4C2-sense repeats) and orange, green and violet (3×V5 tags). Sequences highlighted in black/underlined correspond to the 3'end of the promoter sequence and in black/italics to the start of the terminator sequence. Note the absence of initiating codons (ATG) in the transcript generated from the RAN-dependent DPR-expression construct. Sequencing and size analysis further showed that the number of repeats remained stable over multiple rounds of transformation and replication in NEB® 10-beta E. coli (New England Biolabs);

FIG. 30 iNPC-differentiation of neurons derived from patient fibroblasts. Tuj1 immunofluorescence microscopy was performed on neurons differentiated from induced-Neural Progenitor Cells (iNPCs) derived from control (Ctrl-pat154) or C9ORF72-ALS (C9-ALS-pat78) patient fibroblasts using the red channel. DAPI was used to stain nuclei in blue;

FIG. 31 Evaluating the efficiency of lentiviral-mediated SRSF1-RNAi depletion in iNeurons derived from control and C9ORF72-ALS patients. SRSF1 transcript levels were quantified in transfected HEK cells and iAstrocytes transduced with increased MOI doses of LV-SRSF1-RNAi. snRNA U1 transcript levels were used for normalization in two control (pat154, pat 155) or C9-ALS (pat78, pat183) cell lines in duplicates (mean±SEM; two-way ANOVA; N (qPCR reactions)=8); and FIG. 32 An SRSF1 inhibitory cell permeable peptide inhibits the production of DPRs expressed in a disease relevant RAN-dependent manner in human HEK cells transfected with a G4C2×38 repeat construct that expresses 3×V5 tags in all frames. Sequence of the peptide: PRSGRGT-GRGGGGGGGGGGAPRGRYGPPSRRSE GG GKPIPN-PLLGLDST GG YGRKKRRQRRR (SEQ ID NO: 153).

TABLE 1

|  | MOI = 0 | | | MOI = 5 | | | MOI = 7 | | |
| --- | --- | --- | --- | --- | --- | --- | --- | --- | --- |
|  | C9 Pat. 78 | C9 Pat. 183 | C9 Pat. 201 | C9 Pat. 78 | C9 Pat. 183 | C9 Pat. 201 | C9 Pat. 78 | C9 Pat. 183 | C9 Pat. 201 |
| RNA Foci/cell | | | | | | | | | |
| Nuclear RNA foci | 0.86 | 0.95 | 0.88 | 1.20 | 1.08 | 1.48 | 1.82 | 1.68 | 1.95 |
| Cyto RNA foci | 0.71 | 0.71 | 0.58 | 0.35 | 0.50 | 0.35 | 0.23 | 0.27 | 0.23 |
| SEM | | | | | | | | | |
| Nuclear RNA foci | 0.14 | 0.18 | 0.15 | 0.17 | 0.18 | 0.18 | 0.20 | 0.26 | 0.23 |
| Cyto RNA foci | 0.16 | 0.12 | 0.13 | 0.13 | 0.13 | 0.10 | 0.09 | 0.10 | 0.09 |

TABLE 2

Examples of human SRSF1 miRNA sequences
These involve expression of pre-miRNA cassettes
which are processed in the cell using the
physiological RNAi machinery (Dicer cleavage to
generate-22 nucleotides mature miRNA and incorporation into RISC (RNA-induced silencing complex).
10 sequences of human SRSF1 mRNA targeted
by mature miRNA:

| SEQ ID NO | miRNA number | SRSF1 region | Start | 21nt SRSF1 sequence target (5'-3') |
| --- | --- | --- | --- | --- |
| 5 | 1 | RRM2 | 767 | AACTGCCTACATCCGGGTTAA |
| 6 | 2 | RRM2 | 784 | TTAAAGTTGATGGGCCCAGAA |
| 7 | 3 | RRM2 | 795 | GGGCCCAGAAGTCCAAGTTAT |
| 8 | 4 | RS domain | 900 | AGCAGAGGATCACCACGCTAT |
| 9 | 5 | 3'UTR | 1422 | TCAATAATGGAGGCAATGGTA |
| 10 | 6 | 3'UTR | 1436 | AATGGTATGACTCCAAGTGCT |

TABLE 2 -continued

Examples of human SRSF1 miRNA sequences
These involve expression of pre-miRNA cassettes which are processed in the cell using the physiological RNAi machinery (Dicer cleavage to generate-22 nucleotides mature miRNA and incorporation into RISC (RNA-induced silencing complex).
10 sequences of human SRSF1 mRNA targeted by mature miRNA:

| SEQ ID NO | miRNA number | SRSF1 region | Start | 21nt SRSF1 sequence target (5'-3') |
|---|---|---|---|---|
| 11 | 7 | 3'UTR | 1695 | GCTAATTTGTCACAGTGCTTA |
| 12 | 8 | 3'UTR | 1725 | GTTAATGTGTGACCTGCTGTT |
| 13 | 9 | 3'UTR | 1804 | ACTGCTAAATCTGCATGTCCT |
| 14 | 10 | 3'UTR | 1834 | TGATAGAGCGTTGCTATTTCA |

RRM2: RNA recognition motif 2;
RS: Arginine-Serine rich;
3'UTR: 3' untranslated region

TABLE 3

Examples of mouse SRSF1 miRNA sequences
10 sequences of mouse SRSF1 mRNA targeted by mature miRNA:

| SEQ ID NO | miRNA number | SRSF1 region | Start | 21nt SRSF1 sequence target (5'-3') |
|---|---|---|---|---|
| 5 | 1 | RRM2 | 656 | AACTGCCTACATCCGGGTTAA |
| 6 | 2 | RRM2 | 673 | TTAAAGTTGATGGGCCCAGAA |
| 49 | 3 | RRM2 | 684 | GGGCCCAGAAGTCCAAGTTAT |
| 7 | 4 | RS domain | 789 | AGCAGAGGATCACCACGCTAT |
| 51 | 5 | 3'UTR | 1105 | AATGTCTATTCTGCTCTGGTT |
| 52 | 6 | 3'UTR | 1843 | AAATTGCAGATGGGAGCAATA |
| 53 | 7 | 3'UTR | 1846 | TTGCAGATGGGAGCAATAGTT |
| 54 | 8 | 3'UTR | 1853 | TGGGAGCAATAGTTTAGGTTT |
| 55 | 9 | 3'UTR | 1866 | TTAGGTTTAGGTGGGTAGTAA |
| 56 | 10 | 3'UTR | 1867 | TAGGTTTAGGTGGGTAGTAAT |

RRM2: RNA recognition motif 2;
RS: Arginine-Serine rich;
3'UTR: 3' untranslated region

TABLE 4

Number and cellular distribution of G4C2 RNA foci in iNPCs-derived astrocytes treated with increasing MOI of LV-SRSF1-RNAi

| | iAstrocytes C9ORF72-ALS Patient 78 | | | | | | iAstrocytes C9ORF72-ALS Patient 183 | | | | | | iAstrocytes C9ORF72-ALS Patient 201 | | | | | |
|---|---|---|---|---|---|---|---|---|---|---|---|---|---|---|---|---|---|---|
| | SRSF1-RNAi MOI | | | | | | | | | | | | | | | | | |
| | 0 | | 5 | | 7 | | 0 | | 5 | | 7 | | 0 | | 5 | | 7 | |
| | Foci | | | | | | | | | | | | | | | | | |
| | Nuc | Cyto | Nuc | Cyto | Nuc | Cyto | Nuc | Cyto | Nuc | Cyto | Nuc | Cyto | Nuc | Cyto | Nuc | Nuc | Nuc | Cyto |
| Raw counts | 1 | 0 | 0 | 1 | 2 | 1 | 0 | 1 | 1 | 0 | 1 | 0 | 1 | 0 | 1 | 0 | 4 | 1 |
| | 2 | 0 | 1 | 0 | 1 | 0 | 2 | 0 | 1 | 0 | 1 | 0 | 2 | 0 | 1 | 0 | 2 | 1 |
| | 1 | 0 | 2 | 0 | 1 | 0 | 1 | 0 | 1 | 0 | 1 | 0 | 1 | 0 | 2 | 0 | 4 | 0 |
| | 1 | 1 | 0 | 2 | 2 | 0 | 1 | 0 | 0 | 1 | 2 | 1 | 1 | 0 | 1 | 0 | 1 | 1 |
| | 1 | 0 | 1 | 0 | 1 | 0 | 1 | 1 | 0 | 1 | 1 | 1 | 1 | 3 | 1 | 3 | 3 | 0 |
| | 0 | 2 | 1 | 0 | 2 | 1 | 0 | 1 | 3 | 0 | 1 | 0 | 3 | 1 | 1 | 0 | 1 | 0 |
| | 0 | 1 | 1 | 0 | 3 | 0 | 1 | 1 | 2 | 0 | 1 | 0 | 2 | 0 | 2 | 0 | 2 | 0 |
| | 0 | 1 | 1 | 0 | 2 | 0 | 1 | 1 | 3 | 0 | 1 | 0 | 0 | 1 | 2 | 0 | 1 | 0 |
| | 0 | 1 | 2 | 0 | 1 | 0 | 2 | 0 | 1 | 2 | 1 | 0 | 1 | 0 | 1 | 0 | 3 | 0 |
| | 1 | 0 | 1 | 0 | 1 | 0 | 0 | 1 | 0 | 1 | 3 | 0 | 1 | 0 | 1 | 1 | 3 | 0 |
| | 1 | 1 | 2 | 0 | 4 | 1 | 0 | 1 | 0 | 1 | 1 | 1 | 1 | 1 | 0 | 1 | 2 | 0 |
| | 1 | 1 | 1 | 0 | 1 | 0 | 1 | 0 | 1 | 0 | 1 | 0 | 1 | 1 | 1 | 3 | 0 | |
| | 2 | 0 | 3 | 1 | 2 | 0 | 1 | 0 | 5 | 1 | 0 | 2 | 2 | 0 | 1 | 0 | | |
| | 1 | 2 | 2 | 0 | 1 | 0 | 0 | 1 | 1 | 2 | 4 | 1 | 1 | 0 | 1 | 0 | 2 | 0 |
| | 0 | 1 | 1 | 0 | 3 | 0 | 2 | 1 | 0 | 1 | 2 | 0 | 1 | 2 | 2 | 1 | 1 | 0 |
| | 1 | 0 | 1 | 1 | 4 | 1 | 1 | 2 | 1 | 1 | 0 | 0 | 1 | 1 | 0 | 3 | 1 | |
| | 1 | 0 | 1 | 0 | 1 | 0 | 1 | 1 | 3 | 0 | 1 | 0 | 0 | 1 | 1 | 0 | | |
| | 0 | 2 | 0 | 1 | 1 | 0 | 1 | 0 | 1 | 0 | 1 | 0 | 2 | 0 | 1 | 0 | | |
| | 2 | 1 | 1 | 0 | 2 | 0 | 1 | 0 | 3 | 1 | 1 | 0 | 1 | 1 | 2 | 0 | | |
| | 1 | 0 | 2 | 1 | 1 | 0 | 1 | 1 | 0 | 2 | 0 | 0 | 1 | 1 | 2 | 0 | | |
| | 1 | 1 | | | 2 | 0 | 3 | 1 | 0 | 1 | 0 | 1 | 0 | 1 | 0 | 1 | 0 | |
| | | | | | 2 | 1 | | | 0 | 1 | 0 | 1 | 0 | 1 | 4 | 1 | | |
| | | | | | | | | | 0 | 1 | | | 0 | 1 | | | | |
| | | | | | | | | | 3 | 1 | | | 0 | 1 | | | | |
| Average | 0.857 | 0.714 | 1.200 | 0.350 | 1.818 | 0.227 | 0.952 | 0.714 | 1.083 | 0.500 | 1.682 | 0.273 | 0.875 | 0.583 | 1.478 | 0.348 | 1.955 | 0.227 |
| S.E.M. | 0.143 | 0.156 | 0.172 | 0.131 | 0.204 | 0.091 | 0.176 | 0.122 | 0.180 | 0.135 | 0.258 | 0.097 | 0.151 | 0.133 | 0.176 | 0.102 | 0.232 | 0.091 |

Nuc = Nuclear;
Cyto = Cytoplasmic

TABLE 5

List and characteristics of patient-derived cells used in this study.

| Patient Sample | Ethnicity | Gender | Cell type | Age at biopsy collection |
|---|---|---|---|---|
| 78 | Caucasian | Male | C9ORF72 | 66 |
| 183 | Caucasian | Male | C9ORF72 | 49 |
| 201 | Caucasian | Female | C9ORF72 | 66 |
| 154 | Caucasian | Female | Control | 55 |
| 155 | Caucasian | Male | Control | 40 |
| 209 | Caucasian | Female | Control | 69 |

TABLE 6

Examples of shRNAs that target human SRSF1 (NM_006924.4)

| SEQ ID NO | shRNA number | SRSF1 regionStart | | 21nt SRSF1 sequence target (5'-3') |
|---|---|---|---|---|
| 47 | 1 | 5'UTR | 25 | GGGATCGAATCGCTGTTTCCT |
| 48 | 2 | 5'UTR | 26 | GCTGTTTCCTTCCGCTTCTCT |
| 50 | 3 | ORF | 657 | GCTGATGTTTACCGAGATGGC |
| 99 | 4 | ORF | 689 | GGAGTTTGTACGGAAAGAAGA |
| 154 | 5 | ORF | 700 | GGAAAGAAGATATGACCTATG |
| 155 | 6 | ORF | 760 | AGGGAGAAACTGCCTACATCC |
| 156 | 7 | 3'UTR | 1673 | GGGACTAATGTGGGAAGAACT |
| 157 | 8 | 3'UTR | 2084 | GCAACCACGAAACCTGTAATA |
| 158 | 9 | 3'UTR | 2470 | GGGATCAGATTACCAGGAACA |
| 60 | 10 | 3'UTR | 3120 | GCATCTGAAAGATAAGCTTCT |

Materials and Methods

*Drosophila* Inducible Short-Hairpin RNAi Lines.

Lines (UAS-RNAi) were obtained from the Vienna *Drosophila* Resource Centre: http://stockcenter.vdrc.at/contro/main

```
SRSF1 (SF2/ASF)-RNAi lines:
v27775: FlyBase ID = FBst0457117
v27776: FlyBase ID = FBst0457118
Independent insertion lines, both lines carry the following inverted
repeat sequence:
                                                      (SEQ ID NO 57)
ATGCCGACGA TGCGGTGAAG GCGCGCGACG GCTACGACTA CGATGGGTAT

CGTCTGCGCG TGGAGTTCCC GCGGGGCGGT GGTCCTGGAA GCTACCGCGG

CGGCAACCGC AATGACCGAA GCCGCGACGG TGGGGACGG ATGGGCGGAC

GCGGACCGCC AGCCAAGCGC TCGCAGTACC GCGTCATGGT TACTGGACTG

CCCGCCTCCG GATCGTGGCA AGATCTCAAG GATCACATGC GCGAGGCCGG

CGACGTCTGC TTCGCGGACA CTTACAAGGA TGGTTCCGGC GTCGTTGAGT

TCCTGCGCCA CGAGGACATG AAGTACGCAA TCAAAAAATT GGACGACTCT

CGCTTCCGA

ALYREF (Ref1)-RNAi lines:
v12301 (GD): FlyBase ID = FBst0450381-the line carry the following
inverted repeat sequence
                                                      (SEQ ID NO 58)
GGTCCGATAA AGAAGGCGGC AGTGCACTAC GATCGCTCCG GTCGCTCGTT

GGGCACCGCT GACGTGATTT TCGAACGTCG CGCCGACGCC TTGAAGGCCA

TTAAACAGTA CCATGGCGTA CCTTTGGACG GACGCCCTAT GACCATTCAG

CTGGCCGTCT CAGACGTGGC CGTGTTGACC CGTCCCGTAG CCGCCACCGA

TGTCAAGCGT CGCGTGGGTG GTACTGCACC AACTTCATTC AAGCGTGGTG

GTGGCCAAGC TGGTGGCACG GCGCGTCGCG GCTTCAAACG TCCGGTCGGT

GGCAAGCCGG CGGCAGGCGG CCAGCGACGG GAGCGCAAGG CCCCGCCCAC

TGCTGAGGAG CTGGACGCCG AACTGGACTC A v104471 (KK): FlyBase ID = FBst0476329-the line carry the following
inverted repeat sequence
                                                      (SEQ ID NO 59)
GTCGAACTTG ATAAAGCGCA TTTCTAAATA CAATAAATAC AGCATCAAAT

GTATTTCAGT TATCTTAACA TCCGCCGCAT GGCAAAACT AACAATTAAT
```

```
                          -continued
GGATAAATGC GCAAGTGGTT GATTGATTTG ATGTCCGATG CTTTCAAAGA

TCTGCTCCTG GGCGCGGCGT TGTCGATGCG TTTGCATTTA TGTACCATGC

GGGGGGTGTC CATATGGTAG GCTTAAAACT ATAGATTGGG CTGCTCTTCT

ATTCTTGTTA GACTAATTCA GACTATTCAC TATTTAGATC TTCATGTCGT

TGATGTATGA GTCCAGTTCG GCGT
```

AAV Vectors

Suitable AAV vectors are self-complementary scAAV and AAV vectors of varied serotypes (for examples, serotypes 2, 5, 6, 9 and AAV9 derivatives such as AAV-PHP.A and AAV-PHP. Further alternatives are AAV9: (Valori et al. Sci Transl Med. 2010; 2:35ra42) and AAV-PHP-A and B) Deverman et al. Nature Biotech 2016: 34:204-9) (see also FIG. 19)

Promoter Elements for Driving Expression of the SRSF1 Antagonists:

SRSF1-RNAi cassettes would be driven using H1 or U6 promoters; Expression of SRSF1 proteins or peptides using CBA, CAG, PGK, EFS1a or CMV; further examples are listed in FIG. 18.

Drosophila Husbandry and Locomotor Assays

Drosophila were raised under standard conditions on food consisting of agar, cornmeal, molasses and yeast unless otherwise stated. All C9orf72 related transgenic lines (14) were a gift from Adrian Isaacs and Linda Partridge (University College London). GMR-GAL4 (#1104), D42-GAL4 (#8816), nSyb-GAL4 (#51635) da-GAL4, UAS-sbr-RNAi [P{TRiP.HM05135}attP2] and UAS-luciferase-RNAi (#31603), used as the control RNAi, were obtained from the Bloomington Drosophila Stock Centre (Bloomington, Ind.).

Eye phenotypes were analyzed by induction of transgene expression by GMR-GAL4 raised at 25° C. For larval crawling assays, transgenes were expressed by nSyb-GAL4 and animals were grown at 29° C. Wandering third instar larvae were collected from vials, briefly rinsed with distilled water, and placed in petri dishes with a 1% agarose matrix. Larvae were observed directly for 2 minutes and the number of peristaltic waves recorded.

Climbing assays were performed as previously described (32) with transgenic expression induced by D42-GAL4. Crosses were started at 25° C. for 3 days and transferred to 29° C. for a further 7 days. Adult flies were tested 1-3 days after eclosion.

For all the experiments only male flies were used. Drosophila were housed in 12:12 light:dark cycle.

Drosophila Light Microscopy Imaging and Scanning Electron Microscopy

For light microscopy of Drosophila eyes, stacks of images were collected on a Nikon motorized SMZ stereo zoom microscope fitted with 1× Apo lens. Extended focus images were then generated using Nikon Elements software. Scanning electron microscopy (SEM) was performed according to a standard protocol (33) and images were captured using a Philips XL-20 SEM microscope. All animals of a given genotype displayed essentially identical phenotypes and randomly selected representative images are shown.

Plasmids

The FLAG-tagged SRSF1/SF2/ASF plasmids were generated as in reference (23) by cloning of a full-length human SRSF1/SF2/ASF PCR fragment into p3×FLAG-myc-CMV26 (Sigma).

miRNA oligonucleotide sequences were designed using the "miR RNAi" Block-IT RNAi designer tool (Thermo-Fisher).

Two miRNA hairpins were designed against human SRSF1 (GenBank: NM_006924.4, mRNA) and mouse SRSF1 (GenBank: BC046773.1, mRNA NCBI Reference Sequence: NM_173374.4, ) and rat SRSF1 (NCBI Reference Sequence: NM_001109552.2, mRNA). The SRSF1 sequence targeted by miRNA hairpin 1 is identical in human, mouse and rat SRSF1. The bold regions in sequences below represent the mature miR RNAi sequences which targets the complementary sense sequences on SRSF1 (italics):

Targeted human and mouse and rat SRSF1 miR1 sequence (TTAAAGTTGATGGGCCCAGAA; SEQ ID NO 6) starts at 784 nt (NCBI RefSeq NM_006924.4—RRM2 region), and 673 nt respectively (RRM2 region), 1,041 nt (NCBI RefSeq NM_173374.4—RRM2 region) and 699 nt (NCBI RefSeq: NM_001109552.2—RRM2 region):

```
human/mouse SRSF1-miR1-Top strand
                                          (SEQ ID NO 61)
5'-TGCTGTTCTGGGCCCATCAACTTTAAGTTTTGGCCACTGACTGACTT

AAAGTTTGGGCCCAGAA-3' human/mouse/rat SRSF1-miR1-Bottom strand:
                                          (SEQ ID NO 62)
5'-CCTGTTCTGGGCCCAAACTTTAAGTCAGTCAGTGGCCAAAAC

TTAAAGTTGATGGGCCCAGAAC-3'

Targeted human SRSF1 miR2 sequence
                                          (SEQ ID NO 10)
(AATGGTATGACTCCAAGTGCT)
starts at 1436 nt (3'UTR region):

human SRSF1-miR2-Top strand:
                                          (SEQ ID NO 63)
5'-TGCTGAGCACTTGGAGTCATACCATTGTTTTGGCCACTGACT

GACAATGGTATCTCCAAGTGCT-3' human SRSF1-miR2-Bottom strand:
                                          (SEQ ID NO 64)
5'-CCTGAGCACTTGGAGATACCATTGTCAGTCAGTGGCCAAAAC

AATGGTATGACTCCAAGTGCTC-3'

Targeted mouse SRSF1 miR2 sequence
                                          (SEQ ID NO 65)
(AATGTCTATTCTGCTCTGGTT)
starts at 1,105 nt (3'UTR region):

Targeted mouse SRSF1 miR2 sequence
                                          (SEQ ID NO 66)
(AATGTCTATTCTGCTCTGGTT)
starts at 1,473 nt
(NCBI RefSeq NM_173374.4-3'UTR region):

mouse SRSF1-miR2-Top strand:
                                          (SEQ ID NO 67)
5'-TGCTGAACCAGAGCAGAATAGACATTGTTTTGGCCACTGACT

GACAATGTCTACTGCTCTGGTT-3'
```

```
mouse SRSF1-miR2-Bottom strand:
                                        (SEQ ID NO 68)
5'-CCTGAACCAGAGCAGTAGACATTGTCAGTCAGTGGCCAAAAC
AATGTCTATTCTGCTCTGGTTC-3'
```

Figure 1A:
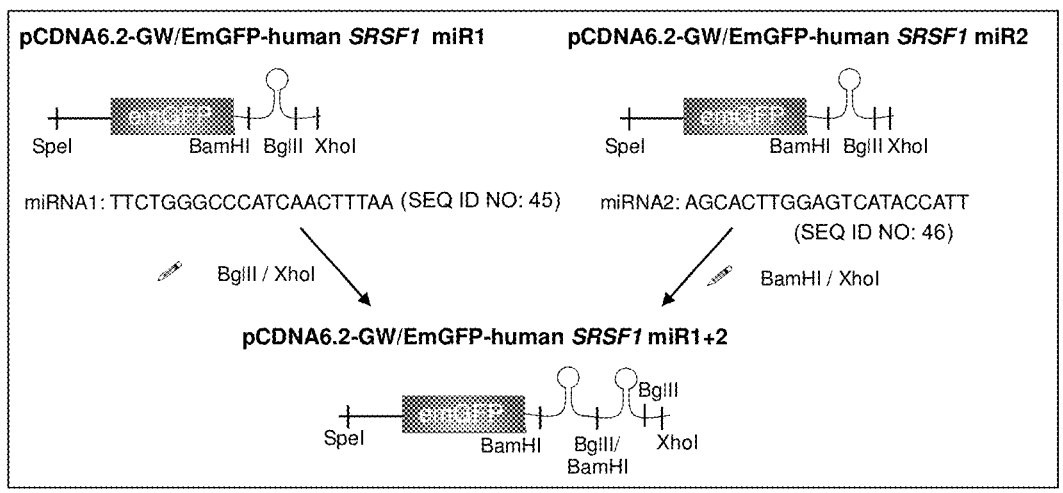
FIGS. 1A-1B: Engineering human SRSF1-RNAi depletion vectors. (A) Diagrams of pCDNA6.2-GW/EmGFP-SRSF1 miR1, EmGFP-SRSF1 miR2 and EmGFP-SRSF1 miR1+2. The pCDNA6.2-GW/EmGFP-SRSF1 miR1 and EmGFP-SRSF1 miR2 were built separately using the BLOCK-iT Pol II miR RNAi Expression Vector Kit with EmGFP (see online methods). The human SRSF1 pre-miR2 RNAi cassette was then chained by subcloning the BamHI/XhoI-cut fragment into the BGlII and XhoI sites of pcDNA6.2 GW/EmGFP-human SRSF1 miR1. miR1 shown in SEQ ID NO: 45, miR2 shown in SEQ ID NO: 46. (B) Plasmid diagram of EmGFP-human SRSF1 miR1+2 cloned into the self-inactivating lentiviral (SIN-W-PGK) vector using the restriction sites SpeI and XhoI.
Figure 1B:
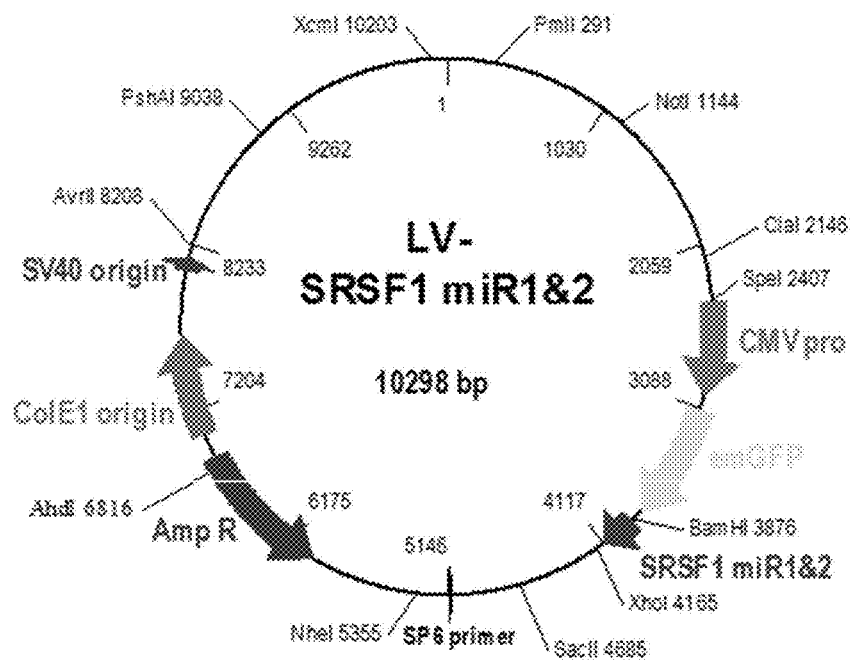
Figure 5:
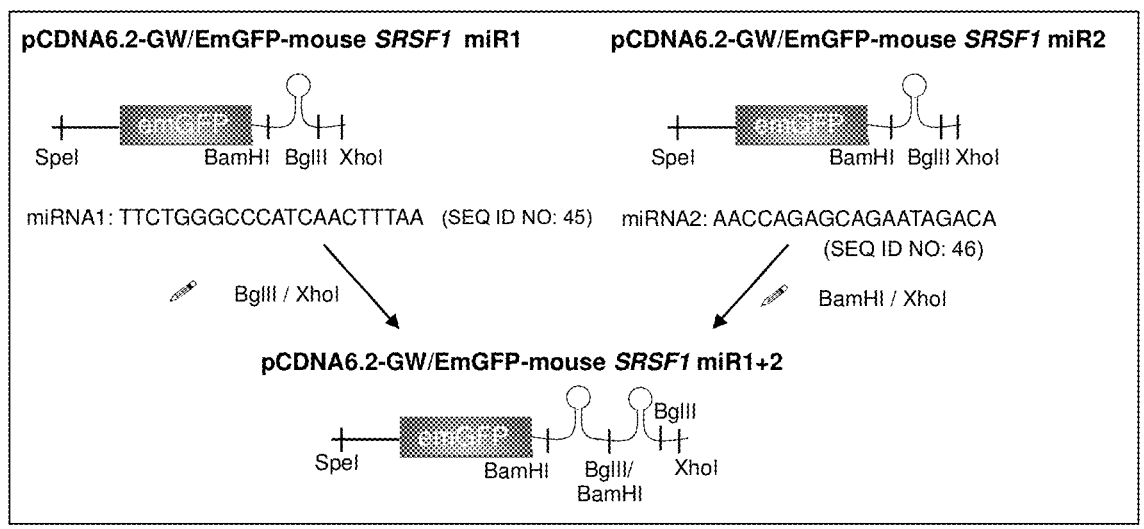
FIG. 5: Engineering mouse SRSF1-RNAi depletion vectors. Diagrams of the mouse EmGFP-SRSF1 miR1, EmGFP-SRSF1 miR2 and EmGFP-SRSF1 miR1+2. The pCDNA6.2-GW/EmGFP-SRSF1 miR1 and EmGFP-SRSF1 miR2 were built separately using the BLOCK-iT Pol II miR RNAi Expression Vector Kit with EmGFP (see online methods). The mouse SRSF1 pre-miR2 RNAi cassette was then chained by subcloning the BamHI/XhoI-cut fragment into the BGIII and XhoI sites of pcDNA6.2 GW/EmGFP-mouse SRSF1 miR1.

Synthesised oligonucleotides (Sigma) were annealed and ligated into pcDNA6.2 GW/EmGFP using the BLOCK-iT Pol II miR RNAi Expression Vector Kit with EmGFP (ThermoFisher, catalogue number K4936-00). Furthermore, the pre-miR2 RNAi cassettes were each chained by sub-cloning BamHI/XhoI-cut fragments into the BGlII and XhoI sites of pcDNA6.2 GW/EmGFP-SRSF1 miR1. The PCR fragments encompassing EmGFP and the chained SRSF1 pre-miRNA cassette were additionally cloned into the lentiviral expression plasmid SIN-PGK-cPPT-GDNF-WHV(9) (5) using the restriction enzymes SpeI and XhoI. Restriction of the SIN-PGK-cPPT-GDNF-WHV(9) by SpeI/XhoI allows removal of the GDNF insert and cloning of the human or mouse EmGFP-SRSF1 RNAi cassette (FIGS. 1 and 5).

Uninterrupted hexanucleotide sense GGGGCCx38 (SEQ ID NO 69) and antisense CCCCGGx39 (SEQ ID NO 70) C9ORF72 repeats were built using the synthetic oligonucleotides 5'-(GGGGCC)$_{15}$-3' and 5'-CCCC-(GGCCCC)$_{14}$-GG-3' (SEQ ID NO 71). Oligonucleotides were annealed by heating to 99° C. for 30 minutes and cooling 0.5° C./min to ambient with incubation at 70° C. for 10 minutes. Oligonucleotides were phosphorylated with T4-Polynucleotide Kinase (New England Biolabs), ligated using T4 DNA Ligase (ThermoFisher) and treated with Mung Bean nuclease (New England Biolabs) for blunt ligation. Oligomeric forms of annealed oligonucleotides were confirmed following analysis on agarose gel (FIG. 4). The band corresponding to trimeric oligonucleotides was then excised, gel purified and ligated into pcDNA3.1 (Invitrogen) with blunted EcoRI ends to allow cloning in both sense and antisense orientation. Sequences are presented in FIG. 4.

Synthetic sequences encoding poly-Gly-Pro and poly-Gly-Ala x36 DPRs independently of G4C2 repeats were first cloned into pcDNA3.1 (Invitrogen) using the EcoRI and NotI sites. Synthetic sequences encoding poly-Gly-Pro and poly-Gly-Ala x36 were then subcloned using BamHI/NotI into pCI-neo-V5-N using BclII/NotI. BclII restriction site was previously introduced into pCI-neo-V5-N by site directed mutagenesis using forward actctagaggtaccacgtgatcattctcgagggtgctatccaggc (SEQ ID NO 72) and reverse gcctggatagcaccctcgagaatgatcacgtggtacctctagagt (SEQ ID NO: 73) primers (QuikChange Lightning Site-Directed Mutagenesis Kit, Agilent).

Lentivirus Production

The miRNA construct was sub-cloned into a self-inactivating lentiviral (SIN-W-PGK) vector using standard cloning methods. Lentiviruses were propagated in HEK293T cells using calcium phosphate transfection (34). 13 µg pCMVΔR8.92, 3.75 µg pM2G, 3 µg pRSV and 13 µg SIN-CMV-miRNA were transfected into HEK293T cells. Twenty 10 cm dishes seeded with 3×10$^6$ HEK293T cells/dish were each transfected with 13 µg pCMVΔR8.92, 3.75 µg pM2G, 3 µg pRSV and 13 µg SIN-CMV-miRNA using calcium phosphate transfection[41] Cells were allowed to produce virus for 72 hours, then the supernatant was collected, filtered using a 0.45 µm filter and centrifuged at 24,000 rpm for 90 minutes at 4° C. The supernatant was discarded and the viral pellet was resuspended in 1% BSA in PBS and stored at −80'C. The biological titre of the viral vector was determined by transducing HeLa cells with $10^{-2}$, $10^{-3}$ and $10^{-4}$ dilutions of the vector. 72 hours post transduction cells were fixed in 4% paraformaldehyde, washed in PBS, and the percentage of GFP positive cells was measured with a Fluorescent-Activated cell sorter (FACS, LSRII). The biological titer is expressed as the number of transducing units per mL (TU/ml) and can be calculated with the following formula: Vector titer=[(% positive cells×number of cells during transduction)×dilution factor×2] TU/ml.

Tissue Culture and Transfection or Transduction

HEK293T cells were cultured in Dulbecco's Modified Eagle Medium (Sigma) supplemented with 10% fetal bovine serum [FBS] (Gibco) and 5 U/ml Penstrep (Lonza). Cells were maintained in a 37° C. incubator with 5% $CO_2$. For qRT-PCR analysis 50,000 HEK cells were split into each well of 24-well plates and transfected for 72 h with 700 ng pcDNA6.2-GW/EmGFP-Control or human SRSF1 miR RNAi constructs using 3.5 µg PEI/ml media and one tenth medium volume OptiMEM (ThermoFisher). For Western blot analysis, HEK cells were transfected for 72 h with 650 ng pcDNA6.2-GW/EmGFP-Control miRNA, pCDNA6.2-GW/EmGFP-human SRSF1 miR1+2 RNAi or LV-EmGFP-human SRSF1 miR1+2 RNAi constructs and 50 ng p3×FLAG/human-SRSF1 using 3.5 µg PEI/ml media and one tenth medium volume of OptiMEM.

Neuro-2a (ATCC) cells were cultured in Dulbecco's Modified Eagle Medium (Sigma) supplemented with 10% fetal bovine serum [FBS] (Gibco), 5 U/ml Penstrep (Lonza) and 5 mM sodium pyruvate. Cells were maintained in a 3TC incubator with 5% $CO_2$. 75,000 Neuro-2a cells were split into each well of 24-well plates and transfected for 72 h with 500 ng pcDNA6.2-GW/EmGFP-Control miR RNAi (ThermoFisher) or pcDNA6.2-GW/EmGFP-mouse SRSF1 miR1+2 RNAi and 200 ng pcDNA 3.1/RAN-G4C2×38-sense or RAN-C4G2×39-antisense using 3 µg PEI/1 µg DNA and one tenth medium volume OptiMEM (ThermoFisher).

Hb9GFP mouse stem cells were cultured as previously described (35) and differentiated into motor neurons with 2 µM retinoic acid (Sigma) and 1 µM Smoothened Agonist (SAG) (Millipore) for 5 days. Embryoid bodies were then dissociated with papain and sorted using the FACSAria™ III (BD Biosciences). Cells were maintained in a 3TC incubator with 5% $CO_2$.

Human patient-derived differentiated astrocytes (iAstrocytes) were differentiated from induced Neural Progenitor Cells (iNPCs) as previously described (29) and cultured in DMEM Glutamax (Gibco) with 10% FBS (Sigma) and 0.02% N2 (Invitrogen). Cells were maintained in a 3TC incubator with 5% $CO_2$.

For Hb9GFP+motor neuron and patient-derived iAstrocytres co-cultures, 20,000 induced neural progenitor cells (iNPCs) were plated in 6-well plates in astrocyte medium. The day after plating, iAstrocytes were transduced with adenovirus expressing red fluorescent protein (RFP) since the co-culture experiments were performed using GFP+ motor neurons from Hb9GFP+ mouse stem cells and with lentivirus co-expressing human SRSF1-RNAi and GFP at an MOI of 5, 7 or 10. GFP expression in iAstrocytes was used to monitor transduction efficiency of the SRSF1-RNAi. Cells were maintained in a 3TC incubator with 5% $CO_2$.

For patient-derived cell cultures, informed consent was obtained from all subjects before sample collection (Study number STH16573, Research Ethics Committee reference 12/YH/0330). Human patient-derived differentiated astrocytes (iAstrocytes) were differentiated from induced Neural Progenitor Cells (iNPCs) as previously described 52 and cultured in DMEM Glutamax (Gibco) with 10% FBS (Sigma) and 0.02% N2 (Invitrogen). Cells were maintained in a 3TC incubator with 5% CO2.

Human patient and control-derived neurons (iNeurons) were differentiated from the previously established iNPCs. iNPCs were then differentiated into neurons using a modified version of the protocol described in reference[40]. Briefly, 30,000 iNPCs were plated in a 6-well plate coated with fibronectin (Millipore) and expanded to 70-80% confluence. Once they reached this confluence, iNPC medium was replaced with neuron differentiation medium (DMEM/F-12 with Glutamax supplemented with 1% N2, 2% B27 (Gibco)). On day one of differentiation the cells were treated with 2.5 µM of DAPT (Tocris) to promote differentiation towards neuronal lineage. On day three the neuron differentiation medium is supplemented with 1 µM retinoic acid (Sigma), 0.5 µM Smoothened Agonist (SAG) (Millipore) and 2.5 µM Forskolin (Sigma) for 7 days. This protocol leads to typical yields of 70% µ-III tubulin (Tuj1) positive cells.

To obtain iMotor Neurons, iNeurons were re-plated on fibronectin and cultured in retinoic acid, SAG and Forskolin for 14 more days with addition of BDNF, CNTF and GDNF (all at 20 ng/ml) for the last 10 days of differentiation. For SRSF1 knockdown, cells were transduced with lentivirus expressing control GFP or human SRSF1-RNAi co-expressing GFP at an MOI of 5 at day 14 along with the HB9:RFP adenovirus.

Co-Cultures of Human Patient-Derived iAstrocytes and Mouse or Human Motor Neurons For Hb9GFP motor neuron and patient-derived iAstrocyte co-cultures, 20,000 induced neural progenitor cells (iNPCs) were plated in 6-well plates in astrocyte medium. The day after plating, cells were transduced with lentivirus expressing control GFO or human SRSF1-RNAi at an MOI of 5, 7 or 10. The human SRSF1-RNAi virus also co-expressed GFP to allow evaluation of the transduction efficiency. Since the co-culture experiments were performed using GFP+ motor neurons from Hb9GFP+ mouse stem cells, on the same day cells were also transduced with an adenovirus expressing red fluorescent protein (RFP). Cells were maintained in a 3TC incubator with 5% CO$_2$.

Seven days post-transduction with Ad-RFP and LV-SRSF/-RNAi, iAstrocytes were plated at a density of 10,000 cell/well. The day after, Hb9GFP embryoid bodies were dissociated and sorted for GFP+ cells. 10,000 GFP+ motor neurons were plated onto the astrocytes in motor neuron medium consisting of DMEM/F12, 2% horse serum (Invitrogen), 2% N2, 2% B27 plus GDNF (Invitrogen; 10 ng/ml), BDNF (Invitrogen; 10 ng/ml), CNTF (Invitrogen; 10 ng/ml) and IGF-1 (Invitrogen; 10 ng/ml).

Nine 10× images/well to cover the whole well surface were acquired daily for 3 days using the high content imaging system InCell 2000 (GE Healthcare), gathering data on neuronal cell size and number, axonal length and neurite branching. Data analysis was performed using the InCell Developer software. Data analysis was performed using the Columbus software (PerkinElmer). Data are presented for 3 days of co-culture. The programme designed for co-culture analysis only takes into account GFP+ cells with at least one projection to exclude counts of cell debris. For iMN on iAstrocyte cultures, iAstrocytes were plated in 384-well plates 24 h before plating 1,000 FACS-sorted iMNs. Cultures were maintained for 4 days. Data are presented for 4 days of co-culture.

Cytoplasmic Fractionation

Cytoplasmic fractionation was performed 72 h post-transfection. 300,000 cells from one well of a 6-well plate were removed from the plate using DEPC PBS and pelleted by centrifugation at 800×g for 5 minutes. Cell pellets were quickly washed with hypotonic lysis buffer (10 mM HEPES pH 7.9, 1.5 mM MgCl$_2$, 10 mM KCl, 0.5 mM DTT). Cell pellets were then lysed in hypotonic lysis buffer containing 0.16 U/µL Ribosafe RNase inhibitors (Bioline), 2 mM PMSF (Sigma) and SIGMAFAST™ Protease Inhibitor Cocktail tablets, EDTA free (Sigma) according to manufacturer's instructions. Cells were lysed gently using a cut P1000 tip ensuring no physical force is exerted on the cell pellet. The lysate then underwent differential centrifugation (1500 g, 3 min, 4° C. then 3500 g rpm, 8 min, 4° C. and then 17 000 g, 1 min, 4° C.) transferring the supernatant to a fresh tube after each centrifugation. The supernatant was then added to PureZOL (Biorad) to extract RNA. The nuclear pellet obtained after centrifugation at 1500 g for 3 min was lysed in Reporter lysis buffer (Promega) for 10 minutes on ice before centrifugation at 17000 g, 5 min, 4° C.

Total fractions were collected directly in Reporter lysis buffer (Promega) containing 0.16 U/µL Ribosafe RNase inhibitors (Bioline), 2 mM PMSF (Sigma) and SIGMA-FAST™ Protease Inhibitor Cocktail tablets, EDTA free (Sigma) according to manufacturer's instructions and lysed for 10 min on ice before centrifugation at 17 000 g, 5 min, 4° C. The supernatant was then added to PureZOL (Biorad) to extract RNA.

Equal volumes of total, nuclear and cytoplasmic lysates were resolved using SDS-PAGE, electroblotted onto nitrocellulose membranes and probed using anti-SSRP1 and anti-α-tubulin antibodies (see western blot analysis section below for details on antibodies).

Western Blot Analysis

HEK cells were transfected for 72 h with 650 ng pcDNA6.2-GW/EmGFP-Control miRNA, pCDNA6.2-GW/EmGFP-human SRSF1 miR1+2 RNAi or LV-EmGFP-human SRSF1 miR1+2 RNAi constructs and 50 ng p3×FLAG/human-SRSF1 using 3.5 µg PEI/ml media and one tenth medium volume of OptiMEM. Neuro-2a cells were split into each well of 24-well plates (75,000 cells/well) and transfected for 72 h with 350 ng pcDNA6.2-GW/EmGFP-Control miR RNAi (ThermoFisher), pcDNA6.2-GW/EmGFP-mouse SRSF1 miR1+2 RNAi, p3×FLAG, p3×FLAG/SRSF1 (11-196), p3×FLAG/SRSF1 (11-196)-m2 or p3×FLAG/SRSF1 (11-196)-m4 and 350 ng pcDNA 3.1/RAN-G4C2×38-sense or RAN-C4G2×39-antisense using 3 µg PEI/1 µg DNA and one tenth medium volume OptiMEM.

Proteins were extracted from HEK or Neuro-2a cells 72 hours after transfection. Cells were briefly washed in ice-cold phosphate-buffered saline (PBS) and then scraped into ice-cold lysis buffer (50 mM Hepes pH7.5, 150 mM NaCl, 10% glycerol, 0.5% triton X-100, 1 mM EDTA, 1 mM DTT, protease inhibitor cocktail (Sigma)). Cells were left to lyse on ice for 10 minutes followed by centrifugation at maximum speed at 4° C. for five minutes. Protein extracts were quantified using Bradford Reagent (BioRAD), resolved by SDS-PAGE, electroblotted onto nitrocellulose membrane and probed using the relevant primary antibody. Human/mouse SRSF1/SF2 [1:1000 dilution] (Cell Signaling #8241) and poly-Gly-Pro [1:10,000 dilution] (kindly received from Prof Stuart Pickering Brown) primary antibodies were detected with horseradish peroxidase (HRP)-conjugated rabbit secondary antibody [1:5000 dilution] (Promega), while α-tubulin [1:10000 dilution] (Sigma, clone DM1A), FLAG [1:2000 dilution] (Sigma F1804, clone M2), ALYREF [1:2000 dilution] (Sigma A9979, clone 11G5), SSRP1

[1:500 dilution] (Abcam 26212, clone 10D7) and poly-Gly-Ala [1:500 dilution] (kindly provided from Prof Dieter Edbauer) primary antibodies were detected using HRP-conjugated mouse secondary antibody [1:5000 dilution] (Promega). For dot blot analysis, 50 µg total protein extracts prepared in ice-cold lysis buffer were loaded onto a nitrocellulose membrane using a microfiltration apparatus (Biorad) and analysed by western immunoblotting as previously described.

Cytoplasmic Fractionation

Neuro-2a cells were split into each well of 6 well plates ($2 \times 10^6$ cells/well) and transfected for 72 hours with 1 µg pcDNA6.2-GW/EmGFP-Control miR RNAi, pcDNA6.2-GW/EmGFP-mouse SRSF1 miR1+2 RNAi, p3×FLAG/SRSF1 (11-196), or p3×FLAG/SRSF1 (11-196)-m4 and 1 µg pcDNA 3.1/RAN-G4C2×38-sense or RAN-C4G2×39-antisense using 3 µg PEI/1 µg DNA and one tenth medium volume OptiMEM. iNeurons were cultured in 6-well plates and transduced with 5MOI human LV-SRSF1-RNAi lentivirus for 5 days.

Cytoplasmic fractionation was performed as follows. Cells were removed from the plate using DEPC PBS and pelleted by centrifugation at 800×g for 5 minutes. Cell pellets were quickly washed with hypotonic lysis buffer (10 mM HEPES pH 7.9, 1.5 mM $MgCl_2$, 10 mM KCl, 0.5 mM DTT). Cell pellets were then lysed in hypotonic lysis buffer containing 0.16 U/µL Ribosafe RNase inhibitors (Bioline), 2 mM PMSF (Sigma) and SIGMAFAST™ Protease Inhibitor Cocktail tablets, EDTA free (Sigma) according to manufacturer's instructions. Cells were lysed gently using a cut P1000 tip ensuring no physical force was exerted on the cell pellet. For fly tissue, da-GAL4 was used to drive transgene expression in all tissues, and 10 third instar larvae were homogenised and lysed using the same buffer and a dounce homogenizer. The lysate then underwent differential centrifugation (1,500 g, 3 min, 4° C. then 3,500 g rpm, 8 min, 4° C. and then 17,000 g, 1 min, 4° C.) transferring the supernatant to a fresh tube after each centrifugation. The supernatant was then added to PureZOL (Biorad) to extract RNA. The nuclear pellet obtained after centrifugation at 1,500 g for 3 min was lysed in Reporter lysis buffer (Promega) for 10 minutes on ice before centrifugation at 17,000 g, 5 minutes, 4° C.

Total fractions were collected directly in Reporter lysis buffer (Promega) containing 0.16 U/µL Ribosafe RNase inhibitors (Bioline), 2 mM PMSF (Sigma) and SIGMA-FAST™ Protease Inhibitor Cocktail tablets, EDTA free (Sigma) according to manufacturer's instructions and lysed for 10 min on ice before centrifugation at 17,000 g, 5 minutes, 4° C. The supernatant was then added to PureZOL (Biorad) to extract RNA.

Equal volumes of total, nuclear and cytoplasmic lysates were resolved using SDS-PAGE, electroblotted onto nitrocellulose or PVDF membranes and probed using SSRP1 and α-tubulin (Neuro-2a), SSRP1 and Actin (iNeurons), or α-tubulin and α-Histone H3 (*Drosophila*).

Quantitative RT-PCR

Total RNA was extracted from 5-10 crushed larvae or adult *Drosophila* using 800 µl PureZOL (BioRAD) and a syringe with a 21G gauge needle for homogenization. Lysate was cleared by centrifugation for 10 minutes at 12,000 g at 4° C. 200 µl of chloroform was added to the supernatant and vigorously shaken for 15 seconds. After 10 minutes of incubation at room temperature, tubes were centrifuged at 12,000 g for 10 minutes at 4° C. and supernatants (400 µl) were collected. RNA was precipitated for 30 minutes at room temperature with 2 µl Glycogen (5 mg/ml, Ambion) and 500 µl isopropanol and pelleted at 12,000 g for 20 minutes at 4° C. Pellets were washed with 70% DEPC EtOH and re-suspended in 40 µl DEPC water. Total RNA was then treated with DNaseI (Roche) and quantified using a Nanodrop (NanoDrop®Technologies).

For HEK cells, 50,000 cells were split into each well of 24-well plates and transfected with 700 ng pcDNA6.2-GW/EmGFP-Control or human SRSF1 miR RNAi constructs using 3.5 µg PEI/ml media and one tenth medium volume OptiMEM (ThermoFisher). For iAstrocytes, 20,000 induced neural progenitor cells (iNPCs) were plated in 6-well plates in astrocyte medium. The day after plating, 3 wells were transduced with lentivirus expressing human SRSF1-RNAi at an MOI of 5.

Total RNA was extracted from HEK cells 72 hours after transfection or iAstrocytes 5 days after transduction and RNA extracted using the EZ Total RNA Isolation Kit (Geneflow). Briefly, cells were washed in DEPC-treated PBS before lysis directly in the culture dish at room temperature using the denaturing solution. Lysed cells were scraped and removed from the culture dish and equal volume extraction buffer added, vigorously shaken, incubated at room temperature for 10 minutes and then centrifuged for 15 minutes at 4° C. and 12,000 g. RNA was subsequently precipitated from the upper phase using equal volume isopropanol overnight at −20° C., pelleted at 12,000 g, 4° C. for 15 minutes, washed with 70% DEPC EtOH and re-suspended in 22.5 µl DEPC water. RNA was then treated with DNaseI (Roche) and quantified using a Nanodrop (NanoDrop®Technologies).

Following RNA quantification, 2 µg RNA was converted to cDNA using BioScript™ Reverse Transcriptase (Bioline). qRT-PCR primers were designed using Primer-BLAST (NCBI) and validated using a 1 in 4 serial template dilution series (standard curve with $R^2 > 0.97$). qRT-PCR reactions were performed in duplicate for 3 independent biological repeats using the Brilliant III Ultra-Fast SYBR® Green QPCR Master Mix (Agilent Technologies) on a MX3000P QPCR system (Statagene). qRT-PCR data was analysed using MxPro (Stratagene) and GraphPad Prism (Version 6). The following qPCR primers were used:

```
Drosophila SF2 (designed using Primer-BLAST)
                                  (SEQ ID NO 74/75)
Fwd: 5'-TACCGCGTCATGGTTACTGG-3'

Rev: 5'-GTACGCGAATGTAGGCAACC-3'

Drosophila Ref1 (designed using Primer-BLAST)
                                  (SEQ ID NO 76/77)
Fwd: 5'-CGATATGTACGACGGACCGAA-3'

Rev: 5'-CGGACCAAAGTCGTTGAAGAG-3'

Drosophila Tub84b (described in reference (36))
                                  (SEQ ID NO 78/79)
Fwd: 5'-TGGGOOOGTCTGGACCACAA-3'

Rev: 5'-TCGCCGTCACCGGAGTCCAT-3'

Drosophila C9 3'UTR (described in reference69)
                                  (SEQ ID NO 80/81)
Fwd: 5'-_TTCCAACCTATGGAACTGATGA-3'

Rev: 5'-_GGITTICCTCATTAAAGGCATTC-3'
```

-continued

Human SRSF1 (designed using Primer-BLAST)
(SEQ ID NO 82/83)
Fwd: 5'-CCGCATCTACGTGGGTAACT-3'

Rev: 5'-TCGAACTCAACGAAGGCGAA-3'

Human ALYREF/THOC4 (designed using Primer-BLAST)
(SEQ ID NO 84/85)
Fwd: 5'-TCTGGTCGCAGCTTAGGAAC-3'

Rev: 5'-CCACCTCTGTTTACGCTCTGT-3'

Human U1 snRNA (designed using Primer-BLAST)
(SEQ ID NO 86/87)
Fwd: 5'-CCATGATCACGAAGGTGGTT-3'

Rev: 5'-ATGCAGTCGAGTTTCCCACA-3'

Human SMN (described in reference[70])
(SEQ ID NO 88/89)
Fwd 5'-CTTGTGAAACAAAATGCTTTTTAACATCCAT-3'

Rev 5'-GAATGTGAGCACCTTCCTTCTTTTT-3'

Human JUN (designed using Primer BLAST)
(SEQ ID NO 90/91)
Fwd 5'-GAACTGCACABCCAGAACAC-3'

Rev 5'TGGGTTGAAGTTGCTGAGG-3'

C9RAN (designed using Primer-BLAST). Primers anneal downstream of the G402 or C4G2 repeat sequences in the 3'UTR of mRNA transcribed from pcDNA3.1 constructs.
(SEQ ID N 92/93)
Fwd 5'-GGGCCCTTCGAACCCCCGTC-3'

Rev: 5'GGGAGGGGCAAACAACAGAT-3'

Human C9ORF72 Exon-1 Forward (designed using Primer BLAST)
(SEQ ID NO 94)
5'-TCAAACAGCGACAAGTTCCG-3'

Human C9ORF72 Exon-3 Reverse (designed using Primer BLAST)
(SEQ ID NO 95)
5'-GTCGACATGACTGCATTCCA-3'

Human C9ORF72 Intron-1 Reverse (designed using Primer BLAST)
(SEQ ID NO 96)
5'-GGAGAGAGGGTGGGAAAAAC-3'

MTT Cell Proliferation Assay

Neuro-2a (N2A) cells were split into each well of a 24 well plate (30,000 cells/well). Each plate contained 4 wells with only media to serve as a blank and 4 wells/treatment. Cells were transfected for 72 hours with either 500 ng pcDNA 3.1, pcDNA 3.1/RAN-G4C2×15 RAN-G4C2×38-sense, RAN-C4G2×15 or RAN-C4G2×39-antisense; or 250 ng pcDNA6.2-GW/EmGFP-Control miR RNAi, pcDNA6.2-GW/EmGFP-mouse SRSF1 miR1+2 RNAi, p3×FLAG/SRSF1 (11-196), or p3×FLAG/SRSF1 (11-196)-m4 and 250 ng pcDNA 3.1, pcDNA 3.1/RAN-G4C2×38-sense or RAN-C4G2×39-antisense.

250 mg Thiazolyl Blue Tetrazolum Bromide reagent (MTT) was added to each well and incubated in the dark at 3TC for 1 hour. Cells were subsequently lysed with equal volume MTT lysis buffer (20% SDS, 50% Dimethylformamide (DMF)) and incubated, shaking, at room temperature for 1 hour. Absorbance at 595 was then assessed with a PHERAstar FS (BMG Labtech). Experiments were performed in triplicate for each treatment. Absorbance data was analysed using PHERAstar MARS (BMG Labtech) and GraphPad Prism (version 6).

Immunofluorescence of Rat Cortical Neurons

Cortical neurons were isolated, cultured and transfected as described previously[36]. Briefly, neurons were transfected using Lipofectamine LTX with PLUS reagent according to the manufacturer's instructions (Thermofisher; DNA:PLUS:LTX ratio of 1:0.5:0.5 with 2 µg DNA/100,000 cells/cm$^2$). After 6 hours, the transfection mix was replaced with conditioned medium.

Immunofluorescence staining of rat cortical neurons was performed 72 hours after transfection as described previously[36]. Briefly, cells cultured on glass coverslips were fixed with 3.7% formaldehyde in PBS at room temperature for 20 minutes. Cells were washed once with PBS and residual formaldehyde was quenched with 50 mM NH$_4$Cl in PBS at room temperature for 10 minutes. Cells were subsequently washed in PBS and permeabilised with 0.2% Triton X-100 in PBS at room temperature for 5 minutes. Cells were washed in PBS to remove excess Triton X-100, blocked with 4% goat serum in PBS for 2 hours at room temperature and then incubated with the V5 antibody [1:1000 dilution] (ThermoFisher Scientific # R96025) in PBS containing 4% goat serum overnight at 4° C. Cells were washed 3 times with PBS containing 4% goat serum and incubated for 1 hour with PBS containing 4% goat serum & goat anti-mouse secondary antibody, Alexa Fluor 594 [1:1000 dilution] (ThermoFisher Scientific). Cell transfected with pcDNA6.2-GW/EmGFP-Control or human SRSF1 miR RNAi constructs were subsequently stained with Hoechst 33342 for 10 minutes at room temperature, washed with 3 times PBS and mounted in fluorescence mounting medium (Dako). After incubation in the secondary antibody, cells transfected with p3×FLAG/SRSF1 (11-196) or p3×FLAG/SRSF1-m4 were washed 3 times with PBS containing 4% goat serum, incubated at room temperature for one hour with PBS containing 4% goat serum & anti-FLAG® M2-FITC antibody [10 µg/ml] (Sigma-Aldrich # F4049) and subsequently stained with Hoechst 33342. Cells were then washed with 3 times PBS and mounted in fluorescence mounting medium (Dako).

Co-Immunoprecipitation

Cells were split into 1×10 cm plates/treatment (1.5×10$^6$ cells/plate) and transfected with 15 µg p3×FLAG, p3×FLAG/SRSF1 (11-196), p3×FLAG/SRSF1 (11-196)-m2 or p3×FLAG/SRSF1(11-196)-m4 using 3 µg PEI/1 µg DNA and one tenth medium volume OptiMEM.

Proteins were extracted from Neuro-2a cells 48 hours after transfection. Cells were briefly washed in ice cold PBS, scraped into 500 µl ice cold lysis buffer, passed through a 21G gauge needle 10 times and left to lyse on ice for 10 minutes. Lysed cells were cleared by centrifugation at maximum speed at 4° C. for five minutes and protein extracts were quantified using Bradford Reagent. 2 mg of total protein in 1 ml lysis buffer was incubated with 30 µl anti-FLAG® M2 affinity resin slurry (Sigma A2220) (which had been blocked overnight with 1% BSA in IP lysis buffer) for 2 hours at 4° C. on a rotating wheel. The anti-FLAG® M2 affinity resin captured protein complexes were washed 5 times with ice-cold lysis buffer and eluted in 50 µl IP lysis buffer supplemented with 100 µg/ml 3×FLAG peptide (Sigma # F4799) for 30 minutes at 4° C. on a rotating wheel. 30 µg total protein and 15 µl captured protein complexes were resolved by SDS-PAGE, electroblotted onto nitrocellulose membrane and probed using FLAG, NXF1 clone 53H8 [1:2000] (Abcam ab50609) and ☐-tubulin.

RNA:Protein UV Crosslinking Assays

Recombinant proteins expressed in 1.51 of E. coli BL21 (DE3)-RP (Novagen) cell cultures were purified by IMAC chromatography on TALON/Cobalt beads (Clontech) in 1M NaCl containing buffers to prevent the potential co-purification of *E. coli* RNA (Lysis buffer: 50 mM TRIS-HCl pH8.0, 1M NaCl, 0.5% Triton X-100; Wash buffer: 50 mM TRIS-HCl pH8.0, 1M NaCl, 0.5% Triton X-100, 5 mM imidazole). Elution was achieved in step in buffer containing 200 mM imidazole (50 mM TRIS-HCl pH8.0, 500 mM NaCl, 200 mM imidazole) and 50 mM L-Arg and L-Glu to prevent protein precipitation while retaining interaction with RNA and NXF1[38,39]. $^{32}$P-radiolabelled probes (synthetic G4C2×5 or C4G2×5 RNA oligonucleotides purchased from Dharmacon) for 10 min at room temperature and 10 min on ice prior to UV-crosslinking or not (10 min, 1.5 J/cm$^2$). Binding reactions were resolved on SDS-PAGE prior to analysis by Coomassie staining and Phosphoimaging.

RNA Immunoprecipitation (RIP) Assays

Cells were split into 1×T-175 flasks/treatment (5×10$^6$ cells/plate) and transfected with 30 µg p3×FLAG, p3×FLAG/SRSF1 (11-196) or p3×FLAG/SRSF1 (11-196)-m4 and 10 µg pcDNA 3.1/RAN-G4C2×15-sense, RAN-G4C2×38-sense, RAN-G4C2×15-antisense or RAN-C4G2× 39-antisense using 3 µg PEI/1 µg PEI and one tenth volume OptiMEM.

Protein-RNA complexes were extracted from Neuro-2a cells 48 hours after transfection. Protein-RNA complexes were cross-linked using 1% formaldehyde for 10 minutes, shaking at room temperature. Residual formaldehyde was quenched with 250 mM Glycine at room temperature for 5 minutes, shaking. Cross-linked cells were subsequently washed in ice cold DEPC treated PBS and scraped into ice cold RNase free lysis buffer (DEPC treated water containing 50 mM Hepes pH7.5, 150 mM NaCl, 10% glycerol, 0.5% triton X-100, 1 mM EDTA, 1 mM DTT, 1 µl RNase inhibitor, protease inhibitor cocktail). Cells were passed through a 21G gauge needle 10 times and left to lyse on ice for 10 minutes, followed by centrifugation at maximum speed at 4° C. for five minutes and quantification using Bradford Reagent. 2.5 mg of total protein at a 1 mg/ml concentration was incubated with 40 µl anti-FLAG® M2 affinity resin slurry (which had been blocked overnight with 1% BSA and 5 µl/ml ssDNA) overnight at 4° C. on a rotating wheel. One 15th of the total protein extract was retained for an input sample.

The anti-FLAG® M2 affinity resin captured protein-RNA complexes were washed 5 times with ice-cold RNase free lysis buffer. Complexes were subsequently reverse-cross-linked and eluted from the resin in EZ RNA extraction denaturing buffer for 1 hour at 70° C., re-suspending the resin every 10 minutes. The formaldehyde crosslinks were reversed by heating the samples for 1 hour at 70° C. and RNA was extracted using PureZOL (for total samples) or the EZ Total RNA Isolation Kit (for eluted complexes) as described in the qRT-PCR section. Extracted RNA samples were re-suspended in 25 µl RNase-free water.

Extracted RNA samples were DNase treated and 10 µl input or eluate RNA was converted to cDNA as described previously in the quantitative RT-PCR section. qRT-PCR primers were designed using Primer-BLAST and validated using a 1 in 4 serial template dilution series (standard curve with $R^2 > 0.97$). qRT-PCR reactions were performed in duplicate for 3 independent biological repeats using the Brilliant III Ultra-Fast SYBR® Green QPCR Master Mix (Agilent Technologies) on a CFX 96™ Real-Time System (BIO-RAD). qRT-PCR data was analysed using CFX Manager 3.1 (BIO-RAD) and GraphPad Prism (Version 6). The relative concentration of cDNA was calculated for each sample and the input samples multiplied by 15 to obtain a total input value. Eluate samples were expressed as a percentage of the input total input values. qPCR primers were described above in the qRT-PCR section.

RNA Fluorescence In Situ Hybridisation (FISH) and Visualization of RNA Foci

To visualize sense RNA foci, RNA fluorescence in situ hybridisation (FISH) was performed as described previously (9). Briefly, iAstrocyte cells were grown on 13 mm coverslips for 5 days following LV-SRSF1-RNAi transduction, before being fixed and permeabilised in 4% paraformaldehyde & 0.2% Tween-20 (Sigma) for 10 minutes. Fixed cells were subsequently washed in DEPC-treated PBS and were blocked with hybridization solution [50% formamide, 2× saline sodium citrate (SSC), 100 mg/ml dextran sulphate & 50 mM sodium phosphate pH 7.0] for 1 h at 66° C. Cells were then incubated with 400 ng/ml of denatured probe (a 5' TYE-563-labelled LNA (16-mer fluorescent)-incorporated DNA probe against the sense C9orf72 RNA hexanucleotide repeat (Exiqon, Inc.)) in hybridization solution overnight at 66° C. After hybridization, cells were washed once in 2×SSC & 0.1% Tween-20 at room temperature for 15 minutes, followed by three 15 minutes washes in 0.1×SSC at 65° C. Coverslips were mounted using a DAPI-containing mounting medium (Vector Labs, Inc.). All solutions were made with DEPC-treated water.

RNA foci were visualized using a Leica SP5 confocal microscope system and a 63/1.4 oil immersion objective lens. The presence of foci was assessed within a high resolution (848 µm$^2$ per image, 393×393 pixels) using 0.9 µm z-stacks through the entire volume of the cell.

Confocal Immunofluorescence Microscopy in Human Post Mortem Spinal Cord Tissue from C9ORF72-ALS Patients This study was approved by the South Sheffield Research Ethics Committee and informed consent was obtained for all samples. Brain and spinal cord tissues were donated to the Sheffield Brain Tissue Bank for research, with the consent of the next of kin. IHC and RNA fluorescence in situ hybridisation (FISH) were performed on formalin fixed paraffin-embedded (FFPE) tissues from four C9ORF72+ patients with ALS. After wax removal, antigen retrieval was performed by microwaving for 10 min in 0.8 mM EDTA pH9.5. A 5' TYE-563-labelled LNA (16-mer fluorescent)-incorporated DNA probe was used against the sense (Exiqon, Inc.; batch number 607323) RNA hexanucleotide repeat as described in previous section. Slides were then immediately transferred to PBS/5% BSA for protein staining using anti-SRSF1 antibody (Cell Signaling #8241) at a dilution of 1:200. After incubation with the primary antibodies overnight at 4° C. in DEPC-treated PBS/5% BSA, slides were washed in DEPC PBS and incubated with fluorescent secondary anti-rabbit Alexa Fluor 488 antibodies (Abcam ab150077). Mounted slides were visualised by confocal microscopy as described in previous section.

Statistical Analysis of Data

We have used one-way or two-way ANOVA (analysis of variance) to statistically evaluate and plot our data using the GraphPad Prism version 6 (GraphPad Software Inc., San Diego, Calif.). All files and data points are available on request. RNA foci were counted in a blinded manner and several researchers carried out the analysis. Several researchers were also involved in producing the qRT-PCR and western blot data showing that depleting SRSF1 or inhibiting the interaction of SRSF1 with NXF1 lead to nuclear export alteration of C0ORF72 repeat transcripts and both sense and antisense DPRs.

Either one-way or two-way ANOVA (analysis of variance) with Tukey's correction for multiple comparisons was used for most experiments with the following exceptions: DPR analysis in primary neurons used Fisher's exact test; adult fly climbing ability was analysed by Kruskal-Wallis non-parametric test with Dunn's correction for multiple comparisons; and the analysis of G4C2×36 transcripts in Drosophila used paired two-tailed t-test. No randomization was used in the animal studies. Data were plotted using GraphPad Prism 6. Significance is indicated as follows; NS: non-significant, *: p<0.05, : p<0.01, *: p<0.001, ****: p<0.0001; All files and data points are available on request. RNA foci, DPR-positive neurons, crawling and climbing assays were analysed in a blinded manner and several investigators carried out the analysis. Several researchers were also involved in producing the qRT-PCR and western blot data showing that depleting SRSF1 or inhibiting the interaction of SRSF1 with NXF1 lead to nuclear export alteration of C9ORF72 repeat transcripts and reduction of both sense and antisense DPRs.

SRSF1 Expression and RNAi Gene Therapy Vectors shRNA Design for SRSF1 Knockdown

Initial shRNA design was conducted using the Invitrogen Block-it RNAi designer (https://rnaidesigner.thermofisher.com/rnaiexpress/). Input sequence was the NCBI accession number: NM_001078166.1—corresponding to short isoform transcript variant 2 of the SRSF1 mRNA, ensuring both SRSF1 isoforms are targeted. The ORF was selected as the region for target design and GC content was set at the default values of 35-55%. Output sequence strand orientation was sense-loop-antisense. The selected loop sequence was CGAA but this can be modified to incorporate different loop sequences if necessary. The top 10 output sequences ranked by likelihood of target knockdown are shown in Table 7.

TABLE 7

Invitrogen RNAi design output

| SEQ ID NO | Rank | Start | Sense shRNA | | GC% |
|---|---|---|---|---|---|
| 97 | 1 | 259 | GCATCTACGTGGGTAACTTAC | ORF | 47.62 |
| 98 | 2 | 244 | GGAACAACGATTGCCGCATCT | ORF | 52.39 |
| 99 | 3 | 689 | GGAGTTTGTACGGAAAGAAGA | ORF | 42.86 |
| 100 | 4 | 603 | GGAAGTTGGCAGGATTTAAAG | ORF | 42.86 |
| 101 | 5 | 761 | GGTAGGTTATACACGTATTCT | ORF | 38.1 |
| 102 | 6 | 639 | GCAGGTGATGTATGTTATGCT | ORF | 42.86 |
| 103 | 7 | 657 | GCTGATGTTTACCGAGATGGC | ORF | 52.39 |
| 104 | 8 | 604 | GAAGTTGGCAGGATTTAAAGG | ORF | 42.86 |
| 105 | 9 | 701 | GAAAGAAGATATGACCTATGC | ORF | 38.1 |
| 106 | 10 | 632 | GCGTGAAGCAGGTGATGTATG | ORF | 52.39 |

These 10 highest ranked sequences were interrogated for their off-target potential by in silico analysis of the antisense strand using the siSPOTR online tool In siSPOTR, shRNA sequences are given a potential of off-targeting score (POTS) where a score of ≤30 is considered ideal. A higher score suggests a high likelihood of off-targeting. The results of this analysis are shown in Table 8.

TABLE 8 siSPOTR analysis of Invitrogen designed shRNA

| SEQ ID NO | Sequence | Antisense | POTS | % worse | SEQ ID NO | Seed |
|---|---|---|---|---|---|---|
| 107 | 1 | GTAAGTTACCC ACGTAGATGC | 343.584 | 28.50% | 108 | TAAGTTA |
| 109 | 2 | AGATGCGGCAA TCGTTGTTCC | 40.8429 | 87.04% | 110 | GATGCGG |
| 111 | 3 | TCTTCTTTCCG TACAAACTCC | 588.488 | 5.44% | 112 | CTTCTTT |
| 113 | 4 | CTTTAAATCCT GCCAACTTCC | 1794 | 0.11% | 114 | TTTAAAT |
| 115 | 5 | AGAATACGTGT ATAACCTACC | 171.811 | 65.49% | 116 | GAATACG |
| 117 | 6 | AGCATAACATA CATCACCTGC | 217.02 | 57.33% | 118 | GCATAAC |
| 119 | 7 | GCCATCTCGGT AAACATCAGC | 463.716 | 12.93% | 120 | CCATCTC |
| 121 | 8 | CCTTTAAATCC TGCCAACTTC | 773.609 | 2.09% | 122 | CTTTAAA |
| 123 | 9 | GCATAGGTCAT ATCTTCTTTC | 167.649 | 66.20% | 124 | CATAGGT |
| 125 | 10 | CATACATCACC TGCTTCACGC | 465.8 | 12.79% | 126 | ATACATC | siSPOTR also contains a function enabling the design of minimal off-targeting shRNA sequences irrespective of potential efficacy. Using the CDS of the short SRSF1 isoform as an input, 8 sequences with a POTS score lower than 30 were generated and are shown in Table 9.

TABLE 9 shRNA sequences with low off-targeting potential designed by siSPOTR

| SEQ ID NO | rank | position | POTS | percentile_worse | sense shrna | SEq ID NO | Seed | gc_content_percent |
|---|---|---|---|---|---|---|---|---|
| 127 | 1 | 119 | 22 | 96.99% | GCGCTATC CGCGACAT CGACCT | 128 | GGU CGA U | 63.64% |
| 129 | 2 | 24 | 30 | 92.95% | TGGCCCCG CAGGGAAC AACGAT | 130 | UCG UUG U | 63.64% |
| 131 | 3 | 219 | 33 | 91.33% | TCGCGACG GCTATGAT TACGAT | 132 | UCG UAAU | 50% |
| 133 | 4 | 117 | 34 | 90.84% | CGGCGCTA TCCGCGAC ATCGAC | 134 | UCG AUG U | 68.18% |
| 135 | 5 | 33 | 37 | 88.84% | AGGGAACA ACGATTGC CGCATC | 136 | AUG CGG C | 54.55% |
| 137 | 6 | 208 | 39 | 88.01% | GCGGTGTA TGGTCGCG ACGGCT | 138 | GCC GUC G | 68.18% |

TABLE 9 -continued shRNA sequences with low off-targeting potential designed by siSPOTR

| SEQ ID NO | posi- rank | tion | POTS | percen- tile_ worse | sense shrna | SEq ID NO Seed | gc_ content_ percent |
|---|---|---|---|---|---|---|---|
| 139 | 7 | 250 | 52 | 81.52% | CTGCGGGT GGAGTTTC CTCGAA | 140 UCG AGG A | 59.09% |
| 141 | 8 | 256 | 54 | 80.66% | GTGGAGTT TCCTCGAA GCGGCC | 142 GCC GCU U | 63.64% |

As the siSPOTR algorithm does not rank sequences based on their ability to knockdown the target transcript it would be sensible to choose a number of shRNA sequences from both design tools and validate their ability to silence SRSF1 mRNA in vitro. siSPOTR indicates that several of the shRNAs from the Invitrogen design tool have an extremely high POTS score far in excess of the recommended score of 30, perhaps excluding them from an initial knockdown screen in favour of lower scored sequences. siSPOTR reference: Boudreau, R. L. et al., 2013. siSPOTR: a tool for designing highly specific and potent siRNAs for human and mouse. *Nucleic Acids Research*, 41(1), p.e9.

EXAMPLE 1

Figure 9A:
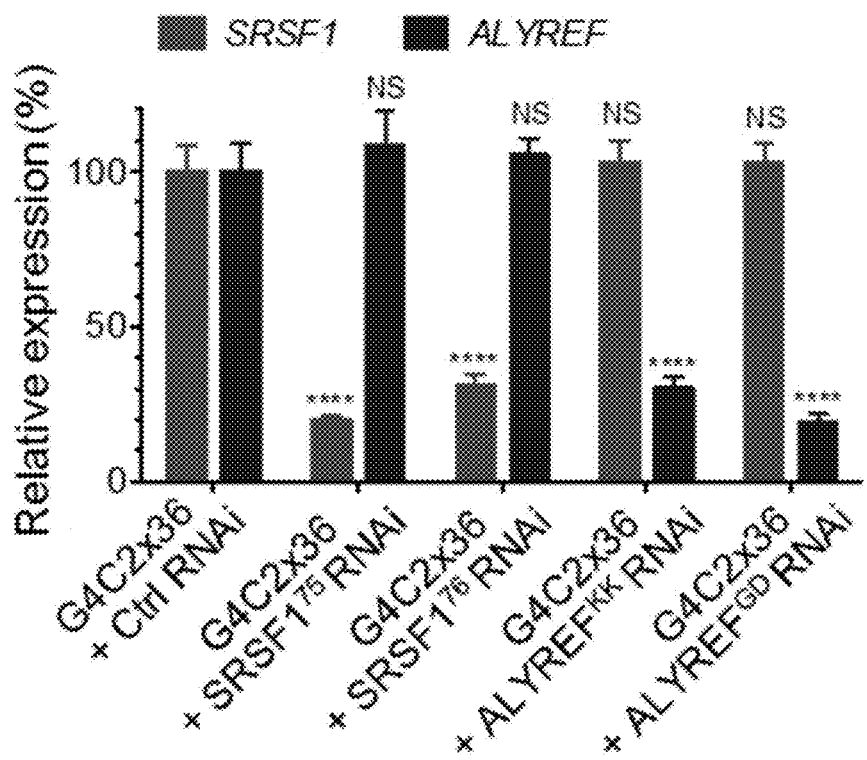
FIGS. 9A-9F: Depletion of SRSF1 prevents in vivo neurodegeneration and rescues locomotor function. (A) SRSF1 (red) and ALYREF (blue) transcript levels were quantified by qRT-PCR analysis in independent knockdown lines in G4C2×36 flies. Tub84b transcript levels were used for normalization in triplicate experiments (mean±SEM; two-way ANOVA, NS: non-significant, **: $p<0.001$; N (qRT-PCR reactions)=6). (B) Targeted expression of G4C2×36 causes a rough eye phenotype which is fully rescued by SRSF1-knockdown. Normal eye phenotypes are presented for Ctrl-RNAi and control G4C2×3 flies. Representative scanning electron micrographs are presented below light microscopy images. Scale bar: 100 µm. (C and D) Neuronal expression of G4C2×36 causes larval crawling (C) and adult climbing (D) deficits that are both rescued by SRSF1-depletion (mean±SEM normalized to control (Ctrl)-RNAi); Kruskal-Wallis with Dunn's multiple comparison test, NS: non-significant, : $p<0.01$, *: $p<0.005$, **: $p<0.001$; N (larvae)=10; N (adults)=Control: 93, G4C2×3: 62, G4C2×36+Ctrl-RNAi: 51, G4C2×36+SRSF1-RNAi: 50, G4C2×36+ALYREF-RNAi: 36)(e) SRSF1 depletion in *Drosophila* models expressing DPRs independently of G4C2 repeat expansions and RAN translation 16. (f) Neuronal expression of poly-Gly-Arg DPRs (GR36) and poly-Pro-Arg DPRs (PR36) causes adult climbing deficits that are not restored by SRSF1 depletion (mean±95% CI normalized to Control; N=Control (GAL4/luciferase-RNAi): 239, GR36+Ctrl-RNAi: 12, GR36+SRSF1-RNAi: 7, PR36+Ctrl-RNAi: 125, PR36+SRSF1-RNAi: 119)
Figure 9B:
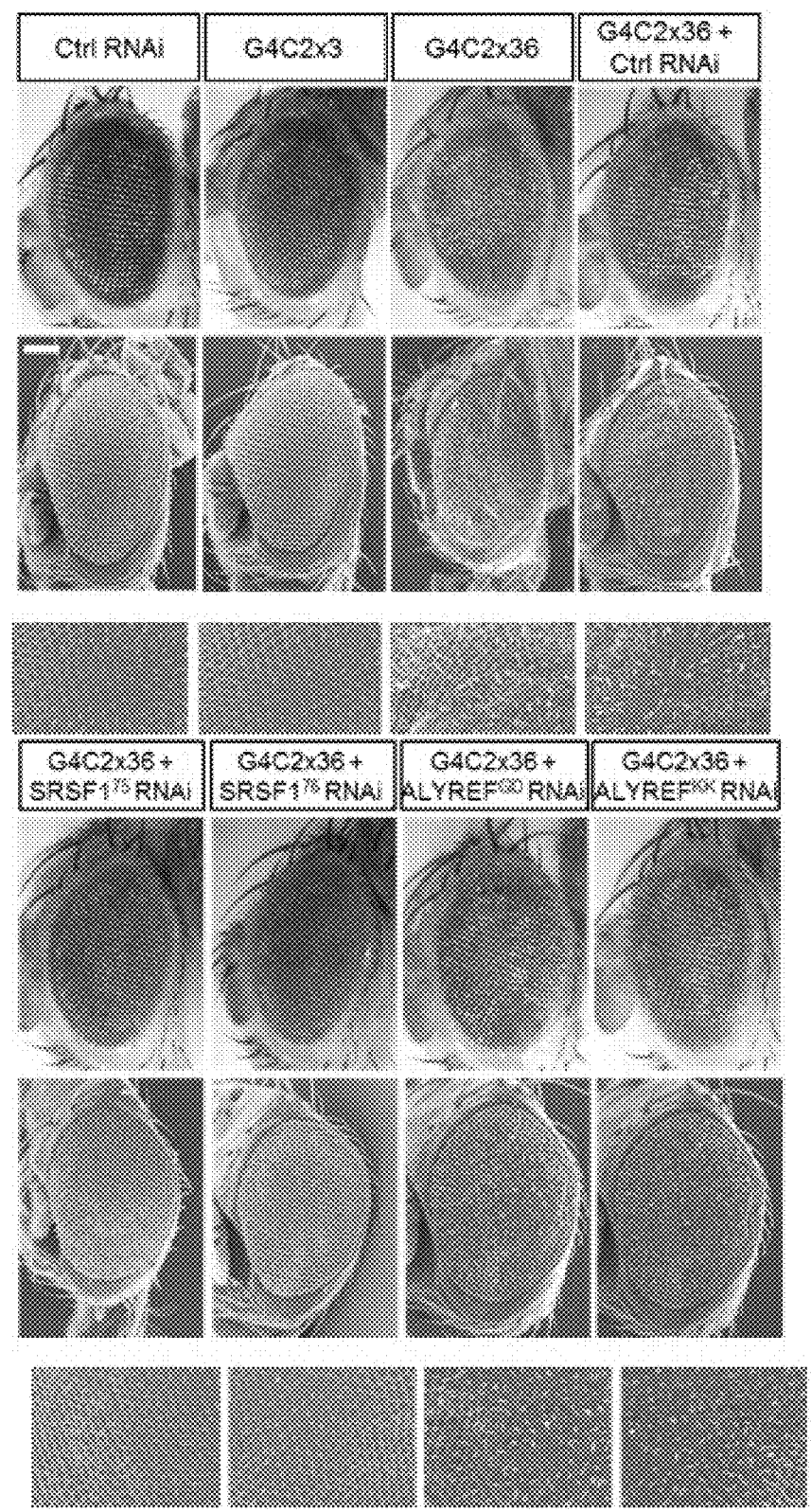
Figure 9C:
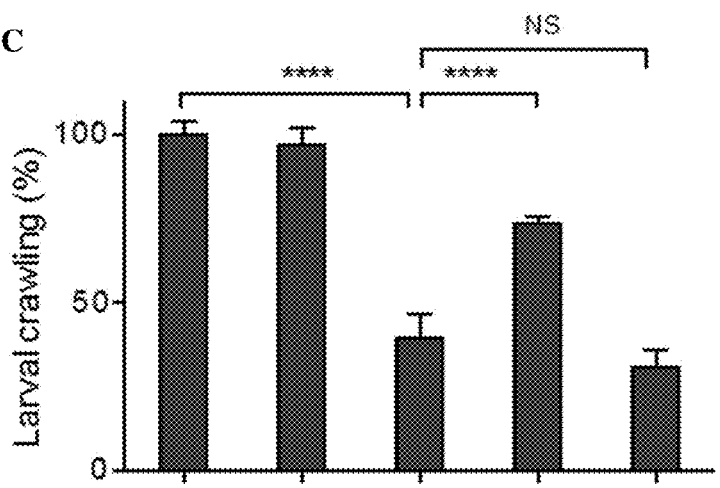
Figure 9D:
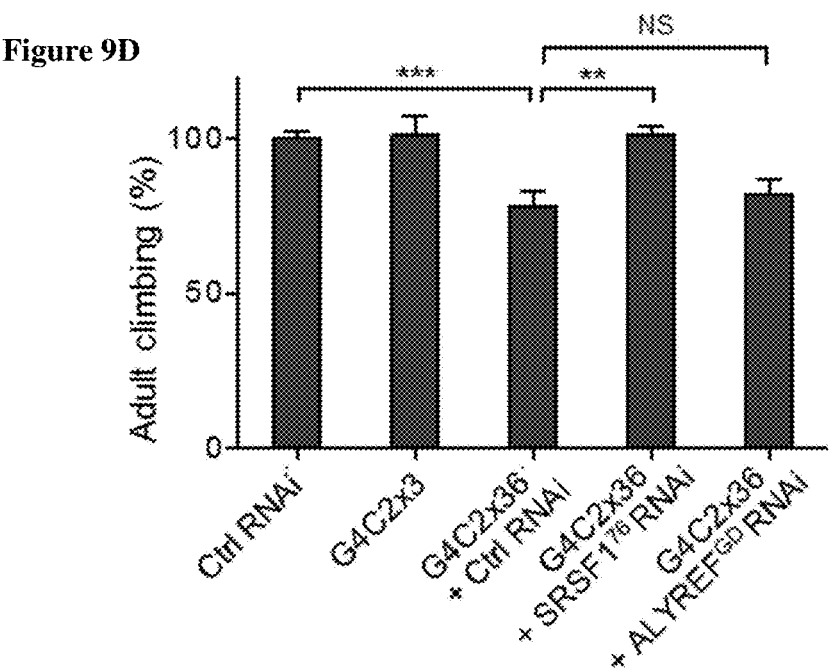
Figure 9E:
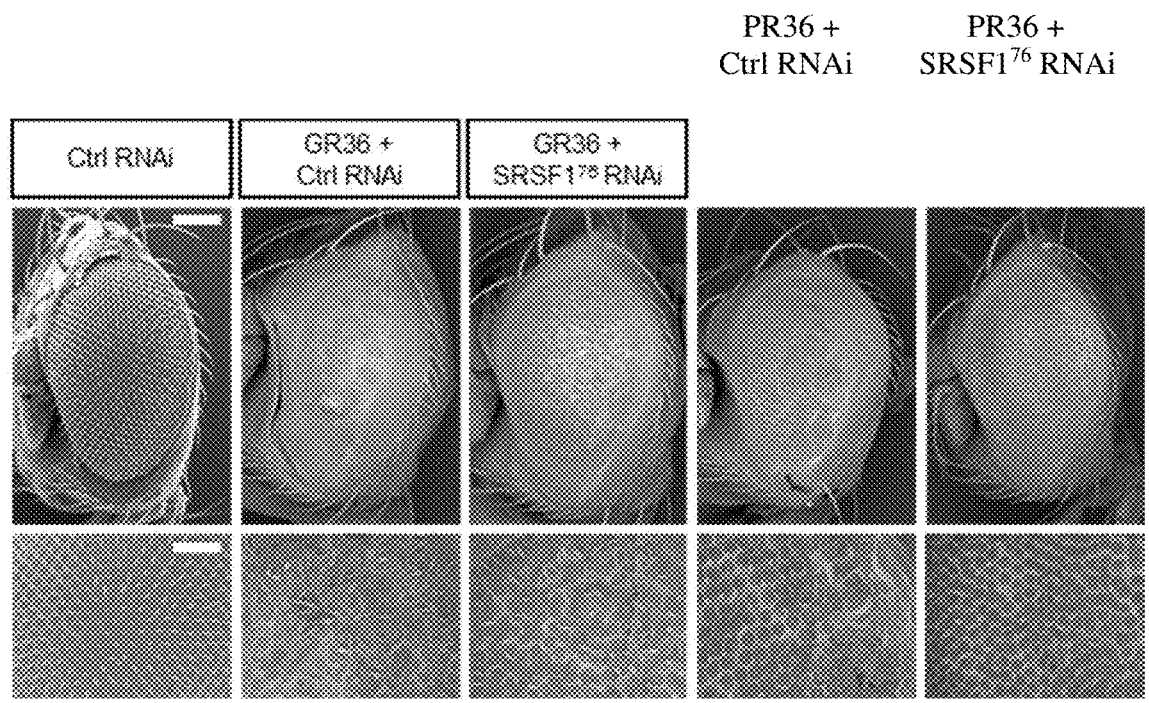
Figure 9F:
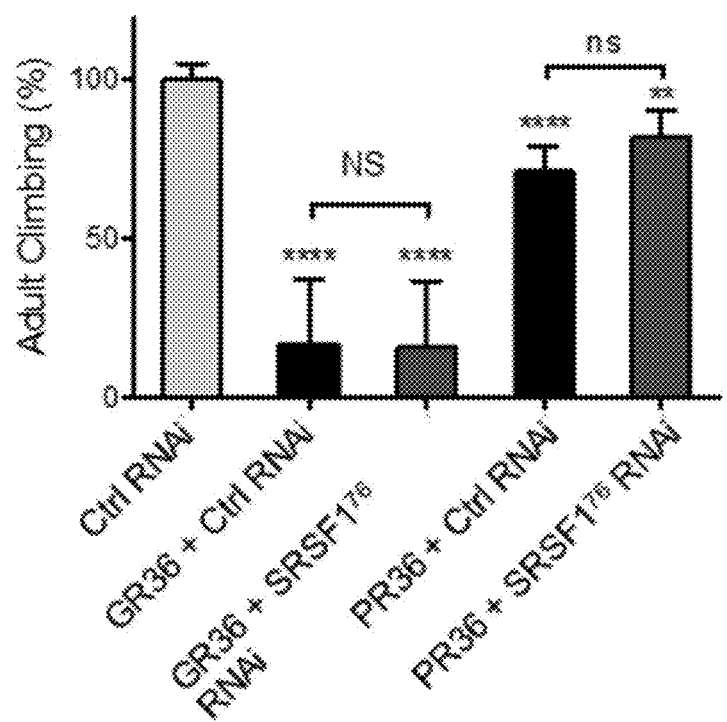

To gain functional insight into the nuclear export dependence of G4C2 repeat transcripts, we tested whether reducing the expression levels of the conserved nuclear export adaptors SRSF1 (26) and ALYREF (27) might rescue neurodegeneration in C9ORF72-ALS *Drosophila* which exhibits both RNA and DPR-mediated neurotoxicity (14). Flies expressing 36 uninterrupted repeats (pure G4C2x36) were crossed with two independent transgenic RNAi lines each targeting SRSF1 or REFALY (28), overall achieving 70-80% reduction in mRNA expression levels (FIG. 9A). Targeted expression of G4C2x36 disrupts the compound eye and is minimally altered by co-expression of a control RNAi (14) (FIG. 9B). In contrast, co-expression of two different SRSF1-RNAi (also called SF2/ASF) sequences completely prevented neurodegeneration, while two knockdown lines of REFALY (also called Ref1 or ALYREF) only showed a modest rescue of the neurodegenerative phenotype. We validated the successful knockdown of SRSF1 and ALYREF in the corresponding flies showing 70-80% reduction in mRNA expression levels (FIG. 9b).Moreover, neuronal expression of G4C2x36 causes both larval and adult locomotor deficits in this model[44]. Consistent with the previous results, SRSF1-depletion restored locomotor function while Ref1-RNAi provided no rescue of the behavioural phenotype (FIGS. 9, C and D).

Figure 25A:
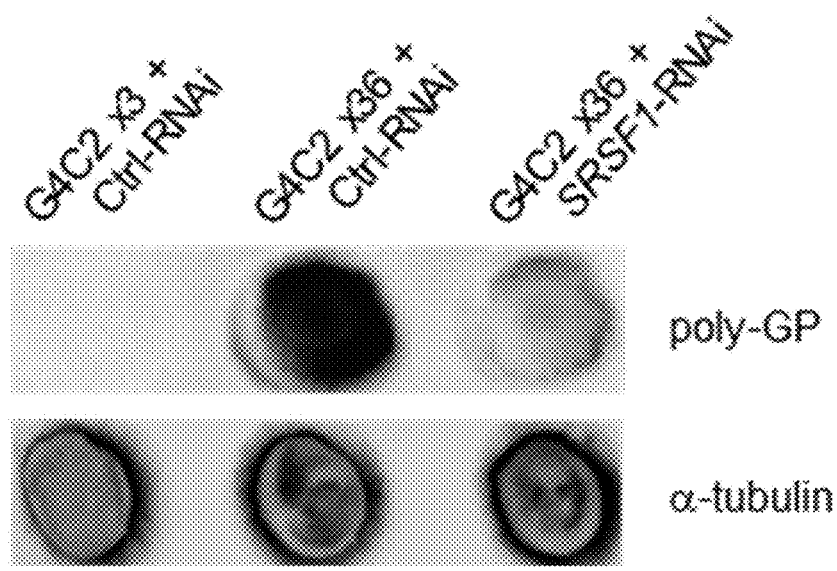
FIGS. 25A-25B: Partial depletion of SRSF1 leads to prominent reduction of sense and antisense poly-GP DPRs in Drosophila and motor neurons derived from C9ORF72-ALS patients. (A) Total protein extracts from G4C2×3+Ctrl-RNAi, G4C2×36+Ctrl RNAi and G4C2×36+SRSF1-RNAi Drosophila larvae were analysed by dot blots using poly-GP and loading control α-tubulin antibodies. (B) Total protein extracts from HEK cells transfected with either Ctrl or GP36 plasmids and patient-derived iMNs transduced (MOI=5) or not (MOI=0) with LV-SRSF1-RNAi viruses are analysed by dot blots using poly-GP DPRs and loading control alpha-tubulin antibodies.

This effect is specific of SRSF1 since depletion of ALYREF showed no effect, which is in agreement with the rough eye phenotypes. The neurotoxicity effects observed in the G4C2x36 C9ORF72-ALS model of *Drosophila* were primarily attributed to the expression of DPRs16. Accordingly, we now show that the depletion of SRSF1 leads to prominent reduction in the production of both sense and antisense poly-GP DPRs (FIG. 25a).

EXAMPLE 2

To test for the hexanucleotide-repeat expansion specificity of the SRSF1-RNAi rescued phenotypes, we used the previously established GR36 and PR36 flies 16 which respectively express 36-repeat poly-Gly-Arg and poly-Pro-Arg DPRs using alternative codons. As reported in the original study 16, the GR36 flies have a high rate of mortality and only a few GR36 flies crossed with Ctrl or SRSF1-RNAi survived to adulthood. Nonetheless, the partial depletion of SRSF1 did not significantly ameliorate the rough eye phenotypes (FIG. 9e) or the locomotor deficits (FIG. 9f) induced by the G4C2-independent expression of DPRs in both GR36 and PR36-expressing flies. These results indicate that partial depletion of SRSF1 exerts neuroprotection through direct effects on the C9ORF72 hexanucleotide repeat expansion rather than indirect effect on gene expression alteration or downstream accumulation of DPRs.

Figure 10A:
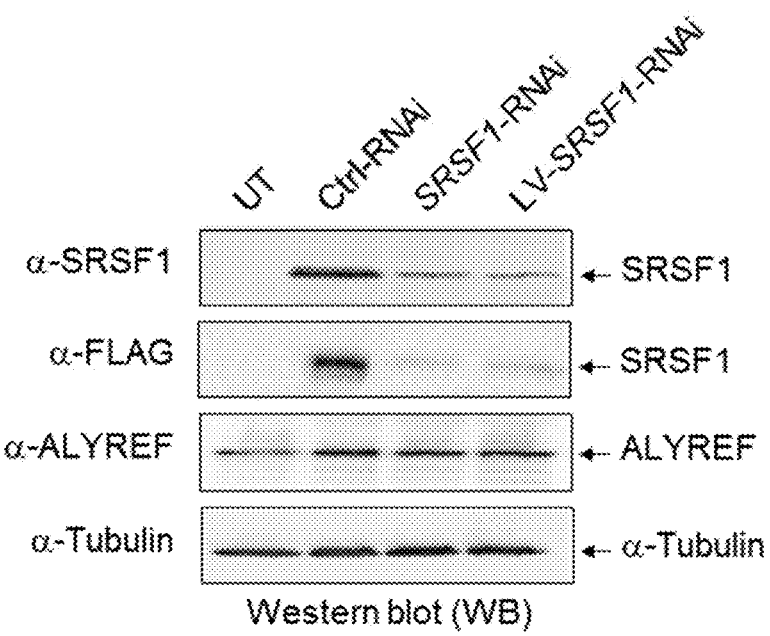
FIGS. 10A-10E: Depletion of SRSF1 suppresses patient-derived C9ORF72-mediated astrocytic toxicity and motor neuron death. (A) Untransfected HEK293T (UT), control (Ctrl)-RNAi, SRSF1-RNAi or LV-SRSF1-RNAi and FLAG-tagged SRSF1 transfected cells were analyzed 72 h post-transfection by immunoblotting using anti-FLAG, anti-ALYREF and loading control anti-α-Tubulin antibodies. (B) SRSF1 and ALYREF transcript levels were quantified by qRT-PCR analysis following normalization to U1 snRNA levels in triplicate experiments (mean±SEM; two-way ANOVA, NS: non-significant, **: $p<0.001$; N (qRT-PCR reactions)=6). Three control (Ctrl-pat) and three C9ORF72-ALS (C9-ALS-pat) color-coded patient lines were used. (C) Representative immunofluorescence microscopy images from iAstrocytes and motor neuron co-cultures. Arrows point to examples of axons of motor neurons. Scale bar: 100 µm. (D) Same control (Ctrl-pat) and C9ORF72-ALS (C9-ALS-pat) color-coded patient lines (panel B) are used for quantification of Hb9-GFP+ motor neuron (MN) counts in four replicate co-cultures of astrocytes and motor neurons (mean±SEM; one-way ANOVA, NS: non-significant, *: $p<0.005$, **: $p<0.001$; N (cells)=Ctrl-pat154: 567/589/582/500, Ctrl-pat154+SRSF1-RNAi: 620/543/504/349, Ctrl-pat155: 602/610/553/571, Ctrl-pat155+SRSF1-RNAi: 554/584/532/516, Ctrl-pat209: 519/599/584/535, Ctrl-pat209+SRSF1-RNAi: 617/486/425/572, C9-ALS-pat78: 352/279/294/258, C9-ALS-pat78+SRSF1-RNAi: 569/451/398/583, C9-ALS-pat183: 200/188/154/145, C9-ALS-pat183+SRSF1-RNAi: 480/420/380/399, C9-ALS-pat201: 201/243/261/224, C9-ALS-pat201+SRSF1-RNAi: 486/463/444/485). (E) Quantification of nuclear and cytoplasmic sense RNA foci in SRSF1-RNAi-transduced iAstrocytes (mean±SEM; two-way ANOVA, NS: non-significant, : $p<0.01$, *: $p<0.005$, **: $p<0.001$; N (cells with 1-5 RNA foci)=C9-ALS-pat78+M010: 21, C9-ALS-pat78+M015: 20, C9-ALS-pat78+M017: 22, C9-ALS-pat183+M010: 21, C9-ALS-pan 83+M015: 24, C9-ALS-pat183+M017: 22, C9-ALS-pat201+M010: 24, C9-ALS-pat201+M015: 23, C9-ALS-pat201+M017: 22). >95% of cells with RNA foci presented a total of 5 or fewer foci.

Partial depletion of SRSF1 prevents patient-derived astrocytic neurotoxicity and motor neuron death. To apply our in vivo findings to human C9ORF72-related ALS, we sought to deplete SRSF1 in patient-derived cell models. Human SRSF1-knockdown plasmids co-expressing a GFP reporter and a pre-miRNA cassette were engineered to produce recombinant SRSF1-RNAi lentivirus (LV-SRSF1-RNAi) (FIG. 1). HEK293T cells co-transfected with SRSF1-RNAi constructs and a FLAG-tagged SRSF1 expression plasmid showed efficient and specific depletion of SRSF1 (FIG. 10A). The survival of C9ORF72-ALS patient-derived neurons is not impaired in vitro (6, 7) but altered microglial function was recently reported to contribute in vivo to C9ORF72-related neurodegeneration (16). The survival and morphology of C9ORF72-ALS patient-derived neurons is indistinguishable from control neurons 45, 46.

We thus assessed motor neuron survival in co-cultures with patient-derived astrocytes using our recently developed assay that recapitulates the astrocyte-mediated neurotoxicity observed in ALS for both primary mouse and human derived neurons (29).

Figure 2A:
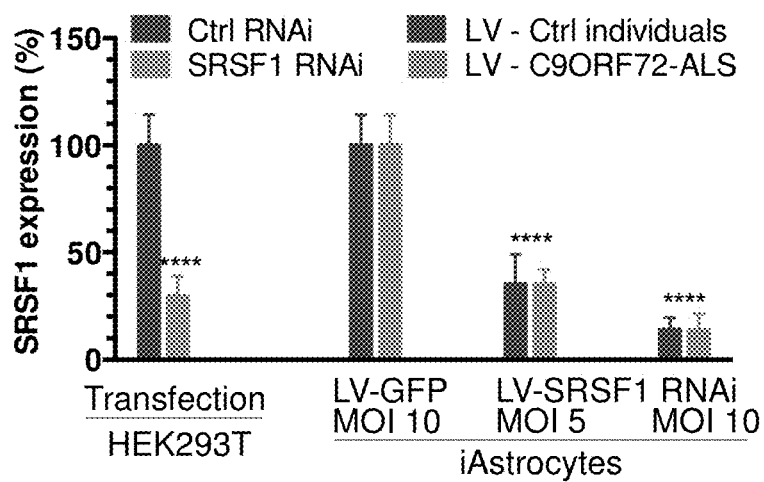
FIGS. 2A-2B: Co-cultures of mouse HB9:GFP motor neurons and SRSF1-RNAi transduced patient-derived astrocytes. A) Evaluating the efficiency of lentiviral-mediated SRSF1-RNAi depletion in HEK cells and iAstrocytes derived from control and C9ORF72-ALS patients. SRSF1 transcript levels were quantified in transfected HEK cells and iAstrocytes transduced with increased MOI doses of LV-SRSF1-RNAi. snRNA U1 transcript levels were used for normalization in triplicate experiments (Mean±SEM; two-way ANOVA, NS: non-significant, ****: $p<0.001$; N (qPCR reactions)=6); (b) High content imaging pictures showing how the Columbus analysis software recognizes Hb9:GFP motor neurons and the axons sprouting from them over SRSF1-RNAi-transduced astrocyte background.
Figure 2B:
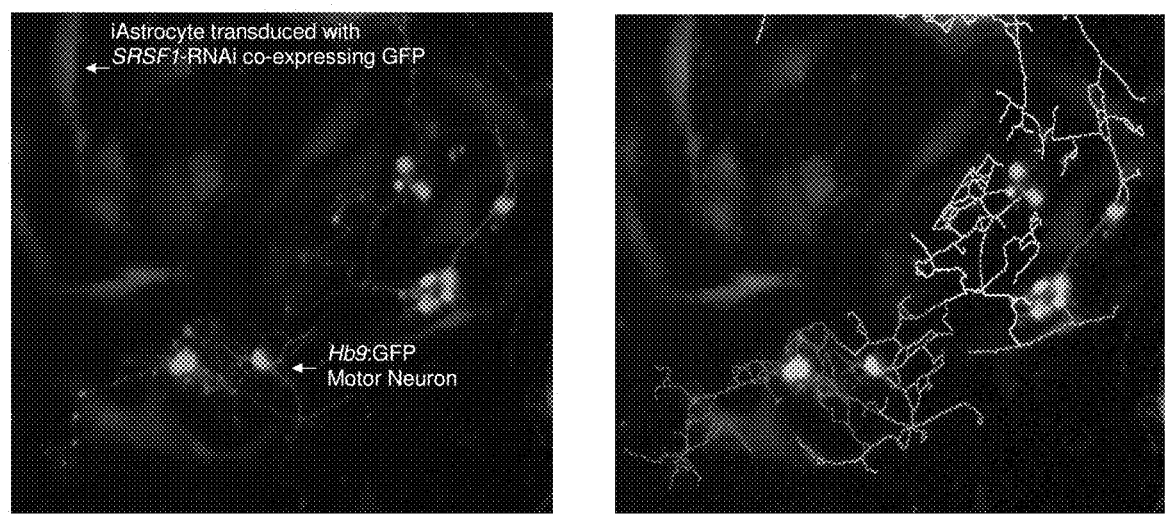

Transduction of human iNPC-derived astrocytes (iAstrocytes) using a viral multiplicity of infection (MOI) of 5 led to efficient transcript knockdown comparable to levels achieved in vivo in neuro-protected G4C2x36+SRSF1-RNAi *Drosophila* (FIG. 2). Mouse GFP-Hb9+ motor neurons were plated onto LV-SRSF1-RNAi transduced astrocytes derived from three controls and three C9ORF72-ALS patient fibroblast lines (table 5) and survival was quantified using a high-throughput imaging system (Online methods, FIG. 2b, methods).

Figure 10B:
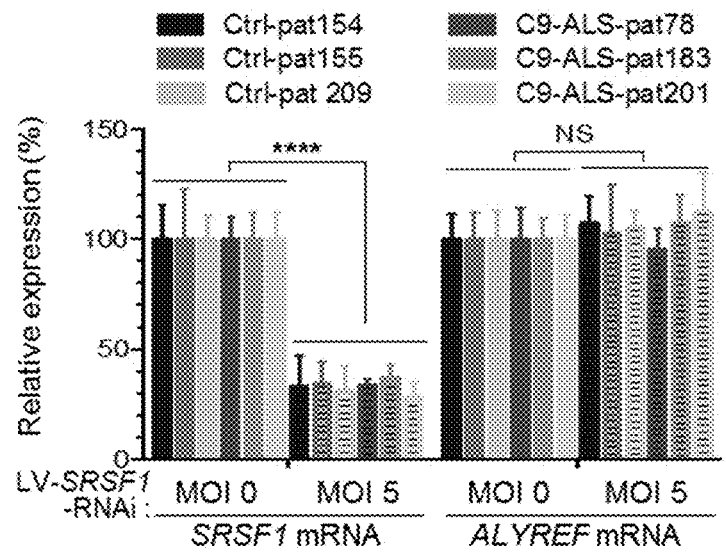
Figure 10C:
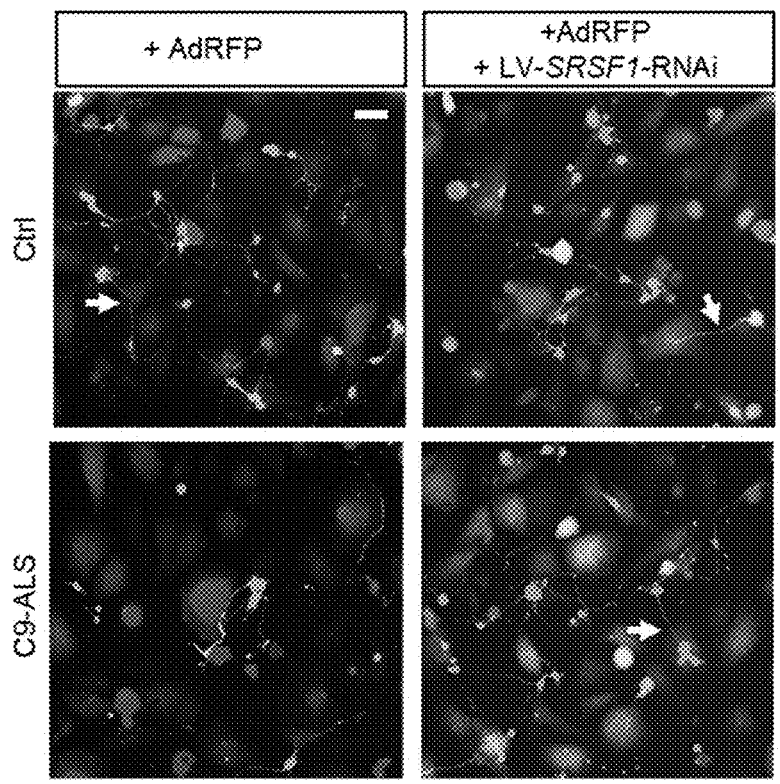
Figure 10D:
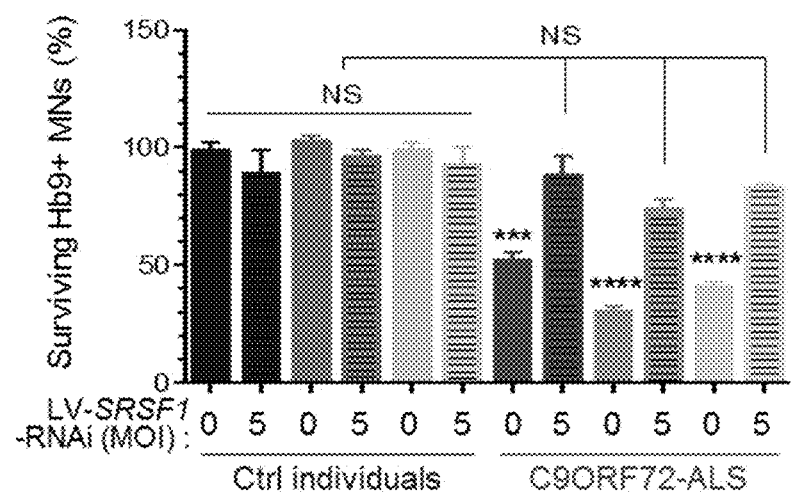
Figure 10E:
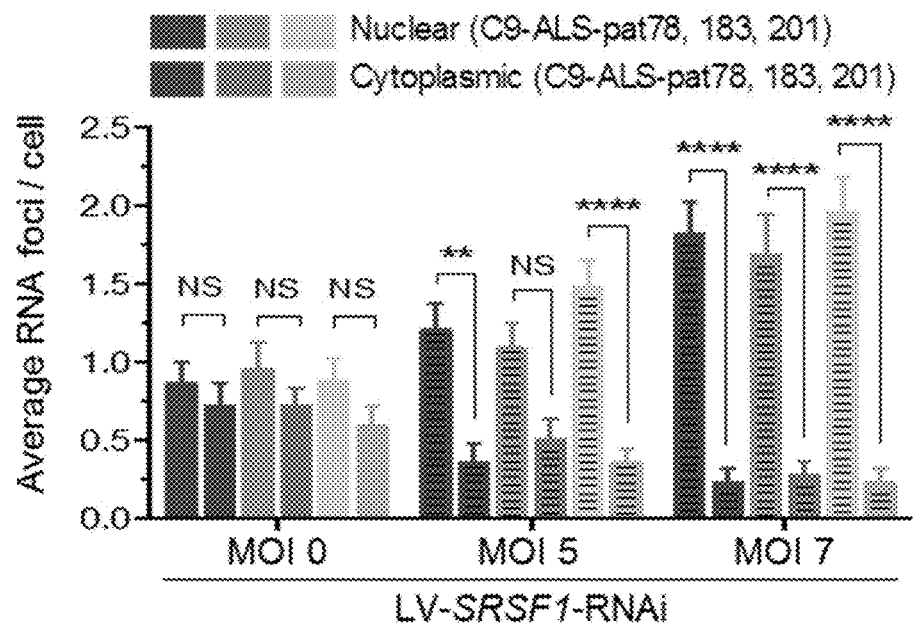

Quantification of SRSF1 and ALYREF mRNA levels confirmed the specific and partial knockdown of SRSF1 transcripts in both control and C9ORF72-ALS iAstrocytes (FIG. 10B). Control iAstrocytes transduced with an RFP-adenovirus (red) efficiently support the growth of GFP-Hb9+ motor neurons (green) while fewer motor neurons survived when co-cultured with astrocytes derived from C9ORF72-ALS patient fibroblasts (29) (FIG. 10C). Quantification of surviving motor neurons from four replicate experiments showed that while depletion of SRSF1 is not detrimental to control co-cultures, motor neuron death was prevented by depletion of SRSF1 in co-cultures derived from three separate C9ORF72-ALS cases (FIG. 10D).

EXAMPLE 3

To investigate potential nuclear export alteration of G4C2 repeat transcripts, we quantified nuclear and cytoplasmic sense RNA foci in the C9ORF72-ALS iAstrocytes. Representative images (FIG. 3) and individual counts are reported in Additional Data table 1. Upon depletion of SRSF1, the number of cytoplasmic RNA foci decreased, while nuclear RNA foci concomitantly increased (FIG. 11E) consistent with the predicted nuclear export inhibition of G4C2-repeat transcripts.

Figure 7:
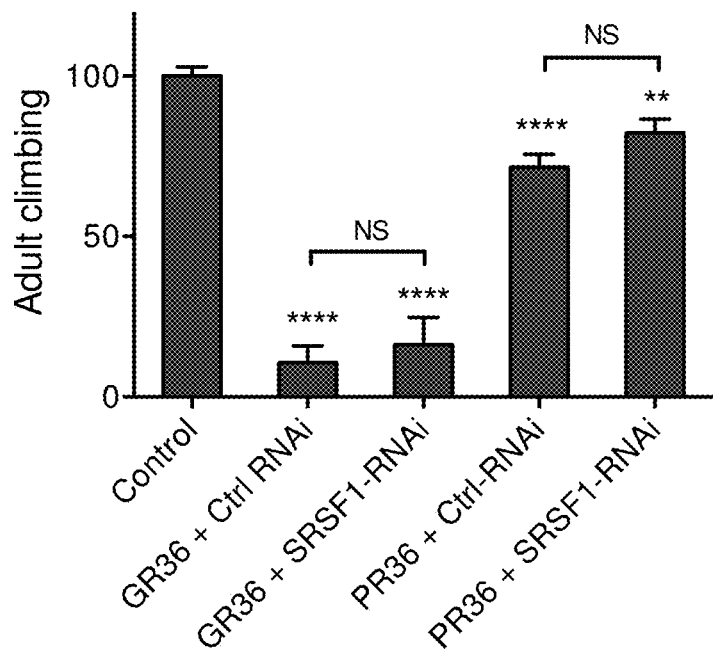
FIG. 7: SRSF1 depletion in *Drosophila* models expressing DPRs independently of G4C2 repeat expansions. Neuronal expression of Gly-Arg (GR36) and Pro-Arg (PR36) dipeptide repeats causes adult climbing deficits that are not rescued by SRSF1-depletion (mean±SEM normalized to Control (GAL4/Control-RNAi); Kruskal-Wallis with Dunn's multiple comparison test, NS: non-significant, : $p<0.01$, **: $p<0.001$; N=Control: 188, GR36+Ctrl-RNAi: 8, GR36+SRSF1-RNAi: 7, PR36+Ctrl-RNAi: 125, PR36+SRSF1-RNAi: 119)
Figure 11A:
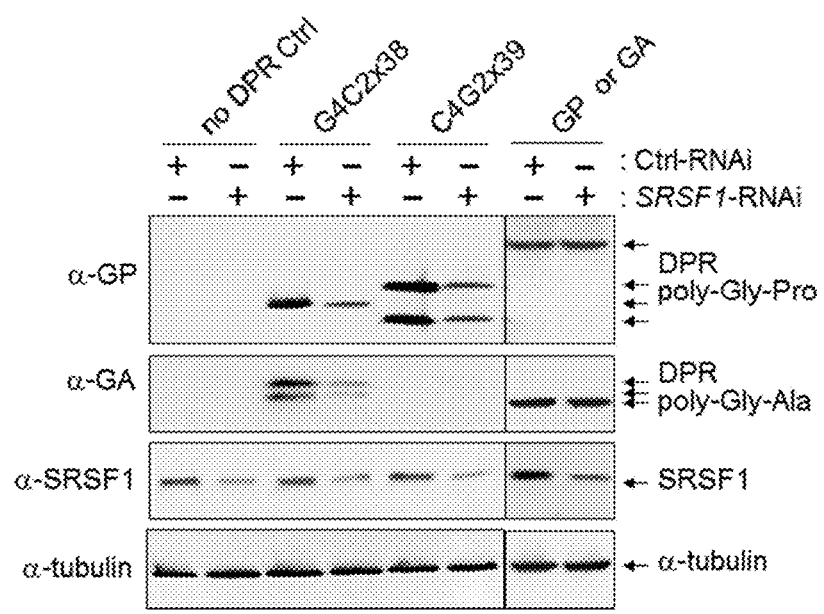
FIGS. 11A-11D: SRSF1-depletion and blocked SRSF1:TAP/NXF1 interaction both inhibit the nuclear export of C9ORF72-repeat RAN-translated transcripts and DPR production. (A) Western blots from N2A cells co-transfected with either a Ctrl or SRSF1-RNAi vector and control backbone plasmid (no DPR Ctrl) or the same plasmid expressing 38 uninterrupted G4C2-sense-repeats (G4C2×38) or 39 uninterrupted C4G2-antisense-repeats (C4G2×39). Sense/antisense poly-Gly-Pro and sense poly-Gly-Ala DPR proteins are produced by internal repeat RAN translation in the absence of an initiating start codon (FIG. 4) (nucleotide sequences in FIG. 4e. A hexanucleotide-repeat specificity control was provided by co-transfection of plasmids expressing poly-Gly-Ala (GAx36) or poly-Gly-Pro (GPx36) independently of the G4C2/C4G2-repeat sequences nucleotide sequences in FIG. 26) and either Ctrl or SRSF1-RNAi vectors. (B) N2A cells co-transfected with G4C2×38 and either Ctrl or SRSF1-RNAi plasmids (left part) and either FLAG-tagged SRSF1 aa11-196 wild type (SRSF1) or SRSF1-m4 (right part) were subjected to cellular fractionation using hypotonic lysis to yield cytoplasmic fractions (FIG. 8e). Cytoplasmic and whole-cell (total) G4C2-repeat sense transcript levels were normalized to U1 snRNA levels in triplicate experiments prior to plotting as a ratio to account for potential changes in mRNA transcription/stability (mean±SEM; one-way ANOVA, NS: non-significant, : $p<0.01$; N (qRT-PCR reactions)=6). (C) Western blots from N2A cells co-transfected with either G4C2×38 or C4G2×39 plasmids and control (FLAG Ctrl) or FLAG-tagged SRSF1 aa11-196 wild type (SRSF1), SRSF1-m2 or SRSF1-m4. (D) MTT cell proliferation assay performed on N2A cells transfected with either G4C2×38 or C4G2×39 plasmids and Ctrl-RNAi, SRSF1-RNAi, FLAG Ctrl, SRSF1 or SRSF1-m4 in triplicate experiments (mean±SEM; one-way ANOVA, NS: non-significant, : $p<0.01$, *: $p<0.005$, **: $p<0.001$; N ($OD_{650}$ values)=12)

Due to poor detection of DPRs in flies or patient-derived iAstrocytes and iNeurons (not shown), we engineered plasmids expressing 38 uninterrupted G4C2-sense or 39 uninterrupted C4G2-antisense repeat transcripts that are substrates for specific RAN translation of DPRs (FIG. 4). Transfection of mouse neuronal N2A cells with sense or antisense repeat constructs led to specific DPR production of poly-Gly-Pro (expressed from both sense and antisense transcripts and poly-Gly-Ala (expressed from sense transcripts) (FIG. 11A). However, co-transfection of a mouse SRSF1-RNAi plasmid (FIG. 5) led to a marked reduction in the RAN translation of both sense and antisense DPRs (FIG. 11A, left panels; quantification in FIG. 6A). This does not depend on reduced splicing activity of SRSF1 since the RAN constructs were engineered without splicing sites. Moreover, it is specific for the hexanucleotide-repeat sequences since expression of synthetic poly-Gly-Ala ×36 or poly-Gly-Pro ×36 using alternatives codons (GGA/T, GCA/T, CCA/T) is not altered upon SRSF1 depletion (FIG. 11A, right panels). Supporting this, SRSF1-RNAi did not ameliorate locomotor deficits conferred by DPR expression Drosophila (FIG. 7). These data are consistent with our previous reported findings that showed specific and direct binding of SRSF1 onto G4C2-repeat transcripts (9).

EXAMPLE 4

Figure 11B:
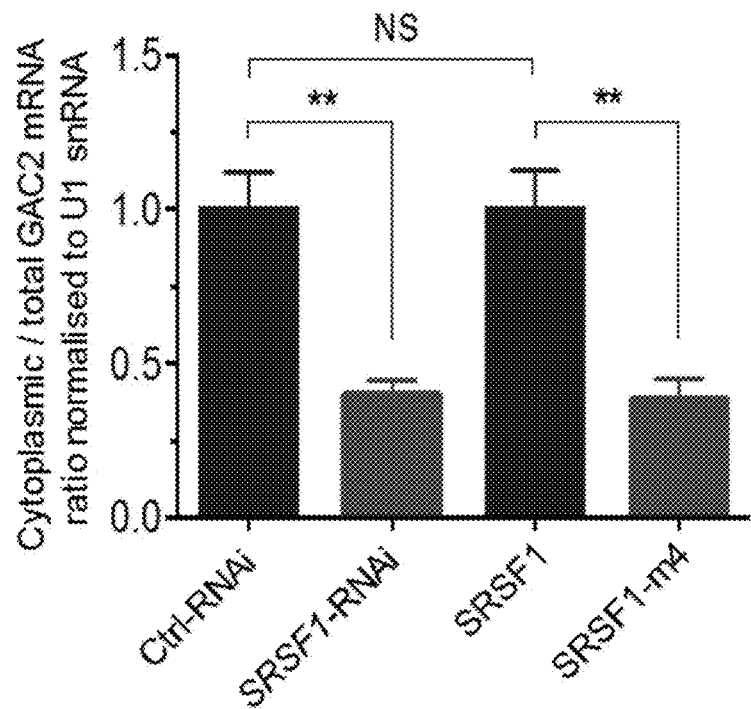
Figure 11C:
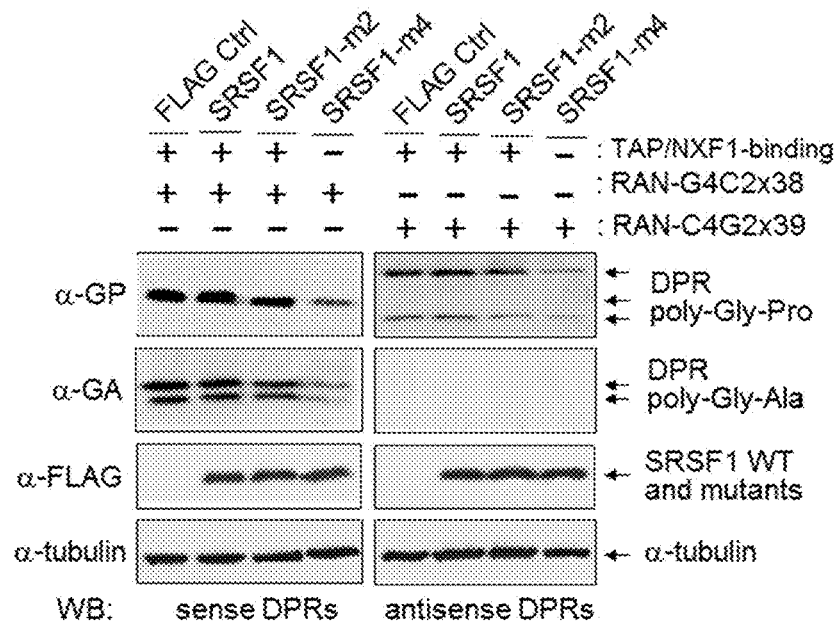
Figure 11D:
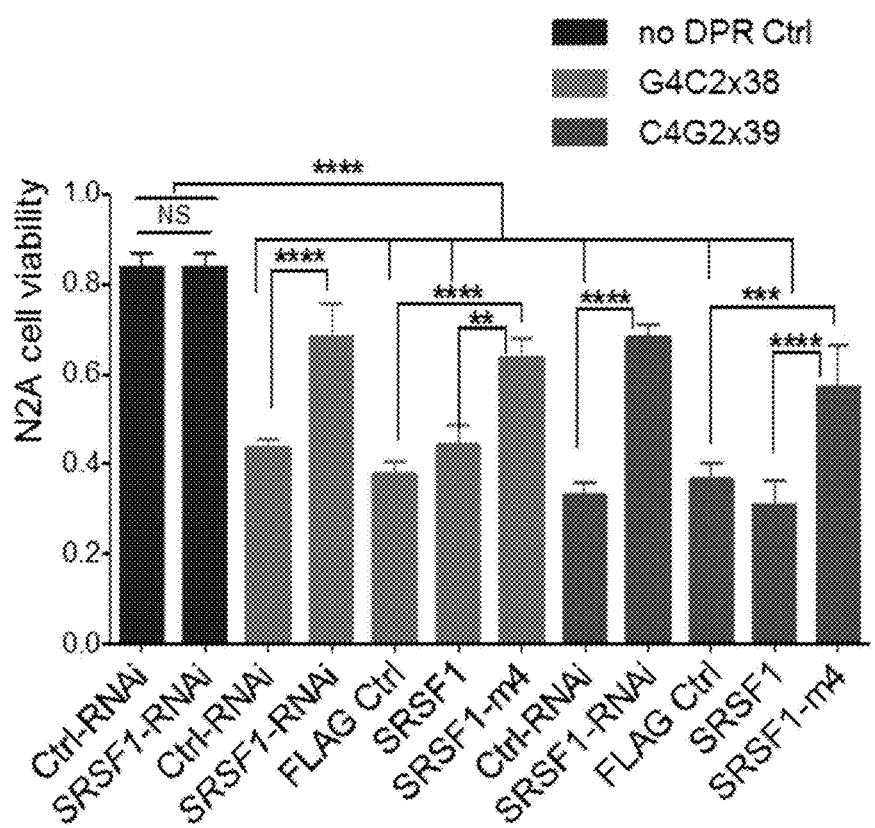

To identify potential impairment in the nuclear export of C9ORF72 repeat transcripts, we measured the cytoplasmic expression levels of G4C2 transcripts in the presence of Ctrl or SRSF1-RNAi constructs. Cytoplasmic repeat transcript levels normalized to total levels are markedly reduced upon exposure to SRSF1-RNAi (FIG. 11B, left image) indicating that the nuclear export of C9ORF72-repeat transcripts is inhibited by the depletion of SRSF1. The quality of cellular fractionation was checked by immunoblotting using antibodies against the chromatin-remodeling SSRP1 factor, showing absence of nuclear contamination in the cytoplasmic fractions (FIG. 8). SRSF1 mediates mRNA nuclear export through binding to NXF1 (26, 30). We previously showed that four arginine residues lying in the unstructured linker between the two RNA recognition motifs of SRSF1 (amino-acids 11-196) are required both for RNA nuclear export and interaction with NXF1, while mutations of only two arginine residues lead to reduced binding to NXF1 (23). Co-transfection of the quadruple SRSF1 point mutant (SRSF1-m4) which does not interact with TAP/NXF1 (23) led to marked reduction in the normalized cytoplasmic repeat transcript levels (FIG. 10B, right image) and production of sense and antisense DPRs while the wild type region or the same sequence bearing only two arginine mutations (SRSF1-m2) respectively had no or little effect (FIG. 11C, quantification in FIGS. 6 B and C) demonstrating that C9ORF72-repeat transcripts are exported from the nucleus via a mechanism that requires the interaction of SRSF1 and NXF1. Accordingly, both the depletion of SRSF1 and the expression of the dominant negative mutant SRSF1-m4 suppress the neurotoxicity mediated by expression of the C9ORF72-repeat transcripts in neuronal N2A cells (FIG. 11D).

In this report, we show for the first time that the nuclear export of C9ORF72 repeat transcripts and subsequent RAN translation depends on the interaction of the nuclear export adaptor SRSF1 with the NXF1 export receptor. Inhibiting this interaction or depleting SRSF1 lead to marked inhibition of the nuclear export of C9ORF72 repeat transcripts and reduced RAN translation of both sense and antisense DPRs. Moreover, partial depletion of SRSF1 prevents in vivo neurodegeneration and rescues locomotor deficits in a Drosophila model of C9ORF72-ALS, consistent with previous work which showed that DPRs cause neurodegeneration in Drosophila (14). Depletion of SRSF1 also suppresses neurotoxicity in co-cultures of motor neurons and human-derived C9ORF72-ALS astrocytes and in neuronal N2A cells. Hence, this represents a promising prospect for the development of an effective neuroprotective strategy in C9ORF72-related ALS. It is noteworthy that SRSF1-RNAi depletion was used as a therapeutic approach to prevent oncogenic transformation both in vitro and in vivo in mice (31). The cellular pathways causing neurodegeneration following nuclear export of C9ORF72 G4C2 repeat sequences and the precise mechanism(s) of neuroprotection conferred by the partial depletion of SRSF1 remain to be elucidated in future studies.

EXAMPLE 5

Figure 20B:
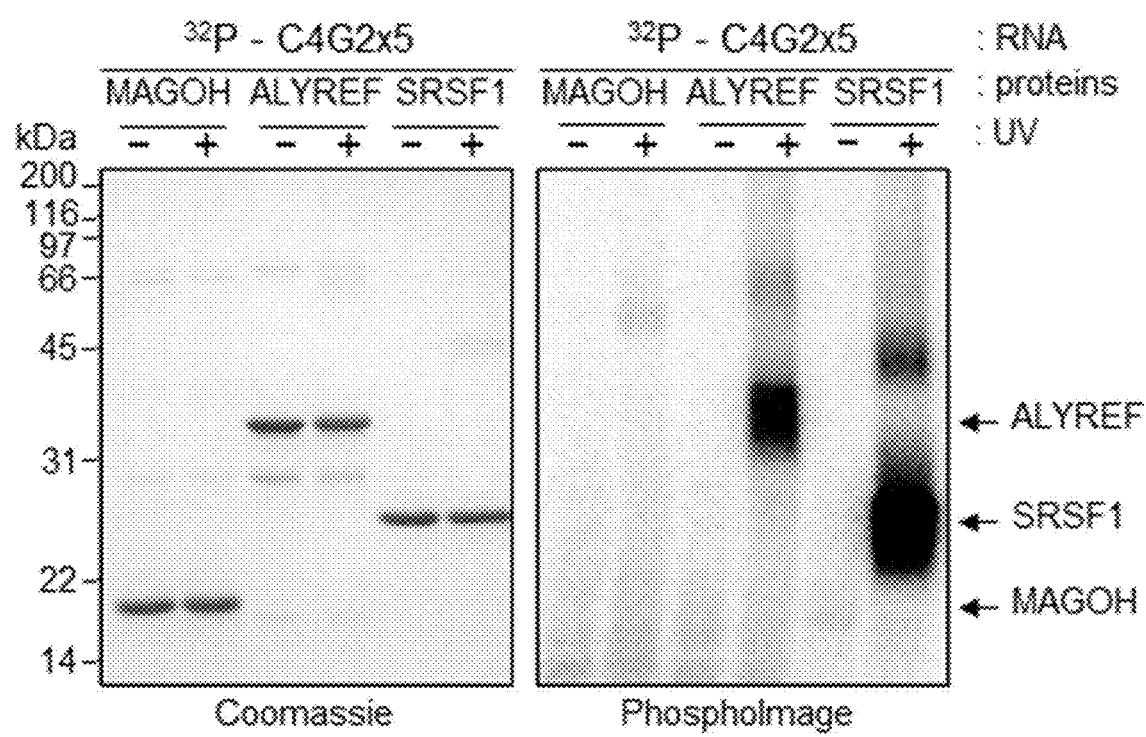

ALYREF and SRSF1 directly bind G4C2 and C4G2 repeat RNA. We performed in vitro UV-crosslinking assays using purified recombinant proteins and synthetic G4C2×5 and C4G2×5 RNA probes to investigate direct protein:RNA interactions. Recombinant hexa-histidine-tagged human ALYREF, SRSF1 amino-acids 11-196 which retains wild type ability to bind RNA and NXF136, and MAGOH, a control protein which does not bind RNA49, were purified by ion metal affinity chromatography in high salt to disrupt potential interactions with bacterial RNA. Purified proteins were incubated with 5'-end 32P-radiolabelled G4C2×5 (FIG. 20a) or C4G2×5 (FIG. 20b) RNA probes prior to irradiation with UV where indicated (+) and resolved by SDS-PAGE. As shown on the Phosphoimages, covalently-bound RNA molecules remained associated with ALYREF and SRSF1 visualised on the Coomassie-stained panels during the denaturing electrophoresis. These data demonstrate direct interactions of ALYREF and SRSF1 with both sense and antisense repeat RNA in agreement with our previous studies[42, 43]. The interactions are specific since no binding of RNA was detected in absence of UV-irradiation or with the negative control protein MAGOH. These direct interactions are also consistent with our previously reported co-localization of ALYREF with RNA foci in motor neurons from C9ORF72-ALS patients[42]. Furthermore, we show that SRSF1 co-localizes with RNA foci in motor neurons from human post mortem spinal cord tissue of C9ORF72-ALS cases (FIG. 20c).

EXAMPLE 6

Figure 21A:
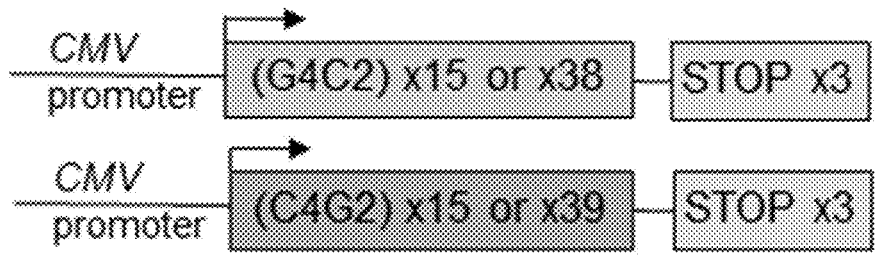
FIGS. 21A-21D: Generation of neuronal cell models recapitulating the RAN-dependent translation of sense and antisense DPRs. (A) diagrammatic representations of constructs. (B) Sense G4C2 RNA foci stained with Cy3-labelled antisense C4G2 probe. DAPI was used to stain nuclei of neuronal N2A cells in blue. Scale bar: 5 µm. (C) Western blots from N2A cells transfected with a control backbone plasmid (no DPR Ctrl) or the same plasmid expressing either 15 uninterrupted G4C2-sense repeat (G4C2×15), 38 uninterrupted G4C2-sense-repeats (G4C2×38), 15 uninterrupted C4G2-antisense repeat (C4G2×15) or 39 uninterrupted C4G2-antisense-repeats (C4G2×39). Membranes were probed with antibodies against poly-Gly-Pro DPRs, poly-Gly-Ala DPRs or loading control α-tubulin. (D) MTT cell proliferation assay performed on N2A cells transfected with either a control backbone plasmid (no DPR Ctrl) or the same plasmid expressing various length of uninterrupted hexanucleotide repeat transcripts in triplicate experiments (mean±SEM; one-way ANOVA; N (OD650 values)=12)
Figure 21B:
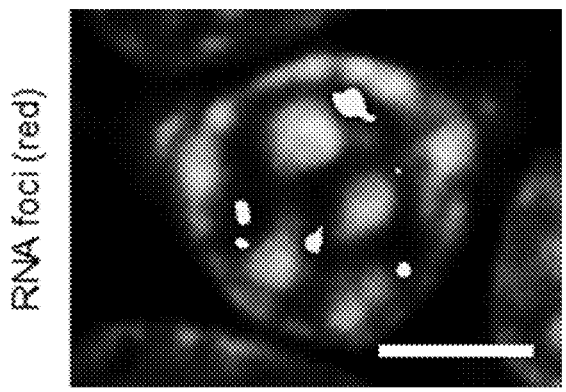
Figure 21C:
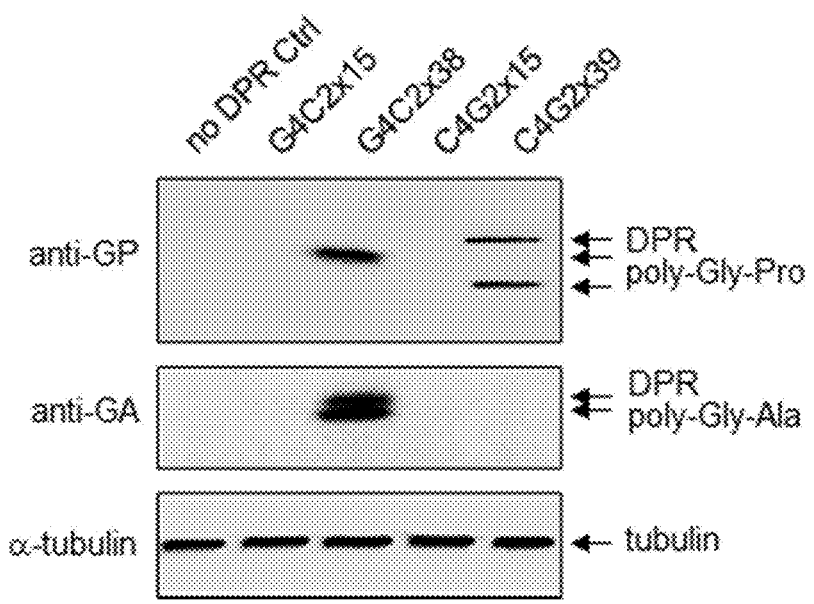
Figure 21D:
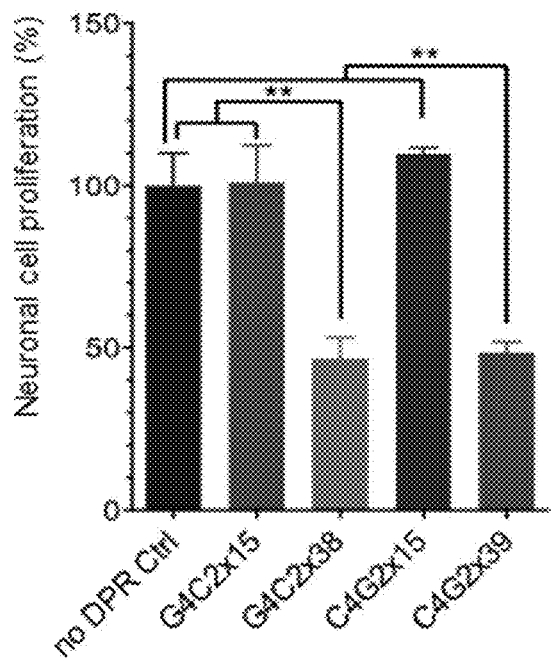

Generation of neuronal cell models recapitulating the RAN-dependent translation of sense and antisense DPRs. To investigate whether the binding of SRSF1 to G4C2-sense and C4G2-antisense repeat RNA sequences has the ability to trigger the nuclear export of repeat transcripts, we generated synthetic mammalian expression constructs bearing increasing lengths of pure repeat sequences in the absence of ATG or Kozak elements to specifically investigate RAN-dependent translation of dipeptide repeat proteins. Following annealing of synthetic G4C2 or C4G2 repeat oligonucleotides as described in Methods and FIG. 4a-d, we engineered plasmids expressing transcripts containing 15 or 38 uninterrupted sense repeats (G4C2×15 or G4C2×38) and 15 or 39 uninterrupted antisense repeats (G4C2×15 or C4G2×39) with 3'-end stop codons in each of the three frames (FIG. 21a). The lengths of repeats were confirmed by sequencing and poly-acrylamide gel electrophoresis. The nucleotide sequences are presented in Supplementary FIG. 4e. In mammals, the bulk nuclear export of mRNA is predominantly coupled to the recruitment of the TREX complex during splicing[47]. Three C9ORF72 transcripts, each containing 4 or 10 introns, are transcribed from the C9ORF72 gene. The synthetic repeat constructs were engineered without splicing elements or intronic sequences to investigate the nuclear export potential of G4C2 and C4G2 repeat RNA sequences in repeat transcripts independently of functional coupling to pre-mRNA splicing. Transfections of mouse neuronal N2A cells with sense or antisense repeat constructs led to the formation of RNA foci for all repeat transcripts (FIG. 21b, data shown for the G4C2×38 construct) and to specific DPR production of poly-Gly-Pro (expressed from both sense and antisense transcripts) and poly-Gly-Ala (expressed from sense transcripts) for repeat transcripts bearing 38 sense or 39 antisense repeats (FIG. 21c). Interestingly, the expression of DPRs correlated with neurotoxic effects in MTT cell proliferation assays, while the control plasmid or the constructs expressing 15 sense or antisense repeats but no DPRs did not exhibit significant cytotoxicity in the neuronal cells (FIG. 21d). We conclude that the minimal G4C2×38 sense and C4G2×39 antisense repeat RNA transcripts can be exported into the cytoplasm independently of functional coupling to pre-mRNA splicing and are substrates for subsequent RAN translation of DPRs.

EXAMPLE 7

Depletion of SRSF1 inhibits the production of sense and antisense DPRs in neuronal cells. A mouse SRSF1-knockdown plasmid co-expressing a GFP reporter and a pre-miRNA cassette was engineered similarly to the previously described human SRSF1-RNAi (FIG. 5). Transfection of mouse neuronal N2A cells with G4C2×38 or C4G2×39 repeat constructs and the mouse SRSF1-RNAi plasmid led to a marked reduction in the RAN translation of both sense and antisense DPRs (FIG. 11a, left panels and FIG. 6b for quantification). The SRSF1-RNAi dependent inhibition of DPR production does not depend on the splicing activity of SRSF1 since the RAN constructs are devoid of splicing sites. Moreover, the SRSF1 depletion is specific to the hexanucleotide-repeat sequences since expression of synthetic 36-repeat poly-Gly-Pro (GP36) or 36-repeat poly-Gly-Ala (GA36) DPRs using alternative codons (sequences available in FIG. 27) is not altered upon SRSF1 depletion (FIG. 11a, right panels and FIG. 6e-f for respective quantifications of GP36 and GA36). These results support our previous findings that the depletion of SRSF1 did not ameliorate the rough eye phenotypes (FIG. 9e) or the locomotor deficits (FIG. 9f) conferred by G4C2-independent GR36 and PR36 DPRs expression in Drosophila.

Figure 28A:
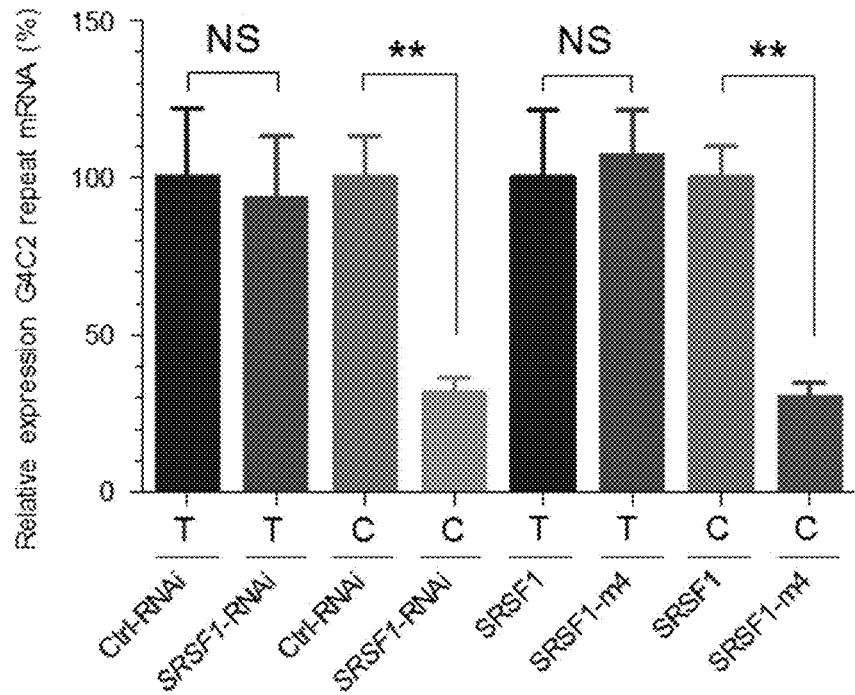
FIGS. 28A-28B: Depleting SRSF1 or inhibiting its sequestration and interaction with NXF1 alter the cytoplasmic levels of hexanucleotide repeat transcripts but not their total levels.
Figure 28B:
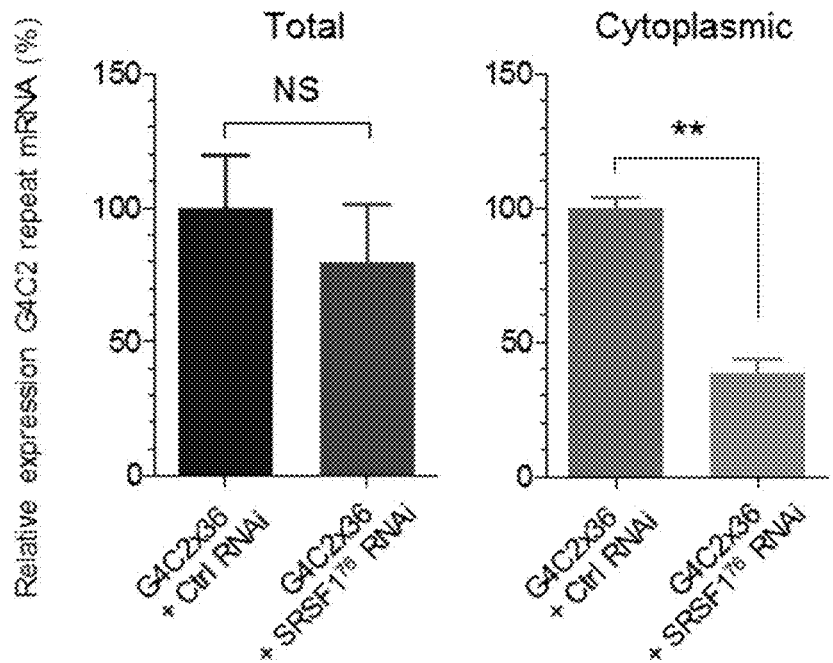

SRSF1 mediates mRNA nuclear export through binding to NXF1[34,54]. We previously showed that four arginine residues lying in the unstructured linker between the two RNA recognition motifs of SRSF1 (amino-acids 11-196) are required both for RNA nuclear export and interaction with NXF1, while mutations of only two arginine residues lead to slightly reduced binding to NXF1 in human embryonic kidney cells [36]. Similarly, endogenous NXF1 is specifically immunoprecipitated in neuronal N2A cells transfected with FLAG-tagged SRSF1 11-196 wild type or double R117, 118A mutant (SRSF1-m2). In contrast, the co-immunoprecipitation of NXF1 is severely impaired by the quadruple R93,94,117,118A mutations of SRSF1 (SRSF1-m4) (FIG. 6g). Co-transfection of the quadruple SRSF1-m4 dominant mutant further led to a marked reduction in the production of both sense and antisense DPRs while the wild type sequence or the variant bearing two arginine mutations (SRSF1-m2) respectively had no or little effect (FIG. 11c). This was statistically assessed for both poly-GP and poly-GA DPRs produced by sense repeat transcripts (FIG. 6c) and poly-GP DPRs generated from antisense repeat transcripts (FIG. 56b. Taken together our data demonstrate that the expression of the C9ORF72 repeat transcripts is dependent on a mechanism that requires the interaction of SRSF1 with the nuclear export receptor NXF1. Accordingly, both the depletion of SRSF1 and the expression of the dominant negative mutant SRSF1-m4 suppress the neurotoxicity mediated by expression of the C9ORF72 repeat transcripts in neuronal N2A cells (FIG. 11d). Supporting this, RNAi-mediated depletion of the Drosophila NXF1 homologue, sbr, could rescue the locomotor deficits in larvae and adult flies expressing G4C2×36 (FIG. 28).

EXAMPLE 8

Sequestration of SRSF1 triggers the NXF1-dependent nuclear export of hexanucleotide repeat transcripts in neuronal cells. Our result showing that expression of the SRSF1-m4 mutant protein acts as a dominant negative mutant for DPR production suggests that the SRSF1-m4 protein is sequestered onto the hexanucleotide repeat transcripts instead of the endogenous SRSF1 protein, preventing in turn interactions of repeat transcripts with NXF1 and nuclear export. Using in vitro UV cross-linking assays, we confirmed that the purified recombinant hexa-histidine-tagged SRSF1-m4 protein retains the ability to directly interact with synthetic 5'-end 32P-radiolabelled sense G4C2×5 (FIG. 8a) and antisense C4G2×5 (FIG. 8b) repeat RNA. These interactions are specific since no binding of RNA was detected in absence of UV-irradiation or with the negative control protein MAGOH. We next sought to investigate whether this was also true in live N2A cells using RNA immunoprecipitation (RIP) assays. N2A cells were transfected with FLAG control, FLAG-tagged SRSF1 or FLAG-tagged SRSF1-m4 and various lengths of sense or antisense repeat transcript constructs prior to fixing of ribonucleoprotein complexes. Cell extracts were then subjected to anti-FLAG immunoprecipitation under the same conditions used in the co-immunoprecipitation of NXF1 (FIG. 6g) prior to the qRT-PCR analysis of SRSF1-cross-linked RNA molecules. Validating our RIP assay, immunoprecipitation of both SRSF1 or SRSF1-m4 led to specific co-precipitation of SMN, a known SRSF1-binder 55, but not of JUN, an intronless control transcript not expected to be bound by SRSF156, in N2A cells expressing either sense (FIG. 8c) or antisense (FIG. 8d) repeat transcripts. In sharp contrast, the levels of immunoprecipitated G4C2-sense or C4G2-antisense repeat transcripts significantly increased with the number of hexanucleotide repeats (FIG. 8c, d) showing length-dependent repeat-RNA sequestration of SRSF1 and SRSF1-m4 in neuronal cells.

Figure 8A:
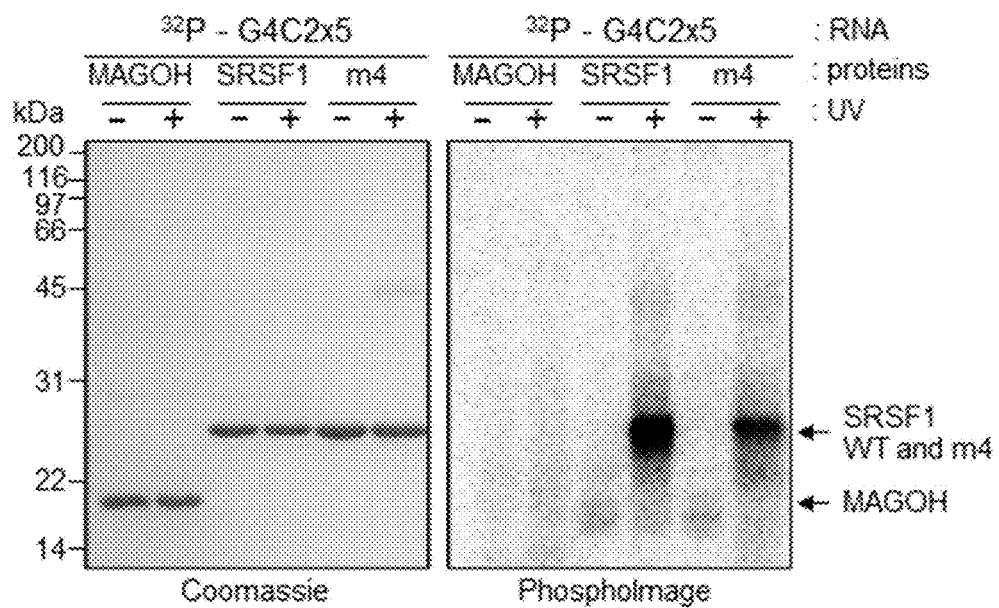
FIGS. 8A-8G: Depleting SRSF1 or inhibiting its repeat-RNA sequestration and interaction with NXF1 inhibit the nuclear export of RAN-translated transcripts to alleviate neurotoxicity. (a, b) Protein:RNA UV crosslinking assays using purified recombinant proteins and 32P-end-radiolabeled G4C2×5 (a) and C4G2×5 (b) repeat RNA probes. Proteins are visualised on SDS-PAGE stained with Coomassie blue (left panels) and covalently linked RNA:protein complexes by autoradiography on PhosphoImages (Right panels). (c, d) RNA immunoprecipitation (RIP) assays. Formaldehyde was added to the medium of live N2A cells co-transfected with G4C2×15, G4C2×38 (c), C4G2×15 or C4G2×39 (d) and either FLAG control (FLAG Ctrl), FLAG-tagged SRSF1 aa11-196 wild type (SRSF1) or SRSF1-m4 were subjected to anti-FLAG immunoprecipitation. Purified RNA was analysed by qRT-PCR following normalization to U1 snRNA levels in triplicate experiments (mean±SEM; two-way ANOVA; N (qRT-PCR reactions)=6). (e) Cellular fractionation quality check. N2A cells co-transfected with G4C2×38 and either Ctrl or SRSF1-RNAi plasmids or with G4C2×38 and either FLAG-tagged SRSF1 aa11-196 wild type (SRSF1) or SRSF1-m4 were subjected to cellular fractionation using hypotonic lysis conditions to yield cytoplasmic fractions. The quality of the cellular fractionation was checked using antibodies against the nuclear chromatin-remodeling SSRP1 factor and alpha-tubulin. This was repeated for each fractionation and RNA were kept for qRT-PCR analysis if the cytoplasmic fraction showed no nuclear contamination. (f) Western blots of *Drosophila* expressing G4C2×36 and either Ctrl or SRSF1-RNAi, subjected to cellular fractionation using hypotonic lysis to yield cytoplasmic fractions. Histone H3 is used to check for potential nuclear contamination. (g) Cytoplasmic and total G4C2-repeat sense transcript levels were normalized to Tub84b levels in G4C2×36+Ctrl-RNAi or G4C2×36+SRSF1[76]-RNAi *Drosophila* in triplicate experiments prior to plotting as a ratio to account for potential changes in mRNA transcription/stability (mean±SEM; paired t-test; N (qRT-PCR reactions)=3). In contrast to cytoplasmic levels, total levels of hexanucleotide repeat transcripts were not significantly altered upon expression of SRSF1-m4 or depletion of SRSF1 in cells or flies (FIG. 2B)
Figure 8B:
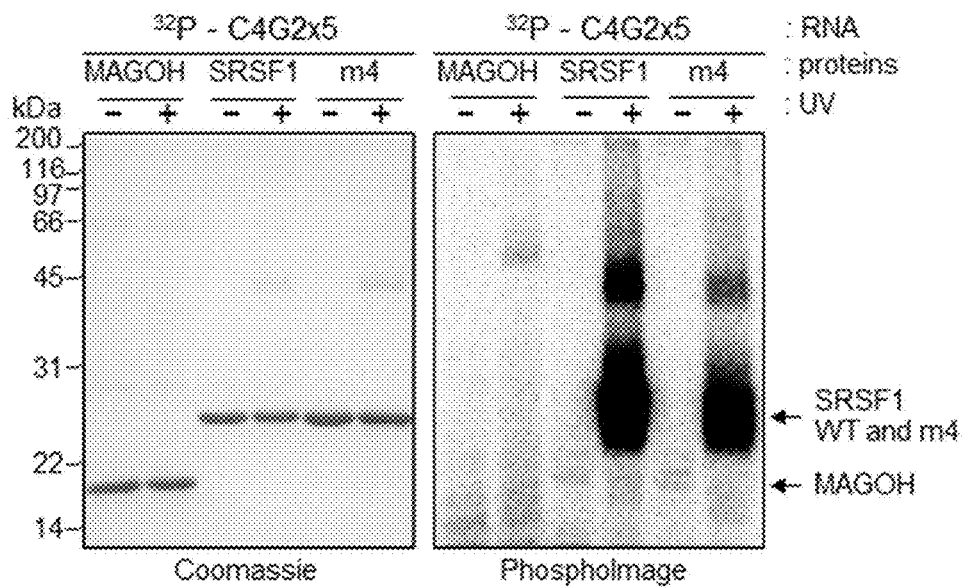
Figure 8C:
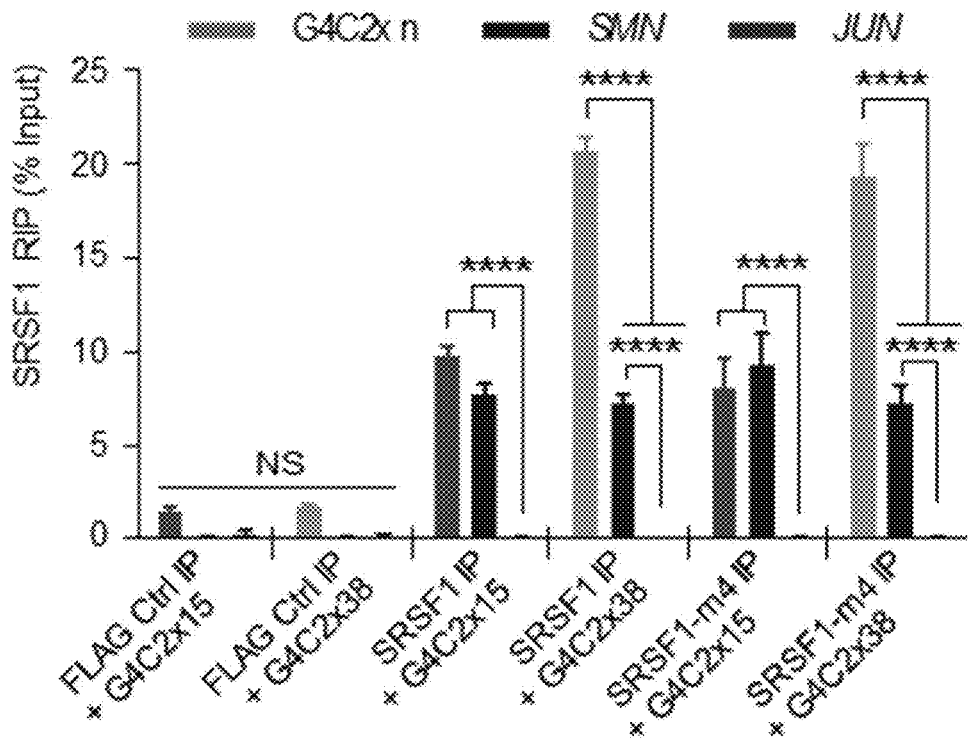
Figure 8D:
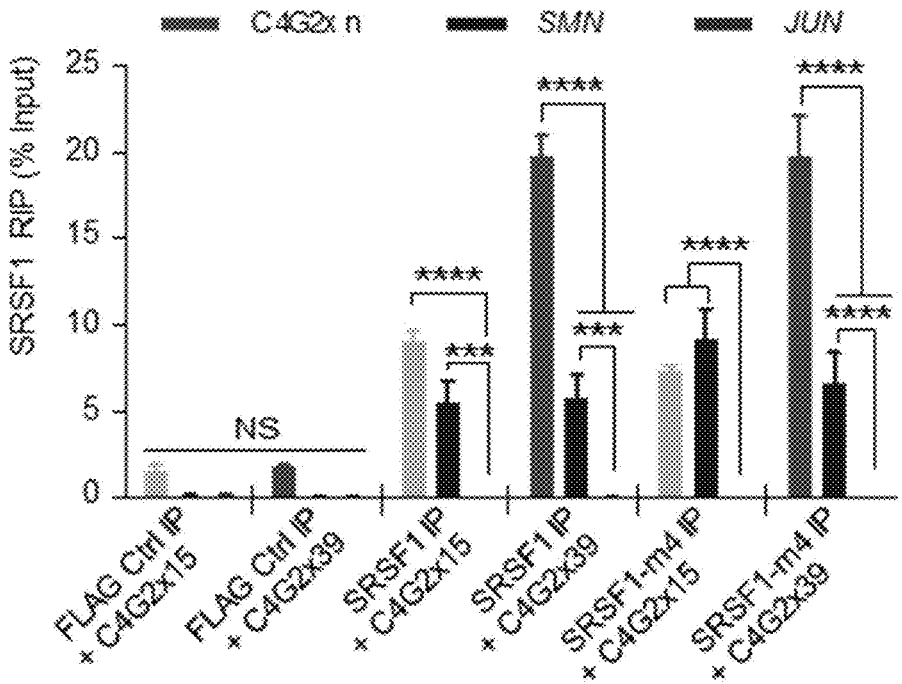
Figure 8E:
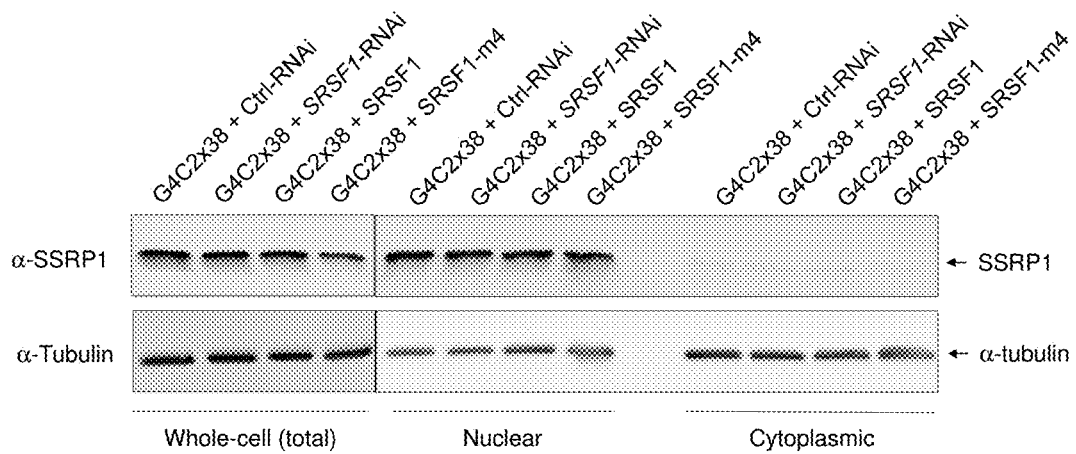
Figure 8F:
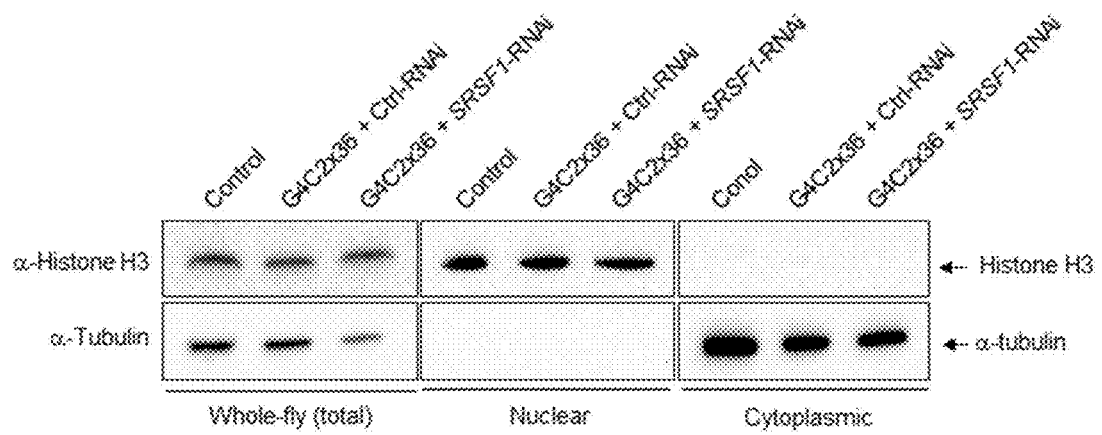
Figure 8G:
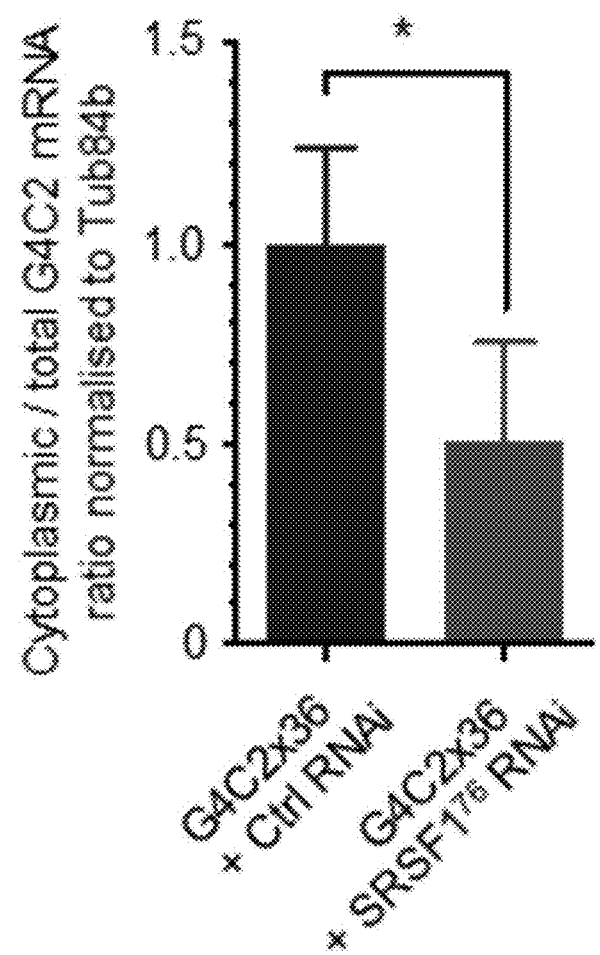

To evaluate the effects of SRSF1 depletion or SRSF1-m4 expression on the nuclear export of C9ORF72 repeat transcripts, we measured the total and cytoplasmic levels of G4C2×38 transcripts in the presence of Ctrl or SRSF1-RNAi and SRSF1 or SRSF1-m4 in transfected N2A cells. The quality of the cellular fractionation was checked by immunoblotting using antibodies against the chromatin-remodeling SSRP1 factor (FIG. 8e) showing absence of significant nuclear contamination in the cytoplasmic fractions. Total levels of G4C2×38 transcripts are not significantly altered upon SRSF1-RNAi or expression of SRSF1-m4 while the cytoplasmic levels of G4C2×38 transcripts are markedly reduced in both conditions (FIG. 29a). Cytoplasmic repeat transcript levels were also normalized to total levels to specifically assess the nuclear export process as in our previous studies[48, 49]. The cytoplasmic/total mRNA level ratios are markedly reduced upon exposure to SRSF1-RNAi (FIG. 8f, Ctrl-RNAi vs. SRSF1-RNAi). Similarly, the co-transfection of the SRSF1-m4 mutant which fails to interact with NXF1 led to marked reduction in the normalized cytoplasmic repeat transcript levels (FIG. 8f, SRSF1 vs. SRSF1-m4). To extend this analysis in vivo, *Drosophila* larvae expressing G4C2×36 and either Ctrl or SRSF1-RNAi were subjected to the same fractionation (FIG. 8g) and transcript analysis. As with cells, total levels of G4C2×36 transcripts are not significantly altered upon SRSF1-RNAi while the cytoplasmic levels of G4C2×36 transcripts are markedly reduced (FIG. 29b). Consequently, the cytoplasmic/total mRNA level ratio is significantly reduced upon exposure to SRSF1-RNAi (FIG. 8h). Together these data demonstrate that depleting SRSF1 or preventing its repeat RNA-sequestration and interaction with NXF1 specifically inhibit the nuclear export of hexanucleotide repeat transcripts in vitro and in vivo.

EXAMPLE 9

Figure 22A:
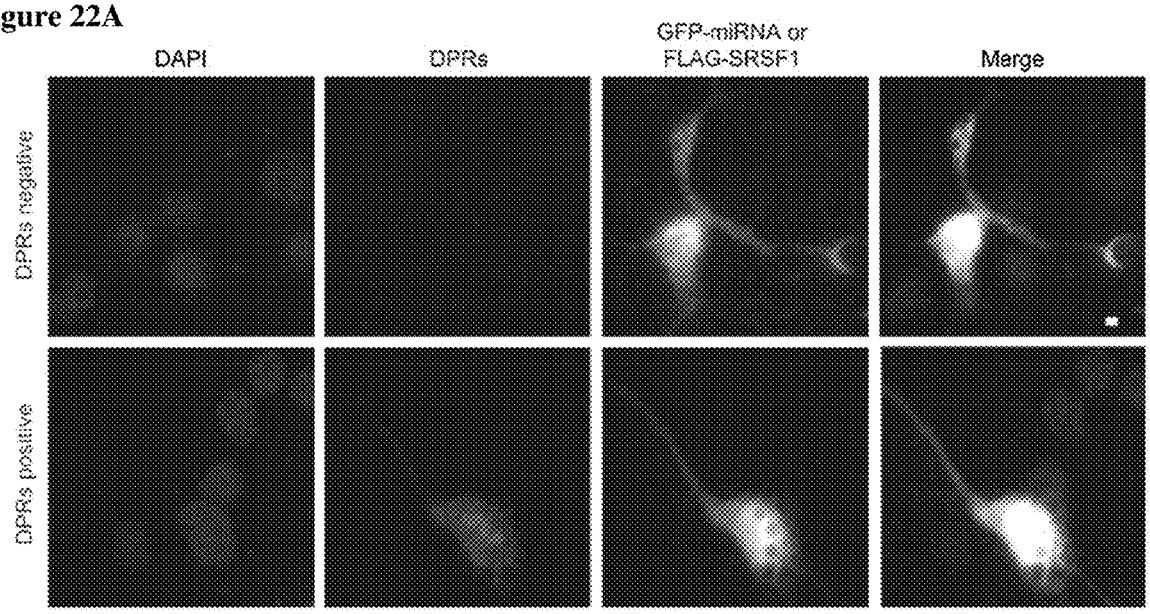
FIGS. 22A-22C: Depleting SRSF1 or inhibiting its repeat-RNA sequestration and interaction with NXF1 inhibit the production of DPRs in primary neurons. (A) Immunofluorescence microscopy of cultured rat cortical neurons. DPRs were detected in the red channel using anti-V5 and anti-mouse ALEXA594 antibodies. The Ctrl-RNAi and SRSF1-RNAi constructs co-express GFP while the FLAG-tagged SRSF1 proteins were stained using an anti-FLAG antibody conjugated to FITC allowing detection and quantification of transfected neurons in the green channel. Scale bar: 5 µm. (B, C) Statistical assessment of the cortical neuron counts was performed from approximately 100 transfected neurons for each group (Fisher's exact test; N (transfected neurons)=Ctrl-RNAi: 95, SRSF1-RNAi: 112, SRSF1: 106, SRSF1-m4: 121)
Figure 22B:
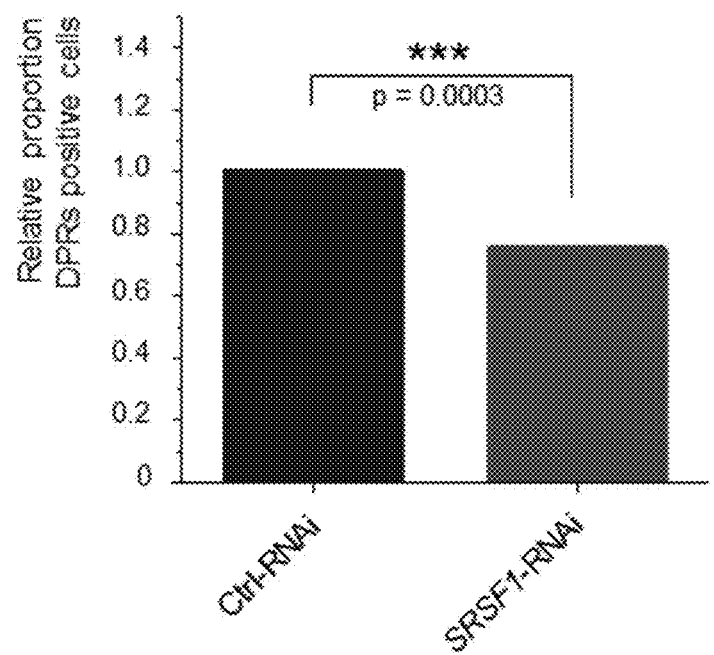
Figure 22C:
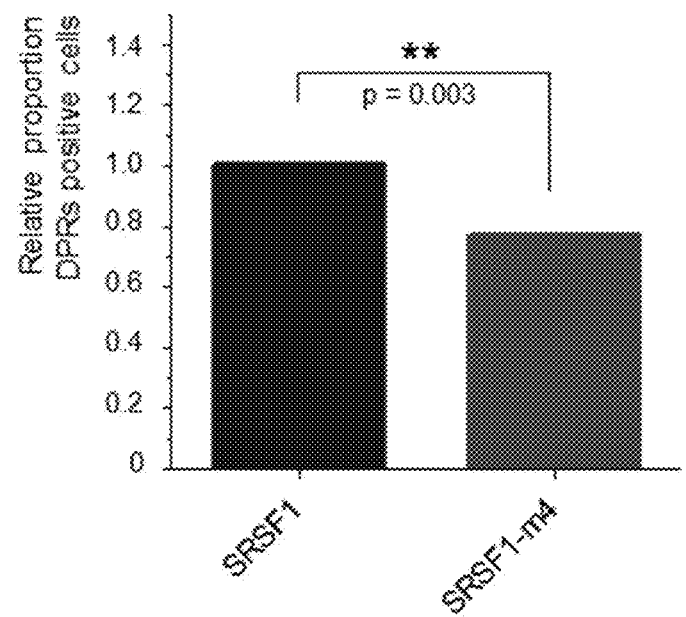

Depleting SRSF1 or inhibiting its RNA-repeat sequestration and interaction with NXF1 prevents the production of DPRs in primary neurons. We next sought to validate our findings in primary neurons. Due to high background staining obtained with poly-GP and poly-GA antibodies, we expressed V5 tags in all three frames downstream of the G4C2×38 repeat sequence (FIG. 30) to simultaneously detect all DPR species using the more specific and sensitive anti-V5 antibody. Cultured rat cortical neurons were transfected with the G4C2×38-3×V5 construct and either the Ctrl-RNAi, SRSF1-RNAi, SRSF1 or SRSF1-m4 expression plasmids prior to immunofluorescence studies. The nucleotide sequence targeted by the SRSF1-RNAi miRNA hairpin-1 is identical in human, mouse and rat SRSF1 (Methods, FIG. 5). Microscopy image examples of DPR-negative and DPR-positive neurons are presented in FIG. 22a. The proportion of DPR-positive neurons in approximately 100 successfully transfected neurons from two independent experiments was quantified in each group and all counts were performed blinded. Depletion of SRSF1 led to a significant reduction (25%) in the proportion of neurons with RAN-translated DPR-staining compared to neurons transfected with Ctrl-RNAi (FIG. 22b). Inhibiting the sequestration of endogenous SRSF1 and the interaction with NXF1 by recruitment of the SRSF1-m4 dominant mutant also led to a similar and significant reduction of neurons expressing DPRs compared to neurons transfected with wild type SRSF1 (FIG. 22c). Only cells showing absence of DPRs were counted DPR-negative. It is very likely that the effects of the SRSF1-RNAi or SRSF1-m4 expression have been under-estimated since neurons expressing reduced amounts of DPRs would still have been scored as DPR-positive. We concluded that our findings in N2A cells were corroborated in cultures of primary neurons.

EXAMPLE 10

Figure 23A:
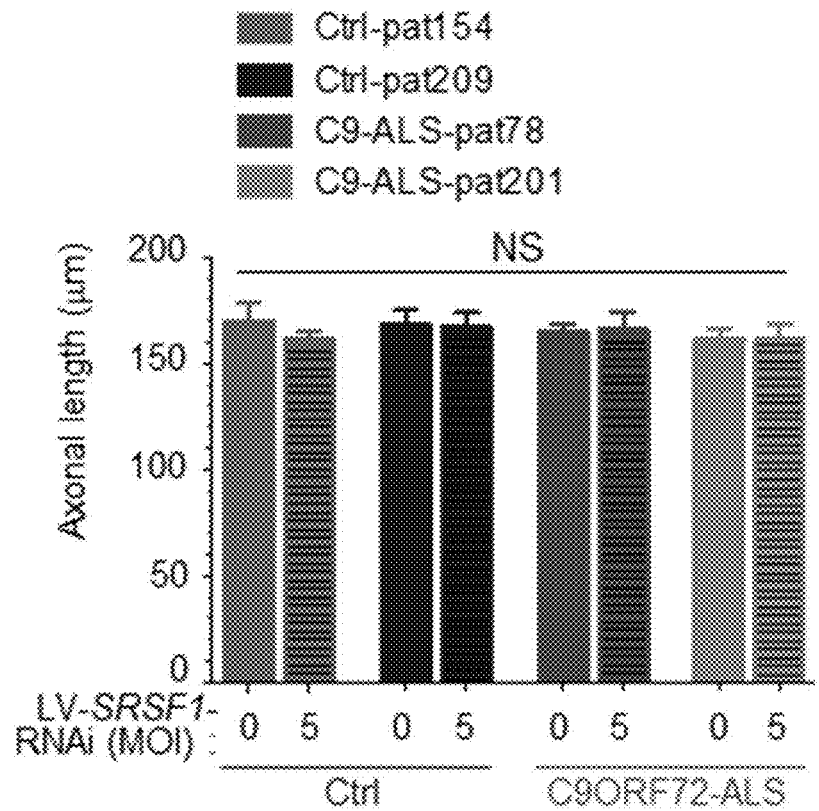
FIGS. 23A-23H: Depletion of SRSF1 specifically inhibits the nuclear export of C9ORF72 repeat transcripts retaining hexanucleotide repeat expansions in intron-1 in patient-derived neurons. (A) The axonal length of patient-derived iMNs treated or not with SRSF1-RNAi was assessed by high content imaging in triplicate experiments (mean±SEM; one-way ANOVA, NS: non-significant; N (average axon length/well)=9). (B) The cell body area of patient-derived iMNs treated or not with SRSF1-RNAi was assessed by high content imaging in triplicate experiments (mean±SEM; one-way ANOVA; N (average cell body area/well)=9). (C) The survival of patient-derived Ctrl or C9ORF72-ALS iMNs treated or not with SRSF1-RNAi was quantified in co-cultures with patient-derived Ctrl or C9ORF72-ALS iAstrocytes in six replicate experiments at day 4 (mean±SEM; one-way ANOVA; N (iMNs)=Ctrl-pat209: 142/165/174/117/122/168, C9-ALS-pat78: 77/65/41/68/71/70; C9-ALS-pat78+SRSF1-RNAi: 106/84/81/97/113/83; C9-ALS-pat201: 68/69/68/62/66/74; C9-ALS-pat201+SRSF1-RNAi: 131/104/96/82/111/104). (D) Western blots of iNeurons differentiated from control (Ctrl-pat 154, Ctrl-pat155) and C9ORF72-ALS (C9-ALS-pat78, C9-ALS-pat183) patients treated or not with LV-SRSF1-RNAi (MOI 0 or 5) were subjected to cellular fractionation using hypotonic lysis to yield cytoplasmic fractions. The chromatin remodeling SSRP1 factor is used to check for potential nuclear contamination in cytoplasmic fractions. Depletion of actin in nuclear fractions was used to check for quality of the nuclear fractions. The efficacy of SRSF1-RNAi was also validated by qRT-PCR achieving approximately 80% SRSF1 mRNA knockdown (FIG. 29). (E) Total, nuclear and cytoplasmic levels of intron1-spliced C9ORF72 transcripts (as measured by the exon1-exon3 junction) were quantified in duplicate experiments by qRT-PCR following normalization to U1 snRNA levels and to 100% in control patients at M010 (mean±SEM; one-way ANOVA, NS: non-significant; N (qRT-PCR reactions)=8). (F Intron1-spliced C9ORF72 transcripts levels normalized to U1 snRNA levels (panel d) were plotted as a ratio SRSF1-RNAi M015 over M010 to evaluate the specific effect due to the SRSF1-RNAi (mean±SEM; one-way ANOVA; N (qRT-PCR reactions)=8). (G) Total, nuclear and cytoplasmic levels of unspliced C9ORF72 transcripts retaining intron1 (as measured by the exon1-intron1 junction) were quantified in duplicate experiments by qRT-PCR following normalization to U1 snRNA levels and to 100% for control patients at M010 (mean±SEM; one-way ANOVA, NS: non-significant; N (qRT-PCR reactions)=8). (H) Unspliced C9ORF72 transcripts retaining intron1 levels normalized to U1 snRNA levels (panel f) were plotted as a ratio SRSF1-RNAi M015 over M010 to evaluate the specific effect due to the SRSF1-RNAi (mean±SEM; one-way ANOVA; N (qRT-PCR reactions)=8)
Figure 23B:
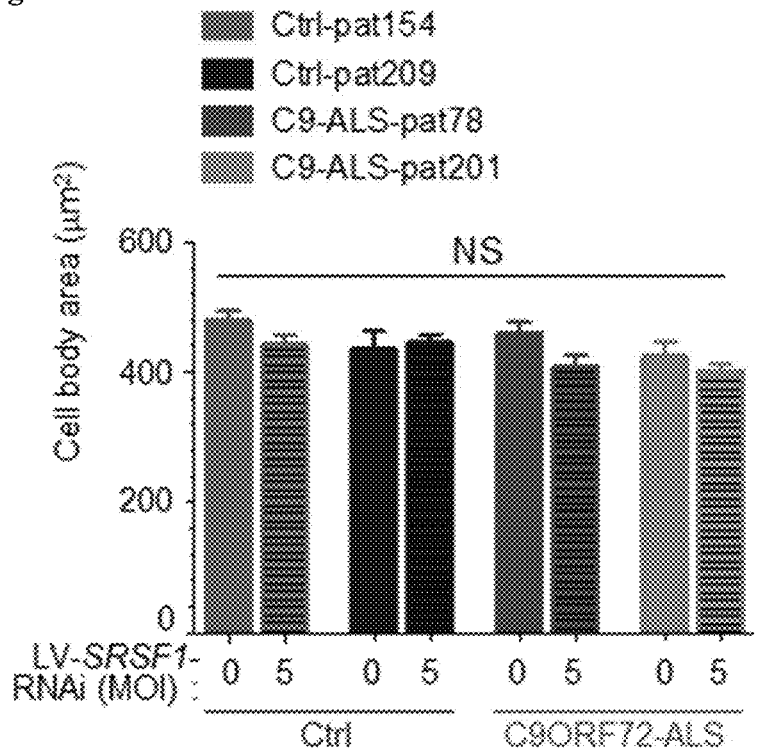
Figure 23C:
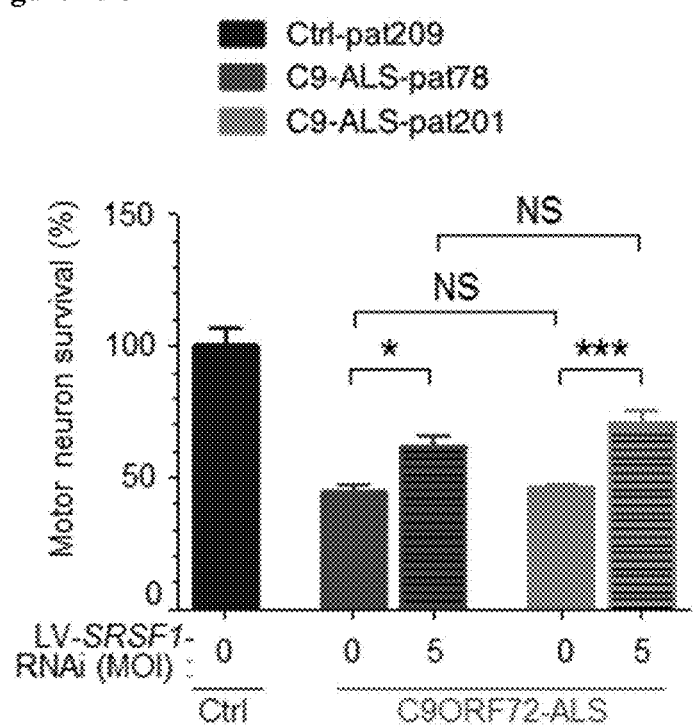
Figure 23D:
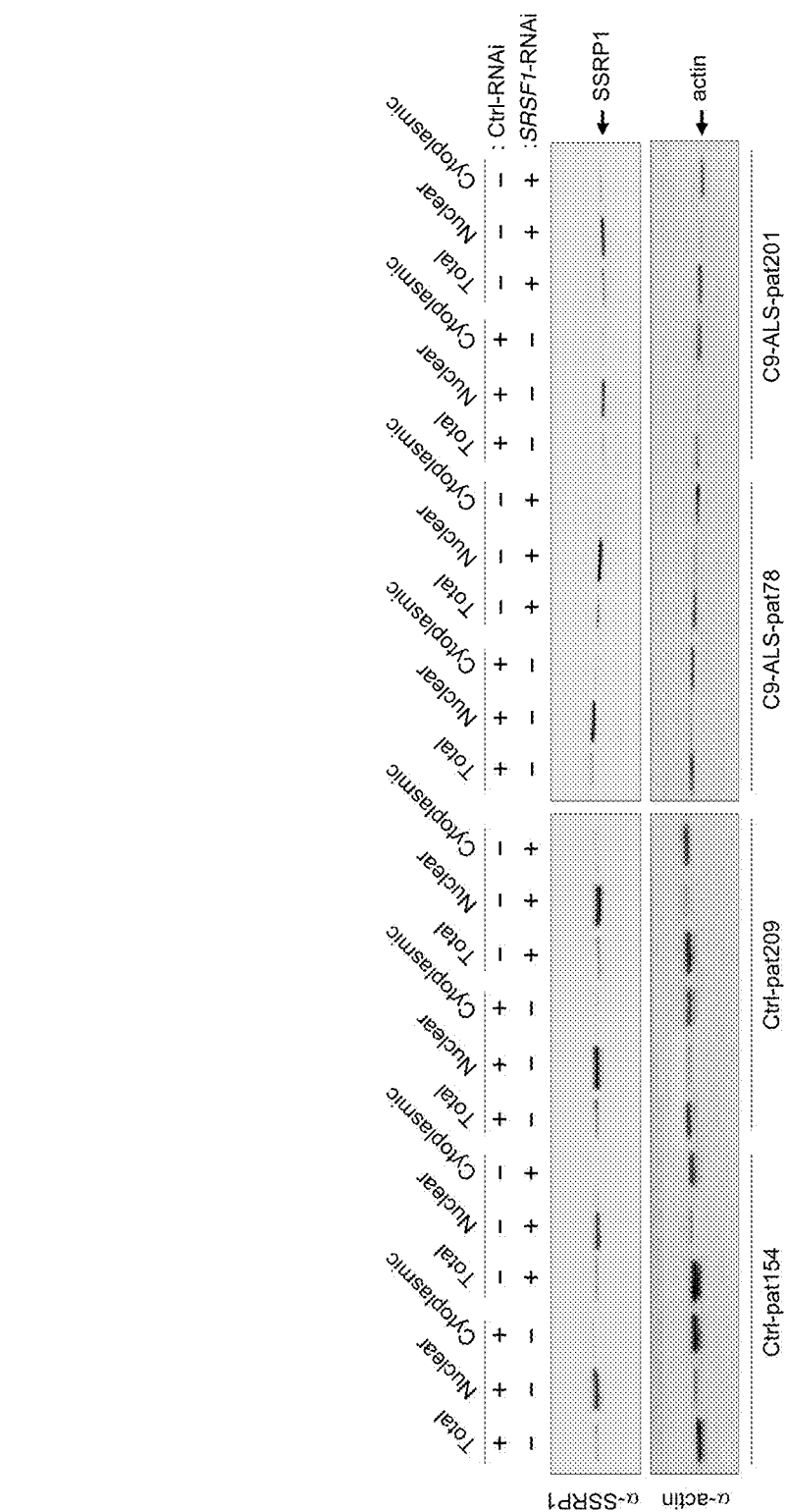
Figure 23E:
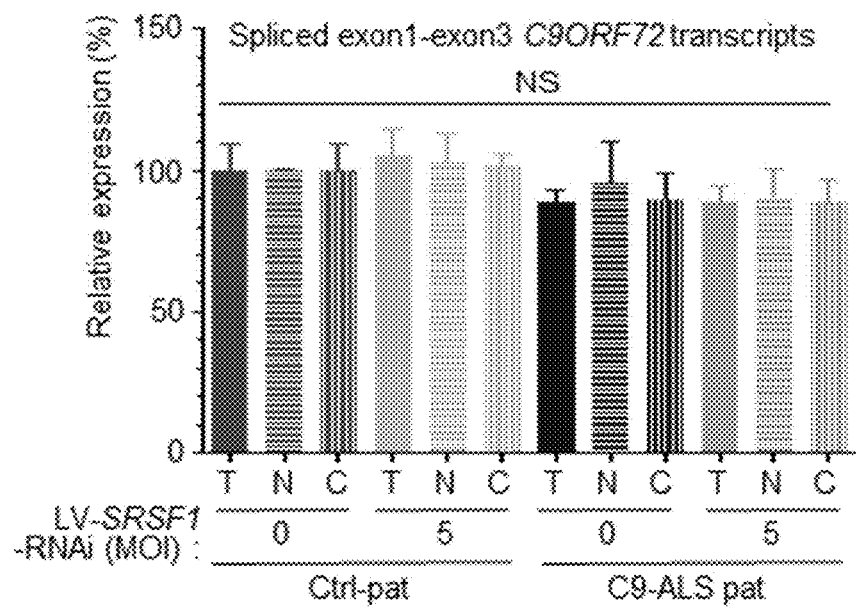
Figure 23F:
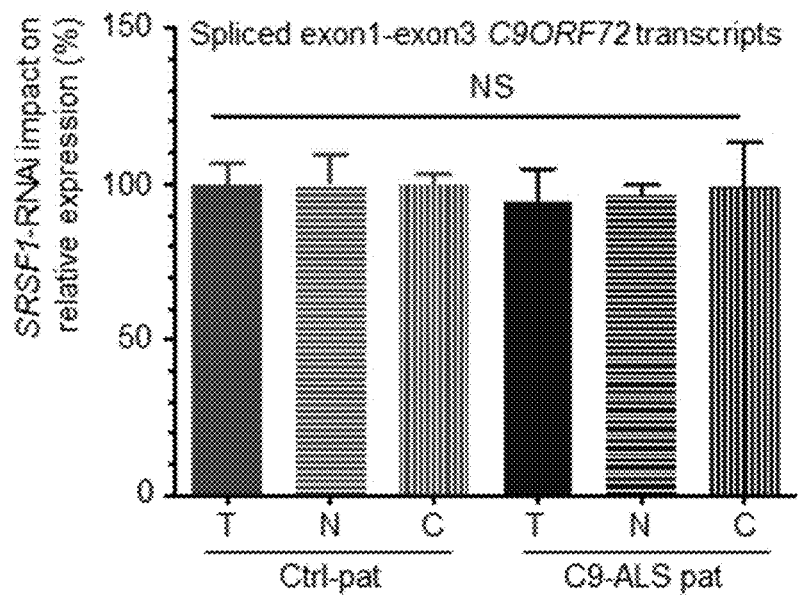
Figure 23G:
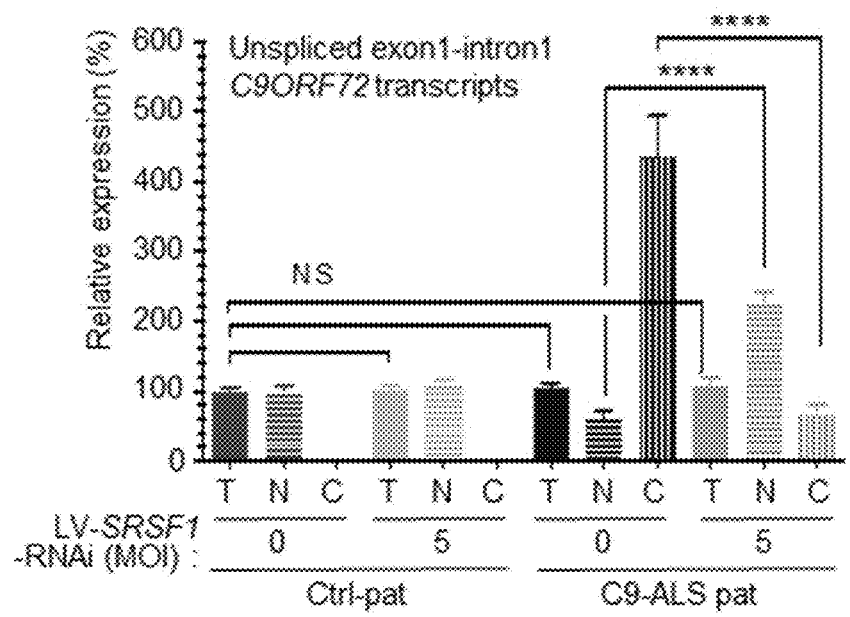
Figure 23H:
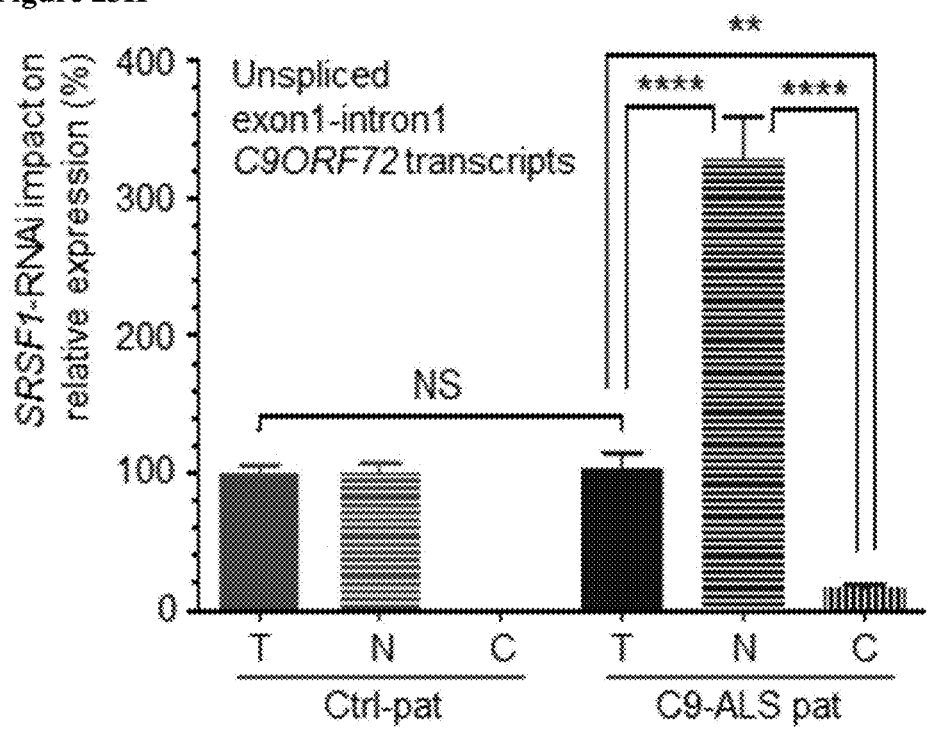
Figure 25B:
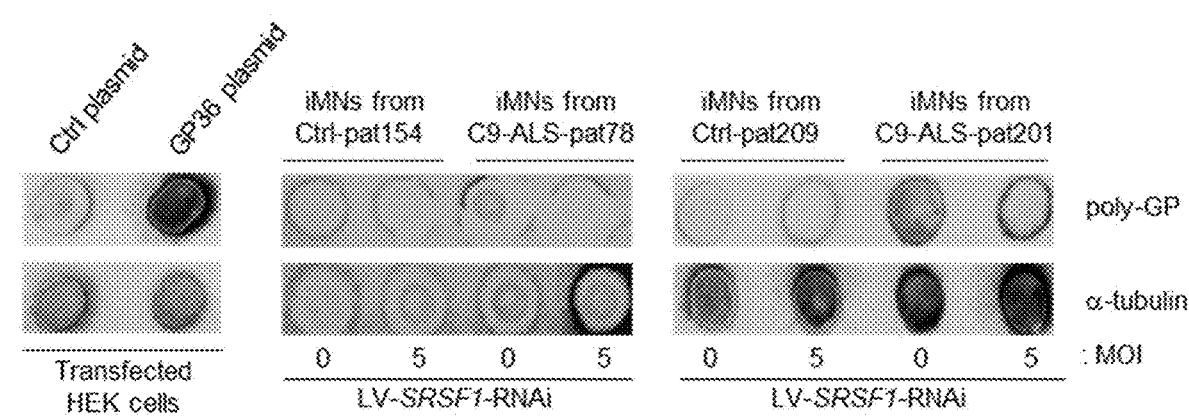

SRSF1 depletion specifically inhibits the nuclear export of pathological transcripts retaining intron-1 hexanucleotide repeat expansions in neurons-derived from C9ORF72-ALS patients. In order to investigate the nuclear export of C9ORF72 transcripts in the context of wild type and repeat-expanded C9ORF72 genes, we differentiated motor neurons from established induced-neural progenitor cells (iNPCs) derived from sex/age matched control and C9ORF72-ALS patient fibroblasts 52. Both control and C9ORF72-ALS induced iNeurons express the neuronal lineage marker Tuj1 and exhibit the propensity to form complex branching (FIG. 31). High content imaging analysis of axonal length (FIG. 23a) and soma cell size (FIG. 23b) did not show any significant differences between control and C9ORF72-ALS differentiated iNeurons under basal culture conditions, in agreement with previous reports[45,46]. To test a potential neuroprotective effect of SRSF1 depletion in disease relevant cells, we next differentiated iNPCs into motor neurons (iMNs), transduced them with an adenoviral vector expressing RFP under the Hb9 promoter and cultured them either in monoculture or in co-culture with control or ALS-derived iAstrocytes. We did not observe increased cell death or morphological abnormalities when the C9ORF72-ALS iMNs were cultured without astrocytes (data not shown). Remarkably, however, the transduction of SRSF1-RNAi lentivirus in iMNs prior to co-cultures with C9ORF72-ALS iAstrocytes resulted in significantly higher survival of iMNs against the astrocytic-derived toxicity (FIG. 23c) indicating a neuroprotective effect of SRSF1 depletion in motor neurons derived from C9ORF72-ALS patients. Consistent with our previous data presented in *Drosophila* and neuronal cells models, we also found that depletion of SRSF1 in C9ORF72-ALS patient-derived iMNs leads to specific reduction in the expression levels of poly-GP DPRs (FIG. 25b). We next quantified the total, nuclear and cytoplasmic levels of intron-1-spliced C9ORF72 transcripts (using qPCR primers annealing in exon-1 and exon-3)[50,51] and unspliced C9ORF72 transcripts retaining intron-1 (using qPCR primers annealing in exon-1 and in intron-1 upstream of the hexanucleotide repeat expansion)[50, 51] to evaluate the potential impact of SRSF1-RNAi on the splicing of intron-1 and on the nuclear export of wild type and pathological C9ORF72 transcripts. Depletion of the chromatin-remodeling factor SSRP1 in the cytoplasmic fractions and of actin in the nuclear fractions was used to validate the quality of the subcellular fractionation (FIG. 23d). The relative expression levels of SRSF1 mRNA were down regulated by approximately 80% upon SRSF1-RNAi transduction of iNeurons differentiated from either two control or two sex/age-matched C9ORF72-ALS patient lines FIG. 32). No significant changes in the total, nuclear or cytoplasmic levels of intron-1-spliced transcripts were measured between control and C9ORF72-ALS iNeurons transduced or not with SRSF1-RNAi lentivirus (FIG. 23e). The mRNA level ratios of SRSF1-RNAi (MOI5) over untreated (MOI0) were further plotted to assess the net impact of the SRSF1-RNAi on each cellular compartment and control or C9ORF72-ALS iNeurons (FIG. 23f). These data show that the proportion of exon1-exon3 spliced transcripts is not altered in C9ORF72-ALS neurons and that the presence of the hexanucleotide repeat expansion does not affect the splicing of intron-1, in full agreement with a recent study[50]. In addition, we also show here that the SRSF1-RNAi has no effect on the nuclear export or the splicing of intron-1 in the spliced transcripts that lead to the production of the wild type C9ORF72 protein. The same experimental analysis was carried out for the C9ORF72 transcripts retaining intron-1 (FIGS. 23g and 23h). We were unable to detect significant levels (above non template control qRT-PCR reactions) of intron-1-retaining C9ORF72 transcripts in the cytoplasm of control iNeurons consistent with the nuclear retention of unspliced transcripts. In striking contrast, the presence of the hexanucleotide repeat expansion in C9ORF72-ALS patients triggers the nuclear export of C9ORF72 repeat transcripts retaining intron-1 (FIG. 23g) consistent with our previous data showing that the sequestration of SRSF1 on synthetic hexanucleotide repeat expansions promotes nuclear mRNA export through the interaction with NXF1 (FIG. 8). Whilst the depletion of SRSF1 did not affect the total level and biogenesis/stability of intron-1-retaining transcripts in control or C9ORF72-ALS iNeurons, it specifically triggers a cytoplasmic reduction and nuclear accumulation of pathological C9ORF72 repeat transcripts in C9ORF72-ALS iNeurons (FIG. 23g, h). These data demonstrate that the depletion of SRSF1 specifically inhibits the nuclear export of expanded C9ORF72 repeat transcripts. Taken together, our data show that the SRSF1 depletion has no effect on the expression level, splicing or nuclear export of wild type spliced exon1-exon3 C9ORF72 transcripts while it specifically inhibits the nuclear export of pathological C9ORF72 transcripts retaining the hexanucleotide repeats in intron-1.

EXAMPLE 11

Microsatellite expansions of 3-6 nucleotides in coding and non-coding regions of genes cause neurodegeneration through complex mechanisms involving protein loss-of-function and protein/RNA toxic gain-of-function mechanisms[52]. The production of toxic polymeric repeat proteins by RAN translation has now been characterised in multiple neurodegenerative disorders caused by microsatellite expansions including spinocerebellar ataxia type 8 (SCA8)58, myotonic dystrophy type 1 (DM1)[53], Fragile X-associated tremor and ataxia syndrome (FXTAS)59, C9ORF72-ALS6, 13-16,27 and Huntington disease (HD)60. However, the mechanisms involved in the nuclear export of these disease-related repeat transcripts are currently unknown.

EXAMPLE 12

We previously suggested that the sequestration of nuclear export adaptors onto C9ORF72 repeat transcripts might trigger the abnormal nuclear export of C9ORF72 repeat transcripts and the subsequent RAN translation of DPRs in the cytoplasm 12. In this study, we identified for the first time the molecular mechanism driving the nuclear export of pathological C9ORF72 repeat transcripts. We investigated whether the partial depletion of two evolutionarily conserved nuclear export adaptors which avidly interact with the hexanucleotide repeat transcripts 12, ALYREF and SRSF1, would mitigate DPR-mediated neurotoxicity in an established Drosophila model of C9ORF72-ALS16. We discovered that the partial depletion of SRSF1 prevents in vivo neurodegeneration and suppresses the associated locomotor deficits while the depletion of ALYREF only had marginal effects. The depletion of SRSF1 in C9ORF72-ALS patient-derived motor neurons also conferred neuroprotection of motor neurons in co-culture with C9ORF72-ALS astrocytes. Moreover, we also showed that this intervention does not affect the morphology or the growth of control and C9ORF72-ALS patient-derived motor neurons. On the other hand, the depletion of SRSF1 in patient-derived C9ORF72-ALS astrocytes significantly suppressed motor neuron death in a co-culture system. The mechanisms for suppression of astrocyte-mediated neurotoxicity remain however to be determined. They might involve a modification of the RNA or protein composition in the extra-cellular exosomes released by astrocytes.

EXAMPLE 13

Using neuronal N2A cells, we demonstrated that the nuclear export of C9ORF72 repeat transcripts and subsequent RAN translation depends on the interaction of SRSF1 with the nuclear export receptor NXF1. Depleting SRSF1 or inhibiting its endogenous RNA-repeat sequestration and interaction with NXF1 lead to a marked inhibition of the nuclear export of C9ORF72 repeat transcripts and RAN translation of sense and antisense DPRs to prevent C9ORF72 repeat-mediated neurotoxicity. We also showed that the SRSF1-dependent inhibition of the nuclear export of C9ORF72 repeat transcripts leads to altered production of DPRs in Drosophila and patient-derived motor neurons. Importantly, the depletion of SRSF1 in control or C9ORF72-ALS patient-derived neurons does not affect the expression levels or the nuclear export of intron-1-spliced transcripts required for the translation of the wild type C9ORF72 protein. This also indicates that the nuclear export of non-repeat C9ORF72 transcripts does not depend on the nuclear export adaptor SRSF1. In sharp contrast to control neurons, the presence of the hexanucleotide repeat expansion in intron-1 of C9ORF72 transcripts led to SRSF1-dependent mRNA nuclear export, while depletion of SRSF1 specifically inhibits the nuclear export but not the levels or splicing of C9ORF72 transcripts retaining expanded hexanucleotide repeats in intron-1. Taking these data together, we show that sequestration of SRSF1 onto C9ORF72 hexanucleotide repeats is able to license the NXF1-dependent nuclear export of pathological C9ORF72 repeat transcripts without functional coupling of the nuclear export process to pre-mRNA splicing. This explains in turn why the depletion of SRSF1 has no effect on the level, intron-1-splicing or nuclear export of wild type C9ORF72 transcripts.

EXAMPLE 14

Figure 24A:
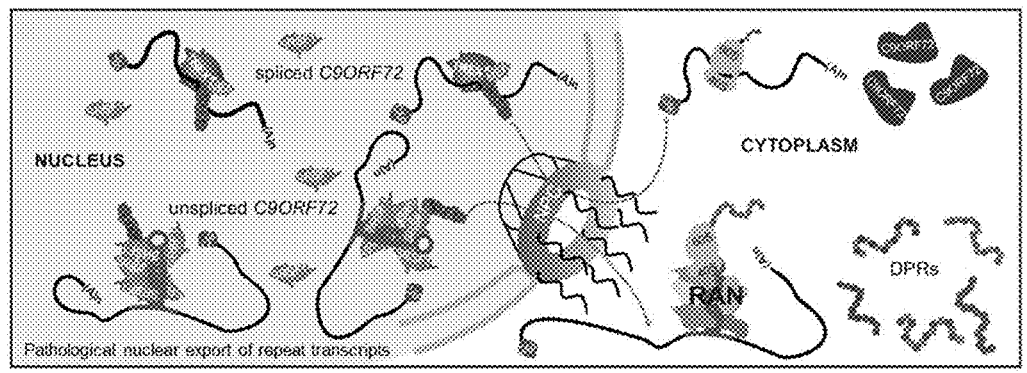
FIGS. 24A-24C: Model for the nuclear export of pathological C9ORF72 hexanucleotide repeat transcripts and therapeutic manipulation. (A) The nuclear export of sense and antisense C9ORF72 transcripts retaining expanded hexanucleotide repeats in intron1 specifically depend on the sequestration of SRSF1 and its interaction with the nuclear export receptor NXF1. In contrast, the nuclear export of intron1-spliced C9ORF72 transcripts required for the production of the C9ORF72 protein does not involve the interaction of SRSF1 with NXF1 however the nuclear export adaptor(s) (NEA) remain to be identified. (B) The depletion of SRSF1 specifically inhibits the nuclear export of C9ORF72 transcripts retaining expanded hexanucleotide repeats in intron1, likely due to a reduction in the sequestration of endogenous SRSF1 onto the C9ORF72 hexanucleotide repeats and failure to abnormally remodel NXF1 in a high RNA-binding mode, while it does not affect the expression levels and splicing/retention of intron1. Moreover, the depletion of SRSF1 does not affect the expression levels, the splicing of intron1 or the nuclear export of wild type intron1-spliced C9ORF72 transcripts required for the production of the C9ORF72 protein. (C) Over-expression of the SRSF1-m4 protein, which fails to interact efficiently with NXF1, competes endogenous SRSF1 for sequestration onto hexanucleotide repeats preventing in turn interactions with NXF1 and nuclear export of C9ORF72 repeat transcripts.
Figure 24B:
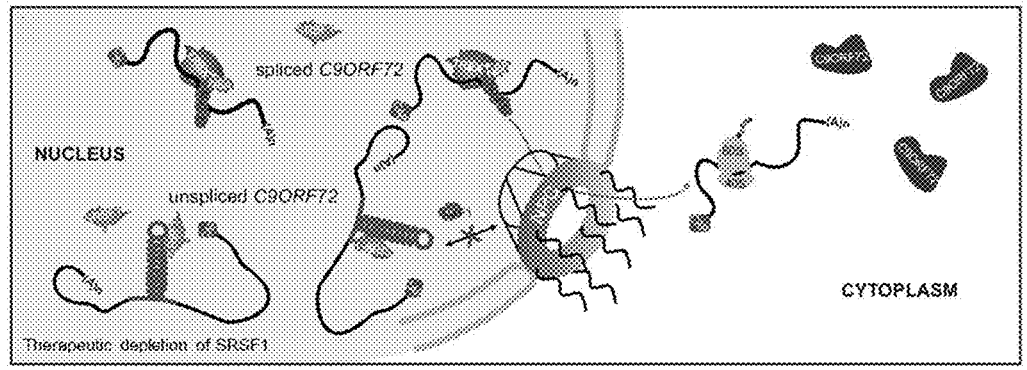
Figure 24C:
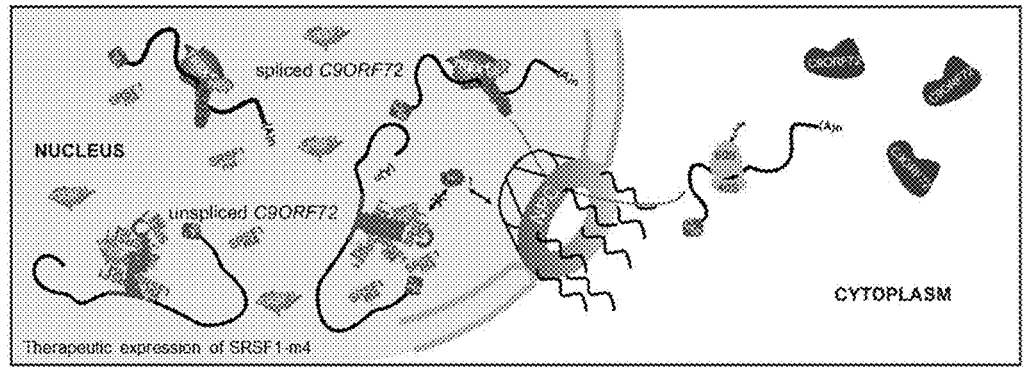

In conclusion, we have elucidated for the first time the molecular mechanism driving the nuclear export of pathological C9ORF72 repeat transcripts which allows for RAN translation of dipeptide repeat proteins in the cytoplasm (FIG. 24a). The depletion of SRSF1 specifically inhibits the nuclear export of the pathologically expanded C9ORF72 transcripts without interfering with biogenesis/processing of the wild type C9ORF72 transcripts (FIG. 24b). The expression of the engineered SRSF1-m4 protein, which retains specific ability to be sequestered on repeat transcripts but fails to effectively interact with NXF1, also inhibits the nuclear export of repeat transcripts and the production of DPRs. (FIG. 24c). Both these interventions represent promising prospects for the development of an effective neuroprotective strategy in C9ORF72-related ALS. The effects of antagonizing SRSF1 in the vertebrate brain remain to be elucidated in wild-type mice as well as in murine C9ORF72-ALS models. Interestingly, it was recently shown that whilst SRSF1 directly binds thousands of transcripts, the depletion of SRSF1 in isolation affects the nuclear export of only 225 transcripts (<1% transcribed coding genes) due to the presence of 6 additional SRSF factors (SRSF2-7) which act as redundant NXF1-dependent nuclear export adaptors 46. The cellular pathways causing C9ORF72 repeat-mediated neurodegeneration and the precise mechanism(s) of neuroprotection conferred by the targeting of SRSF1 remain to be elucidated in future studies.

Inhibiting the nuclear export of repeat transcripts might also confer neuroprotection in other microsatellite expansion disorders. However, it will remain essential to determine pathophysiological contributions between polymeric repeat protein production and RNA-mediated toxicity by nuclear retention of transcripts and/or sequestration of RNA-processing factors on repeat transcripts. While expression of repeat proteins can kill cells in vitro, it is difficult to evaluate the levels of RAN-translation in patients and the thresholds required for triggering neurotoxicity which will differ depending on the nature of the repeat expansions, the disease in question and the cell types. There is however growing evidence for a pathogenic role of RAN-translation and the data presented here fully support this. For example, FXTAS was initially thought to be caused by intranuclear retention of transcripts and sequestration of splicing factors[54,55]. However, the discovery of RAN translation in the same model challenged this view[56]. Similarly, in C9ORF72-ALS, a 10-fold increase in the number of intranuclear RNA foci does not significantly alter survival or global RNA processing, while expression of DPRs caused neurodegeneration[50] in full agreement with the data presented here. Partial depletion of individual nuclear export adaptors does not appear to be detrimental to the functioning of higher eukaryotic cells. Therefore, they might constitute viable therapeutic targets for inhibiting the nuclear export of repeat transcripts and the production of toxic repeat proteins, particularly in neurodegenerative diseases where RAN-translation appears to have a prominent pathological role.

EXAMPLE 15

Expression of cell permeable or AAV-encoded antagonistic SRSF1 peptides that interact with NXF1

```
SRSF1 amino acids 89-120 (SEQ ID NO 15):
PRSGRGTGRGGGGGGGGAPRGRYGPPSRRSE
```

We have used the following peptide and showed reduction in the production of DPRs expressed in a disease relevant RAN-dependent manner in human HEK cells transfected with a G4C2×38 repeat constructs that express 3×V5 tags in all frames (FIG. 33).

```
                                              SEQ ID NO 153
SRSF1 sequence (TAP/NXF1-binding site) V5
tag TAT PTD
PRSGRGTGRGGGGGGGGAPRGRYGPPSRRSE GG GKPIPNPLLGLDST

GG YGRKKRRQRRR
```

EXAMPLE 16

Expression of SRPK1 amino-acids 1-655 (SEQ ID NO 19) to maintain phosphorylation state of SRSF1 for inhibiting interaction of SRSF1 with NXF1.

EXAMPLE 17

Mouse models of C9ORF72 related ALS/FTD
Ranum's mice (Liu Y et al. Neuron 2016; 90:521-34)
BAC mouse model of C9orf72 ALS/FTD that shows decreased survival, paralysis, muscle denervation, motor neuron loss, anxiety-like behavior, and cortical and hippocampal neurodegeneration. These mice express C9ORF72 sense transcripts and upregulated antisense transcripts. This is our first model of choice to test our gene therapy vectors.

Cleveland and Lagier-Tourenne's mice (Jiang et al. Neuron 2016; 90:535-50)

Mice expressing C9ORF72 RNAs with up to 450 GGGGCC repeats or with one or both C9orf72 alleles inactivated.

Virally-delivered models (Chew J. Science 2015; 348: 1151-4)

Expression of (G4C2)66 throughout the murine central nervous system by means of somatic brain transgenesis mediated by adeno-associated virus.

EXAMPLE 18 ROUTES OF ADMINISTRATION

Cerebrospinal fluid (CSF) using cisterna magna or intracerebroventricular delivery of AAV vectors AAV-mediated gene delivery will be applied at 2 different time points; pre-onset and onset of symptoms. Transgenic mice (Liu Y et al. Neuron 2016; 90:521-34) will be divided into 2 groups to be treated either therapeutic vector as described above or control viruses [12 µl (2 µl iodixanol); 1.2×1013/ml], via cisterna magna or intracerebroventricular (ICV). 5 mice per group will be sacrificed 4 weeks post-injection and CNS tissue collected to assess viral biodistribution (in spinal cord) and SRF1 mRNA and protein levels (in spinal cord, striatum, brainstem, cerebellum and cortex). The remaining 15 mice per group underwent behavioural testing to assess effects on disease progression including weekly rotarod analysis after three consecutive days of training and gait analysis. In all studies, onset and progression of disease will be assessed by neurological scoring 3 times per week from 60 days of age and mice were also weighed weekly. Mice will be scored for tremor, hind-limb splay and overall neurological deficit using a previously reported scoring system (Mead R J et al. PLoS One 2011; 6:e23244). All mice continued to end-stage disease and the time to reach this stage will be recorded. All animals will be perfused under terminal anaesthesia and CNS tissue was collected to assess viral biodistribution, SRF1 mRNA and protein levels.

IV Delivery

Mice will be injected in the facial or tail vein under isoflurane anaesthesia with 1-5×1011 vector genome of either therapeutic vectors as described above or control viruses. The mice were then allowed to recover, rolled in the sawdust from their original cage and immediately returned to their cage. Behavioral analysis will be carried using the design described above.

REFERENCES

1. M. DeJesus-Hernandez et al., Expanded GGGGCC hexanucleotide repeat in noncoding region of C9ORF72 causes chromosome 9p-linked FTD and ALS. *Neuron.* 72, 245-256 (2011).
2. A. E. Renton et al., A hexanucleotide repeat expansion in C9ORF72 is the cause of chromosome 9p21-linked ALS-FTD. *Neuron.* 72, 257-268 (2011).
3. J. Cooper-Knock et al., C9ORF72 GGGGCC expanded repeats produce splicing dysregulation which correlates with disease severity in amyotrophic lateral sclerosis. *PLoS ONE.* 10, e0127376 (2015).
4. J. Cooper-Knock et al., Antisense RNA foci in the motor neurons of. *Acta Neuropathol.* 130, 63-75 (2015).

5. K. Mori et al., hnRNP A3 binds to GGGGCC repeats and is a constituent of p62-positive/TDP43-negative inclusions in the hippocampus of patients with C9orf72 mutations. *Acta Neuropathol.* 125, 413-423 (2013).
6. C. J. Donnelly et al., RNA Toxicity from the ALS/FTD C9ORF72 Expansion Is Mitigated by Antisense Intervention. *Neuron.* 80, 415-428 (2013).
7. D. Sareen et al., Targeting RNA Foci in iPSC-Derived Motor Neurons from ALS Patients with a C9ORF72 Repeat Expansion. *Sci Transl Med.* 5, 208ra149 (2013).
8. Y.-B. Lee et al., Hexanucleotide Repeats in ALS/FTD Form Length-Dependent RNA Foci, Sequester RNA Binding Proteins, and Are Neurotoxic. *Cell Rep.* 5, 1178-1186 (2013).
9. J. Cooper-Knock et al., Sequestration of multiple RNA recognition motif-containing proteins by C9orf72 repeat expansions. *Brain.* 137, 2040-2051 (2014).
10. K. Mori et al., The C9orf72 GGGGCC repeat is translated into aggregating dipeptide-repeat proteins in FTLD/ALS. *Science.* 339, 1335-1338 (2013).
11. K. Mori et al., Bidirectional transcripts of the expanded C9orf72 hexanucleotide repeat are translated into aggregating dipeptide repeat proteins. *Acta Neuropathol.* 126, 881-893 (2013).
12. P. E. A. Ash et al., Unconventional translation of C9ORF72 GGGGCC expansion generates insoluble polypeptides specific to c9FTD/ALS. *Neuron.* 77, 639-646 (2013).
13. T. Zu et al., RAN proteins and RNA foci from antisense transcripts in C9ORF72 ALS and frontotemporal dementia. *Proc. Natl. Acad. Sci. U.S.A.* 110, E4968-77 (2013).
14. S. Mizielinska et al., C9orf72 repeat expansions cause neurodegeneration in *Drosophila* through arginine-rich proteins. *Science.* 345, 1192-1194 (2014).
15. S. Ciura et al., Loss of function of C9orf72 causes motor deficits in a zebrafish model of Amyotrophic Lateral Sclerosis. *Ann. Neurol.* 74:180-187 (2013), doi:10.1002/ana.23946.
16. J. G. O'Rourke et al., C9orf72 is required for proper macrophage and microglial function in mice. *Science.* 351, 1324-1329 (2016).
17. M. J. Walsh et al., Invited review: decoding the pathophysiological mechanisms that underlie RNA dysregulation in neurodegenerative disorders: a review of the current state of the art. *Neuropathol Appl. Neurobiol.* 41, 109-134 (2015).
18. J. D. Rohrer et al., C9orf72 expansions in frontotemporal dementia and amyotrophic lateral sclerosis. *Lancet Neurol.* 14, 291-301 (2015).
19. T. W. Todd, L. Petrucelli, Insights into the pathogenic mechanisms of Chromosome 9 open reading frame 72 (C9orf72) repeat expansions. *J Neurochem* (2016), doi: 10.1111/jnc.13623.
20. D. Edbauer, C. Haass, An amyloid-like cascade hypothesis for C9orf72 ALS/FTD. *Curr. Opin. Neurobiol.* 36, 99-106 (2016).
21. B. D. Freibaum et al., GGGGCC repeat expansion in C9orf72 compromises nucleocytoplasmic transport. *Nature.* 525, 129-133 (2015).
22. A. P. Golovanov, G. M. Hautbergue, A. M. Tintaru, L.-Y. Lian, S. A. Wilson, The solution structure of REF2-I reveals interdomain interactions and regions involved in binding mRNA export factors and RNA. *RNA.* 12, 1933-1948 (2006).
23. A. M. Tintaru et al., Structural and functional analysis of RNA and TAP binding to SF2/ASF. *EMBO Rep.* 8, 756-762 (2007).
24. G. M. Hautbergue, M.-L. Hung, A. P. Golovanov, L.-Y. Lian, S. A. Wilson, Mutually exclusive interactions drive handover of mRNA from export adaptors to TAP. *Proc. Natl. Acad. Sci. U.S.A.* 105, 5154-5159 (2008).
25. N. Viphakone et al., TREX exposes the RNA-binding domain of Nxf1 to enable mRNA export. *Nat Commun.* 3, 1006 (2012).
26. Y. Huang, R. Gattoni, J. Stevenin, J. A. Steitz, S R splicing factors serve as adapter proteins for TAP-dependent mRNA export. *Molecular Cell.* 11, 837-843 (2003).
27. F. Stutz et al., REF, an evolutionarily conserved family of hnRNP-like proteins, interacts with TAP/Mex67p and participates in mRNA nuclear export. *RNA.* 6, 638-650 (2000).
28. G. Dietzl et al., A genome-wide transgenic RNAi library for conditional gene inactivation in *Drosophila. Nature.* 448, 151-156 (2007).
29. K. Meyer et al., Direct conversion of patient fibroblasts demonstrates non-cell autonomous toxicity of astrocytes to motor neurons in familial and sporadic ALS. *Proc. Natl. Acad. Sci. U.S.A.* 111, 829-832 (2014).
30. Y. Huang, T. A. Yario, J. A. Steitz, A molecular link between SR protein dephosphorylation and mRNA export. *Proc. Natl. Acad. Sci. U.S.A.* 101, 9666-9670 (2004).
31. R. Karni et al., The gene encoding the splicing factor SF2/ASF is a proto-oncogene. *Nat. Struct. Mol. Biol.* 14, 185-193 (2007).
32. J. C. Greene et al., Mitochondrial pathology and apoptotic muscle degeneration in *Drosophila* parkin mutants. *Proc. Natl. Acad. Sci. U.S.A.* 100, 4078-4083 (2003).
33. W. Sullivan, M. Ashburner, R. S. Hawley, *Drosophila* protocols. (Cold Spring Harbor, N.Y., Cold Spring Harbor Laboratory Press, 2000).
34. N. Deglon, J. L. Tseng, J. C. Bensadoun, Self-inactivating lentiviral vectors with enhanced transgene expression as potential gene transfer system in Parkinson's disease. *Human Gene Ther.* 11, 179-190 (2000).
35. H. Wichterle, I. Lieberam, J. A. Porter, T. M. Jessell, Directed differentiation of embryonic stem cells into motor neurons. *Cell.* 110, 385-397 (2002).
36. D. Ling, P. M. Salvaterra, Robust RT-qPCR data normalization: validation and selection of internal reference genes during post-experimental data analysis. *PLoS ONE.* 6, e17762 (2011).
36. Webster, C. P. et al. The C9orf72 protein interacts with Rab1 a and the ULK1 complex to regulate initiation of autophagy. EMBO J. 35, 1656-1676 (2016).
37. Jovičić, A. et al. Modifiers of C9orf72 dipeptide repeat toxicity connect nucleocytoplasmic transport defects to FTD/ALS. *Nat. Neurosci.* 18, 1226-1229 (2015).
38. Golovanov, A. P., Hautbergue, G. M., Tintaru, A. M., Lian, L.-Y. & Wilson, S. A. The solution structure of REF2-I reveals interdomain interactions and regions involved in binding mRNA export factors and RNA. *RNA* 12, 1933-1948 (2006).
39. Tintaru, A. M. et al. Structural and functional analysis of RNA and TAP binding to SF2/ASF. *EMBO Rep.* 8, 756-762 (2007).
40. Meyer, K. et al. Direct conversion of patient fibroblasts demonstrates non-cell autonomous toxicity of astrocytes to motor neurons in familial and sporadic ALS. *Proc. Natl. Acad. Sci. U.S.A.* 111, 829-832 (2014).
41. Deglon, N., Tseng, J. L. & Bensadoun, J. C. Self-inactivating lentiviral vectors with enhanced transgene expression as potential gene transfer system in Parkinson's disease. *Human Gene Ther.* 11, 179-190 (2000).

42. Cooper-Knock, J. et al. Sequestration of multiple RNA recognition motif-containing proteins by C9orf72 repeat expansions. *Brain* 137, 2040-2051 (2014).
43. Cooper-Knock, J. et al. Antisense RNA foci in the motor neurons of. *Acta Neuropathol* 130, 63-75 (2015).
44 Mizielinska, S. et al. C9orf72 repeat expansions cause neurodegeneration in *Drosophila* through arginine-rich proteins. *Science* 345, 1192-1194 (2014).
45. Donnelly, C. J. et al. RNA Toxicity from the ALS/FTD C9ORF72 Expansion Is Mitigated by Antisense Intervention. *Neuron* 80, 415-428 (2013).
46. Sareen, D. et al. Targeting RNA Foci in iPSC-Derived Motor Neurons from ALS Patients with a C9ORF72 Repeat Expansion. *Sci Transl Med* 5, 208ra149 (2013).
47. Masuda, S. et al. Recruitment of the human TREX complex to mRNA during splicing. *Genes & Development* 19, 1512-1517 (2005).
48. Chang, C.-T. et al. Chtop is a component of the dynamic TREX mRNA export complex. *EMBO J.* 32, 473-486 (2013).
49. Hautbergue, G. M. et al. UIF, a New mRNA export adaptor that works together with REF/ALY, requires FACT for recruitment to mRNA. *Curr. Biol.* 19, 1918-1924 (2009).
50. Tran, H. et al. Differential Toxicity of Nuclear RNA Foci versus Dipeptide Repeat Proteins in a *Drosophila* Model of C9ORF72 FTD/ALS. *Neuron* 87, 1207-1214 (2015).
51. Niblock, M. et al. Retention of hexanucleotide repeat-containing intron in C9orf72 mRNA: implications for the pathogenesis of ALS/FTD. *Acta Neuropathol Commun* 4, 18 (2016).
52. Loureiro, J. R., Oliveira, C. L. & Silveira, I. Unstable repeat expansions in neurodegenerative diseases: nucleocytoplasmic transport emerges on the scene. *Neurobiol. Aging* 39, 174-183 (2016).
53. Zu, T. et al. Non-ATG-initiated translation directed by microsatellite expansions. *Proc. Natl. Acad. Sci. U.S.A.* 108, 260-265 (2011).
54. Jin, P. et al. Pur alpha binds to rCGG repeats and modulates repeat-mediated neurodegeneration in a *Drosophila* model of fragile X tremor/ataxia syndrome. *Neuron* 55, 556-564 (2007).
55. Sofola, O. A. et al. RNA-binding proteins hnRNP A2/B1 and CUGBP1 suppress fragile X CGG premutation repeat-induced neurodegeneration in a *Drosophila* model of FXTAS. *Neuron* 55, 565-571 (2007).
56. Todd, P. K. et al. CGG repeat-associated translation mediates neurodegeneration in fragile X tremor ataxia syndrome. *Neuron* 78, 440-455 (2013).
63. Greene, J. C. et al. *Mitochondrial pathology and apoptotic muscle degeneration in Drosophila parkin mutants. Proc. Natl. Acad. Sci. U.S.A.* 100, 4078-4083 (2003).
64. Sullivan, W., Ashburner, M. & Hawley, R. S. *Drosophila protocols.* (Cold Spring Harbor, N.Y., Cold Spring Harbor Laboratory Press., 2000).
65 Deglon, N., Tseng, J. L. & Bensadoun, R. S. Self-inactivating lentiviral vectors with enhanced transgene expression as potential gene transfer system in Parkinson's disease. *Human Gene The.* 11, 179-190 (2000).
66. Wichterle, H., Lieberam, I., Porter, J. A. & Jessell, T. M. Directed differentiation of embryonic stem cells into motor neurons. *Cell* 110, 385-397 (2002).
67. Ye, J. et al. Primer-BLAST: a tool to design target-specific primers for polymerase chain reaction. *BMC Bioinformatics* 13, 134 (2012).
68. Ling, D. & Salvaterra, P. M. Robust RT-qPCR data normalization: validation and selection of internal reference genes during post-experimental data analysis. *PLoS ONE* 6, e17762 (2011).
69. Yang, D. et al. FTD/ALS-associated poly(GR) protein impairs the Notch pathway and is recruited by poly(GA) into cytoplasmic inclusions. *Acta Neuropathol* (2015). doi:10.1007/s00401-015-1448-6
70. Maranda, B., Fan, L., Soucy, J.-F., Simard, L. & Mitchell, G. A. Spinal muscular atrophy: clinical validation of a single-tube multiplex real time PCR assay for determination of SMN1 and SMN2 copy numbers. *Clin. Biochem.* 45, 88-91 (2012).

The invention claimed is:

1. A method of treating amyotrophic lateral sclerosis resulting from expression of polymorphic repeat expansions in a first intron of C9ORF72 in a subject, comprising:
administering to the subject an effective amount of a viral based expression vector comprising a transcription cassette comprising:
a promoter operably linked to a nucleic acid molecule encoding an shRNA that inhibits the expression of a nucleic acid encoding a Serine/Arginine-Rich Splice Factor (SRSF1) encoded by the nucleotide sequence of SEQ ID NO: 1, or encoded by a polymorphic sequence variant comprising 90% to 99 sequence identity over the full length nucleotide sequence of SEQ ID NO: 1, thereby treating amyotrophic lateral sclerosis in the subject.

2. A method of treating frontotemporal lobar dementia resulting from expression of polymorphic repeat expansions in a first intron of C9ORF72 in a subject, comprising:
administering to the subject an effective amount of a viral based expression vector comprising a transcription cassette comprising: a promoter operably linked to a nucleic acid molecule encoding an shRNA that inhibits the expression of a nucleic acid encoding a Serine/ Arginine-Rich Splice Factor (SRSF1) encoded by the nucleotide sequence set forth in SEQ ID NO: 1, or encoded by a polymorphic sequence variant that has 90% to 99 sequence identity over the full length nucleotide sequence of SEQ ID NO: 1, wherein said promoter is adapted to express said antagonistic agent, thereby treating frontotemporal lobar dementia in the subject.

3. The method according to claim 1, wherein said inhibitory RNA comprises the nucleotide sequence of SEQ ID NO: 5, 6, 7, 8, 9, 10, 11, 12, 13, or 14.

4. The method according to claim 2, wherein said inhibitory RNA comprises the nucleotide sequence of SEQ ID NO: 5, 6, 7, 8, 9, 10, 11, 12, 13 or 14.

5. The method according to claim 1, wherein said inhibitory RNA consists of the nucleotide sequence of SEQ ID NO: 5, 6, 7, 8, 9, 10, 11, 12, 13, or 14.

6. The method according to claim 2, wherein said inhibitory RNA consists of the nucleotide sequence of SEQ ID NO: 5, 6, 7, 8, 9, 10, 11, 12, 13 or 14.

7. The method according to claim 1, wherein said subject is a mammalian subject.

8. The method according to claim 2, wherein said subject is a mammalian subject.

9. The method according to claim 1, wherein said mammalian subject is a human subject.

10. The method according to claim 2, wherein said mammalian subject is a human subject.

11. The method according to claim 1, wherein said promoter is a constitutive promoter.

12. The method according to claim 2, wherein said promoter is a constitutive promoter.

13. The method according to claim 1, wherein said promoter is a regulated promoter.

14. The method according to claim 2, wherein said promoter is a regulated promoter.

15. The method according to claim 1, wherein said viral based expression vector is an adeno-associated virus (AAV) vector.

16. The method according to claim 2, wherein said viral based expression vector is an adeno-associated virus (AAV) vector.

17. The method according to claim 9, wherein said AAV vector is AAV9.

18. The method according to claim 10, wherein said AAV vector is AAV9.

19. The method according to claim 1, wherein said viral based vector is a lentiviral vector.

20. The method according to claim 2, wherein said viral based vector is a lentiviral vector.

21. The method according to claim 1, wherein said nucleic acid encoding SRSF1 is encoded by the nucleotide sequence of SEQ ID NO: 1.

22. The method according to claim 2, wherein said nucleic acid encoding SRSF1 is encoded by the nucleotide sequence of SEQ ID NO: 1.

23. The method according to claim 1, wherein said nucleic acid encoding SRSF1 is encoded by a polymorphic sequence variant comprising 90% to 99 sequence identity over the full length nucleotide sequence of SEQ ID NO: 1.

24. The method according to claim 2, wherein said nucleic acid encoding SRSF1 is encoded by a polymorphic sequence variant comprising 90% to 99 sequence identity over the full length nucleotide sequence of SEQ ID NO: 1.

* * * * *